United States Patent
Ohsawa et al.

(10) Patent No.: US 11,404,656 B2
(45) Date of Patent: Aug. 2, 2022

(54) LIGHT-EMITTING DEVICE, LIGHT-EMITTING APPARATUS, ELECTRONIC DEVICE, AND LIGHTING DEVICE

(71) Applicant: Semiconductor Energy Laboratory Co., Ltd., Kanagawa-ken (JP)

(72) Inventors: Nobuharu Ohsawa, Kanagawa (JP); Satoshi Seo, Kanagawa (JP); Hiroshi Kadoma, Kanagawa (JP)

(73) Assignee: Semiconductor Energy Laboratory Co., Ltd.

( * ) Notice: Subject to any disclaimer, the term of this patent is extended or adjusted under 35 U.S.C. 154(b) by 198 days.

(21) Appl. No.: 16/954,692

(22) PCT Filed: Dec. 17, 2018

(86) PCT No.: PCT/IB2018/060157
§ 371 (c)(1),
(2) Date: Jun. 17, 2020

(87) PCT Pub. No.: WO2019/123190
PCT Pub. Date: Jun. 27, 2019

(65) Prior Publication Data
US 2020/0388779 A1    Dec. 10, 2020

(30) Foreign Application Priority Data
Dec. 22, 2017 (JP) .............. JP2017-246022

(51) Int. Cl.
*H01L 51/50* (2006.01)
*H01L 27/32* (2006.01)
(Continued)

(52) U.S. Cl.
CPC ........ *H01L 51/5004* (2013.01); *H01L 27/322* (2013.01); *H01L 51/0072* (2013.01);
(Continued)

(58) Field of Classification Search
CPC ............... H01L 51/5004; H01L 27/322; H01L 51/0072; H01L 51/0084; H01L 51/5206;
(Continued)

(56) References Cited

U.S. PATENT DOCUMENTS

| 6,914,269 B2 | 7/2005 | Nakamura |
| 7,189,996 B2 | 3/2007 | Nakamura |

(Continued)

FOREIGN PATENT DOCUMENTS

| CN | 001578558 A | 2/2005 |
| CN | 104030974 A | 9/2014 |

(Continued)

OTHER PUBLICATIONS

International Search Report (Application No. PCT/IB2018/060157) dated Apr. 2, 2019.
(Continued)

*Primary Examiner* — Mamadou L Diallo
(74) *Attorney, Agent, or Firm* — Husch Blackwell LLP

(57) ABSTRACT

A light-emitting device with low driving voltage and favorable reliability is provided. The light-emitting device includes an electron-injection layer between a cathode and a light-emitting layer. The electron-injection layer is a mixed film of a metal and an organic compound having a function of interacting with the metal as a tridentate or tetradentate ligand, and the metal atom and the organic compound form SOMO.

29 Claims, 38 Drawing Sheets

(51) Int. Cl.
*H01L 51/00* (2006.01)
*H01L 51/52* (2006.01)

(52) U.S. Cl.
CPC ...... *H01L 51/0084* (2013.01); *H01L 51/5206* (2013.01); *H01L 51/5221* (2013.01)

(58) Field of Classification Search
CPC ............. H01L 51/5221; H01L 27/3244; H01L 51/0052; H01L 51/007; H01L 51/0067; H01L 51/5092; H01L 51/5278; H01L 51/0069; H01L 51/50; H05B 33/12; C07F 1/08; C07F 1/10; C09K 11/06; C07D 213/53; C07D 401/14; C07D 403/14; C07D 413/14
See application file for complete search history.

(56) References Cited

U.S. PATENT DOCUMENTS

| | | |
|---|---|---|
| 7,659,556 B2 | 2/2010 | Nakamura |
| 10,068,948 B2 | 9/2018 | Yun et al. |
| 10,476,009 B2 | 11/2019 | Yamada et al. |
| 2002/0043663 A1 | 4/2002 | Seo et al. |
| 2004/0251466 A1 | 12/2004 | Nakamura |
| 2005/0112400 A1 | 5/2005 | Seo et al. |
| 2005/0147847 A1 | 7/2005 | Nakamura |
| 2007/0164285 A1 | 7/2007 | Nakamura |
| 2007/0228380 A1* | 10/2007 | Yoshinaga .......... H01L 51/5092 257/40 |
| 2008/0233432 A1 | 9/2008 | Inoue et al. |
| 2009/0015143 A1 | 1/2009 | Inoue et al. |
| 2011/0245495 A1 | 10/2011 | Inoue et al. |
| 2013/0137866 A1 | 5/2013 | Inoue et al. |
| 2015/0041789 A1 | 2/2015 | Ozeki |
| 2015/0333279 A1* | 11/2015 | Kamatani ........... C07F 15/0033 257/40 |
| 2015/0364703 A1* | 12/2015 | Miyashita .............. C09K 11/06 345/204 |
| 2016/0168162 A1* | 6/2016 | Chae .................. H01L 51/0072 546/85 |
| 2016/0240794 A1 | 8/2016 | Yamada et al. |
| 2016/0276600 A1* | 9/2016 | Park ..................... C09K 11/025 |
| 2016/0372524 A1 | 12/2016 | Yun et al. |
| 2017/0331067 A1* | 11/2017 | Park ....................... C09K 11/06 |
| 2018/0212155 A1* | 7/2018 | Hung ................... H01L 27/302 |
| 2019/0036032 A1* | 1/2019 | Denker ............... H01L 51/5092 |
| 2019/0280211 A1* | 9/2019 | Jung ................... H01L 51/0067 |

FOREIGN PATENT DOCUMENTS

| | | |
|---|---|---|
| CN | 106257704 A | 12/2016 |
| CN | 107250131 A | 10/2017 |
| CN | 107464885 A | 12/2017 |
| EP | 1 486 551 A1 | 12/2004 |
| EP | 3 107 131 A1 | 12/2016 |
| JP | 2001-102175 A | 4/2001 |
| JP | 2005-026221 A | 1/2005 |
| JP | 2006-032683 A | 2/2006 |
| JP | 2015-130319 A | 7/2015 |
| JP | 2016-153400 A | 8/2016 |
| JP | 2018-201012 A | 12/2018 |
| KR | 2004-0107399 A | 12/2004 |
| KR | 2012-0013283 A | 2/2012 |
| KR | 2016-0150184 A | 12/2016 |
| KR | 2017-0117084 A | 10/2017 |
| TW | 201638082 | 11/2016 |
| TW | 201743441 | 12/2017 |
| WO | WO 2013/137234 A1 | 9/2013 |
| WO | WO 2013/141097 A1 | 9/2013 |
| WO | WO 2016/132250 A1 | 8/2016 |
| WO | WO 2017/211100 A1 | 12/2017 |
| WO | WO 2018/185642 A1 | 10/2018 |

OTHER PUBLICATIONS

Written Opinion (Application No. PCT/IB2018/060157) dated Apr. 2, 2019.
Liu, W. et al., "Efficient Inverted Organic Light-Emitting Devices with Self or Intentionally Ag-Doped Interlayer Modified Cathode," Applied Physics Letters, Mar. 6, 2014, vol. 104, pp. 093305-1-093305-4.
Khadir, S. et al., "Localized Surface Plasmon Enhanced Emission of Organic Light Emitting Diode Coupled to DBR-Cathode Microcavity by Using Silver Nanoclusters," Optics Express, Aug. 31, 2015, vol. 23, No. 18, pp. 23647-23659.
Yan, F. et al., "A Plasmonically Enhanced Charge Generation Layer for Tandem Organic Light Emitting Device," Applied Physics Letters, Jan. 30, 2013, vol. 102, pp. 043303-1-043303-4.

* cited by examiner

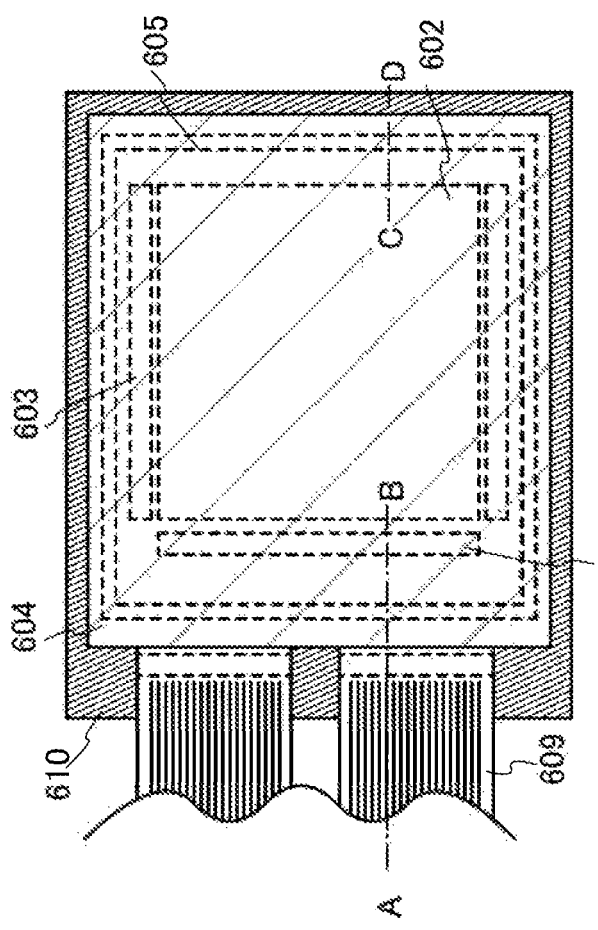
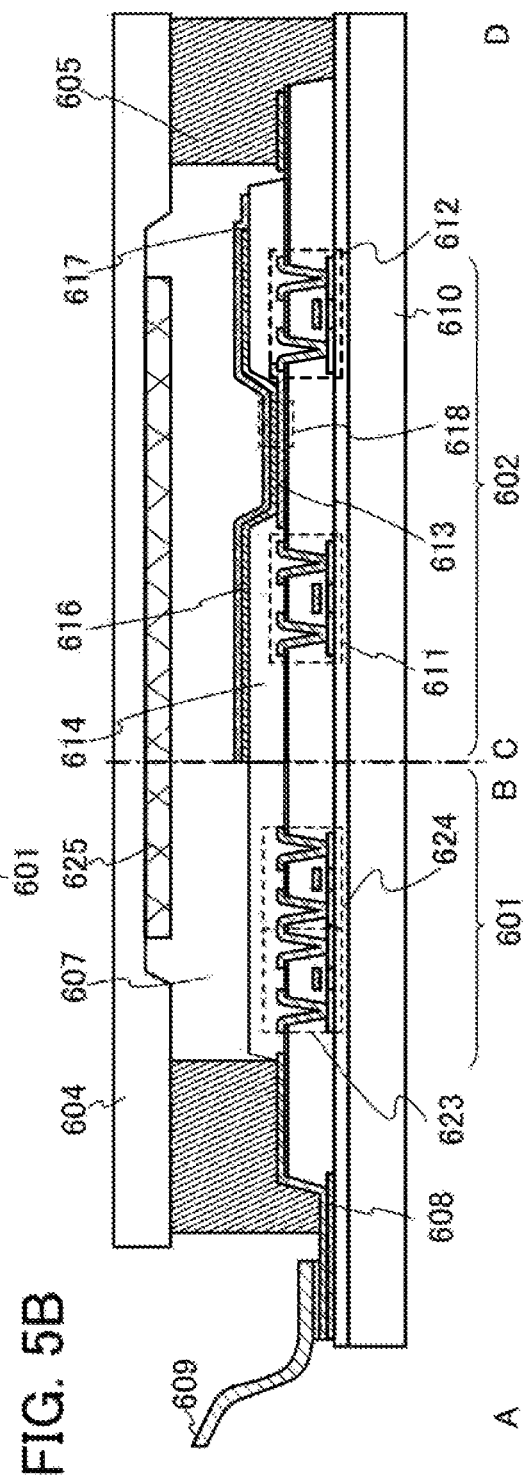
FIG. 5A
FIG. 5B

LIGHT-EMITTING DEVICE, LIGHT-EMITTING APPARATUS, ELECTRONIC DEVICE, AND LIGHTING DEVICE

This application is a 371 of international application PCT/IB2018/060157 filed on Dec. 17, 2018 which is incorporated herein by reference.

TECHNICAL FIELD

One embodiment of the present invention relates to a novel light-emitting device including an electron-injection layer. Another embodiment of the present invention also relates to a display device, an electronic device, and a lighting device each including the light-emitting device.

Note that one embodiment of the present invention is not limited to the above technical field. The technical field of one embodiment of the invention disclosed in this specification and the like relates to an object, a method, or a manufacturing method. Alternatively, one embodiment of the present invention relates to a process, a machine, manufacture, or a composition of matter. Accordingly, specific examples of the technical field of one embodiment of the present invention disclosed in this specification include a semiconductor device, a display device, a liquid crystal display device, a light-emitting apparatus, a lighting device, a power storage device, a memory device, a method for driving any of them, and a method for manufacturing any of them.

BACKGROUND ART

In recent years, research and development have been extensively conducted on light-emitting devices utilizing electroluminescence (EL). The basic structure of these light-emitting devices is a structure in which a layer containing a light-emitting substance (an EL layer) is interposed between a pair of electrodes. By application of a voltage between the electrodes of this element, light emission from the light-emitting substance can be obtained.

Since the above light-emitting device is a self-luminous type, a display device using this has advantages such as high visibility, no necessity of a backlight, and low power consumption. The display device also has advantages in that it can be manufactured to be thin and lightweight and has high response speed.

In general, an electron-injection layer is provided between a cathode and a light-emitting layer to reduce the driving voltage of an EL element. In the electron-injection layer, a metal having a low work function, such as an alkali metal or an alkaline earth metal, typically lithium (Li) or calcium (Ca), or a compound thereof is used to reduce a barrier to electron injection between the cathode and the EL layer (e.g., Patent Document 1).

PRIOR ART DOCUMENT

Patent Document

[Patent Document 1] Japanese Published Patent Application No. 2001-102175

SUMMARY OF THE INVENTION

Problems to be Solved by the Invention

A metal having a low work function and a compound thereof are difficult to handle because of their high reactivity with oxygen or water. When the metal or the metal compound is used for a light-emitting device, a reduction in the emission efficiency, an increase in the driving voltage, a reduction in the reliability, or the like of the light-emitting device is caused by the influence of oxygen or water in some cases. Accordingly, there is a demand for the development of an electron-injection layer that is hardly affected by oxygen and water and forms a low barrier to electron injection between the cathode and the EL layer.

In view of the above-described problems, an object of one embodiment of the present invention is to provide a light-emitting device with low driving voltage. Another object of one embodiment of the present invention is to provide a light-emitting device having high moisture resistance. Another object of one embodiment of the present invention is to provide a light-emitting device having high oxygen resistance. Another object of one embodiment of the present invention is to provide a light-emitting device with reduced power consumption. Another object of one embodiment of the present invention is to provide a light-emitting device with high reliability. Another object of one embodiment of the present invention is to provide a novel light-emitting device. Another object of one embodiment of the present invention is to provide a novel semiconductor device. Another object of one embodiment of the present invention is to provide an organic compound that can be used for a light-emitting device having high moisture resistance.

Another object of one embodiment of the present invention is to provide an electronic device and a lighting device each having high moisture resistance and including the light-emitting device. Another object of one embodiment of the present invention is to provide a light-emitting apparatus with reduced power consumption in which the light-emitting device is used. Another object of one embodiment of the present invention is to provide a light-emitting apparatus having a long lifetime in which the light-emitting device is used.

Note that the descriptions of the above objects do not disturb the existence of other objects. Note that in one embodiment of the present invention, there is no need to achieve all the objects. Other objects are apparent from the descriptions of the specification and the like and can be derived from the descriptions of the specification and the like.

Means for Solving the Problems

As described above, development of a light-emitting device having high moisture resistance and a high electron-injection property is required. Thus, development of a light-emitting device that does not use a metal with a low work function is required.

Accordingly, one embodiment of the present invention is a light-emitting device including a light-emitting layer between an anode and a cathode and a first layer between the light-emitting layer and the cathode. The first layer includes a first organic compound and a metal; the metal belongs to any of Group 3 to Group 13 of the periodic table; the first organic compound includes a substituted or unsubstituted heteroaromatic ring having 1 to 30 carbon atoms; the heteroaromatic ring includes nitrogen; the first organic compound has a function of interacting with the metal at the nitrogen as a tridentate or tetradentate ligand; and the first organic compound and the metal form SOMO (Single Occupied Molecular Orbital).

Another embodiment of the present invention is a light-emitting device including a first light-emitting unit and a second light-emitting unit between an anode and a cathode, and a first layer between the first light-emitting unit and the second light-emitting unit. The first layer includes a first organic compound and a metal; the metal belongs to any of Group 3 to Group 13 of the periodic table; the first organic compound includes a substituted or unsubstituted heteroaromatic ring having 1 to 30 carbon atoms; the heteroaromatic ring includes nitrogen; the first organic compound has a function of interacting with the metal at the nitrogen as a tridentate or tetradentate ligand; and the first organic compound and the metal form SOMO.

In the above structure, the first organic compound is preferably an organic compound represented by a general formula (G0).

[Chemical Formula 1]

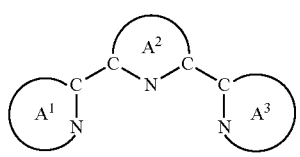

(G0)

In the general formula (G0), $A^1$, $A^2$, and $A^3$ independently represent a substituted or unsubstituted heteroaromatic ring having 1 to 30 carbon atoms, and $A^1$, $A^2$, and $A^3$ may form a condensed ring.

Furthermore, in the above structure, the first organic compound is preferably an organic compound represented by a general formula (G1).

[Chemical Formula 2]

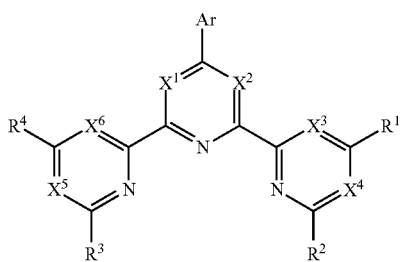

(G1)

In the general formula (G1), $X^1$ to $X^6$ independently represent carbon (C) or nitrogen (N), the carbon includes hydrogen, an alkyl group having 1 to 4 carbon atoms, a substituted or unsubstituted cycloalkyl group having 3 to 7 carbon atoms, a substituted or unsubstituted aromatic hydrocarbon group having 6 to 25 carbon atoms, or a substituted or unsubstituted heteroaromatic hydrocarbon group having 3 to 30 carbon atoms. $R^1$ to $R^4$ independently represent hydrogen, an alkyl group having 1 to 4 carbon atoms, a substituted or unsubstituted cycloalkyl group having 3 to 7 carbon atoms, a substituted or unsubstituted aromatic hydrocarbon group having 6 to 25 carbon atoms, or a substituted or unsubstituted heteroaromatic hydrocarbon group having 3 to 30 carbon atoms. Ar represents hydrogen, an alkyl group having 1 to 4 carbon atoms, a substituted or unsubstituted cycloalkyl group having 3 to 7 carbon atoms, a substituted or unsubstituted aromatic hydrocarbon group having 6 to 60 carbon atoms, or a substituted or unsubstituted heteroaromatic hydrocarbon group having 2 to 60 carbon atoms.

Furthermore, in the above structure, the first organic compound is preferably an organic compound represented by a general formula (G2).

[Chemical Formula 3]

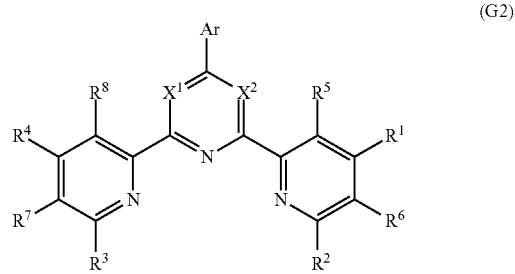

(G2)

In the general formula (G2), $X^1$ and $X^2$ independently represent carbon (C) or nitrogen (N), the carbon includes hydrogen, an alkyl group having 1 to 4 carbon atoms, a substituted or unsubstituted cycloalkyl group having 3 to 7 carbon atoms, a substituted or unsubstituted aromatic hydrocarbon group having 6 to 25 carbon atoms, or a substituted or unsubstituted heteroaromatic hydrocarbon group having 3 to 30 carbon atoms. $R^1$ to $R^8$ independently represent hydrogen, an alkyl group having 1 to 4 carbon atoms, a substituted or unsubstituted cycloalkyl group having 3 to 7 carbon atoms, a substituted or unsubstituted aromatic hydrocarbon group having 6 to 25 carbon atoms, or a substituted or unsubstituted heteroaromatic hydrocarbon group having 3 to 30 carbon atoms. Ar represents hydrogen, an alkyl group having 1 to 4 carbon atoms, a substituted or unsubstituted cycloalkyl group having 3 to 7 carbon atoms, a substituted or unsubstituted aromatic hydrocarbon group having 6 to 60 carbon atoms, or a substituted or unsubstituted heteroaromatic hydrocarbon group having 2 to 60 carbon atoms.

Furthermore, in the above structure, the first organic compound is preferably an organic compound represented by any one of general formulae (G3-1) to (G3-3).

[Chemical Formula 4]

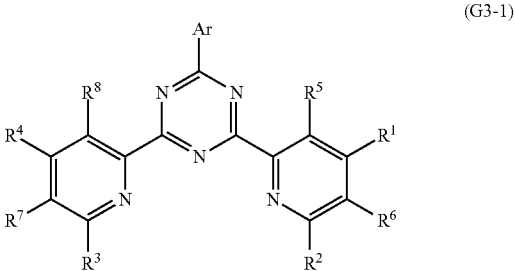

(G3-1)

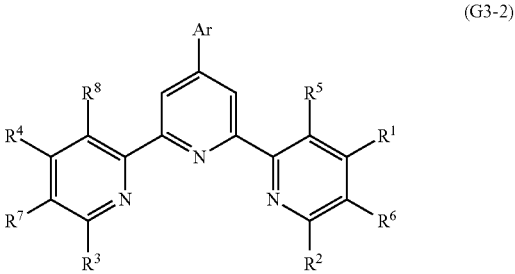

(G3-2)

-continued

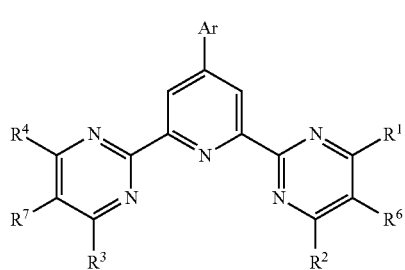
(G3-3)

In the general formulae (G3-1) to (G3-3), $R^1$ to $R^8$ independently represent hydrogen, an alkyl group having 1 to 4 carbon atoms, a substituted or unsubstituted cycloalkyl group having 3 to 7 carbon atoms, a substituted or unsubstituted aromatic hydrocarbon group having 6 to 25 carbon atoms, or a substituted or unsubstituted heteroaromatic hydrocarbon group having 3 to 30 carbon atoms; and Ar represents hydrogen, an alkyl group having 1 to 4 carbon atoms, a substituted or unsubstituted cycloalkyl group having 3 to 7 carbon atoms, a substituted or unsubstituted aromatic hydrocarbon group having 6 to 60 carbon atoms, or a substituted or unsubstituted heteroaromatic hydrocarbon group having 2 to 60 carbon atoms.

Furthermore, in the above structure, the first organic compound is preferably an organic compound represented by any one of general formulae (G4-1) to (G4-3).

[Chemical Formula 5]

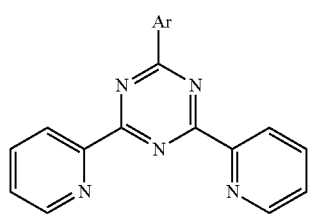
(G4-1)

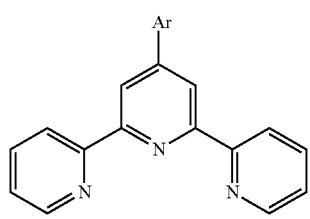
(G4-2)

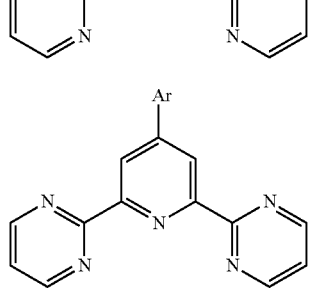
(G4-3)

In the general formula (G4-1) to the general formula (G4-3), Ar represents hydrogen, an alkyl group having 1 to 4 carbon atoms, a substituted or unsubstituted cycloalkyl group having 3 to 7 carbon atoms, a substituted or unsubstituted aromatic hydrocarbon group having 2 to 60 carbon atoms, or a substituted or unsubstituted heteroaromatic hydrocarbon group having 2 to 60 carbon atoms.

Furthermore, in the above structure, the first organic compound is preferably an organic compound represented by any one of the following structural formulae (100) to (103).

[Chemical Formula 6]

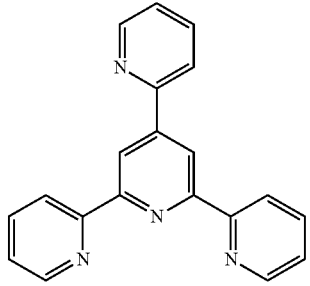
(100)

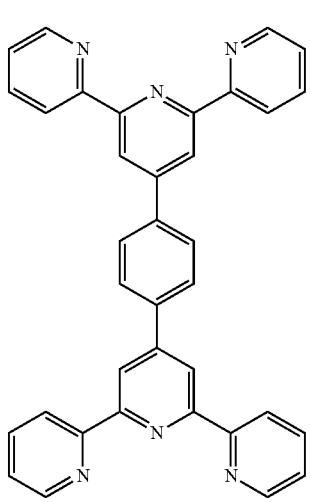
(101)

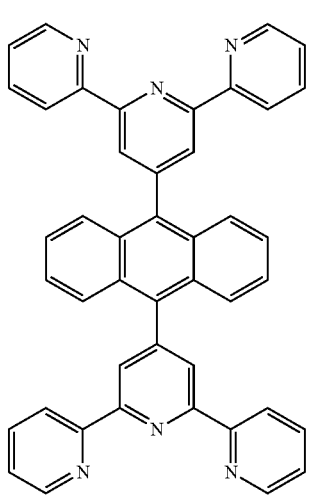
(102)

(103)

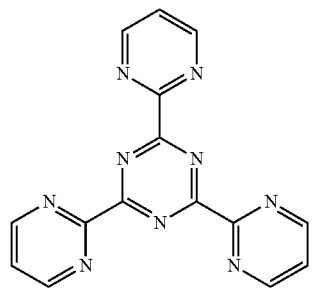

[Chemical Formula 7]

(200)

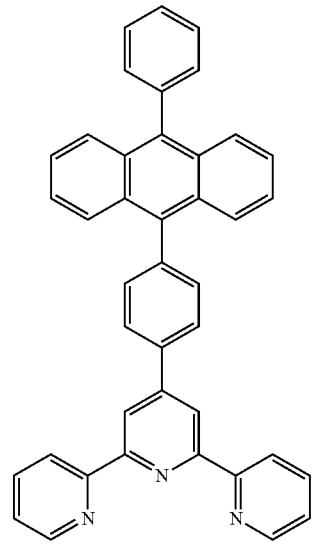

Furthermore, in the above structure, the work function of the metal is preferably higher than or equal to 4.0 eV and lower than or equal to 5.3 eV.

Furthermore, in the above structure, a LUMO (Lowest Unoccupied Molecular Orbital) level of the first organic compound is preferably higher than or equal to −3.6 eV and lower than or equal to −2.3 eV.

Furthermore, in the above structure, the metal is preferably a transition metal, further preferably a metal belonging to Group 5, Group 7, Group 9, or Group 11, still further preferably a transition metal belonging to Group 11, and yet further preferably Ag or Cu.

Furthermore, in the above structure, the heteroaromatic ring preferably includes a substituted or unsubstituted electron deficient heteroaromatic ring, and further preferably includes any one of a pyridine ring, a diazine ring, and a triazine ring.

Furthermore, in the above structure, it is preferable that the second layer be also included between the cathode and the first layer and the second layer include a second organic compound having an electron deficient heteroaromatic ring.

In the above structure, a LUMO level of the second organic compound is preferably lower than the energy level of SOMO.

In the above structure, it is preferable that the first layer of the light-emitting device include neither an alkali metal nor an alkaline earth metal.

In the above structure, it is preferable that a molar ratio of the metal to the first organic compound in the first layer be higher than or equal to 0.2 and lower than or equal to 0.8.

In the above structure, the cathode preferably includes the same metal as that in the first layer.

Another embodiment of the present invention is an organic compound represented by structural formulae (200) to (203).

(201)

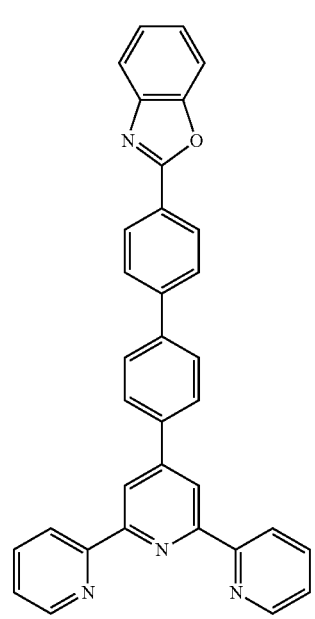

-continued

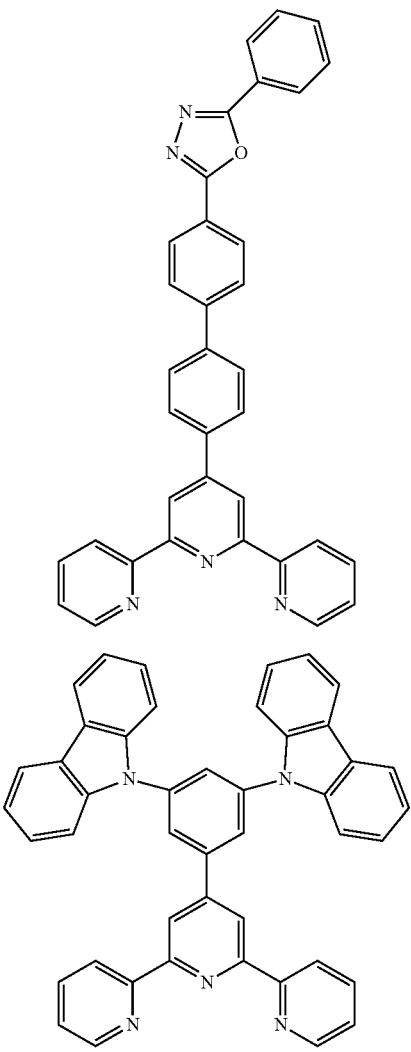

(202)

(203)

Another embodiment of the present invention is an electronic device including the display device having any of the above structures and at least one of a housing and a touch sensor. Another embodiment of the present invention is a lighting device including the light-emitting device having any of the above structures and at least one of a housing and a touch sensor. The category of one embodiment of the present invention includes not only the light-emitting apparatus including the light-emitting device but also an electronic device including the light-emitting apparatus. Thus, the light-emitting apparatus in this specification refers to an image display device or a light source (including a lighting device). A display module in which a connector such as an FPC (Flexible Printed Circuit) or a TCP (Tape Carrier Package) is connected to a light-emitting device, a display module in which a printed wiring board is provided on the tip of a TCP, and a display module in which an IC (integrated circuit) is directly mounted on a light-emitting device by a COG (Chip On Glass) method are also embodiments of the present invention.

Effect of the Invention

According to one embodiment of the present invention, a light-emitting device with low driving voltage can be provided. According to another embodiment of the present invention, a light-emitting device with high moisture resistance can be provided. According to another embodiment of the present invention, a light-emitting device with high oxygen resistance can be provided. According to another embodiment of the present invention, a light-emitting device with reduced power consumption can be provided. According to another embodiment of the present invention, a light-emitting device with high reliability can be provided. According to another embodiment of the present invention, a novel light-emitting device can be provided. According to another embodiment of the present invention, a novel semiconductor device can be provided. According to another embodiment of the present invention, an organic compound that can be used in a light-emitting device having high moisture resistance can be provided.

According to another embodiment of the present invention, an electronic device and a lighting device each having high moisture resistance and including the light-emitting device can be provided. According to another embodiment of the present invention, a light-emitting apparatus with reduced power consumption in which the light-emitting device is used can be provided. According to one embodiment of the present invention, a light-emitting apparatus having a long lifetime in which the light-emitting device is used can be provided.

Note that the descriptions of these effects do not disturb the existence of other effects. Note that one embodiment of the present invention does not necessarily have all the effects. Other effects will be apparent from the descriptions of the specification, the drawings, the claims, and the like, and other effects can be derived from the descriptions of the specification, the drawings, the claims, and the like.

BRIEF DESCRIPTION OF THE DRAWINGS

FIGS. 5A-5B are a top view and a schematic cross-sectional view illustrating a display device of one embodiment of the present invention.

MODE FOR CARRYING OUT THE INVENTION

Figure 1A:
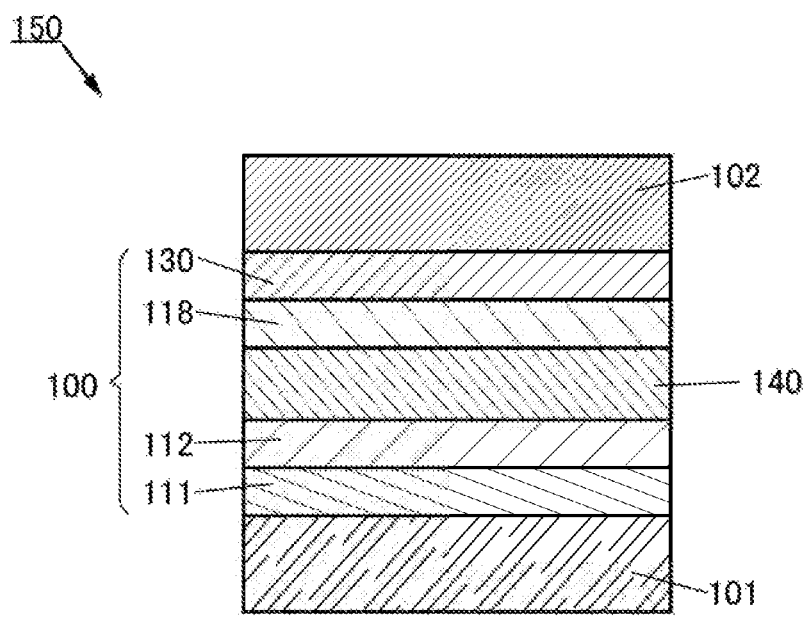
FIGS. 1A-1C are schematic cross-sectional views illustrating a light-emitting device of one embodiment of the present invention and a diagram illustrating the correlation of energy levels in an electron-injection layer.

Embodiments of the present invention will be described in detail below with reference to the drawings. However, the present invention is not limited to the following description, and the modes and details can be variously changed without departing from the spirit and scope of the present invention. Accordingly, the present invention should not be interpreted as being limited to the description of the embodiments below.

Note that the position, size, range, or the like of each structure illustrated in the drawings and the like do not represent the actual position, size, range, or the like in some cases for easy understanding. Therefore, the disclosed invention is not necessarily limited to the position, size, range, or the like disclosed in the drawings and the like.

In this specification and the like, the ordinal numbers such as first and second are used for convenience, and do not denote the order of steps or the stacking order of layers in some cases. Therefore, for example, description can be made even when "first" is replaced with "second," "third," or the like as appropriate. In addition, the ordinal numbers in this specification and the like are not necessarily the same as those used to specify one embodiment of the present invention.

Furthermore, when describing the structures of the invention with reference to the drawings in this specification and the like, the reference numerals denoting the same components are commonly used in different drawings.

In this specification and the like, the term "film" and the term "layer" can be interchanged with each other. For example, the term "conductive layer" can be changed into the term "conductive film" in some cases. For another example, the term "insulating film" can be changed into the term "insulating layer" in some cases.

Embodiment 1

In this embodiment, a light-emitting device of one embodiment of the present invention is described below with reference to FIG. 1.

<Structure Example 1 of Light-Emitting Device>

FIG. 1(A) is a schematic cross-sectional view of a light-emitting device 150 of one embodiment of the present invention.

The light-emitting device 150 includes a pair of electrodes (an electrode 101 and an electrode 102) and an EL layer 100 provided between the pair of electrodes. The EL layer 100 includes at least a light-emitting layer 140 and an electron-injection layer 130.

The EL layer 100 shown in FIG. 1(A) includes functional layers such as a hole-injection layer 111, a hole-transport layer 112, and an electron-transport layer 118, in addition to the light-emitting layer 140 and the electron-injection layer 130.

Note that in this embodiment, although description is given assuming that the electrode 101 and the electrode 102 of the pair of electrodes serve as an anode and a cathode, respectively, the structure of the light-emitting device 150 is not limited thereto. That is, the electrode 101 may serve as a cathode, the electrode 102 may serve as an anode, and the stacking order of layers between the electrodes may be reversed. In other words, the hole-injection layer 111, the hole-transport layer 112, the light-emitting layer 140, the electron-transport layer 118, and the electron-injection layer 130 may be stacked in this order from the anode side.

Note that the structure of the EL layer 100 is not limited to the structure shown in FIG. 1(A); the structure of the EL layer 100 includes at least the light-emitting layer 140 and the electron-injection layer 130, and does not necessarily include the hole-injection layer 111, the hole-transport layer 112, and the electron-transport layer 118.

The layers corresponding to the required functions may be formed in the EL layer between the pair of electrodes, and the layers are not limited to them. In other words, the EL layer between the pair of electrodes may have a structure including a layer which has a function of reducing a barrier to hole or electron injection, enhancing a hole- or electron-transport property, inhibiting a hole- or electron-transport property, suppressing a quenching phenomenon due to an electrode, or the like.

The light-emitting layer 140 preferably includes a host material and a guest material (a light-emitting material).

As the host material, it is preferable to use one or both of a material having a function of transporting holes (hole-transport property) and a material having a function of transporting electrons (electron-transport property), and a material having a hole-transport property and an electron-transport property may be used.

Furthermore, in the case where the host material is a combination (a mixed host) of an electron-transport material and a hole-transport material, the carrier balance can be easily controlled depending on the mixture ratio. Specifically, the ratio of the electron-transport material to the hole-transport material is preferably within a range of 1:9 to 9:1 (weight ratio). Since the carrier balance can be easily controlled with the structure, a carrier recombination region can also be controlled easily.

As the guest material, a light-emitting compound may be used, and the light-emitting compound is preferably a substance capable of exhibiting fluorescence (hereinafter also referred to as a fluorescent compound) or a substance capable of exhibiting phosphorescence (hereinafter also referred to as a phosphorescent compound).

In order to reduce the driving voltage of the light-emitting device, it is necessary to lower a barrier to electron injection between the light-emitting layer 140 and the electrode 102. Hence, it is preferable to provide the electron-injection layer 130 between the light-emitting layer 140 and the electrode 102. In a conventional light-emitting device, a metal material including an alkali metal or an alkaline earth metal, which has a low work function, is used for the electron-injection layer 130. However, a metal material having a low work function has high reactivity with oxygen or water; accordingly, when the reaction between oxygen and water occurs in the light-emitting device, a reduction in emission efficiency, an increase in driving voltage, a reduction in element lifetime, generation of shrinkage (a non-emission region at the end portion of a light-emitting portion), or the like occurs, leading to deterioration in the characteristics or a reduction in the reliability of the light-emitting device in some cases. In other words, a metal material having a low work function can cause element degradation. Thus, a light-emitting device that does not include an alkali metal or an alkaline earth metal is preferable in terms of suppressing deterioration in the characteristics or a reduction in the reliability of the light-emitting device.

Meanwhile, a metal having a high work function has low reactivity with oxygen and water, but causes an increase in a barrier to electron injection between the light-emitting layer 140 and the electrode 102 when used for the electron-injection layer 130, which causes a problem such as an increase in driving voltage or a reduction in emission efficiency of the light-emitting device.

The present inventors have found that SOMO can be formed by interaction between a metal and an organic compound having a function of interacting with the metal as a tridentate or tetradentate ligand, and using a composite material including such a combination of the metal and the organic compound that form SOMO for the electron-injection layer enables a light-emitting device with a reduced barrier to electron injection from the cathode to the light-emitting layer and high moisture resistance to be obtained. That is, they have found that the electron-injection layer 130 can be fabricated without using an alkali metal or an alkaline earth metal.

Thus, the light-emitting device of one embodiment of the present invention is a light-emitting device that uses the composite material of a metal and an organic compound having a function of interacting with the metal as a tridentate or tetradentate ligand for the electron-injection layer.

SOMO is formed by the interaction between the organic compound and the metal. The SOMO is an orbital originating from an unpaired electron of a metal and is distributed also on the orbital of the organic compound. Accordingly, it is shown that the electron orbital of a metal and the electron orbital of the organic compound interact with each other. For efficient interaction between the organic compound and the metal, the organic compound preferably has a large number of atoms that causes interaction. Since the organic compound having a large number of atoms that causes interaction easily interacts with a metal, such an organic compound can easily form SOMO when mixed with a metal. Thus, the organic compound used for the light-emitting device of one embodiment of the present invention preferably has a function of interacting with a metal as a tridentate or tetradentate ligand. Furthermore, SOMO formed by a metal and the organic compound having a large number of atoms that causes interaction is likely to have a high SOMO level, leading to a favorable electron-injection property from the cathode to the light-emitting layer. In addition, such an organic compound can form SOMO by interacting with a metal having a high work function. Thus, the organic compound used for the light-emitting device of one embodiment of the present invention preferably has a function of interacting with a metal as a tridentate or tetradentate ligand.

Examples of the atom that interacts with a metal include a heteroatom having an unshared electron pair in an organic compound. For example, oxygen (O), nitrogen (N), sulfur (S), and phosphorus (P) are given, and nitrogen is preferable. Nitrogen is likely to interact with a metal because of its high electronegativity. Furthermore, the organic compound having a function of interacting with a metal as a tridentate or tetradentate ligand, which is used for the light-emitting device of one embodiment of the present invention, preferably has an electron-transport property to be used for the electron-injection layer. Thus, the organic compound is preferably an organic compound in which the conjugation is extended in the whole molecule. Here, since nitrogen can form a conjugated bond in an organic compound, nitrogen enables the organic compound to have a high carrier-transport property when used in the molecule, particularly in a heteroaromatic ring. Thus, it is preferable that the atom that interacts with a metal be nitrogen, and further preferable that the nitrogen be included in the heteroaromatic ring in the organic compound. With this structure, the organic compound can have a high carrier-transport property and a function of interacting with a metal. Moreover, it is further preferable that the heteroaromatic ring be an even-numbered ring such as a six-membered ring or an eight-membered ring. Since the unshared electron pair of nitrogen does not contribute to the conjugation in this structure, nitrogen is likely to interact with a metal.

In order to form SOMO by interaction between a metal and the organic compound having a function of interacting with the metal as a tridentate or tetradentate ligand, the sum of the number of electrons of the organic compound and the metal is preferably an odd number. Accordingly, in the case where the number of electrons of the organic compound is an even number, the metal preferably belongs to an odd-numbered group in the periodic table. In the case where the number of electrons of the organic compound is an odd number, the metal preferably belongs to an even-numbered group in the periodic table.

In addition, as the compound having a function of interacting with a metal as a tridentate or tetradentate ligand, an organic compound having a function of transporting electrons is preferable. Furthermore, an organic compound that functions as an electron acceptor with respect to the metal is preferable.

Furthermore, the organic compound used for one embodiment of the present invention interacts with the metal as a tridentate or tetradentate ligand, and thus is highly likely to interact with a metal. Thus, not only transition metals of Groups 3 to 11, but also metals of Group 12 and Group 13 that have a closed-shell d orbital can be used for one embodiment of the present invention. In addition, metals having an extremely high work function such as gold (Au) or cobalt (Co) can also be used suitably.

A metal having a high work function such as a metal belonging to Group 3 to Group 13 has low reactivity with water and oxygen; accordingly, in a light-emitting device using such a metal, element degradation due to water and oxygen, which might occur in the case of using a metal having a low work function, hardly occurs. Specifically, the work function of the metal is preferably higher than or equal to 4.0 eV and lower than or equal to 5.3 eV, further preferably higher than or equal to 4.2 eV and lower than or equal to 5.0 eV, still further preferably higher than or equal to 4.5 eV and lower than or equal to 5.0 eV, yet further preferably higher than or equal to 4.7 eV and lower than or equal to 5.0 eV. With this structure, one embodiment of the present invention can provide a light-emitting device having high moisture resistance and high oxygen resistance.

Figure 1B:
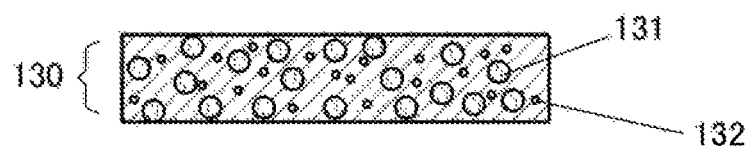

FIG. 1(B) is a schematic view of the electron-injection layer 130 in the light-emitting device of one embodiment of the present invention. The electron-injection layer 130 includes a compound 131 and a metal 132. The compound 131 has a function of interacting with the metal 132 as a tridentate or tetradentate ligand.

Figure 1C:
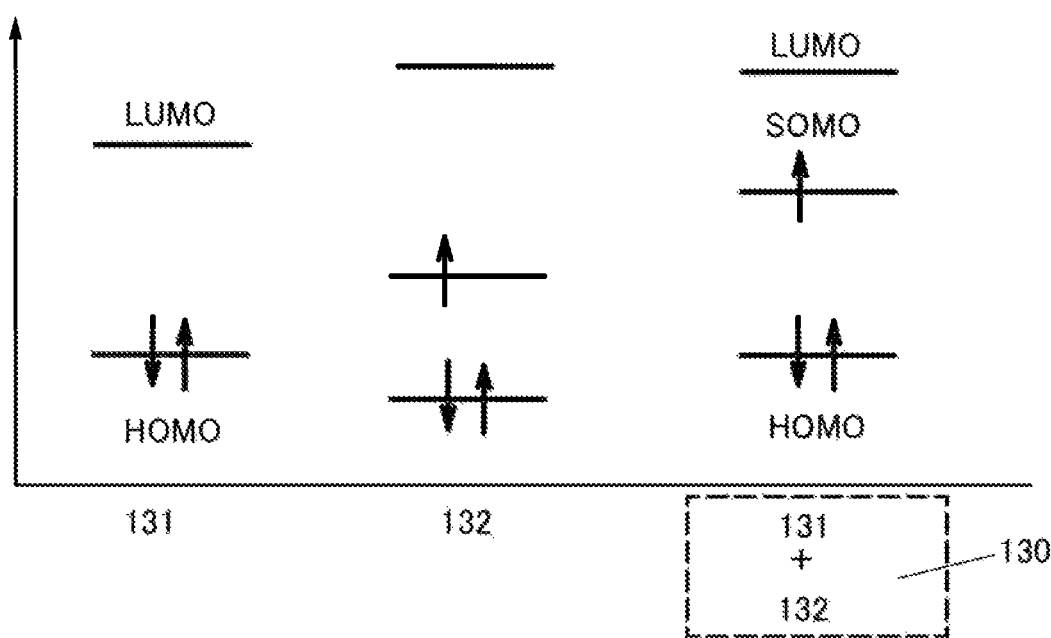

FIG. 1(C) is a diagram showing energy in the electron-injection layer 130 of the light-emitting device of one embodiment of the present invention. When the metal 132 and the compound 131 are mixed, the compound 131 interacts with an atom of the metal 132, whereby SOMO is formed. At this time, it is preferable that a HOMO (Highest Occupied Molecular Orbital) level formed by interaction between the compound 131 and the atom of the metal 132 be approximately equal to the HOMO level of the original compound 131. In the case where an organic compound having a function of transporting electrons is used for the compound 131, the HOMO level of the compound 131 is low, and holes are not easily injected into the compound 131. Therefore, it is preferable that the HOMO level formed by the interaction between the compound 131 and the metal 132 be approximately equal to the HOMO level of the original compound 131, in which case a barrier to hole injection between the electron-injection layer 130 and the electrode 102 is high; accordingly, a hole does not easily pass through from the electron-injection layer 130 to the electrode 102, resulting in improvement in the carrier balance in the light-emitting device. Note that HOMO in this specification and the like refers to a molecular orbital having the highest energy of orbitals occupied by electrons.

SOMO is an orbital having only one electron; thus, when a voltage is applied to the light-emitting device 150, the electron in the SOMO serves as a carrier in the light-emitting device and is transported to the electron-transport layer 118 and the light-emitting layer 140. In addition, electrons can be easily injected from the electrode 102 into the electron-injection layer 130, and furthermore, the electrons can be easily injected from the electron-injection layer 130 into the light-emitting layer 140 through the electron-transport layer 118. That is, when the electron-injection layer 130 includes materials which form SOMO in combination, electrons can be easily injected from the electrode 102 into the light-emitting layer 140. The SOMO level is preferably lower than the LOMO level of the compound 131. Accordingly, the LUMO level of the compound 131 is preferably high. Specifically, the LUMO level of the compound 131 is preferably higher than or equal to −3.6 eV and lower than or equal to −2.3 eV. When an organic compound having such a LUMO level and a metal are mixed, a SOMO level suitable for electron injection is formed by the interaction, whereby a barrier to electron injection from the electrode 102 into the light-emitting layer 140 can be reduced.

Note that the HOMO level and the LUMO level of an organic material are generally estimated by CV (cyclic voltammetry), photoelectron spectroscopy, optical absorption spectroscopy, inverse photoemission spectroscopy, or the like. In the case where values of different compounds are compared with each other, it is preferable that values estimated by the same measurement be used.

The above-described metal preferably belongs to any of Group 3, Group 5, Group 7, Group 9, Group 11, and Group 13. Metals belonging to the odd-numbered groups have one electron (an unpaired electron) in the orbital of the outermost shell is particularly preferable because of the properties of easily forming SOMO by combination with the compound 131.

<Estimation of SOMO Level Formed by Interaction Between Metal 132 and Compound 131 by Quantum Chemistry Calculations>

In the light-emitting device of one embodiment of the present invention, the compound 131 and the metal 132 form SOMO; however, in the case where the SOMO level is extremely low, they are not suitable as the electron-injection layer. Here, the levels of SOMO formed by the interaction between the compound 131 and metal atoms were estimated by quantum chemistry calculation. The results are shown in Table 1. Note that as the organic compound having a function of interacting with a metal as a tridentate or tetradentate ligand, the following are used: 4',4''''-(1,4-Phenylene)bis(2,2':6',2''-terpyridine) (abbreviation: tPy2P), 4',4''-(9,10-anthryl)bis(2,2':6',2''-terpyridine) (abbreviation: tPy2A), 2,2'-(pyridine-2,6-diyl)bis(4-phenylbenzo[h]quinazoline) (abbreviation: 2,6(P-Bqn)2Py), 2,2'-(2,2'-bipyridine-6,6'-diyl)bis(4-phenylbenzo[h]quinazoline) (abbreviation: 6,6'(P-Bqn)2BPy), 2,4,6-tris(2-pyridyl)-1,3,5-triazine (abbreviation: 2Py3Tzn), and 2,4,6-tris(5-phenylpyrimidine-2-yl)-1,3,5-triazine (abbreviation: PPm3Tzn).

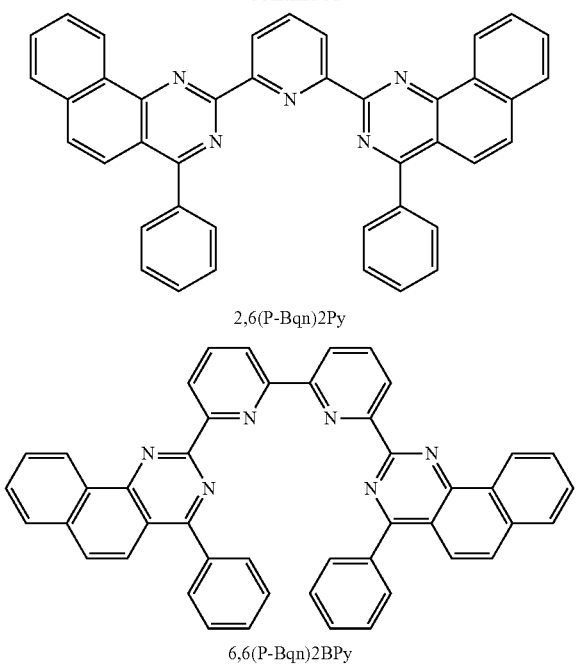

[Chemical Formula 8]

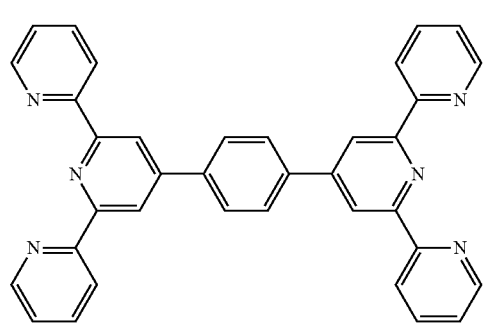

tPy2P

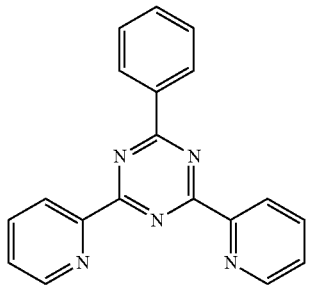

2Py3Tzn

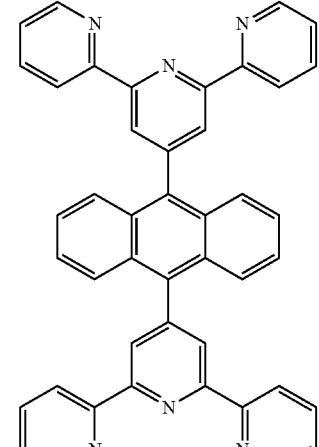

tPy2A

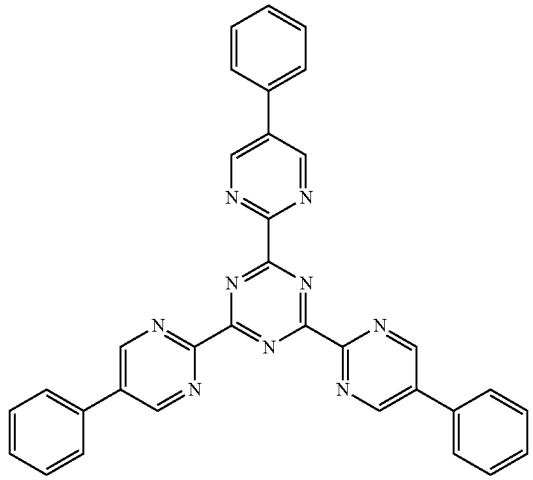

PPm3Tzn

TABLE 1

| Organic Compound Figures in parentheses indicates | Metal Figures in parentheses indicates work function (eV) | | | | | | |
|---|---|---|---|---|---|---|---|
| LLTMO level (eV) | Li (2.9) | In (4.1) | Mn (4.1) | Al (4.2) | Ag (4.5) | Cu (4.7) | Co (5.0) Au (5.1) |
| tPy2P (−2.85) | −3.30 | −3.39 | — | −3.60 | −2.97 | −3.02 | −3.30 −3.15 |
| tPy2A (−2.91) | −2.92 | −3.32 | −3.22 | −3.61 | −2.89 | −2.93 | −3.20 −3.08 |
| 2,6(P-Bqn)2Py (−2.92) | −2.94 | −3.16 | −3.51 | −3.37 | −2.93 | −3.00 | −3.07 −2.99 |
| 6.6'(P-Bqn)2BPy (−2.92) | −2.88 | −3.06 | −3.64 | −3.40 | −2.86 | −2.89 | −3.48 −2.87 |
| 2Py3Tzn (−3.15) | −3.27 | −3.67 | −3.63 | −3.97 | −3.28 | −3.37 | −3.46 −3.51 |
| PPm3Tzn (−3.41) | −3.50 | −3.82 | −3.96 | −4.09 | −3.49 | −3.63 | −3.69 −3.70 |

In addition, the LUMO levels of the organic compounds in Table 1 were calculated by cyclic voltammetry (CV) measurement.

An electrochemical analyzer (ALS model 600A or 600C, manufactured by BAS Inc.) is used as a measurement apparatus. To prepare a solution for the CV measurement, dehydrated dimethylformamide (DMF) (produced by Sigma-Aldrich Inc., 99.8%, catalog No. 22705-6) is used as a solvent, tetra-n-butylammonium perchlorate (n-Bu$_4$NClO$_4$) (produced by Tokyo Chemical Industry Co., Ltd., catalog No. T0836) as a supporting electrolyte is dissolved at a concentration of 100 mmol/L, and the object to be measured is also dissolved at a concentration of 2 mmol/L. A platinum electrode (PTE platinum electrode, manufactured by BAS Inc.) is used as a working electrode, another platinum electrode (Pt counter electrode for VC-3 (5 cm), manufactured by BAS Inc.) is used as an auxiliary electrode, and an Ag/Ag$^+$ electrode (RE7 reference electrode for non-aqueous solvent, manufactured by BAS Inc.) is used as a reference electrode. Note that the measurement is performed at room temperature (20° C. to 25° C.). In addition, the scan speed in the CV measurement is fixed to 0.1 V/sec, and an oxidation potential Ea [V] and a reduction potential Ec [V] with respect to the reference electrode are measured. Ea is an intermediate potential of an oxidation-reduction wave, and Ec is an intermediate potential of a reduction-oxidation wave. Here, since the potential energy of the reference electrode used in this example with respect to the vacuum level is known to be −4.94 [eV], the HOMO level and the LUMO level can be calculated by the following formulae: HOMO level [eV]=−4.94−Ea and LUMO level [eV]=−4.94−Ec.

As the quantum chemistry computational program, Gaussian 09 is used. A high performance computer (ICE X, manufactured by SGI Japan, Ltd.) is used for the calculations. First, the most stable structures in the ground state of the organic compound alone, the ground state of each metal alone, and the ground state of a composite material of the organic compound and each metal are calculated by density functional theory (DFT). As basis functions, 6-311G(d,p) and LanL2DZ are used, and as a functional, B3LYP is used. Next, the stabilization energy is calculated by subtracting the sum of the total energy of the organic compound alone and the total energy of the metal alone from the total energy of the composite material of the organic compound and the metal. That is, (stabilization energy)=(the total energy of the composite material of the organic compound and the metal)−(the total energy of the organic compound alone)−(the total energy of the metal alone) is satisfied. In the DFT, the total energy is represented as the sum of potential energy, electrostatic energy between electrons, electronic kinetic energy, and exchange-correlation energy including all the complicated interactions between electrons. Also in the DFT, exchange-correlation interaction is approximated by a functional (a function of another function) of one electron potential represented in terms of electron density to enable high-accuracy calculations.

Table 1 shows the calculation results of the levels of SOMO formed by the organic compounds and metals: manganese (Mn) that is a transition metal of Group 7; cobalt (Co) that is a transition metal of Group 9; copper (Cu) that is a transition metal of Group 11; silver (Ag); gold (Au); and aluminum (Al) and indium (In) that are metals of Group 13. In addition, the levels of SOMO formed by lithium (Li), which is widely used as a material for an electron-injection layer, and each of the organic compounds are also calculated. The results obtained by the calculation show that, in any of the combinations of the organic compound and the metal shown in Table 1, the organic compound and the metal interact with each other to be stable at the vicinity of nitrogen in the heteroaromatic ring included in the organic compound, and the stabilization energy has a negative value. That is, in the case where any of these organic compounds and the metals are mixed, energy is more stable when the organic compound and the metal interact with each other than when they do not interact with each other. As described above, a stable composite material can be obtained by the interaction between a metal and the organic compound having a function of interacting with the metal as a tridentate or tetradentate ligand. Furthermore, Table 1 shows that the levels of SOMO formed by the metals and the organic compounds having a function of interacting with the metals as a tridentate or tetradentate ligand are substantially equal to the levels of SOMO formed by Li and each of the organic compounds. Accordingly, it is found that the composite material of the metal and the organic compound having a function of interacting with the metal as a tridentate or tetradentate ligand has a high electron-injection property. In addition, it is found that the composite material particularly using Cu, Ag, or Au that is a Group 11 element or Co that is a Group 9 element has a high SOMO level, and the composite material of the organic compound having a function of interacting with the metal as a tridentate or tetradentate ligand and the metal belonging to Group 9 or Group 11 has a high electron-injection property.

Table 1 also indicates that the levels of SOMO formed by the metals and the organic compounds having a function of interacting with the metals as a tridentate or tetradentate ligand are more affected by the LUMO levels of the organic compounds than by the work functions of the metals. Thus, with the use of an organic compound with a high LUMO level, a composite material of an organic compound and a metal having a high SOMO level and a high electron-injection property can be fabricated. As described above, the LUMO level of the organic compound is preferably higher than or equal to −3.6 eV and lower than or equal to −2.3 eV.

Meanwhile, considering a fabrication process of a light-emitting device, an EL layer of a light-emitting device, particularly an electron-injection layer, and a cathode are generally formed by a vacuum evaporation method. In that case, it is preferable to use a material that can be easily deposited by vacuum evaporation, that is, a material with a low melting point, a low boiling point, or a low sublimation point, and it is preferable to use a material that has a low temperature corresponding to the vapor pressure at the time of vacuum evaporation. A Group 11 or Group 13 element has a lower melting point than a Group 7 or Group 9 element, and thus can be suitably used for deposition by vacuum evaporation. In particular, a Group 11 element such as Ag and a Group 13 element such as Al that have a low melting point is preferable because such a metal atom is easily mixed with the organic compound by a vacuum evaporation method.

Furthermore, Ag, Cu, Au, Al, or In can be used also as a cathode material. Using the same material for the electron-injection layer 130 and the electrode 102 is preferable because the light-emitting device can be manufactured easily. Furthermore, using the same material for the electron-injection layer 130 and the electrode 102 can increase the adhesion between the electron-injection layer 130 and the electrode 102, and accordingly improve the reliability of the light-emitting device. Moreover, the manufacturing cost of the light-emitting device can be reduced.

Furthermore, the light-emitting device of one embodiment of the present invention can use a metal having a high work function for the electron-injection layer 130. Thus, a metal having a work function higher than or equal to the work function of the metal included in the electrode 102 can be used for the electron-injection layer 130. The light-emitting device of one embodiment of the present invention can have a reduced barrier to electron injection between the electrode 102 and the electron-injection layer 130 even when using a metal having a high work function, and thus can have a reduced driving voltage.

In addition, in the case where the compound 131 interacts with the metal 132, it is preferable that the metal 132 and the compound 131 serve as an electron donor and an electron acceptor, respectively. In this case, the compound 131 preferably has a plurality of electron deficient heteroaromatic rings. In such a structure, the compound 131 is likely to accept electrons, and thus is likely to form SOMO when interacting with the atom of the metal 132. A compound having an electron deficient heteroaromatic ring has a favorable electron-transport property, and thus is preferably used as the compound 131 of the electron-injection layer in terms of reducing the driving voltage of the light-emitting device.

The electron deficient heteroaromatic ring is preferably a nitrogen-containing heteroaromatic ring, further preferably includes at least one of a pyridine ring, a diazine ring (a pyrimidine ring, a pyrazine ring, or a pyridazine ring), and a triazine ring. Since these rings have high electrochemical stability, light-emitting devices having high reliability can be provided. Moreover, the light-emitting devices with reduced driving voltage can be provided owing to their excellent electron-transport properties. Note that the compound having the electron deficient heteroaromatic ring may be a metal complex.

In the case where an organic compound is used as the compound 131, the number of carbon atoms is preferably greater than or equal to 25 and less than or equal to 100. The organic compound having such number of carbon atoms can have a high sublimation property, and accordingly, the thermal decomposition of the organic compound in vacuum evaporation can be suppressed, whereby favorable material use efficiency can be achieved. Furthermore, the glass transition point (Tg) is preferably 100° C. or higher. When an organic compound with such Tg is used for the EL layer, the light-emitting device can have high heat resistance.

Note that the organic compound used for this calculation includes N that is a coordinating atom in the heteroaromatic ring and includes a conjugated double bond arranged in the order of N—C—C—N. This is because such a bonding portion allows a chelate ring to be formed by interaction between the compound 131 and the metal 132 (a ring structure is formed by the interaction between the compound 131 and the metal 132). The combination of the compound 131 and the metal 132 that can form a chelate ring is preferable because it facilitates the interaction therebetween and formation of SOMO.

Thus, an organic compound having a function of interacting with a metal as a tridentate or tetradentate ligand, which can be suitably used for the light-emitting device of one embodiment of the present invention, has a structure represented by the following general formula (G0).

[Chemical Formula 9]

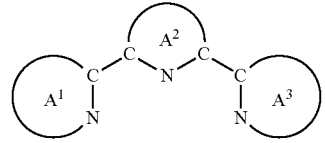

(G0)

In the general formula (G0), $A^1$, $A^2$, and $A^3$ independently represent a substituted or unsubstituted heteroaromatic ring having 1 to 30 carbon atoms, and $A^1$, $A^2$, and $A^3$ may form a condensed ring.

The organic compound represented by the general formula (G0) includes a conjugated double bond in which N in the heteroaromatic ring are arranged in the order of N—C—C—N, and have a function of interacting with a metal as a ligand of tridentate or more. Since the organic compound having such a structure easily forms SOMO when mixed with a metal as described above, and thus can be suitably used for the light-emitting device of one embodiment of the present invention.

Examples of the substituted or unsubstituted heteroaromatic ring having 1 to 30 carbon atoms represented by $A^1$, $A^2$, and $A^3$ in the general formula (G0) include a pyridine ring, a diazine ring (a pyrimidine ring, a pyrazine ring, or a pyridazine ring), a triazine ring, a quinoline ring, a quinoxaline ring, a quinazoline ring, a benzoquinazoline ring, a phenanthroline ring, an azafluoranthene ring, an imidazole ring, an oxazole ring, and an oxadiazole ring. Specifically, heteroaromatic rings represented by the following (A-1) to (A-16) can be given. Note that the substituted or unsubstituted heteroaromatic ring having 1 to 30 carbon atoms represented by $A^1$, $A^2$, and $A^3$ is not limited to these. $A^1$, $A^2$, and $A^3$ may form a condensed ring. For example, $A^1$ and $A^2$ may be bonded to each other to form a phenanthroline ring.

[Chemical Formula 10]

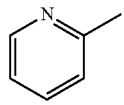

(A-1)

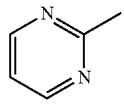

(A-2)

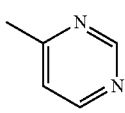 (A-3)

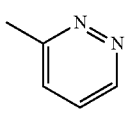 (A-4)

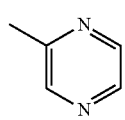 (A-5)

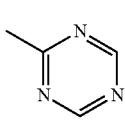 (A-6)

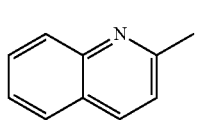 (A-7)

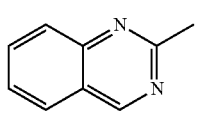 (A-8)

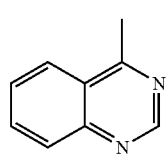 (A-9)

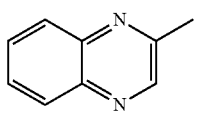 (A-10)

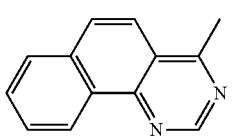 (A-11)

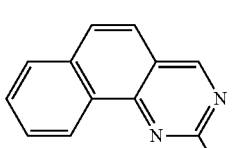 (A-12)

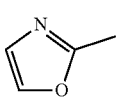 (A-13)

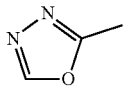 (A-14)

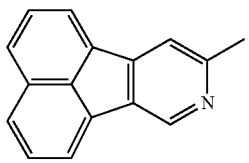 (A-15)

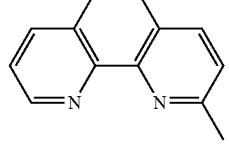 (A-16)

Alternatively, an organic compound having a function of interacting with a metal as a tridentate or tetradentate ligand, which can be suitably used for the light-emitting device of one embodiment of the present invention, has a structure represented by the following general formula (G1).

[Chemical Formula 11]

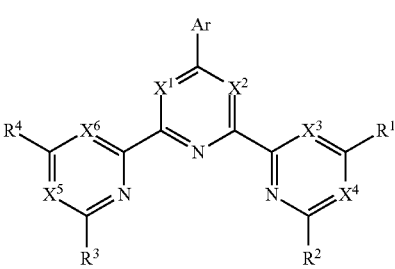 (G1)

In the general formula (G1), $X^1$ to $X^6$ independently represent carbon (C) or nitrogen (N), carbon includes hydrogen, an alkyl group having 1 to 4 carbon atoms, a substituted or unsubstituted cycloalkyl group having 3 to 7 carbon atoms, a substituted or unsubstituted aromatic hydrocarbon group having 6 to 25 carbon atoms, or a substituted or unsubstituted heteroaromatic hydrocarbon group having 3 to 30 carbon atoms; $R^1$ to $R^4$ independently represent hydrogen, an alkyl group having 1 to 4 carbon atoms, a substituted or unsubstituted cycloalkyl group having 3 to 7 carbon atoms, a substituted or unsubstituted aromatic hydrocarbon group having 6 to 25 carbon atoms, or a substituted or unsubstituted heteroaromatic hydrocarbon group having 3 to 30 carbon atoms; and Ar represents hydrogen, an alkyl group having 1 to 4 carbon atoms, a substituted or unsubstituted cycloalkyl group having 3 to 7 carbon atoms, a substituted or unsubstituted aromatic hydrocarbon group having 6 to 60 carbon atoms, or a substituted or unsubstituted heteroaromatic hydrocarbon group having 2 to 60 carbon atoms.

As the organic compound represented by the general formula (G1), the organic compound having a function of interacting with a metal as a tridentate or tetradentate ligand preferably includes at least one of a pyridine ring, a diazine ring (a pyrimidine ring, a pyrazine ring, or a pyridazine ring), and a triazine ring. Since these rings have high electrochemical stability, light-emitting devices having high reliability can be provided. Moreover, the light-emitting devices with reduced driving voltage can be provided owing to their high electron-transport properties.

Alternatively, an organic compound having a function of interacting with a metal as a tridentate or tetradentate ligand, which can be suitably used for the light-emitting device of one embodiment of the present invention, has a structure represented by the following general formula (G2).

[Chemical Formula 12]

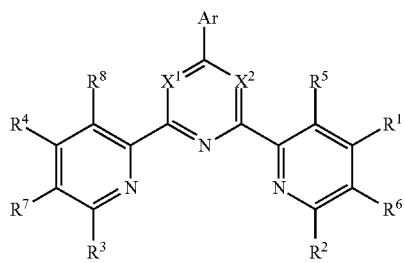

(G2)

In the general formula (G2), $X^1$ and $X^2$ independently represent carbon (C) or nitrogen (N), carbon includes hydrogen, an alkyl group having 1 to 4 carbon atoms, a substituted or unsubstituted cycloalkyl group having 3 to 7 carbon atoms, a substituted or unsubstituted aromatic hydrocarbon group having 6 to 25 carbon atoms, or a substituted or unsubstituted heteroaromatic hydrocarbon group having 3 to 30 carbon atoms; $R^1$ to $R^8$ independently represent hydrogen, an alkyl group having 1 to 4 carbon atoms, a substituted or unsubstituted cycloalkyl group having 3 to 7 carbon atoms, a substituted or unsubstituted aromatic hydrocarbon group having 6 to 25 carbon atoms, or a substituted or unsubstituted heteroaromatic hydrocarbon group having 3 to 30 carbon atoms; and Ar represents hydrogen, an alkyl group having 1 to 4 carbon atoms, a substituted or unsubstituted cycloalkyl group having 3 to 7 carbon atoms, a substituted or unsubstituted aromatic hydrocarbon group having 6 to 60 carbon atoms, or a substituted or unsubstituted heteroaromatic hydrocarbon group having 3 to 60 carbon atoms.

An organic compound having a pyridine skeleton tends to have a high LUMO level. Thus, a composite material having a high SOMO level can be fabricated when the organic compound having a pyridine skeleton represented by the general formula (G2) is mixed with a metal. That is, a composite material having a high electron-injection property can be fabricated when an organic compound having a pyridine ring and a function of interacting with a metal as a tridentate or tetradentate ligand is mixed with a metal.

The organic compound having a function of interacting with a metal as a tridentate or tetradentate ligand, which can be suitably used for the light-emitting device of one embodiment of the present invention, is represented by any one of the following general formulae (G3-1) to (G3-3).

[Chemical Formula 13]

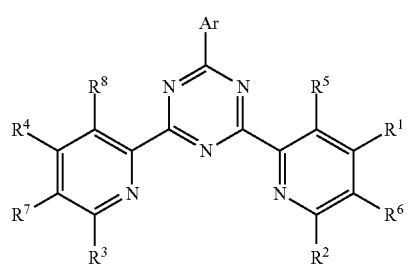

(G3-1)

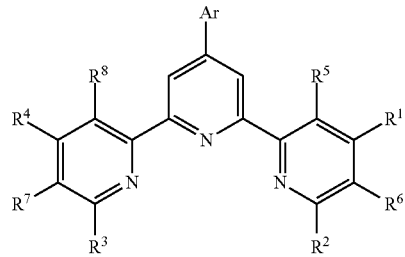

(G3-2)

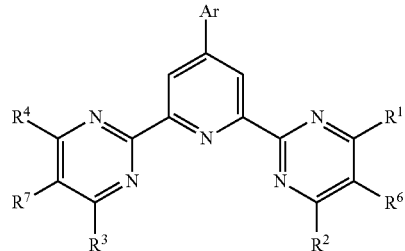

(G3-3)

In the general formulae (G3-1) to (G3-3), $R^1$ to $R^8$ independently represent hydrogen, an alkyl group having 1 to 4 carbon atoms, a substituted or unsubstituted cycloalkyl group having 3 to 7 carbon atoms, a substituted or unsubstituted aromatic hydrocarbon group having 6 to 25 carbon atoms, or a substituted or unsubstituted heteroaromatic hydrocarbon group having 3 to 30 carbon atoms; and Ar represents hydrogen, an alkyl group having 1 to 4 carbon atoms, a substituted or unsubstituted cycloalkyl group having 3 to 7 carbon atoms, a substituted or unsubstituted aromatic hydrocarbon group having 6 to 60 carbon atoms, or a substituted or unsubstituted heteroaromatic hydrocarbon group having 2 to 60 carbon atoms.

Alternatively, the compound having a function of interacting with a metal as a tridentate or tetradentate ligand, which can be suitably used for a light-emitting device of one embodiment of the present invention, is represented by any one of the following general formulae (G4-1) to (G4-3).

[Chemical Formula 14]

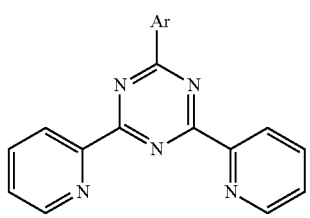

(G4-1)

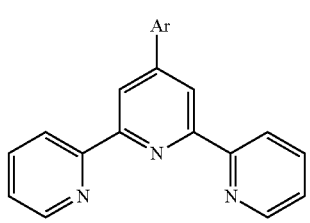

(G4-2)

-continued (G4-3)

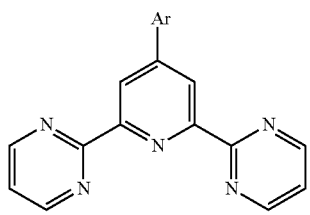

In the general formulae (G4-1) to (G4-3), Ar represents hydrogen, an alkyl group having 1 to 4 carbon atoms, a substituted or unsubstituted cycloalkyl group having 3 to 7 carbon atoms, a substituted or unsubstituted aromatic hydrocarbon group having 2 to 60 carbon atoms, or a substituted or unsubstituted heteroaromatic hydrocarbon group having 2 to 60 carbon atoms.

<Examples of Substituents>

In the general formulae (G0) to (G3), examples of the substituents represented by $R^1$ to $R^8$ or the substituents of C include hydrogen, an alkyl group having 1 to 4 carbon atoms, a substituted or unsubstituted cycloalkyl group having 3 to 7 carbon atoms, a substituted or unsubstituted aromatic hydrocarbon group having 6 to 25 carbon atoms, and a substituted or unsubstituted heteroaromatic hydrocarbon group having 3 to 30 carbon atoms. Specific examples of the alkyl group include a methyl group, an ethyl group, a propyl group, an isopropyl group, a butyl group, an isobutyl group, a tert-butyl group, and an n-hexyl group; specific examples of the cycloalkyl group include a cyclopropyl group, a cyclobutyl group, a cyclopentyl group, and a cyclohexyl group; and specific examples of the aryl group include a phenyl group, a naphthyl group, a biphenyl group, a fluorenyl group, and a spirofluorenyl group. More specific examples include groups represented by the following structural formulae (R-1) to (R-56). Note that the substituents represented by $R^1$ to $R^8$ and the substituents of C are not limited to these.

[Chemical Formula 15]

(R-1)

(R-2)

(R-3)

(R-4)

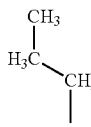

(R-5)

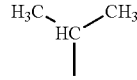

(R-6)

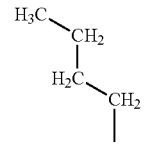

(R-7)

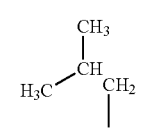

(R-8)

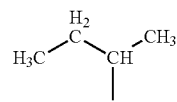

(R-9)

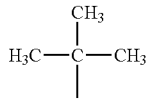

(R-10)

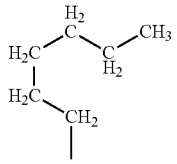

(R-11)

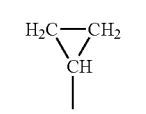

(R-12)

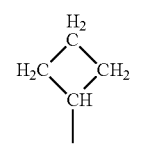

(R-13)

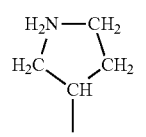

(R-14)

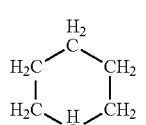

(R-15)

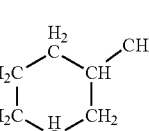

(R-16)

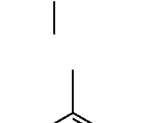

(R-17) 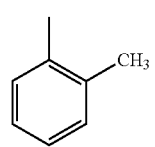
(R-18) 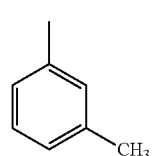
(R-19) 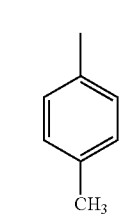
(R-20) 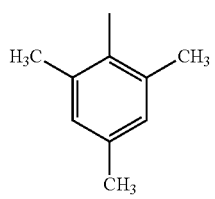
(R-21) 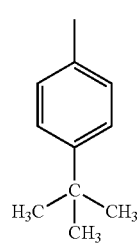
(R-22) 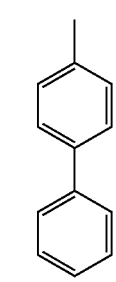
(R-23) 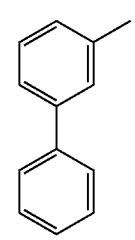
(R-24) 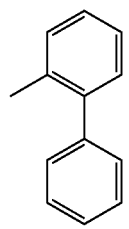
(R-25) 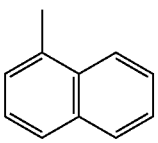
(R-26) 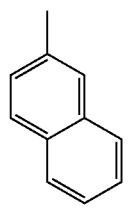
(R-27) 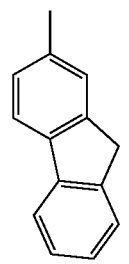
(R-28) 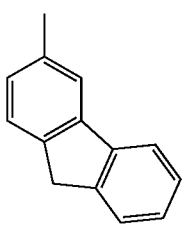
(R-29) 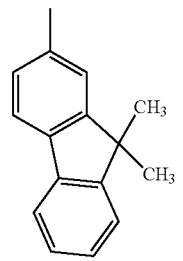
(R-30) 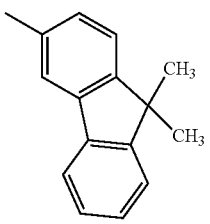

(R-31) 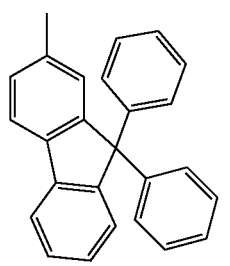
(R-32) 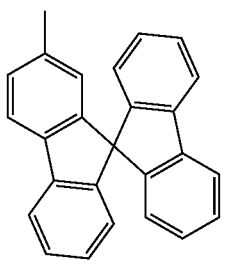
(R-33) 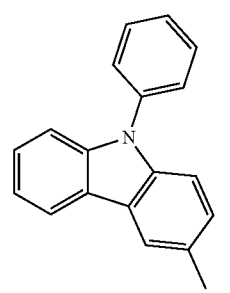
(R-34) 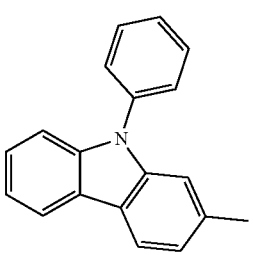
(R-35) 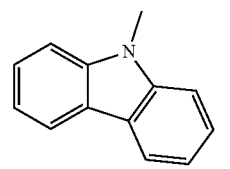
(R-36) 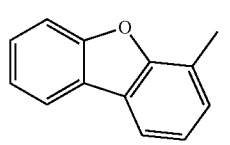
(R-37) 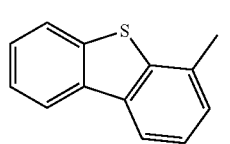
(R-38) 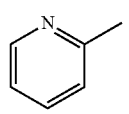
(R-39) 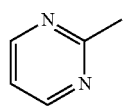
(R-40) 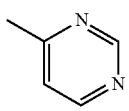
(R-41) 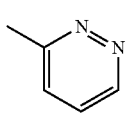
(R-42) 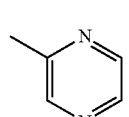
(R-43) 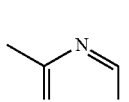
(R-44) 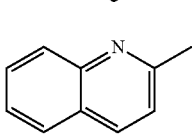
(R-45) 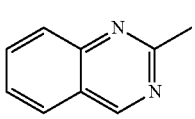
(R-46) 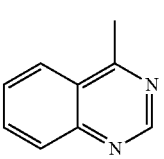
(R-47) 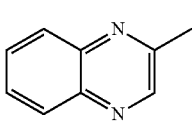
(R-48) 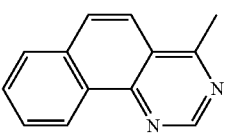
(R-49) 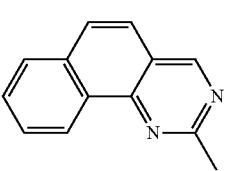

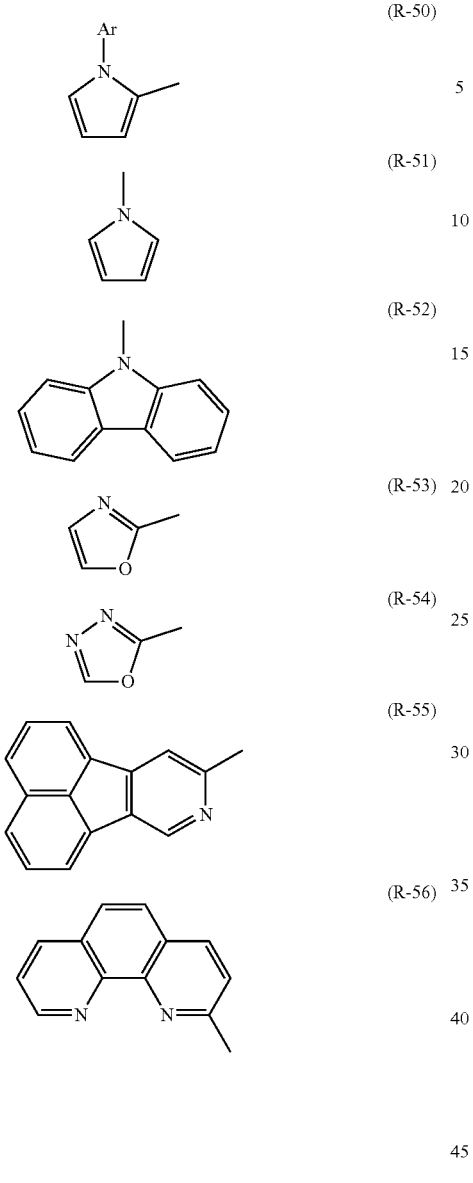

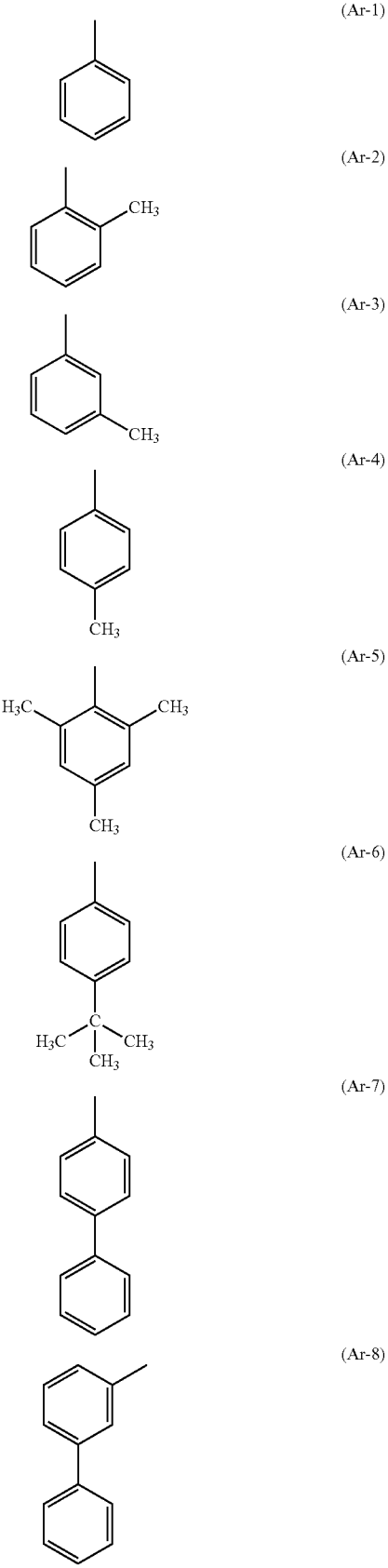

In the general formulae (G0) to (G3), Ar represents hydrogen, an alkyl group having 1 to 4 carbon atoms, a substituted or unsubstituted cycloalkyl group having 3 to 7 carbon atoms, a substituted or unsubstituted aromatic hydrocarbon group having 6 to 60 carbon atoms, or a substituted or unsubstituted heteroaromatic hydrocarbon group having 3 to 60 carbon atoms. Specific examples of the alkyl group include a methyl group, an ethyl group, a propyl group, an isopropyl group, a butyl group, an isobutyl group, a tert-butyl group, and an n-hexyl group; specific examples of the cycloalkyl group include a cyclopropyl group, a cyclobutyl group, a cyclopentyl group, and a cyclohexyl group; and specific examples of the aryl group include a phenyl group, a naphthyl group, a biphenyl group, a fluorenyl group, and a spirofluorenyl group. More specific examples include groups represented by the following structural formulae (Ar-1) to (Ar-48). Note that the group represented by Ar is not limited thereto and may include a substituent.

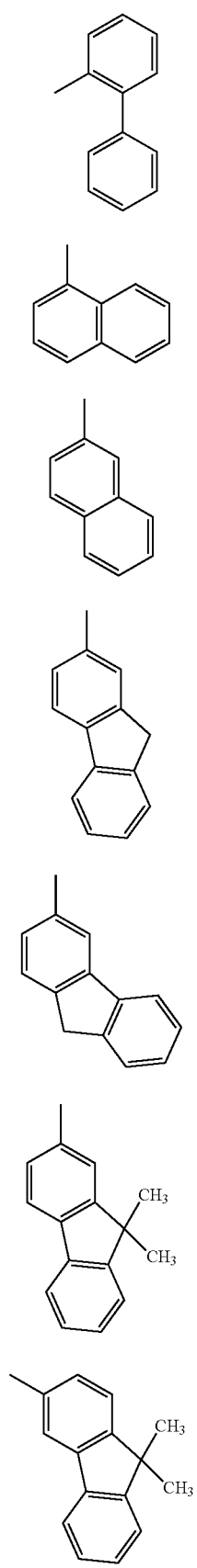
(Ar-9)
(Ar-10)
(Ar-11)
(Ar-12)
(Ar-13)
(Ar-14)
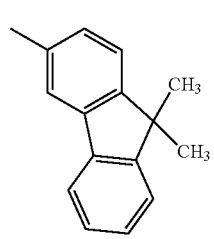
(Ar-15)
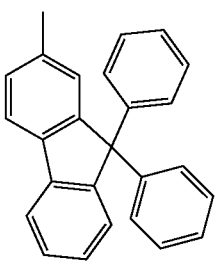
(Ar-16)
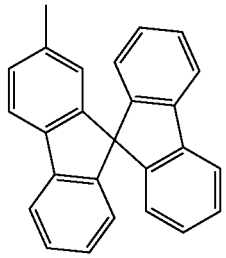
(Ar-17)
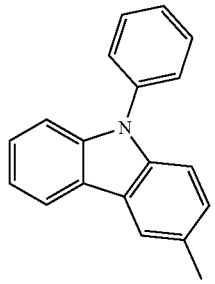
(Ar-18)
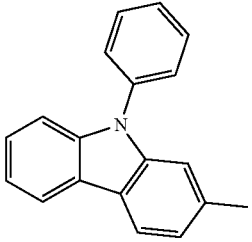
(Ar-19)
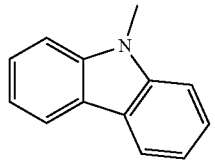
(Ar-20)
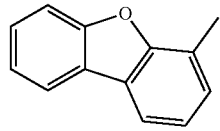
(Ar-21)
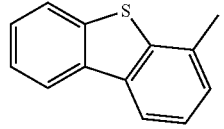
(Ar-22)

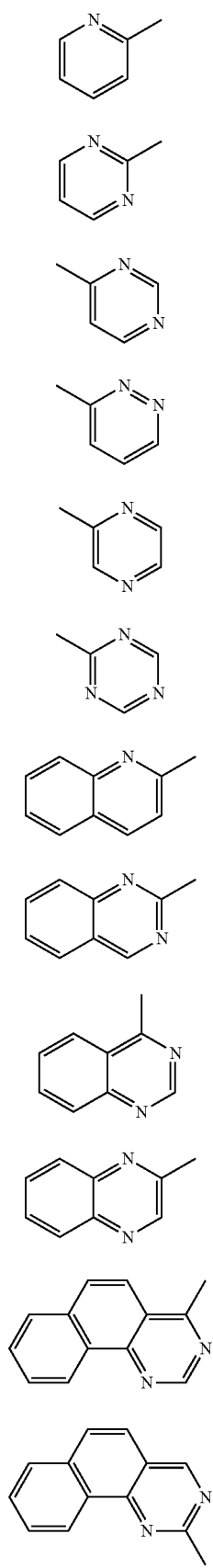
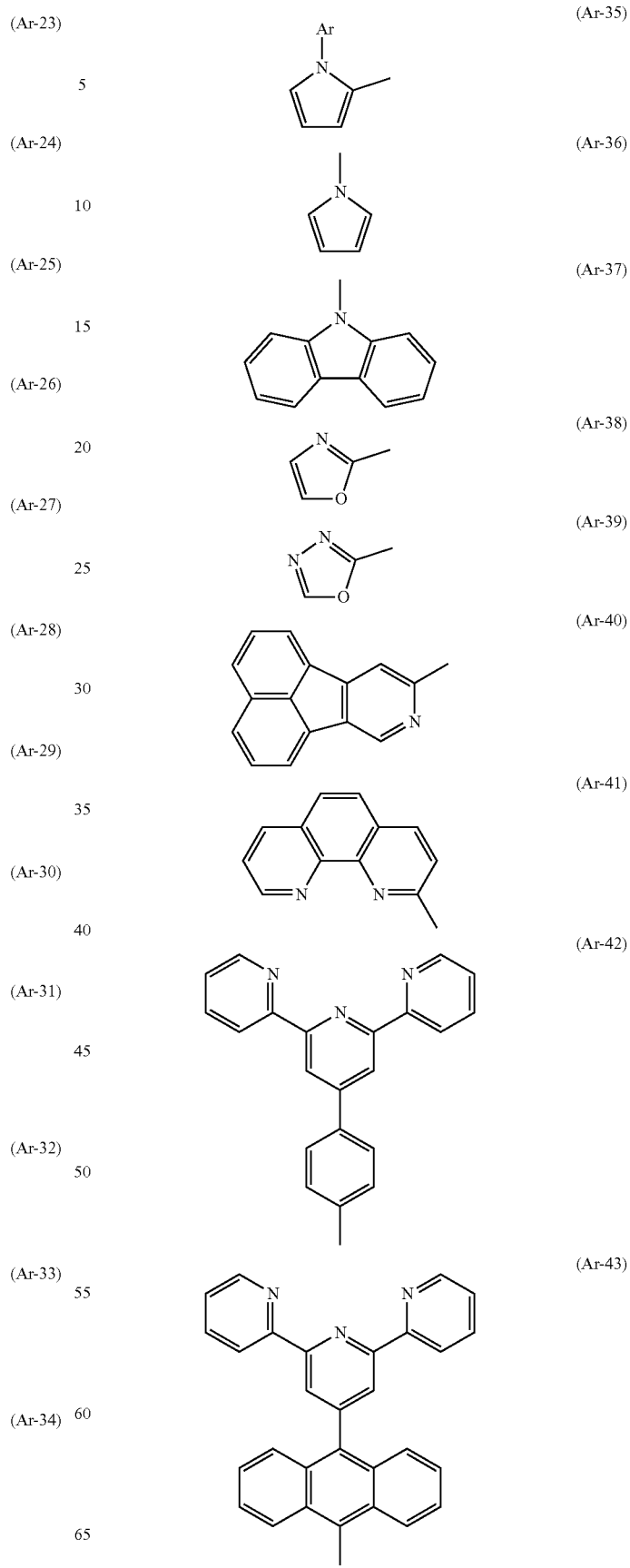

(Ar-44)

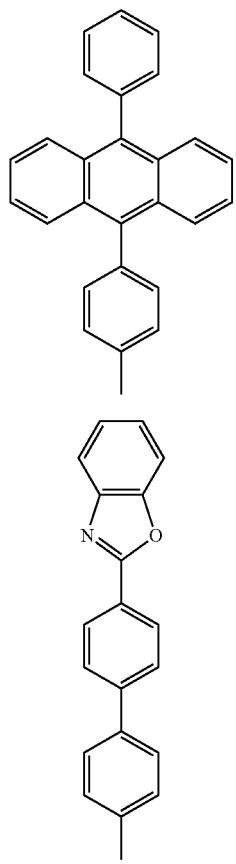

(Ar-45)

(Ar-46)

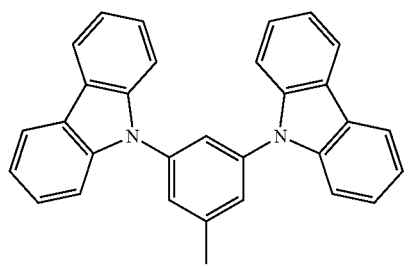

[Chemical Formula 17]

(100)

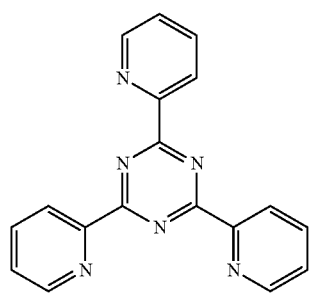

(Ar-47)

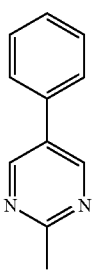

(Ar-48)

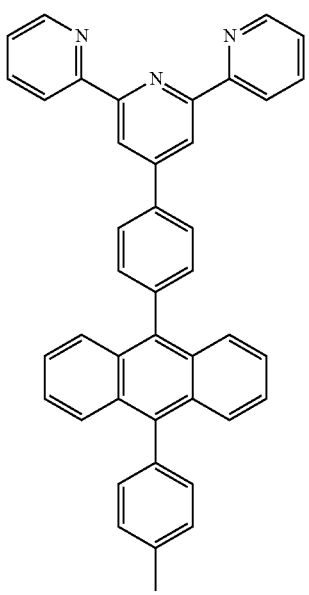

<Specific Examples of Compounds>

Specific structure examples of the compounds represented by the general formulae (G0) to (G3) include organic compounds represented by the following structural formulae (100) to (111) and structural formulae (200) to (211). Note that the organic compounds represented by the general formulae (G0) to (G3) are not limited to the following examples.

(101)

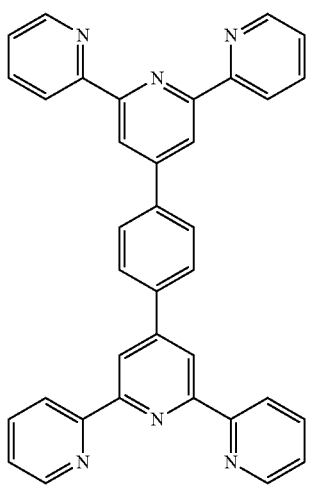

-continued
(102)
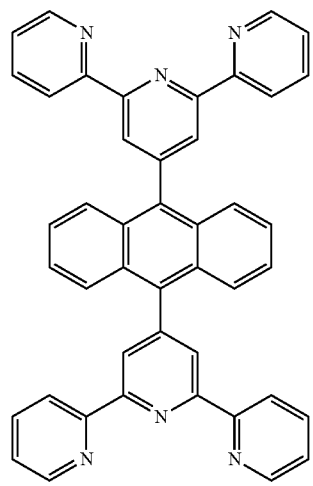
(103)
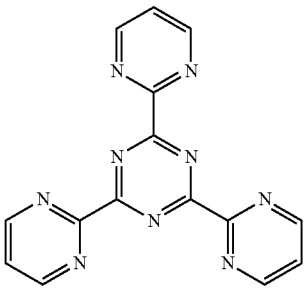
(104)
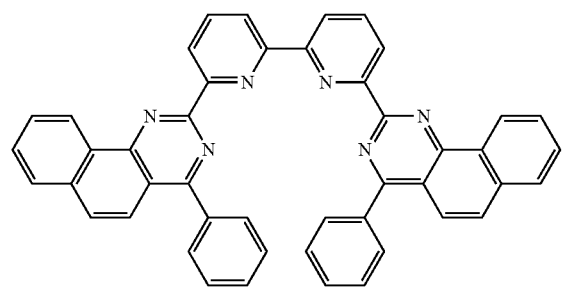
(105)
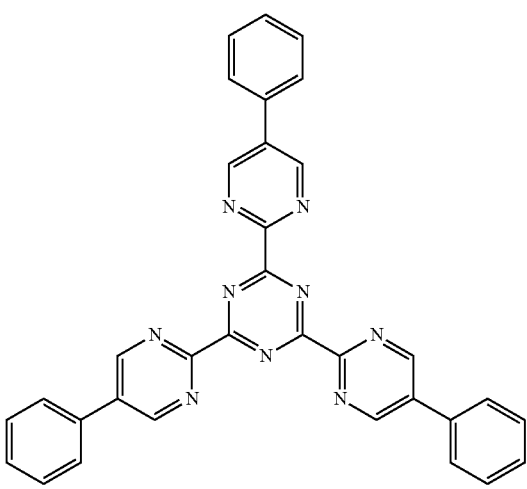
(106)
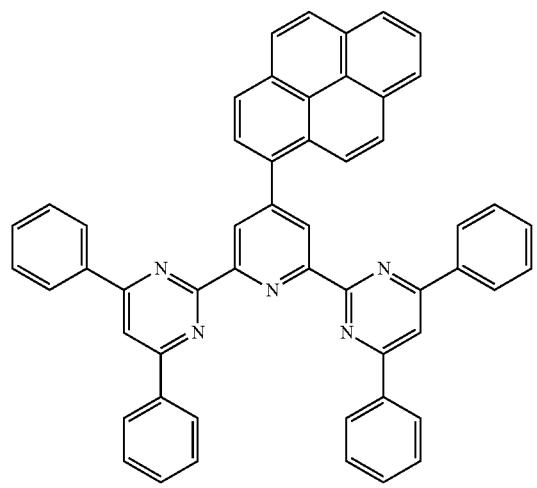
(107)
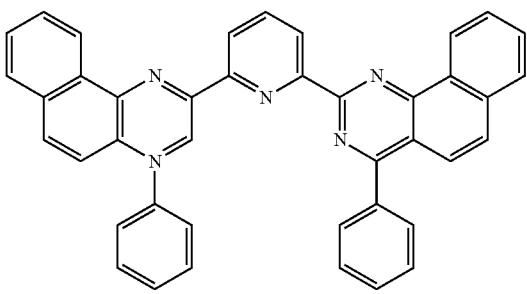

(108)
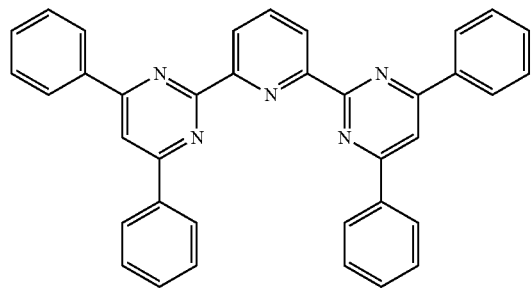
(109)
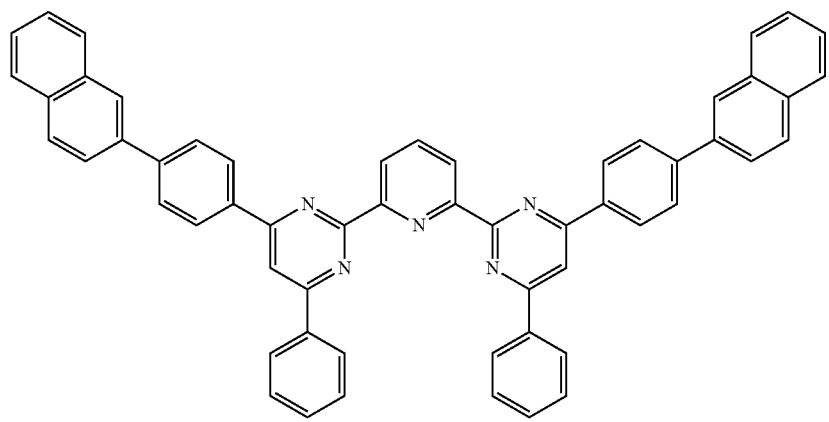
(110)
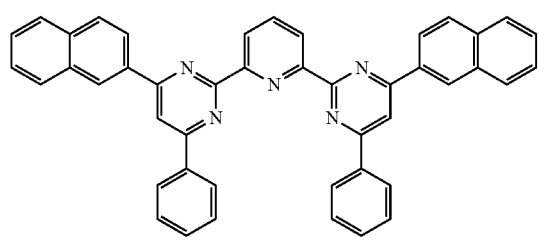
(111)
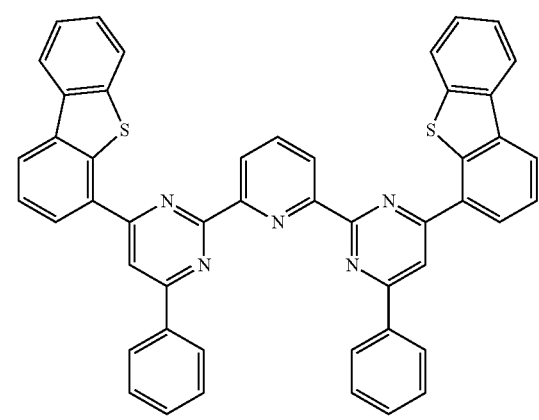

[Chemical Formula 18]
(200) 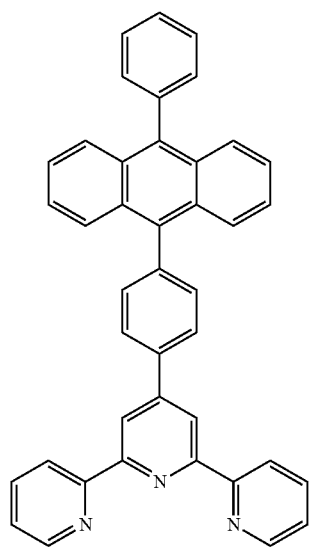
(201) 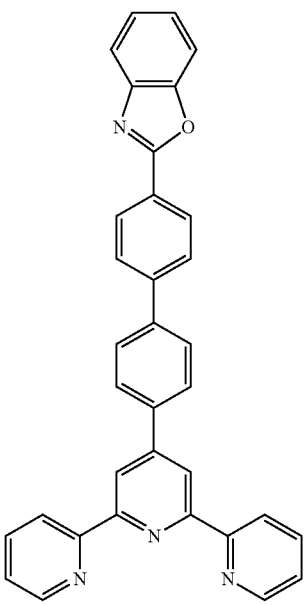
(202) 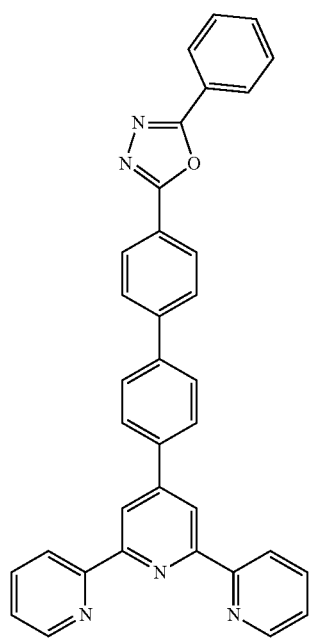
(203) 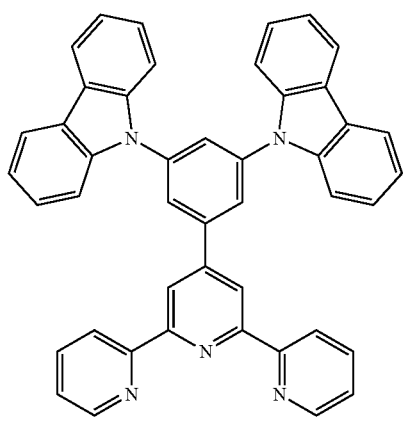
(204) 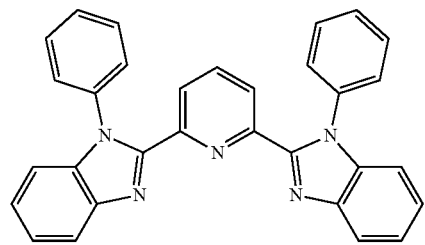
(205) 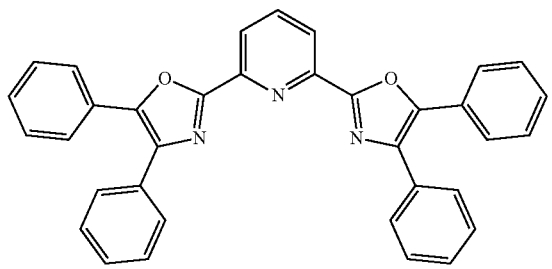

-continued

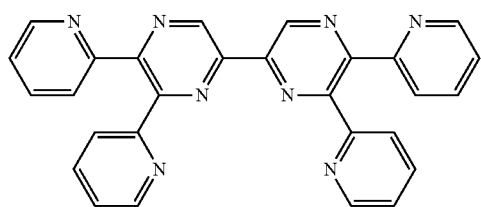
(206)

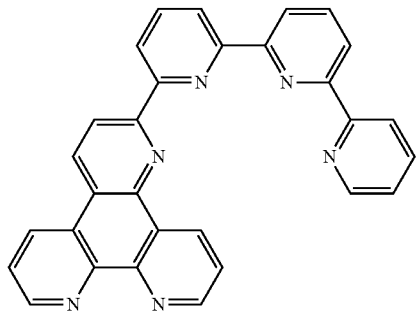
(207)

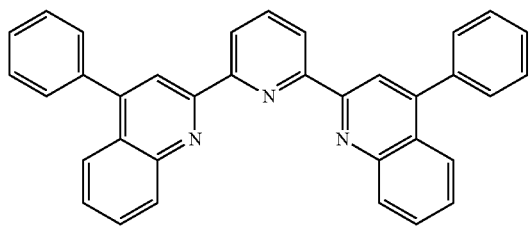
(208)

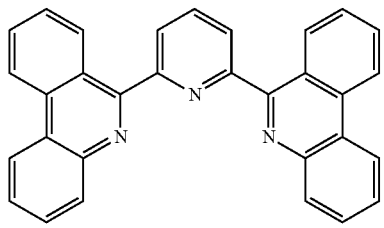
(210)

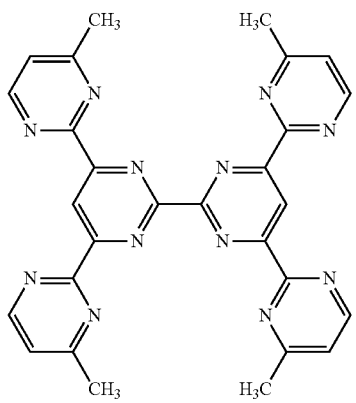
(209)

(211)

The molar ratio of the metal 132 to the compound 131 is preferably higher than or equal to 0.1 and lower than or equal to 10, further preferably higher than or equal to 0.2 and lower than or equal to 2, still further preferably higher than or equal to 0.2 and lower than or equal to 0.8. When the metal 132 and the compound 131 are mixed in such a ratio, a light-emitting device with a favorable electron-injection property can be provided. In the case where the molar ratio of the metal 132 to the compound 131 is too low compared with the above-described ratio, the amount of the compound 131 that interacts with the metal 132 to form SOMO is small, resulting in an inferior electron-injection property in some cases. In the case where the molar ratio of the metal 132 to the compound 131 is too high compared with the above-described ratio, the transmittance of the electron-injection layer 130 is reduced, which reduces the emission efficiency of the light-emitting device in some cases.

The LUMO level of the organic compound included in the electron-transport layer 118 is preferably lower than the SOMO level formed in the electron-injection layer 130. This structure reduces the barrier to electron injection between the electron-injection layer 130 and the electron-transport layer 118, and thus can reduce the driving voltage. In addition, the organic compound included in the electron-transport layer 118 is required to have an electron-transport property, and thus preferably has an electron deficient heteroaromatic ring.

The thickness of the electron-injection layer 130 is preferably greater than or equal to 3 nm, further preferably greater than or equal to 5 nm. With the structure, the composite material in which the metal 132 and the compound 131 are mixed can favorably work. The thickness of the electron-injection layer 130 is preferably less than or equal to 50 nm, further preferably less than or equal to 20 nm, still further preferably less than or equal to 10 nm. This structure reduces the influence of light absorption by the electron-injection layer 130, whereby the light-emitting device having high emission efficiency can be provided.

<Structure Example 2 of Light-Emitting Device>

Next, structure examples different from that of the light-emitting device 150 illustrated in FIG. 1 will be described below with reference to FIG. 2(A).

Figure 2A:
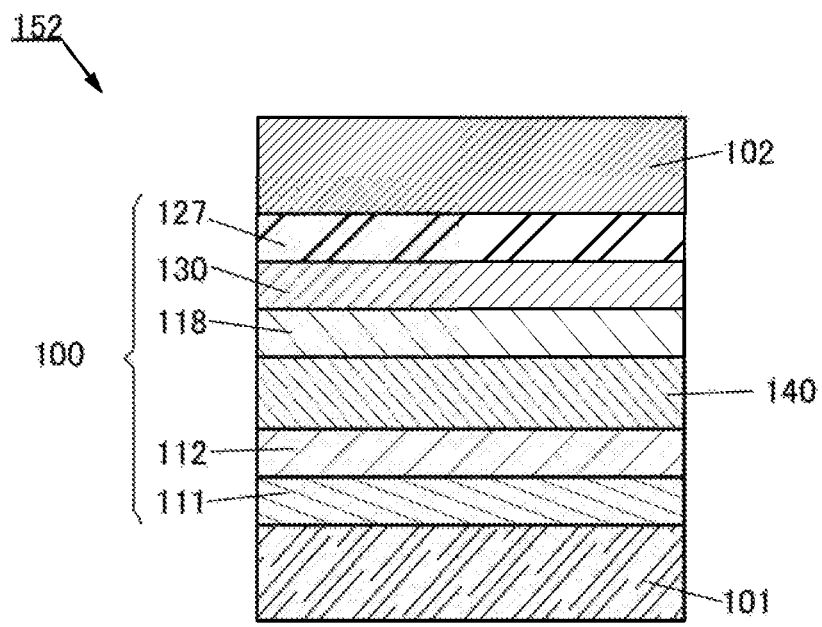
FIGS. 2A-2B are schematic cross-sectional views each illustrating a light-emitting device of one embodiment of the present invention.

FIG. 2(A) is a schematic cross-sectional view illustrating a light-emitting apparatus of one embodiment of the present invention. Note that in FIG. 2(A), a portion having a function similar to that in FIG. 1 is represented using the same hatch pattern and a reference numeral thereof is omitted in some cases. In addition, common reference numerals are used for portions having similar functions, and a detailed description thereof is omitted in some cases.

A light-emitting device 152 includes the pair of electrodes (the electrode 101 and the electrode 102) and the EL layer 100 provided between the pair of electrodes. The EL layer 100 includes at least the light-emitting layer 140 and the electron-injection layer 130. In addition, a buffer layer 127 is included. The buffer layer 127 is provided between the electron-injection layer 130 and the electrode 102.

The EL layer 100 shown in FIG. 2(A) includes functional layers such as the hole-injection layer 111, the hole-transport layer 112, and the electron-transport layer 118 in addition to the light-emitting layer 140.

In one embodiment of the present invention, the above-described composite material of the compound 131 and the metal 132 is used for the electron-injection layer 130, and a compound 133 having an electron deficient heteroaromatic ring is used for the buffer layer 127. An electron deficient heteroaromatic ring has a high electron-transport property, and accordingly, the driving voltage of the light-emitting device can be reduced.

The buffer layer 127 is preferably sandwiched between the electron-injection layer 130 and the electrode 102, in which case a barrier to electron injection between the electrode 102 and the electron-injection layer 130 can be reduced. Furthermore, the thickness of the buffer layer 127 is preferably greater than or equal to 1 nm and less than or equal to 20 nm. With such a structure, a barrier to electron injection can be reduced while a high electron-transport property is maintained.

The LUMO level of the compound 133 is preferably lower than the SOMO level formed in the electron-injection layer 130. Such a structure is preferable because a barrier to electron injection between the electron-injection layer 130 and the electrode 102 can be reduced.

<Structure Example 3 of Light-Emitting Device>

Next, a structure example different from the light-emitting device 150 illustrated in FIG. 1(A) and the light-emitting device 152 illustrated in FIG. 2(A) is described below with reference to FIG. 2(B).

Figure 2B:
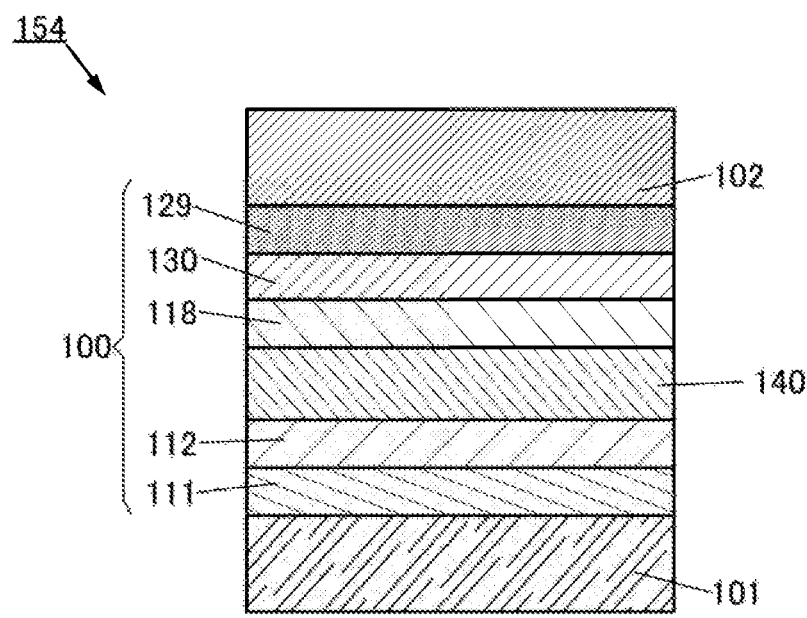

FIG. 2(B) is a schematic cross-sectional view of a light-emitting device of one embodiment of the present invention. Note that in FIG. 2(B), a portion having a function similar to that in FIG. 1 is represented using the same hatch pattern and a reference numeral thereof is omitted in some cases. In addition, common reference numerals are used for portions having similar functions, and a detailed description thereof is omitted in some cases.

A light-emitting device 154 includes a pair of electrodes (the electrode 101 and the electrode 102) and the EL layer 100 provided between the pair of electrodes. The EL layer 100 includes at least the light-emitting layer 140 and the electron-injection layer 130. In addition, a charge-generation layer 129 is included. The charge-generation layer 129 is provided between the electron-injection layer 130 and the electrode 102.

The EL layer 100 illustrated in FIG. 2(B) includes functional layers such as the hole-injection layer 111, the hole-transport layer 112, and the electron-transport layer 118 in addition to the light-emitting layer 140.

The charge-generation layer 129 provided between the electrode 102 and the electron-injection layer 130 as illustrated in FIG. 2(B) reduces the possibility that the electron-injection layer 130 will contact oxygen and moisture; accordingly, the moisture resistance and the oxidation resistance of the light-emitting device can be increased.

The charge-generation layer 129 may have either a structure in which an electron-accepting material is added to a hole-transport material or a structure in which an electron-donating material is added to an electron-transport material. Although both of these structures may be stacked, a structure in which an electron-accepting material is added to a hole-transport material is preferable because the moisture resistance is improved and the number of stacked layers is reduced.

As described above, in the case where the charge-generation layer 129 has a structure including a hole-transport material and an electron-accepting material and the electron-injection layer 130 includes a metal material including an alkali metal or an alkaline earth metal with a low work function, the electron-accepting material of the charge-generation layer 129 extracts an electron from a material used for the electron-injection layer 130; accordingly, a depletion layer is formed in the vicinity of the interface between the charge-generation layer 129 and the electron-injection layer 130. Thus, the driving voltage is increased in some cases. In order to prevent the generation of the depletion layer, provision of a layer having a function of transferring an electron between the electron-injection layer 130 and the charge-generation layer 129 has conventionally been needed.

Meanwhile, in the light-emitting device of one embodiment of the present invention, the electron-injection layer 130 includes the composite material of the transition metal and the organic compound having a function of interacting a metal as a tridentate or tetradentate ligand, in which case the charge-generation layer 129 can be provided without generation of the above-described depletion layer, so that a light-emitting device with a small number of stacked layers and low driving voltage can be fabricated.

The thickness of the charge-generation layer 129 is not particularly limited and can be adjusted as appropriate. For example, by adjusting the thickness from the light-emitting layer 140 to the electrode 102, light emission obtained from the light-emitting layer 140 can be extracted to the outside of the light-emitting device efficiently. That is, by adjusting the thickness of the charge-generation layer 129, the light extraction efficiency can be increased.

It is preferable that the charge-generation layer 129 be provided in contact with the electrode 102. With the structure, a barrier to electron injection between the electrode 102 and the EL layer 100 can be reduced, whereby the driving voltage of the light-emitting device can be reduced. It is further preferable that the charge-generation layer 129 be in contact with the electron-injection layer 130. In one embodiment of the present invention, a light-emitting device with low driving voltage can be fabricated even when the charge-generation layer 129 is in contact with the electron-injection layer 130; thus, with the structure, the number of stacked layers in the EL layer 100 can be reduced.

As the electron-accepting material of the charge-generation layer 129, a transition metal oxide can be suitably used. Examples of the transition metal oxide include titanium oxide, vanadium oxide, tantalum oxide, molybdenum oxide, tungsten oxide, rhenium oxide, ruthenium oxide, chromium oxide, zirconium oxide, hafnium oxide, and silver oxide. Among these, molybdenum oxide is particularly preferable because of its high stability in the air, low hygroscopicity, and inexpensiveness. Using the transition metal oxide is preferable because a barrier to electron injection between the electrode 102 and the charge-generation layer 129 can be reduced. Thus, one embodiment of the present invention is a light-emitting device in which the electron-injection layer 130 includes a transition metal element and the charge-generation layer 129 includes a transition metal element. Note that the electron-accepting material of the charge-generation layer 129 is not limited to the above-described compounds.

As the hole-transport material of the charge-generation layer 129, an organic compound having any one of a pyrrole skeleton, a thiophene skeleton, a furan skeleton, and an aromatic amine skeleton is preferably used. The organic compound having the skeleton has a high hole-transport property, and thus can reduce the driving voltage of the light-emitting device when used for the charge-generation layer 129. The hole-transport material of the charge-generation layer 129 is not limited to the above-described compound.

Note that the composite material of the metal 132 and the compound 131 having a function of interacting with the metal as a tridentate or tetradentate ligand can be used for a thin-film solar cell. Specifically, the above-described composite material can also be suitably used for an electron-injection layer of a thin-film solar cell.

<Components of Light-Emitting Devices>

Next, the components of the light-emitting devices illustrated in FIG. 1 and FIG. 2 are described in detail below.

<<Electron-Injection Layer>>

The electron-injection layer 130 is a layer including a substance having a high electron-injection property, and the above-described composite material of the metal and the organic compound having a function of interacting with the metal as a tridentate or tetradentate ligand can be suitably used. As the organic compound having a function of interacting with the metal as a tridentate or tetradentate ligand, the organic compounds represented by the general formulae (G0) to (G4-3) can be used; specifically, the organic compounds represented by the structural formulae (100) to (111) and the structural formulae (200) to (211) can be used. Heterocyclic compounds having diazine (pyrimidine or pyrazine) skeletons and triazine skeletons are particularly preferable because they have a high electron-transport property and contribute to a reduction in driving voltage. Furthermore, the metal and the organic compound having a function of interacting with the metal as a tridentate or tetradentate ligand each preferably have an electron mobility of $1\times10^{-6}$ cm$^2$/Vs or higher. Note that other substances may also be used for the electron-injection layer 130 as long as their electron-transport properties are higher than their hole-transport properties.

<<Hole-Injection Layer>>

The hole-injection layer 111 and the charge-generation layer 129 have a function of promoting hole injection by reducing a barrier to hole injection from one of the pair of electrodes (the electrode 101 or the electrode 102), and is formed using a transition metal oxide, a phthalocyanine derivative, or an aromatic amine, for example. Examples of the transition metal oxide include molybdenum oxide, vanadium oxide, ruthenium oxide, tungsten oxide, and manganese oxide. Examples of the phthalocyanine derivative include phthalocyanine and metal phthalocyanine. Examples of the aromatic amine include a benzidine derivative and a phenylenediamine derivative. It is also possible to use a high molecular compound such as polythiophene or polyaniline; a typical example thereof is poly(ethylenedioxythiophene)/poly(styrenesulfonic acid), which is self-doped polythiophene.

As the hole-injection layer 111 and the charge-generation layer 129, a layer containing a composite material of a hole-transport material and a material having a property of accepting electrons from the hole-transport material can also be used. Alternatively, a stack of a layer containing a material having an electron-accepting property and a layer containing a hole-transport material may also be used. In a steady state or in the presence of an electric field, electric charge can be transferred between these materials. Examples of the material having an electron-accepting property include organic acceptors such as a quinodimethane derivative, a chloranil derivative, and a hexaazatriphenylene derivative. A specific example is a compound having an electron-withdrawing group (in particular, a cyano group or a halogen group such as a fluoro group), such as 7,7,8,8-tetracyano-2,3,5,6-tetrafluoroquinodimethane (abbreviation: F$_4$-TCNQ), chloranil, 2,3,6,7,10,11-hexacyano-1,4,5,8,9,12-hexaazatriphenylene (abbreviation: HAT-CN), and 1,3,4,5,7,8-hexafluorotetracyano-naphthoquinodimethane (abbreviation: F6-TCNNQ). A compound in which electron-withdrawing groups are bonded to a condensed aromatic ring having a plurality of heteroatoms, such as HAT-CN, is particularly preferable because it is thermally stable. A [3]radialene derivative including an electron-withdrawing group (in particular, a cyano group or a halogen group such as a fluoro group) has a very high electron-accepting property and thus is preferable; specific examples include α,α',α"-1,2,3-cyclopropanetriylidenetris[4-cyano-2,3,5,6-tetrafluorobenzeneacetonitrile], α,α',α"-1,2,3-cyclopropanetriylidenetris[2,6-dichloro-3,5-difluoro-4-(trifluoromethyl)benzeneac etonitrile], and α,α',α"-1,2,3-cyclopropanetriylidenetris[2,3,4,5,6-pentafluorobenzeneacetonitrile]. Alternatively, a transition metal oxide such as an oxide of metal from Group 4 to Group 8 can be used. Specifically, vanadium oxide, niobium oxide, tantalum oxide, chromium oxide, molybdenum oxide, tungsten oxide, manganese oxide, rhenium oxide, or the like can be used. Among these, molybdenum oxide is preferable because of its stability in the air, a low hygroscopic property, and easiness of handling.

As the hole-transport material, a material having a property of transporting more holes than electrons can be used, and a material having a hole mobility of $1\times10^{-6}$ cm$^2$/Vs or higher is preferable. Specifically, any of the aromatic amine, carbazole derivative, aromatic hydrocarbon, stilbene derivative, and the like described as examples of the hole-transport material that can be used in the light-emitting layer 140 can be used, and a heteroaromatic skeleton having 1 to 20 carbon atoms is particularly preferable. In particular, a nitrogen-containing five-membered heterocyclic skeleton is preferable. Furthermore, the hole-transport material may be a high molecular compound.

Other examples of the hole-transport material include aromatic hydrocarbons such as 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 2-tert-butyl-9,10-bis[2-(1-naphthyl)phenyl]anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, and 2,5,8,11-tetra(tert-butyl)perylene. Besides, pentacene, coronene, and the like can be used. It is particularly preferable to use the aromatic hydrocarbon having a hole mobility of $1\times10^{-6}$ cm$^2$/Vs or higher and having 14 to 42 carbon atoms.

Note that the aromatic hydrocarbon may include a vinyl skeleton. As the aromatic hydrocarbon having a vinyl group, for example, 4,4'-bis(2,2-diphenylvinyl)biphenyl (abbreviation: DPVBi), 9,10-bis[4-(2,2-diphenylvinyl)phenyl]anthracene (abbreviation: DPVPA), and the like can be given.

In addition, thiophene compounds, furan compounds, fluorene compounds, triphenylene compounds, phenanthrene compounds, and the like such as 4-{3-[3-(9-phenyl-9H-fluoren-9-yl)phenyl]phenyl}dibenzofuran (abbreviation: mmDBFFLBi-II), 4,4',4"-(benzene-1,3,5-triyl)tri(dibenzofuran) (abbreviation: DBF3P-II), 1,3,5-tri(dibenzothiophen-4-yl)benzene (abbreviation: DBT3P-II), 2,8-diphenyl-4-[4-(9-phenyl-9H-fluoren-9-yl)phenyl]dibenzothiophene (abbreviation: DBTFLP-III), 4-[4-(9-phenyl-9H-fluoren-9-yl)phenyl]-6-phenyldibenzothiophene (abbreviation: DBTFLP-IV), and 4-[3-(triphenylen-2-yl)phenyl]dibenzothiophene (abbreviation: mDBTPTp-II) can be used. Among the above compounds, compounds having a pyrrole skeleton, a furan skeleton, a thiophene skeleton, or an aromatic amine skeleton are preferable because of their high stability and reliability. In addition, the compounds having such skeletons have a high hole-transport property to contribute to a reduction in driving voltage.

<<Hole-Transport Layer>>

The hole-transport layer 112 is a layer including a hole-transport material and can be formed using any of the materials given as examples of the materials of the hole-injection layer 111. The hole-transport layer 112 has a function of transporting, to the light-emitting layer 140, a hole injected from the hole-injection layer 111.

In that case, a hole-transport material whose HOMO level is between the LUMO level of the acceptor material of the hole-injection layer 111 and the HOMO level of the material of the light-emitting layer 140 is preferably used for the hole-transport layer 112. The hole-transport layer 112 is not limited to a single layer and may include a stack of two or more layers. In that case, it is preferable to stack hole-transport materials such that HOMO levels decrease in order from the hole-injection layer 111 side to the light-emitting layer 140 side. In the case where the hole-transport layer 112 includes a stack of two or more layers, in order to transport holes smoothly, the difference in the HOMO level between hole-transport materials is preferably greater than or equal to 0 eV and less than or equal to 0.5 eV, further preferably greater than or equal to 0 eV and less than or equal to 0.3 eV, still further preferably greater than or equal to 0 eV and less than or equal to 0.2 eV.

Examples of the material having a hole-transport property include a compound having an aromatic amine skeleton, such as 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-(9-phenyl-9H-carbazol-3-yl)triphenylamine (abbreviation: PCBA1BP), 4,4'-diphenyl-4"-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4"-(9-phenyl-9H-carbazol-3-yl)triphenylamine (abbreviation: PCBNBB), 9,9-dimethyl-N-phenyl-N-[4-(9-phenyl-9H-carbazol-3-yl)phenyl]fluoren-2-amine (abbreviation: PCBAF), or N-phenyl-N-[4-(9-phenyl-9H-carbazol-3-yl)phenyl]spiro-9,9'-bifluoren-2-amine (abbreviation: PCBASF), a compound having a carbazole skeleton, such as 1,3-bis(N-carbazolyl)benzene (abbreviation: mCP), 4,4'-di(N-carbazolyl)biphenyl (abbreviation: CBP), 3,6-bis(3,5-diphenylphenyl)-9-phenylcarbazole (abbreviation: CzTP), or 3,3'-bis(9-phenyl-9H-carbazole) (abbreviation: PCCP), a compound having a thiophene skeleton, such as 4,4',4"-(benzene-1,3,5-triyl)tri(dibenzothiophene) (abbreviation: DBT3P-II), 2,8-diphenyl-4-[4-(9-phenyl-9H-fluoren-9-yl)phenyl] dibenzothiophene (abbreviation: DBTFLP-III), or 4-[4-(9-phenyl-9H-fluoren-9-yl)phenyl]-6-phenyldibenzothiophene (abbreviation: DBTFLP-IV), and a compound having a furan skeleton, such as 4,4',4"-(benzene-1,3,5-triyl)tri(dibenzofuran) (abbreviation: DBF3P-II) or 4-{3-[3-(9-phenyl-9H-fluoren-9-yl)phenyl]phenyl}dibenzofuran (abbreviation: mmDBFFLBi-II) can be given. Among the above, the compound having an aromatic amine skeleton and the compound having a carbazole skeleton are preferable because these have favorable reliability, have high hole-transport properties, and contribute to a reduction in driving voltage. Hole-transport materials may be selected from a variety of substances as well as from the hole-transport materials described above.

Furthermore, examples of the substance having a high hole-transport property include compounds having aromatic amine skeletons, such as 3-[4-(1-naphthyl)-phenyl]-9-phenyl-9H-carbazole (abbreviation: PCPN), 3-[4-(9-phenanthryl)-phenyl]-9-phenyl-9H-carbazole (abbreviation: PCPPn), 4-phenyl-4'-(9-phenyl-9H-carbazol-3-yl)triphenylamine (abbreviation: PCBA1BP), 4,4'-di(1-naphthyl)-4"-(9-phenyl-9H-carbazol-3-yl)triphenylamine (abbreviation: PCBNBB), 4-phenyldiphenyl-(9-phenyl-9H-carbazol-3-yl)amine (abbreviation: PCA1BP), 3,3'-bis(9-phenyl-9H-carbazole) (abbreviation: PCCP), N-[4-(9H-carbazol-9-yl)phenyl]-N-(4-phenyl)phenylaniline (abbreviation: YGA1BP), 1,3,5-tri(dibenzothiophen-4-yl)-benzene (abbreviation: DBT3P-II), 4,4',4"-(benzene-1,3,5-triyl)tri(dibenzofuran) (abbreviation: DBF3P-II), 4-phenyl-4'-(9-phenylfluoren-9-yl)triphenylamine (abbreviation: BPAFLP), 4-[3-(triphenyl en-2-yl)phenyl]dibenzothiophene (abbreviation: mDBTPTp-II), 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), 4,4',4"-tris(carbazol-9-yl)triphenylamine (abbreviation: TCTA), 4,4',4"-tris(N,N'-diphenylamino)triphenylamine (abbreviation: TDATA), 4,4',4"-tris[N-(3-methylphenyl)-N-phenylamino]triphenylamine (abbreviation: MTDATA), and 4,4'-bis[N-(spiro-9,9'-bifluoren-2-yl)-N-phenylamino]biphenyl (abbreviation: BSPB); 3-[N-(9-phenylcarbazol-3-yl)-N-phenylamino]-9-phenylcarbazole (abbreviation: PCzPCA1); 3,6-bis[N-(9-phenylcarbazol-3-yl)-N-phenylamino]-9-phenylcarbazole (abbreviation: PCzPCA2); and 3-[N-(1-naphthyl)-N-(9-phenylcarbazol-3-yl)amino]-9-phenylcarbazole (abbreviation: PCzPCN1). Other examples include carbazole compounds such as 4,4'-di(N-carbazolyl)biphenyl (abbreviation: CBP) and 1,3,5-tris[4-(N-carbazolyl)phenyl]benzene (abbreviation: TCPB); amine compounds; dibenzothiophene compounds; dibenzofuran compounds; fluorene compounds; triphenylene compounds; and phenanthrene compounds. The substances given here are mainly substances having a hole mobility of $1\times10^{-6}$ cm$^2$/Vs or higher. Note that other substances may also be used as long as their hole-transport properties are higher than their electron-transport properties.

Note that any of these compounds that can be used for the hole-transport layer can also be used for the hole-injection layer. The compounds can also be suitably used as the hole-transport material used for the charge-generation layer 129.

<<Light-Emitting Layer>>

The light-emitting layer 140 includes a light-emitting material having a function of emitting at least one of violet light, blue light, blue green light, green light, yellow green light, yellow light, orange light, and red light. In addition, the light-emitting layer 140 includes one or both of an electron-transport material and a hole-transport material as a host material in addition to the light-emitting material.

As the light-emitting material, any of light-emitting substances capable of converting singlet excitation energy into luminescence and light-emitting substances capable of converting triplet excitation energy into luminescence can be used. Examples of the light-emitting substance are given below.

Examples of the light-emitting substance capable of converting singlet excitation energy into luminescence include substances that exhibit fluorescence (fluorescent compound). Although there is no particular limitation on the fluorescent compound, an anthracene derivative, a tetracene derivative, a chrysene derivative, a phenanthrene derivative, a pyrene derivative, a perylene derivative, a stilbene derivative, an acridone derivative, a coumarin derivative, a phenoxazine derivative, a phenothiazine derivative, or the like is preferable, and for example, any of the following substances can be used.

Specific examples include 5,6-bis[4-(10-phenyl-9-anthryl)phenyl]-2,2'-bipyridine (abbreviation: PAP2BPy), 5,6-bis[4'-(10-phenyl-9-anthryl)biphenyl-4-yl]-2,2'-bipyridine (abbreviation: PAPP2BPy), N,N'-diphenyl-N,N'-bis[4-(9-phenyl-9H-fluoren-9-yl)phenyl]pyrene-1,6-diamine (abbreviation: 1,6FLPAPrn), N,N'-bis(3-methylphenyl)-N,N'-bis[3-(9-phenyl-9H-fluoren-9-yl)phenyl]pyrene-1,6-diamine (abbreviation: 1,6mMemFLPAPrn), N,N'-bis[4-(9-phenyl-9H-fluoren-9-yl)phenyl]-N,N'-bis(4-tert-butylphenyl) pyrene-1,6-diamine (abbreviation: 1,6tBu-FLPAPrn), N,N'-diphenyl-N,N'-bis[4-(9-phenyl-9H-fluoren-9-yl)phenyl]-3,8-dicyclohexylpyrene-1,6-diamine (abbreviation: ch-1, 6FLPAPrn), N,N'-(pyrene-1,6-diyl)bis[(6,N-diphenylbenzo[b]naphtho[1,2-d]furan)-8-amine] (abbreviation: 1,6BnfAPrn-03), N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), perylene, 2,5,8,11-tetra(tert-butyl)perylene (abbreviation: TBP), 4-(10-phenyl-9-anthryl)-4'-(9-phenyl-9H-carbazol-3-yl)triphenylamine (abbreviation: PCBAPA), N,N"-(2-tert-butylanthracene-9,10-diyldi-4,1-phenylene)bis[N,N',N'-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N'-triphenyl-1,4-phenylenediamine (abbreviation: 2DPAPPA), N,N,N',N',N",N",N"',N"'-octaphenyldibenzo[g,p]chrysene-2,7,10,15-tetraamine (abbreviation: DBC1), coumarin 30, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N"-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), coumarin 6, coumarin 545T, N,N'-diphenylquinacridone (abbreviation: DPQd), rubrene, 2,8-di-tert-butyl-5,11-bis(4-tert-butylphenyl)-6,12-diphenyltetracene (abbreviation: TBRb), Nile red, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N',N'-tetrakis(4-methylphenyl) tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), 2-{2-isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTI), 2-{2-tert-butyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTB), 2-(2,6-bis{2-[4-(dimethylamino)phenyl]ethenyl}-4H-pyran-4-ylidene)propanedinitrile (abbreviation: BisDCM), 2-{2,6-bis[2-(8-methoxy-1,1,7,7-tetramethyl-2,3,6,7-tetrahydro-1H,5H-benzo[ij]quinolizin-9-yl) ethenyl]-4H-pyran-4-ylidene}propanedinitrile (abbreviation: BisDCJTM), and 5,10,15,20-tetraphenylbisbenzo[5,6]indeno[1,2,3-cd:1',2',3'-m]perylene.

As an example of the light-emitting substance capable of converting triplet excitation energy into luminescence, a substance that exhibits phosphorescence (a phosphorescent compound) can be given. As the phosphorescent compound, an iridium-, rhodium-, or platinum-based organometallic complex or metal complex can be given. Furthermore, a platinum complex having a porphyrin ligand, an organoiridium complex, and the like can be given; specifically, an organoiridium complex such as an iridium-based orthometalated complex is preferable. Examples of an orthometalated ligand include a 4H-triazole ligand, a 1H-triazole ligand, an imidazole ligand, a pyridine ligand, a pyrimidine ligand, a pyrazine ligand, and an isoquinoline ligand. In this case, the phosphorescent compound has an absorption band based on triplet MLCT (Metal to Ligand Charge Transfer) transition.

Examples of the substance that has an emission peak in blue or green include organometallic iridium complexes having a 4H-triazole skeleton, such as tris{2-[5-(2-methylphenyl)-4-(2,6-dimethylphenyl)-4H-1,2,4-triazol-3-yl-$\kappa N^2$]phenyl-$\kappa C$}iridium(III) (abbreviation: Ir(mpptz-dmp)$_3$), tris(5-methyl-3,4-diphenyl-4H-1,2,4-triazolato)iridium (III) (abbreviation: Ir(Mptz)$_3$), tris[4-(3-biphenyl)-5-isopropyl-3-phenyl-4H-1,2,4-triazolato]iridium(III) (abbreviation: Ir(iPrptz-3b)$_3$), and tris[3-(5-biphenyl)-5-isopropyl-4-phenyl-4H-1,2,4-triazolato]iridium(III) (abbreviation: Ir(iPr5btz)$_3$); organometallic iridium complexes having a 1H-triazole skeleton, such as tris[3-methyl-1-(2-methylphenyl)-5-phenyl-1H-1,2,4-triazolato]iridium(III) (abbreviation: Ir(Mptz1-mp)$_3$) and tris(1-methyl-5-phenyl-3-propyl-1H-1,2,4-triazolato)iridium(III)(abbreviation: Ir(Prptz1-Me)$_3$); organometallic iridium complexes having an imidazole skeleton, such as fac-tris[1-(2,6-diisopropylphenyl)-2-phenyl-1H-imidazole]iridium(III) (abbreviation: Ir(iPrpmi)$_3$) and tris[3-(2,6-dimethylphenyl)-7-methylimidazo[1,2-f]phenanthridinato]iridium(III) (abbreviation: Ir(dmpimpt-Me)$_3$); and organometallic iridium complexes in which a phenylpyridine derivative having an electron-withdrawing group is a ligand, such as bis[2-(4',6'-difluorophenyl)pyridinato-N,C$^{2'}$]iridium(III) tetrakis(1-pyrazolyl) borate (abbreviation: FIr6), bis[2-(4',6'-difluorophenyl)

pyridinato-N,C²']iridium(III) picolinate (abbreviation: FIrpic), bis{2-[3',5'-bis(trifluoromethyl)phenyl]pyridinato-N,C²'}iridium(III) picolinate (abbreviation: Ir(CF$_3$ppy)$_2$(pic)), and bis[2-(4',6'-difluorophenyl)pyridinato-N,C²'] iridium(III)acetylacetonate (abbreviation: FIr(acac)). Among the above, the organometallic iridium complexes including a nitrogen-containing five-membered heterocyclic skeleton, such as a 4H-triazole skeleton, a 1H-triazole skeleton, or an imidazole skeleton have high triplet excitation energy, reliability, and emission efficiency and thus are especially preferable.

Examples of the substance that has an emission peak in green or yellow include organometallic iridium complexes including a pyrimidine skeleton, such as tris(4-methyl-6-phenylpyrimidinato)iridium(III) (abbreviation: Ir(mppm)$_3$), tris(4-t-butyl-6-phenylpyrimidinato)iridium(III) (abbreviation: Ir(tBuppm)$_3$), (acetylacetonato)bis(6-methyl-4-phenylpyrimidinato)iridium(III) (abbreviation: Ir(mppm)$_2$(acac)), (acetylacetonato)bis(6-tert-butyl-4-phenylpyrimidinato)iridium(III) (abbreviation: Ir(tBuppm)$_2$(acac)), (acetylacetonato)bis[4-(2-norbornyl)-6-phenylpyrimidinato]iridium(III) (abbreviation: Ir(nbppm)$_2$(acac)), (acetylacetonato)bis[5-methyl-6-(2-methylphenyl)-4-phenylpyrimidinato]iridium(III) (abbreviation: Ir(mpmppm)$_2$(acac)), (acetylacetonato)bis{4,6-dimethyl-2-[6-(2,6-dimethylphenyl)-4-pyrimidinyl-κN³]phenyl-κC}iridium(III) (abbreviation: Ir(dmppm-dmp)$_2$(acac)), and (acetylacetonato)bis(4,6-diphenylpyrimidinato)iridium(III) (abbreviation: Ir(dppm)$_2$(acac)); organometallic iridium complexes including a pyrazine skeleton, such as (acetylacetonato)bis(3,5-dimethyl-2-phenylpyrazinato)iridium(III) (abbreviation: Ir(mppr-Me)$_2$(acac)) and (acetylacetonato)bis(5-isopropyl-3-methyl-2-phenylpyrazinato)iridium(III) (abbreviation: Ir(mppr-iPr)$_2$(acac)); organometallic iridium complexes including a pyridine skeleton, such as tris(2-phenylpyridinato-N,C²')iridium(III) (abbreviation: Ir(ppy)$_3$), bis(2-phenylpyridinato-N,C²')iridium(III) acetylacetonate (abbreviation: Ir(ppy)$_2$(acac)), bis(benzo[h]quinolinato)iridium(III) acetylacetonate (abbreviation: Ir(bzq)$_2$(acac)), tris(benzo[h]quinolinato)iridium(III) (abbreviation: Ir(bzq)$_3$), tris(2-phenylquinolinato-N,C²')iridium (III) (abbreviation: Ir(pq)$_3$), and bis(2-phenylquinolinato-N,C²')iridium(III) acetylacetonate (abbreviation: Ir(pq)$_2$(acac)); organometallic iridium complexes such as bis(2,4-diphenyl-1,3-oxazolato-N,C²')iridium(III) acetylacetonate (abbreviation: Ir(dpo)$_2$(acac)), bis{2-[4'-(perfluorophenyl)phenyl]pyridinato-N,C²'}iridium(III) acetylacetonate (abbreviation: Ir(p-PF-ph)$_2$(acac)), and bis(2-phenylbenzothiazolato-N,C²')iridium(III) acetylacetonate (abbreviation: Ir(bt)$_2$(acac)); and a rare earth metal complex such as tris(acetylacetonato) (monophenanthroline)terbium(III) (abbreviation: Tb(acac)$_3$(Phen)). Among the above, the organometallic iridium complexes including a pyrimidine skeleton have distinctively high reliability and emission efficiency and thus are especially preferable.

Examples of the substance that has an emission peak in yellow or red include organometallic iridium complexes including a pyrimidine skeleton, such as (diisobutyrylmethanato)bis[4,6-bis(3-methylphenyl)pyrimidinato]iridium(III) (abbreviation: Ir(5mdppm)$_2$(dibm)), bis[4,6-bis(3-methylphenyl)pyrimidinato](dipivaloylmethanato)iridium(III) (abbreviation: Ir(5mdppm)$_2$(dpm)), and bis[4,6-di(naphthalen-1-yl)pyrimidinato] (dipivaloylmethanato)iridium(III) (abbreviation: Ir(dInpm)$_2$(dpm)); organometallic iridium complexes including a pyrazine skeleton, such as (acetylacetonato)bis(2,3,5-triphenylpyrazinato)iridium(III) (abbreviation: Ir(tppr)$_2$(acac)), bis(2,3,5-triphenylpyrazinato)(dipivaloylmethanato)iridium(III) (abbreviation: Ir(tppr)$_2$(dpm)), and (acetylacetonato)bis[2,3-bis(4-fluorophenyl)quinoxalinato]iridium(III) (abbreviation: Ir(Fdpq)$_2$(acac)); organometallic iridium complexes including a pyridine skeleton, such as tris(1-phenylisoquinolinato-N,C²')iridium(III) (abbreviation: Ir(piq)$_3$) and bis(1-phenylisoquinolinato-N,C²')iridium(III) acetylacetonate (abbreviation: Ir(piq)$_2$(acac)); a platinum complex such as 2,3,7,8,12,13,17,18-octaethyl-21H,23H-porphyrin platinum(II) (abbreviation: PtOEP); and rare earth metal complexes such as tris(1,3-diphenyl-1,3-propanedionato) (monophenanthroline)europium(III) (abbreviation: Eu(DBM)$_3$(Phen)) and tris[1-(2-thenoyl)-3,3,3-trifluoroacetonato](monophenanthroline) europium(III) (abbreviation: Eu(TTA)$_3$(Phen)). Among the above, the organometallic iridium complexes including a pyrimidine skeleton have distinctively high reliability and emission efficiency and thus are especially preferable. Furthermore, the organometallic iridium complex having a pyrazine skeleton can provide red light emission with favorable chromaticity.

Note that as an example of the material capable of converting the triplet excitation energy into luminescence, a thermally activated delayed fluorescence (TADF) material can be given in addition to a phosphorescent compound. Therefore, the term "phosphorescent compound" in the description can be rephrased as the term "thermally activated delayed fluorescent compound". The thermally activated delayed fluorescent compound is a material having a small difference between the singlet excitation energy level and the triplet excitation energy level and a function of converting triplet excitation energy into singlet excitation energy by reverse intersystem crossing. Thus, the thermally activated delayed fluorescent material can up-convert a triplet excited state into a singlet excited state (i.e., reverse intersystem crossing is possible) using a little thermal energy and efficiently exhibit light emission (fluorescence) from the singlet excited state. The thermally activated delayed fluorescence is efficiently obtained under the condition where the difference between the singlet excitation energy level and the triplet excitation energy level is preferably greater than 0 eV and less than or equal to 0.3 eV, further preferably greater than 0 eV and less than or equal to 0.2 eV, still further preferably greater than 0 eV and less than or equal to 0.1 eV.

In the case where the thermally activated delayed fluorescent compound is composed of one kind of material, any of the following materials can be used, for example.

First, a fullerene, a derivative thereof, an acridine derivative such as proflavine, eosin, and the like can be given. In addition, a metal-containing porphyrin containing magnesium (Mg), zinc (Zn), cadmium (Cd), tin (Sn), platinum (Pt), indium (In), palladium (Pd), or the like can be given as examples. Examples of the metal-containing porphyrin include a protoporphyrin-tin fluoride complex (SnF$_2$(Proto IX)), a mesoporphyrin-tin fluoride complex (SnF$_2$(Meso IX)), a hematoporphyrin-tin fluoride complex (SnF$_2$(Hemato IX)), a coproporphyrin tetramethyl ester-tin fluoride complex (SnF$_2$(Copro III-4Me)), an octaethylporphyrin-tin fluoride complex (SnF$_2$(OEP)), an etioporphyrin-tin fluoride complex (SnF$_2$(Etio I)), and an octaethylporphyrin-platinum chloride complex (PtCl$_2$OEP).

As the thermally activated delayed fluorescent compound composed of one kind of material, a heterocyclic compound including a π-electron rich heteroaromatic skeleton and a π-electron deficient heteroaromatic skeleton can also be used. Specific examples include 2-(biphenyl-4-yl)-4,6-bis(12-phenylindolo[2,3-a]carbazol-11-yl)-1,3,5-triazine (abbreviation: PIC-TRZ), 2-{4-[3-(N-phenyl-9H-carbazol-3-yl)-9H-carbazol-9-yl]phenyl}-4,6-diphenyl-1,3,5-triazine (abbreviation: PCCzPTzn), 2-[4-(10H-phenoxazin-10-yl)phenyl]-4,6-diphenyl-1,3,5-triazine (abbreviation: PXZ-TRZ), 3-[4-(5-phenyl-5,10-dihydrophenazin-10-yl)phenyl]-4,5-diphenyl-1,2,4-triazole (abbreviation: PPZ-3TPT), 3-(9,9-dimethyl-9H-acridin-10-yl)-9H-xanthen-9-one (abbreviation: ACRXTN), bis[4-(9,9-dimethyl-9,10-dihydroacridine)phenyl]sulfone (abbreviation: DMAC-DPS), and 10-phenyl-10H,10'H-spiro[acridin-9,9'-anthracen]-10'-one (abbreviation: ACRSA). The heterocyclic compound is preferable because of its high electron-transport property and hole-transport property due to the π-electron rich heteroaromatic skeleton and the π-electron deficient heteroaromatic skeleton. Among the π-electron deficient heteroaromatic skeletons, a diazine skeleton (a pyrimidine skeleton, a pyrazine skeleton, or a pyridazine skeleton) and a triazine skeleton are particularly preferable because of their high stability and reliability. Among the π-electron rich heteroaromatic skeletons, an acridine skeleton, a phenoxazine skeleton, a phenothiazine skeleton, a furan skeleton, a thiophene skeleton, and a pyrrole skeleton have high stability and reliability; therefore, one or more selected from these skeletons are preferably included. As the pyrrole skeleton, an indole skeleton, a carbazole skeleton, or a 9-phenyl-3,3'-bi-9H-carbazole skeleton is particularly preferable. Note that a substance in which the π-electron rich heteroaromatic skeleton is directly bonded to the π-electron deficient heteroaromatic skeleton is particularly preferable because the donor property of the π-electron rich heteroaromatic skeleton and the acceptor property of the π-electron deficient heteroaromatic skeleton are both increased and the difference between the singlet excitation energy level and the triplet excitation energy level becomes small.

The material that exhibits thermally activated delayed fluorescence may be a material that can form a singlet excited state from a triplet excited state by reverse intersystem crossing by itself or may be composed of a plurality of materials that form an exciplex.

As the host material used for the light-emitting layer 140, hole-transport materials and electron-transport materials can be used.

Although there is no particular limitation on a material that can be used as a host material of the light-emitting layer, for example, metal complexes such as tris(8-quinolinolato)aluminum(III) (abbreviation: $Alq_3$), tris(4-methyl-8-quinolinolato)aluminum(III) (abbreviation: $Almq_3$), bis(10-hydroxybenzo[h]quinolinato)beryllium(II) (abbreviation: $BeBq_2$), bis(2-methyl-8-quinolinolato) (4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), and bis[2-(2-benzothiazolyl)phenolato]zinc(II) (abbreviation: $Zn(BTZ)_2$); heterocyclic compounds such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), 2,2',2"-(1,3,5-benzenetriyl)tris(1-phenyl-1H-benzimidazole)(abbreviation: TPBI), bathocuproine (abbreviation: BCP), and 9-[4-(5-phenyl-1,3,4-oxadiazol-2-yl)phenyl]-9H-carbazole (abbreviation: CO11); and aromatic amine compounds such as 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), and 4,4'-bis[N-(spiro-9,9'-bifluoren-2-yl)-N-phenyl-amino]biphenyl (abbreviation: BSPB) can be used. In addition, condensed polycyclic aromatic compounds such as anthracene derivatives, phenanthrene derivatives, pyrene derivatives, chrysene derivatives, and dibenzo[g,p]chrysene derivatives can be used, and specific examples include 9,10-diphenylanthracene (abbreviation: DPAnth), N,N-diphenyl-9-[4-(10-phenyl-9-anthryl)phenyl]-9H-carbazol-3-amine (abbreviation: CzA1PA), 4-(10-phenyl-9-anthryl)triphenylamine (abbreviation: DPhPA), YGAPA, PCAPA, N,9-diphenyl-N-{4-[4-(10-phenyl-9-anthryl)phenyl]phenyl}-9H-carbazol-3-amine (abbreviation: PCAPBA), 2PCAPA, 6,12-dimethoxy-5,11-diphenylchrysene, DBC1,9-[4-(10-phenyl-9-anthracenyl)phenyl]-9H-carbazole (abbreviation: CzPA), 3,6-diphenyl-9-[4-(10-phenyl-9-anthryl)phenyl]-9H-carbazole (abbreviation: DPCzPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9,9'-bianthryl (abbreviation: BANT), 9,9'-(stilbene-3,3'-diyl)diphenanthrene (abbreviation: DPNS), 9,9'-(stilbene-4,4'-diyl)diphenanthrene (abbreviation: DPNS2), and 1,3,5-tri(1-pyrenyl)benzene (abbreviation: TPB3). One or more kinds of substances selected from these substances and a variety of substances having a wider energy gap than the energy gap of the above-described light-emitting material is preferably used. Moreover, in the case where the light-emitting material is a phosphorescent compound, a substance having triplet excitation energy which is higher than the triplet excitation energy of the light-emitting material is preferably selected as the host material.

In the case where a plurality of materials are used as the host material of the light-emitting layer, it is preferable to use a combination of two kinds of compounds which form an exciplex. In this case, a variety of carrier-transport materials can be used as appropriate, and in order to form an exciplex efficiently, it is particularly preferable to combine an electron-transport material and a hole-transport material.

This is because in the case where the combination of an electron-transport material and a hole-transport material which form an exciplex is used as a host material, the carrier balance between holes and electrons in the light-emitting layer can be easily optimized by adjustment of the mixture ratio of the electron-transport material and the hole-transport material. The optimization of the carrier balance between holes and electrons in the light-emitting layer can prevent a region in which recombination of electrons and holes occurs from existing on one side in the light-emitting layer. Preventing the region in which recombination occurs from existing on one side can improve the reliability of the light-emitting device.

As the electron-transport material, a metal complex containing zinc or aluminum, a π-electron deficient heteroaromatic compound such as a nitrogen-containing heteroaromatic compound, or the like can be used. Specifically, any of the following can be used: metal complexes such as bis(10-hydroxybenzo[h]quinolinato)beryllium(II) (abbreviation: $BeBq_2$), bis(2-methyl-8-quinolinolato) (4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), and bis[2-(2-benzothiazolyl)phenolato]zinc(II) (abbreviation: $Zn(BTZ)_2$); heterocyclic compounds having azole skeletons, such as 2-(4-biphenylyl)-5-(4-tert-butylphenyl)-1,3,4-oxadiazole (abbreviation: PBD), 3-(4-biphenylyl)-4-phenyl-5-(4-tert-butylphenyl)-1,2,4-triazole (abbreviation: TAZ), 1,3-bis[5-(p-tert-butylphenyl)-1,3,4-oxadiazol-2-yl]benzene (abbreviation: OXD-7), 9-[4-(5-phenyl-1,3,4-oxadiazol-2-yl)phenyl]-9H-carbazole (abbreviation: CO11), 2,2',2"-(1,3,5-benzenetriyl)tris(1-phenyl-1H-benzimidazole) (abbreviation: TPBI), and 2-[3-(dibenzothiophen-4-yl)phenyl]-1-phenyl-1H-benzimidazole (abbreviation: mDBTBIm-II); heterocyclic compounds having diazine skeletons, such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[3'-(9H-carbazol-9-yl)biphenyl-3-yl]dibenzo[f,h]quinoxaline (abbreviation: 2mCzBPDBq), 2-[4-(3,6-diphenyl-9H-carbazol-9-yl)phenyl]dibenzo[f,h]quinoxaline (abbreviation: 2CzPDBq-III), 7-[3-(dibenzothiophen-4-yl)phenyl]dibenzo[f,h]quinoxaline (abbreviation: 7mDBTPDBq-II), 6-[3-(dibenzothiophen-4-yl)phenyl]dibenzo[f,h]quinoxaline (abbreviation: 6mDBTPDBq-II),4,6-bis[3-(phenanthren-9-yl)phenyl]pyrimidine (abbreviation: 4,6mPnP2Pm), 4,6-bis[3-(4-dibenzothienyl)phenyl]pyrimidine (abbreviation: 4,6mDBTP2Pm-II), 4,6-bis[3-(9H-carbazol-9-yl)phenyl]pyrimidine (abbreviation: 4,6mCzP2Pm), and 4-{3-[3'-(9H-carbazol-9-yl)]biphenyl-3-yl}benzofuro[3,2-d]pyrimidine (abbreviation: 4mCzBPBfpm); heterocyclic compounds having triazine skeletons, such as 2-{4-[3-(N-phenyl-9H-carbazol-3-yl)-9H-carbazol-9-yl]phenyl}-4,6-diphenyl-1,3,5-triazine (abbreviation: PCCzPTzn),2,4,6-tris[3'-(pyridin-3-yl)biphenyl-3-yl]-1,3,5-triazine (abbreviation: TmPPPyTz), and 2,4,6-tris(2-pyridyl)-1,3,5-triazine (abbreviation: 2Py3Tz); and heterocyclic compounds having pyridine skeletons, such as 3,5-bis[3-(9H-carbazol-9-yl)phenyl]pyridine (abbreviation: 35DCzPPy), and 1,3,5-tri[3-(3-pyridyl)phenyl]benzene (abbreviation: TmPyPB). Among the above, heterocyclic compounds having diazine skeletons and triazine skeletons and heterocyclic compounds having pyridine skeletons have high reliability and thus are preferable. In particular, heterocyclic compounds having diazine (pyrimidine or pyrazine) skeletons and triazine skeletons have a high electron-transport property and contribute to a reduction in driving voltage.

As the hole-transport material, a π-electron rich heteroaromatic (e.g., a carbazole derivative or an indole derivative), an aromatic amine, or the like can be favorably used. Specific examples include compounds having aromatic amine skeletons, such as 2-[N-(9-phenylcarbazol-3-yl)-N-phenylamino]spiro-9,9'-bifluorene (abbreviation: PCASF), 4,4',4"-tris[N-(1-naphthyl)-N-phenylamino]triphenylamine (abbreviation: 1'-TNATA), 2,7-bis[N-(4-diphenylaminophenyl)-N-phenylamino]-spiro-9,9'-bifluorene (abbreviation: DPA2SF), N,N'-bis(9-phenylcarbazol-3-yl)-N,N'-diphenyl-benzene-1,3-diamine (abbreviation: PCA2B), N-(9,9-dimethyl-2-diphenylamino-9H-fluoren-7-yl)diphenylamine (abbreviation: DPNF), N,N',N"-triphenyl-N,N',N"-tris(9-phenylcarbazol-3-yl)benzene-1,3,5-triamine (abbreviation: PCA3B), 2-[N-(9-phenylcarbazol-3-yl)-N-phenylamino]spiro-9,9'-bifluorene (abbreviation: PCASF), 2-[N-(4-diphenylaminophenyl)-N-phenylamino]spiro-9,9'-bifluorene (abbreviation: DPASF), N,N'-bis[4-(carbazol-9-yl)phenyl]-N,N'-diphenyl-9,9-dimethylfluorene-2,7-diamine (abbreviation: YGA2F), 4,4'-bis[N-(1-naphthyl)-N-phenylamino]biphenyl(abbreviation: NPB), N,N'-bis(3-methylphenyl)-N,N'-diphenyl-[1,1'-biphenyl]-4,4'-diamine (abbreviation: TPD), 4,4'-bis[N-(4-diphenylaminophenyl)-N-phenylamino]biphenyl (abbreviation: DPAB), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), N-(9,9-dimethyl-9H-fluoren-2-yl)-N-{9,9-dimethyl-2-[N-phenyl-N-(9,9-dimethyl-9H-fluoren-2-yl)amino]-9H-fluoren-7-yl}phenylamine (abbreviation: DFLADFL), 3-[N-(9-phenylcarbazol-3-yl)-N-phenylamino]-9-phenylcarbazole (abbreviation: PCzPCA1), 3-[N-(4-diphenylaminophenyl)-N-phenylamino]-9-phenylcarbazole (abbreviation: PCzDPA1), 3,6-bis[N-(4-diphenylaminophenyl)-N-phenylamino]-9-phenylcarbazole (abbreviation: PCzDPA2), N,N'-bis{4-[bis(3-methylphenyl)amino]phenyl}-N,N'-diphenyl-(1,1'-biphenyl)-4,4'-diamine (abbreviation: DNTPD), 3,6-bis[N-(4-diphenylaminophenyl)-N-(1-naphthyl)amino]-9-phenylcarbazole (abbreviation: PCzTPN2), and 3,6-bis[N-(9-phenylcarbazol-3-yl)-N-phenylamino]-9-phenylcarbazole (abbreviation: PCzPCA2), 4-phenyl-4'-(9-phenyl-9H-carbazol-3-yl)triphenylamine (abbreviation: PCBA1BP), 4,4'-diphenyl-4"-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4"-(9-phenyl-9H-carbazol-3-yl)triphenylamine (abbreviation: PCBNBB), 3-[N-(1-naphthyl)-N-(9-phenylcarbazol-3-yl)amino]-9-phenylcarbazole (abbreviation: PCzPCN1), 9,9-dimethyl-N-phenyl-N-[4-(9-phenyl-9H-carbazol-3-yl)phenyl]fluoren-2-amine (abbreviation: PCBAF), N-phenyl-N-[4-(9-phenyl-9H-carbazol-3-yl)phenyl]spiro-9,9'-bifluoren-2-amine (abbreviation: PCBASF), N-(4-biphenyl)-N-(9,9-dimethyl-9H-fluoren-2-yl)-9-phenyl-9H-carbazol-3-amine (abbreviation: PCBiF), and N-(1,1'-biphenyl-4-yl)-N-[4-(9-phenyl-9H-carbazol-3-yl)phenyl]-9,9-dimethyl-9H-fluoren-2-amine (abbreviation: PCBBiF); compounds having carbazole skeletons, such as 1,3-bis(N-carbazolyl)benzene (abbreviation: mCP),4,4'-di(N-carbazolyl)biphenyl(abbreviation: CBP), 3,6-bis(3,5-diphenylphenyl)-9-phenylcarbazole (abbreviation: CzTP), and 9-phenyl-9H-3-(9-phenyl-9H-carbazol-3-yl)carbazole (abbreviation: PCCP); compounds having thiophene skeletons, such as 4,4',4"-(benzene-1,3,5-triyl)tri(dibenzothiophene) (abbreviation: DBT3P-II), 2,8-diphenyl-4-[4-(9-phenyl-9H-fluoren-9-yl)phenyl]dibenzothiophene (abbreviation: DBTFLP-III), and 4-[4-(9-phenyl-9H-fluoren-9-yl)phenyl]-6-phenyldibenzothiophene (abbreviation: DBTFLP-IV); and compounds having furan skeletons, such as 4,4',4"-(benzene-1,3,5-triyl)tri(dibenzofuran) (abbreviation: DBF3P-II) and 4-{3-[3-(9-phenyl-9H-fluoren-9-yl)phenyl]phenyl}dibenzofuran (abbreviation: mmDBFFLBi-II). Among the above, the compound having an aromatic amine skeleton and the compound having a carbazole skeleton are preferable because these have favorable reliability, have high hole-transport properties, and contribute to a reduction in driving voltage.

Note that the combination of the host materials which form an exciplex is not limited to the above-described compounds, and other materials may be used as long as they can transport carriers, the combination can form an exciplex, and light emission of the exciplex overlaps with an absorption band on the longest wavelength side in an absorption spectrum of a light-emitting material (an absorption corresponding to the transition of the light-emitting material from the singlet ground state to the singlet excited state).

As the host material used for the light-emitting layer, a thermally activated delayed fluorescent material may be used.

As the electron-transport material used for the light-emitting layer, a material that is the same as the electron-transport material used for the electron-injection layer can be used. This can simplify the fabrication of the light-emitting device and can reduce the manufacturing cost of the light-emitting device.

<<Electron-Transport Layer and Buffer Layer>>

The electron-transport layer 118 and the buffer layer 127 are layers including a substance having a high electron-transport property. Examples of the organic compound that can be used for the electron-transport layer 118 and the buffer layer 127 include metal complexes having a quinoline ligand, a benzoquinoline ligand, an oxazole ligand, and a thiazole ligand; an oxadiazole derivative; a triazole derivative; a phenanthroline derivative; a pyridine derivative; a bipyridine derivative; and the like can be used. The organic compound having a function of interacting with the metal as a tridentate or tetradentate ligand, which is shown as an example of the compound that can be used for the electron-injection layer 130, can also be used.

Specifically, as the above-described metal complex including a quinoline ligand, a benzoquinoline ligand, an oxazole ligand, or a thiazole ligand, an oxadiazole derivative, a triazole derivative, a phenanthroline derivative, a pyridine derivative, and a bipyridine derivative, a metal complex such as $Alq_3$, $Almq_3$, $BeBq_2$, BAlq, bis(8-quinolinolato)zinc(II) (abbreviation: Znq), bis[2-(2-benzoxazolyl)phenolato]zinc(II) (abbreviation: ZnPBO), or bis[2-(2-benzothiazolyl)phenolato]zinc(II) (abbreviation: ZnBTZ) can be used. Furthermore, any of the following can be used: heterocyclic compounds having azole skeletons, such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 9-[4-(5-phenyl-1,3,4-oxadiazol-2-yl)phenyl]-9H-carbazole (abbreviation: CO11), 3-(4'-tert-butylphenyl)-4-phenyl-5-(4"-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), 4,4'-bis(5-methylbenzoxazol-2-yl)stilbene (abbreviation: BzOS), 2,2',2"-(1,3,5-benzenetriyl)tris(1-phenyl-1H-benzimidazole) (abbreviation: TPBI), and 2-[3-(dibenzothiophen-4-yl)phenyl]-1-phenyl-1H-benzimidazole (abbreviation: mDBTBIm-II); heterocyclic compounds having diazine skeletons, such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[3'-(9H-carbazol-9-yl)biphenyl-3-yl]dibenzo[f,h]quinoxaline (abbreviation: 2mCzBPDBq), 2-[4-(3,6-diphenyl-9H-carbazol-9-yl)phenyl]dibenzo[f,h]quinoxaline (abbreviation: 2CzPDBq-III), 7-[3-(dibenzothiophen-4-yl)phenyl]dibenzo[f,h]quinoxaline (abbreviation: 7mDBTPDBq-II), 6-[3-(dibenzothiophen-4-yl)phenyl]dibenzo[f,h]quinoxaline (abbreviation: 6mDBTPDBq-II),4,6-bis[3-(phenanthren-9-yl)phenyl]pyrimidine (abbreviation: 4,6mPnP2Pm), 4,6-bis[3-(4-dibenzothienyl)phenyl]pyrimidine (abbreviation: 4,6mDBTP2Pm-II), 4,6-bis[3-(9H-carbazol-9-yl)phenyl]pyrimidine (abbreviation: 4,6mCzP2Pm), and 4-{3-[3'-(9H-carbazol-9-yl)]biphenyl-3-yl}benzofuro[3,2-d]pyrimidine (abbreviation: 4mCzBPBfpm); heterocyclic compounds having triazine skeletons, such as 2-{4-[3-(N-phenyl-9H-carbazol-3-yl)-9H-carbazol-9-yl]phenyl}-4,6-diphenyl-1,3,5-triazine (abbreviation: PCCzPTzn),2,4,6-tris[3'-(pyridin-3-yl)biphenyl-3-yl]-1,3,5-triazine (abbreviation: TmPPPyTz), and 2,4,6-tris(2-pyridyl)-1,3,5-triazine (abbreviation: 2Py3Tz); and heterocyclic compounds having pyridine skeletons, such as 3,5-bis[3-(9H-carbazol-9-yl)phenyl]pyridine (abbreviation: 35DCzPPy), 1,3,5-tri[3-(3-pyridyl)phenyl]benzene (abbreviation: TmPyPB), bathocuproine (abbreviation: BCP), and 2,9-bis(naphthalen-2-yl)-4,7-diphenyl-1,10-phenanthroline (abbreviation: NBPhen). Among the above, heterocyclic compounds having diazine skeletons and triazine skeletons and heterocyclic compounds having pyridine skeletons have high reliability and thus are preferable. In particular, heterocyclic compounds having diazine (pyrimidine or pyrazine) skeletons and triazine skeletons have a high electron-transport property and contribute to a reduction in driving voltage. The substances listed here are mainly substances having an electron mobility of $1\times10^{-6}$ $cm^2/Vs$ or higher. Note that other substances may also be used for the electron-injection layer 130 as long as their electron-transport properties are higher than their hole-transport properties.

The electron-transport layer 118 and the buffer layer 127 are not limited to a single layer and may include a stack of two or more layers containing the aforementioned substances.

A layer that controls transfer of electron carriers may be provided between the electron-transport layer 118 and the light-emitting layer 140. This is a layer formed by addition of a small amount of a substance having a high electron-trapping property to the aforementioned material having a high electron-transport property and is capable of adjusting the carrier balance by retarding transfer of electron carriers. Such a structure is very effective in preventing a problem (such as a reduction in element lifetime) caused when electrons pass through the light-emitting layer.

As the electron-transport material used for the electron-transport layer, a material that is the same as the electron-transport material used for the electron-injection layer can be used. As the electron-transport material used for the electron-transport layer, a material that is the same as the electron-transport material used for the light-emitting layer can be used. This can simplify the fabrication of the light-emitting device and can reduce the manufacturing cost of the light-emitting device.

Note that the hole-injection layer, the hole-transport layer, the light-emitting layer, the electron-transport layer, and the electron-injection layer described above can each be formed by an evaporation method (including a vacuum evaporation method), an inkjet method, a coating method, a gravure printing method, or the like. Besides the above-mentioned materials, an inorganic compound such as a quantum dot or a high molecular compound (e.g., an oligomer, a dendrimer, or a polymer) may be used for the hole-injection layer, the hole-transport layer, the light-emitting layer, the electron-transport layer, and the electron-injection layer described above.

As the quantum dot, a colloidal quantum dot, an alloyed quantum dot, a core-shell quantum dot, a core quantum dot, or the like may be used. The quantum dot containing elements belonging to Group 2 and Group 16, elements belonging to Group 13 and Group 15, elements belonging to Group 13 and Group 17, elements belonging to Group 11 and Group 17, or elements belonging to Group 14 and Group 15 may be used. Alternatively, the quantum dot containing an element such as cadmium (Cd), selenium (Se), zinc (Zn), sulfur (S), phosphorus (P), indium (In), tellurium (Te), lead (Pb), gallium (Ga), arsenic (As), or aluminum (Al) may be used.

As the liquid medium used for the wet process, organic solvents such as ketones, e.g., methyl ethyl ketone and cyclohexanone, fatty acid esters, e.g., ethyl acetate, halogenated hydrocarbons, e.g., dichlorobenzene, aromatic hydrocarbons, e.g., toluene, xylene, mesitylene, and cyclohexylbenzene, aliphatic hydrocarbons, e.g., cyclohexane, decalin, and dodecane, N,N-dimethylformamide (DMF), and dimethyl sulfoxide (DMSO) can be used.

Examples of the high molecular compound that can be used for the light-emitting layer include a polyphenylenevinylene (PPV) derivative such as poly[2-methoxy-5-(2-ethylhexyloxy)-1,4-phenylenevinylene] (abbreviation: MEH-PPV) or poly(2,5-dioctyl-1,4-phenylenevinylene); a polyfluorene derivative such as poly(9,9-di-n-octylfluorenyl-2,7-diyl) (abbreviation: PF8), poly[(9,9-di-n-octylfluorenyl-2,7-diyl)-alt-(benzo[2,1,3]thiadiazole-4,8-diyl)] (abbreviation: F8BT), poly[(9,9-di-n-octylfluorenyl-2,7-diyl)-alt-(2,2'-bithiophene-5,5'-diyl)] (abbreviation: F8T2), poly[(9,9-dioctyl-2,7-divinylenefluorenylene)-alt-(9,10-anthracene)], or poly[(9,9-dihexylfluorene-2,7-diyl)-alt-(2,5-dimethyl-1,4-phenylene)]; a polyalkylthiophene (PAT) derivative such as poly(3-hexylthiophene-2,5-diyl) (abbreviation: P3HT); and a polyphenylene derivative. These high molecular compounds or a high molecular compound such as poly(N-vinylcarbazole) (abbreviation: PVK), poly(2-vinylnaphthalene), or poly[bis(4-phenyl)(2,4,6-trimethylphenyl)amine] (abbreviation: PTAA) may be doped with a light-emitting low molecular compound and used for the light-emitting layer. As the light-emitting low molecular compound, any of the above-described fluorescent compounds can be used.

<<Pair of Electrodes>>

The electrode 101 and the electrode 102 have a function of an anode and a cathode of a light-emitting device. The electrode 101 and the electrode 102 can be formed using a metal, an alloy, a conductive compound, a mixture or a stack thereof, or the like.

One of the electrode 101 and the electrode 102 is preferably formed using a conductive material having a function of reflecting light. Examples of the conductive material include aluminum (Al) and an alloy containing Al. Examples of the alloy containing Al include an alloy containing Al and L (L represents one or more of titanium (Ti), neodymium (Nd), nickel (Ni), and lanthanum (La)), such as an alloy containing Al and Ti and an alloy containing Al, Ni, and La. Aluminum has low resistance and high light reflectivity. Aluminum is included in earth's crust in large amount and is inexpensive; therefore, it is possible to reduce costs for fabricating a light-emitting device with the use of aluminum. In addition, silver (Ag) can be suitably used as an electrode material because it has a high light reflectivity. Furthermore, Ag is a transition metal of Group 11, and Ag is preferably used as the cathode of the light-emitting device of one embodiment of the present invention in which Ag is used for the electron-injection layer, in which case the adhesion between the electrode and the electron-injection layer is improved. Alternatively, an alloy of Ag and N (N represents one or more of yttrium (Y), Nd, magnesium (Mg), ytterbium (Yb), Al, Ti, gallium (Ga), zinc (Zn), indium (In), tungsten (W), manganese (Mn), tin (Sn), iron (Fe), Ni, copper (Cu), palladium (Pd), iridium (Ir), and gold (Au)) may be used. Examples of the alloy containing silver include an alloy containing silver, palladium, and copper, an alloy containing silver and copper, an alloy containing silver and magnesium, an alloy containing silver and nickel, an alloy containing silver and gold, and an alloy containing silver and ytterbium. Besides, a transition metal such as tungsten, chromium (Cr), molybdenum (Mo), copper, or titanium can be used.

Light emission obtained from the light-emitting layer is extracted through one or both of the electrode 101 and the electrode 102. Thus, at least one of the electrode 101 and the electrode 102 is preferably formed using a conductive material having a function of transmitting light. An example of the conductive material is a conductive material having a visible light transmittance higher than or equal to 40% and lower than or equal to 100%, preferably higher than or equal to 60% and lower than or equal to 100%, and a resistivity lower than or equal to $1 \times 10^{-2}$ Ω·cm.

The electrode 101 and the electrode 102 may be formed using a conductive material having a function of transmitting light and a function of reflecting light. Examples of the conductive material include a conductive material having a visible light reflectivity higher than or equal to 20% and lower than or equal to 80%, preferably higher than or equal to 40% and lower than or equal to 70%, and a resistivity lower than or equal to $1 \times 10^{-2}$ Ω·cm. For example, one or more kinds of conductive metals and alloys, conductive compounds, and the like can be used. Specifically, a metal oxide such as indium tin oxide (hereinafter, referred to as ITO), indium tin oxide containing silicon or silicon oxide (abbreviation: ITSO), indium oxide-zinc oxide (Indium Zinc Oxide), indium oxide-tin oxide containing titanium, indium titanium oxide, or indium oxide containing tungsten oxide and zinc oxide can be used. A metal thin film having a thickness that allows transmission of light (preferably, a thickness greater than or equal to 1 nm and less than or equal to 30 nm) can also be used. As the metal, Ag, an alloy of Ag and Al, an alloy of Ag and Mg, an alloy of Ag and Au, an alloy of Ag and Yb, or the like can be used.

In this specification and the like, as the material having a function of transmitting light, a material that has a function of transmitting visible light and has conductivity is used, and examples of the material include, in addition to the above-described oxide conductor typified by an ITO, an oxide semiconductor and an organic conductor containing an organic substance. Examples of the organic conductor containing an organic substance include a composite material in which an organic compound and an electron donor (donor) are mixed and a composite material in which an organic compound and an electron acceptor (acceptor) are mixed. Alternatively, an inorganic carbon-based material such as graphene may be used. The resistivity of the material is preferably lower than or equal to $1 \times 10^5$ Ω·cm, further preferably lower than or equal to $1 \times 10^4$ Ω·cm.

Alternatively, one or both of the electrode 101 and the electrode 102 may be formed by stacking two or more of these materials.

In order to improve the extraction efficiency, a material whose refractive index is higher than that of an electrode having a function of transmitting light may be formed in contact with the electrode. The material may be conductive material or non-conductive material as long as it has a function of transmitting visible light. In addition to the oxide conductors described above, an oxide semiconductor and an organic substance are given as examples. Examples of the organic substance include the materials for the light-emitting layer, the hole-injection layer, the hole-transport layer, the electron-transport layer, and the electron-injection layer given as examples. Furthermore, an inorganic carbon-based material or a metal film thin enough to transmit light can be used, and stacked layers with a thickness of several nanometers to several tens of nanometers may be used.

In the case where the electrode 101 or the electrode 102 have a function of a cathode, the electrode preferably contains a material with a low work function (3.8 eV or lower).

In the case where the electrode 101 or the electrode 102 is used as an anode, a material with a high work function (4.0 eV or higher) is preferably used.

The electrode 101 and the electrode 102 may be a stacked layer of a conductive material having a function of reflecting light and a conductive material having a function of transmitting light. In that case, the electrode 101 and the electrode 102 can have a function of adjusting the optical path length so that light of a desired wavelength emitted from each light-emitting layer resonates and the light of a desired wavelength is intensified, which is preferable.

As the method for forming the electrode 101 and the electrode 102, a sputtering method, an evaporation method, a printing method, a coating method, an MBE (Molecular Beam Epitaxy) method, a CVD method, a pulsed laser deposition method, an ALD (Atomic Layer Deposition) method, or the like can be used as appropriate.

<<Substrate>>

A light-emitting device of one embodiment of the present invention is formed over a substrate of glass, plastic, or the like. As for the order of formation over the substrate, layers may be sequentially stacked from the electrode 101 side or sequentially stacked from the electrode 102 side.

For the substrate over which the light-emitting device of one embodiment of the present invention can be formed, glass, quartz, plastic, or the like can be used, for example. Furthermore, a flexible substrate may be used. The flexible substrate is a substrate that can be bent (is flexible), such as a plastic substrate made of polycarbonate or polyarylate, for example. Furthermore, a film, an inorganic vapor deposition film, or the like can be used. Another material may be used as long as the substrate functions as a support in a fabrication process of the light-emitting devices or the optical elements. Another material having a function of protecting the light-emitting devices or the optical elements may be used.

In this specification and the like, a light-emitting device can be formed using any of a variety of substrates, for example. The type of substrate is not limited particularly. Examples of the substrate include a semiconductor substrate (e.g., a single-crystal substrate or a silicon substrate), an SOI substrate, a glass substrate, a quartz substrate, a plastic substrate, a metal substrate, a stainless steel substrate, a substrate including stainless steel foil, a tungsten substrate, a substrate including tungsten foil, a flexible substrate, an attachment film, cellulose nanofiber (CNF) and paper which include a fibrous material, and a base material film. As examples of the glass substrate, barium borosilicate glass, aluminoborosilicate glass, soda lime glass, and the like can be given. Examples of the flexible substrate, the attachment film, the base material film, and the like are as follows. Examples of the flexible substrate, the attachment film, the base material film, and the like include substrates of plastics typified by polyethylene terephthalate (PET), polyethylene naphthalate (PEN), polyether sulfone (PES), and polytetrafluoroethylene (PTFE). Another example is a resin such as acrylic. Furthermore, polypropylene, polyester, polyvinyl fluoride, and polyvinyl chloride can be given as examples. Furthermore, polyamide, polyimide, aramid, epoxy, an inorganic vapor deposition film, paper, and the like can be given as examples.

Furthermore, a flexible substrate may be used as the substrate and the light-emitting device may be formed directly on the flexible substrate. Alternatively, a separation layer may be provided between the substrate and the light-emitting device. The separation layer can be used when part or the whole of a light-emitting device formed thereover is separated from the substrate and transferred onto another substrate. In such a case, the light-emitting device can be transferred to a substrate having low heat resistance or a flexible substrate as well. For the above separation layer, a stacked structure of inorganic films of a tungsten film, a silicon oxide film, and the like, or a structure in which a resin film of polyimide or the like is formed over a substrate can be used, for example.

In other words, after the light-emitting device is formed using a substrate, the light-emitting device may be transferred to a different substrate and placed over the different substrate. Examples of the substrate to which the light-emitting device is transferred include, in addition to the above substrates, a cellophane substrate, a stone substrate, a wood substrate, a cloth substrate (including a natural fiber (silk, cotton, or hemp), a synthetic fiber (nylon, polyurethane, or polyester), a regenerated fiber (acetate, cupra, rayon, or regenerated polyester), and the like), a leather substrate, and a rubber substrate. With the use of such a substrate, a light-emitting device with high durability, a light-emitting device with high heat resistance, a light-emitting device with reduced weight, or a light-emitting device with reduced thickness can be obtained.

The light-emitting device 150 may be formed over an electrode electrically connected to a field-effect transistor (FET), for example, that is formed over the above-described substrate. Accordingly, an active matrix display device in which the FET controls the driving of the light-emitting device can be fabricated.

The structure described above in this embodiment can be used in appropriate combination with the other embodiments.

Embodiment 2

In this embodiment, a light-emitting device having a structure different from the structure described in Embodiment 1 and a light emission mechanism of the light-emitting device are described below with reference to FIG. 3. In FIG. 3, a portion having a function similar to that in FIG. 1(A) is represented using the same hatch pattern and a reference numeral thereof is omitted in some cases. In addition, common reference numerals are used for portions having similar functions, and a detailed description thereof is omitted in some cases.

<Structure Example 4 of Light-Emitting Device>

FIG. 3 is a schematic cross-sectional view of a light-emitting device 250a and a light-emitting device 250b.

The light-emitting device 250a and the light-emitting device 250b each include an electrode 101, an electrode 102, an electrode 103, and an electrode 104 over a substrate 200. At least a light-emitting unit 106, a light-emitting unit 108, and an electron-injection layer 130 are provided between the electrode 101 and the electrode 102, between the electrode 102 and the electrode 103, and between the electrode 102 and the electrode 104. A charge-generation layer 115 is provided between the light-emitting unit 106 and the light-emitting unit 108. Note that the light-emitting unit 106 and the light-emitting unit 108 may have the same structure or different structures.

The charge-generation layer 115 provided between the light-emitting unit 106 and the light-emitting unit 108 injects electrons into one of the light-emitting units and injects holes into the other of the light-emitting units when a voltage is applied to the electrode 101 and the electrode 102, for example. For example, in FIG. 1, the charge-generation layer 115 injects electrons into the light-emitting unit 106 and injects holes into the light-emitting unit 108 when a voltage is applied such that the potential of the electrode 102 is higher than the potential of the electrode 101.

The light-emitting unit 106 includes a hole-injection layer 111, a hole-transport layer 112, a light-emitting layer 140, and an electron-transport layer 113, for example. The light-emitting unit 108 includes a hole-injection layer 116, a hole-transport layer 117, a light-emitting layer 170, an electron-transport layer 118, and an electron-injection layer 119, for example.

As illustrated in FIG. 3, it is preferable that the electron-injection layer 130 be adjacent to the electron-transport layer 113 and provided between the light-emitting unit 108 and the electron-transport layer 113. In addition, as illustrated in FIG. 3, it is preferable that the charge-generation layer 115 be adjacent to the electron-injection layer 130 and provided between the electron-injection layer 130 and the light-emitting unit 108. With such a structure, electrons can be efficiently transported to the light-emitting unit 106.

Note that in this embodiment, description is made on the assumption that the electrode 101, the electrode 103, and the electrode 104 serve as anodes and the electrode 102 serves as a cathode, but the structures of the light-emitting device 250a and the light-emitting device 250b are not limited thereto. That is, the electrode 101, the electrode 103, and the electrode 104 may be cathodes, the electrode 102 may be an anode, and the stacking order of the layers between the electrodes may be reversed. That is, the hole-injection layer 111, the hole-transport layer 112, the light-emitting layer 140, the electron-transport layer 113, and the electron-injection layer 130 are stacked in this order from the anode side in the light-emitting unit 106, and the hole-injection layer 116, the hole-transport layer 117, the light-emitting layer 170, the electron-transport layer 118, and the electron-injection layer 119 are stacked in this order from the anode side in the light-emitting unit 108.

The structures of the light-emitting device 250a and the light-emitting device 250b are not limited to those shown in FIG. 3, and at least the light-emitting layer 140, the light-emitting layer 170, the charge-generation layer 115, and the electron-injection layer 130 are included, but the hole-injection layer 111, the hole-injection layer 116, the hole-transport layer 112, the hole-transport layer 117, the electron-transport layer 113, the electron-transport layer 118, and the electron-injection layer 119 are not necessarily included.

These layers may be formed between the pair of electrodes, depending on their functions, and are not limited to them. In other words, layers between the pair of electrodes may include a layer which has a function of reducing a barrier to hole or electron injection, enhancing a hole- or electron-transport property, inhibiting a hole- or electron-transport property, suppressing a quenching phenomenon due to an electrode, or the like.

Note that in the case where a surface of a light-emitting unit on the anode side is in contact with the charge-generation layer 115 as in the light-emitting unit 108, the charge-generation layer 115 can also function as a hole-injection layer in the light-emitting unit 108 in some cases, and thus, a hole-injection layer is not necessarily provided in the light-emitting unit in such cases.

The light-emitting device having two light-emitting units has been described with reference to FIG. 3; however, a light-emitting device in which three or more light-emitting units are stacked may be employed. When a plurality of light-emitting units partitioned by the charge-generation layer are arranged between a pair of electrodes as in the light-emitting device 250a and the light-emitting device 250b, a high-luminance light-emitting device with a long lifetime can be achieved while the current density is kept low. Moreover, a light-emitting device having low power consumption can be achieved.

In the light-emitting device 250a, the electrode 101, the electrode 103, and the electrode 104 each have a function of reflecting visible light, and the electrode 102 has a function of transmitting visible light. In the light-emitting device 250b, the electrode 101, the electrode 103, and the electrode 104 each have a function of transmitting visible light, and the electrode 102 has a function of reflecting visible light.

Accordingly, light emitted from the light-emitting device 250a is extracted to the outside through the electrode 102, and light emitted from the light-emitting device 250b is extracted to the outside through the electrode 101, the electrode 103, and the electrode 104. However, one embodiment of the present invention is not limited to this, and a light-emitting device in which light is extracted in both top and bottom directions of the substrate 200 where the light-emitting device is formed may be employed.

The electrode 101 includes a conductive layer 101a and a conductive layer 101b over and in contact with the conductive layer 101a. The electrode 103 includes a conductive layer 103a and a conductive layer 103b over and in contact with the conductive layer 103a. The electrode 104 includes a conductive layer 104a and a conductive layer 104b over and in contact with the conductive layer 104a.

The conductive layer 101b, the conductive layer 103b, and the conductive layer 104b each have a function of transmitting visible light. In the light-emitting device 250a, the conductive layer 101a, the conductive layer 103a, and the conductive layer 104a each have a function of reflecting visible light. In the light-emitting device 250b, the conductive layer 101a, the conductive layer 103a, and the conductive layer 104a each have a function of transmitting visible light.

Figure 3A:
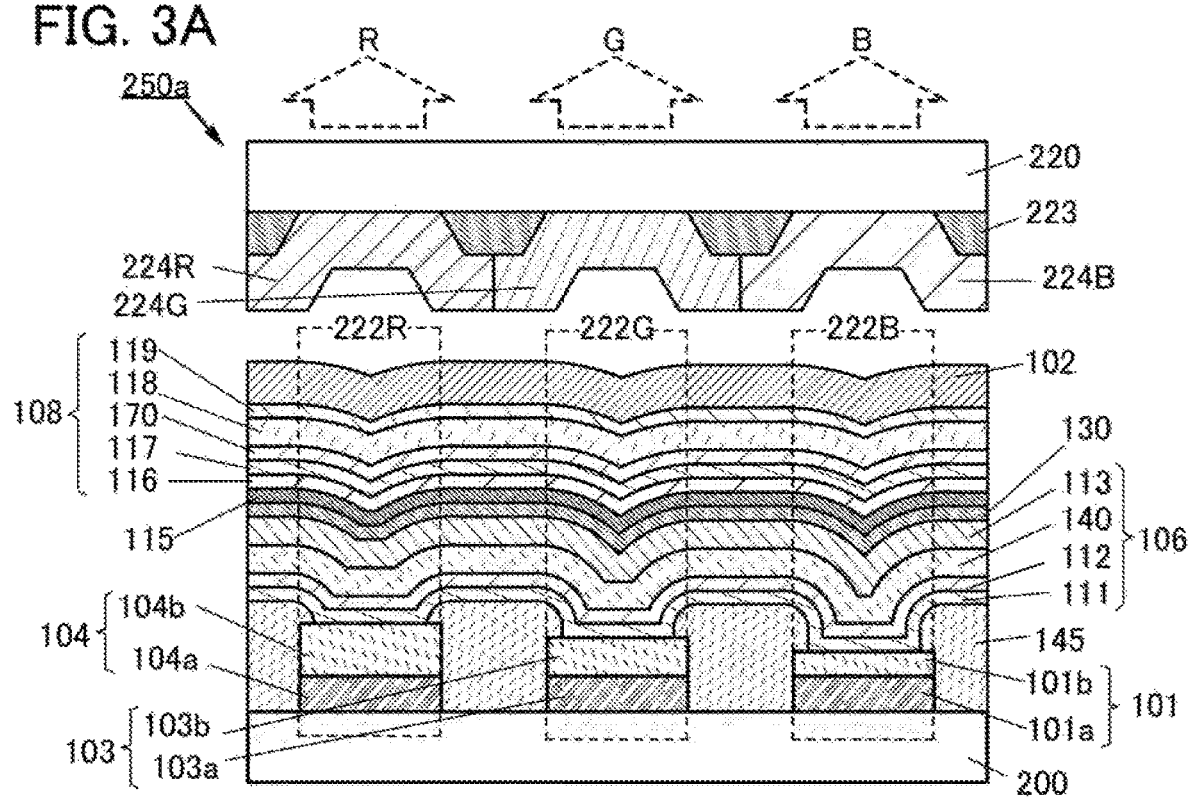
FIGS. 3A-3B are schematic cross-sectional views each illustrating a light-emitting device of one embodiment of the present invention.
Figure 3B:
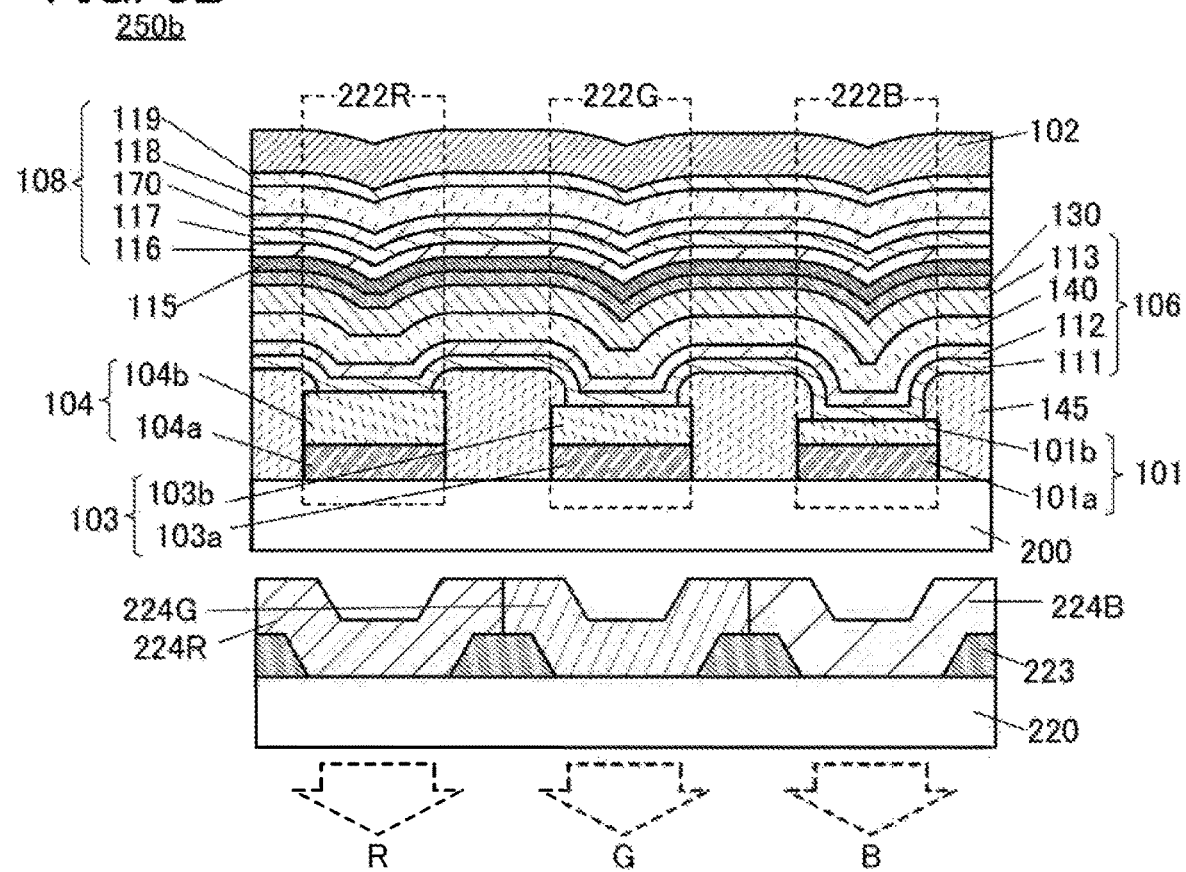

The light-emitting device 250a illustrated in FIG. 3(A) and the light-emitting device 250b illustrated in FIG. 3(B) each include a partition wall 145 between a region 222B sandwiched between the electrode 101 and the electrode 102, a region 222G sandwiched between the electrode 102 and the electrode 103, and a region 222R sandwiched between the electrode 102 and the electrode 104. The partition wall 145 has an insulating property. The partition wall 145 covers end portions of the electrode 101, the electrode 103, and the electrode 104 and has opening portions overlapping with the electrodes. The partition walls 145 are provided, whereby the electrodes over the substrate 200 can be divided to have island shapes in the regions.

In FIG. 3, the hole-injection layer 111, the hole-injection layer 116, the hole-transport layer 112, the hole-transport layer 117, the light-emitting layer 140, the light-emitting layer 170, the electron-transport layer 113, the electron-transport layer 118, the electron-injection layer 119, the charge-generation layer 115, and the electrode 102 are provided in the regions without being separated; however, they may be provided separately in each of the regions.

In each of the light-emitting device 250a and the light-emitting device 250b of one embodiment of the present invention, voltage application between the pair of electrodes (the electrode 101 and the electrode 102) in the region 222B, between the pair of electrodes (the electrode 102 and the electrode 103) in the region 222G, and between the pair of electrodes (the electrode 102 and the electrode 104) in the region 222R allows electron injection from the cathode to the electron-injection layer 119 and hole injection from the anode to the hole-injection layer 111, whereby current flows. Electrons are injected from the charge-generation layer 115 to the electron-injection layer 130 and holes are injected from the charge-generation layer 115 to the hole-injection layer 116. By recombination of the injected carriers (electrons and holes), excitons are formed. When carriers (electrons and holes) recombine and excitons are formed in the light-emitting layer 140 and the light-emitting layer 170 including light-emitting materials, the light-emitting materials included in the light-emitting layer 140 and the light-emitting layer 170 are brought into an excited state, whereby light emission can be obtained from the light-emitting materials.

Each of the light-emitting layer 140 and the light-emitting layer 170 preferably includes any one or more light-emitting materials selected from the ones that emit light of violet, blue, blue green, green, yellow green, yellow, yellow orange, orange, or red.

The light-emitting layer 140 and the light-emitting layer 170 may each have a two-layer structure. With the use of two kinds of light-emitting materials, a first compound and a second compound, for emitting light of different colors for two light-emitting layers, light of a plurality of colors can be obtained at the same time. It is particularly preferable to select the light-emitting materials used for the light-emitting layers such that white light or light of color close to white can be obtained from light emissions exhibited by the light-emitting layer 140 and the light-emitting layer 170.

The light-emitting layer 140 and the light-emitting layer 170 may have a stacked-layer structure of three or more layers, in which a layer not including a light-emitting material may be included.

The light-emitting device 250a and the light-emitting device 250b each include the substrate 220 provided with an optical element 224B, an optical element 224G, and an optical element 224R in the direction in which light emitted from the region 222B, the region 222G, and the region 222R is extracted. The light emitted from each region is emitted to the outside of the light-emitting device through each optical element. In other words, the light emitted from the region 222B is emitted through the optical element 224B, the light emitted from the region 222G is emitted through the optical element 224G, and the light emitted from the region 222R is emitted through the optical element 224R.

The optical element 224B, the optical element 224G, and the optical element 224R each have a function of selectively transmitting light of a particular color out of incident light. For example, the light emitted from the region 222B through the optical element 224B is blue light, the light emitted from the region 222G through the optical element 224G is green light, and the light emitted from the region 222R through the optical element 224R is red light.

Note that in FIGS. 3(A) and 3(B), blue light (B), green light (G), and red light (R) emitted from the regions through the optical elements are schematically illustrated by arrows of dashed lines. The light-emitting device 250a illustrated in FIG. 3(A) is a top-emission light-emitting device, and the light-emitting device 250b illustrated in FIG. 3(B) is a bottom-emission light-emitting device.

A light-blocking layer 223 is provided between the optical elements. The light-blocking layer 223 has a function of blocking light emitted from the adjacent regions. Note that a structure in which the light-blocking layer 223 is not provided may also be employed. A structure in which any one or two or more of the optical element 224B, the optical element 224G, and the optical element 224R are not provided may be employed. With the structure in which the optical element 224B, the optical element 224G, or the optical element 224R is not provided, the extraction efficiency of light emitted from the light-emitting device can be increased.

The charge-generation layer 115 can be formed with a material obtained by adding an electron acceptor (acceptor) to a hole-transport material or a material obtained by adding an electron donor (donor) to an electron-transport material.

Figure 4A:
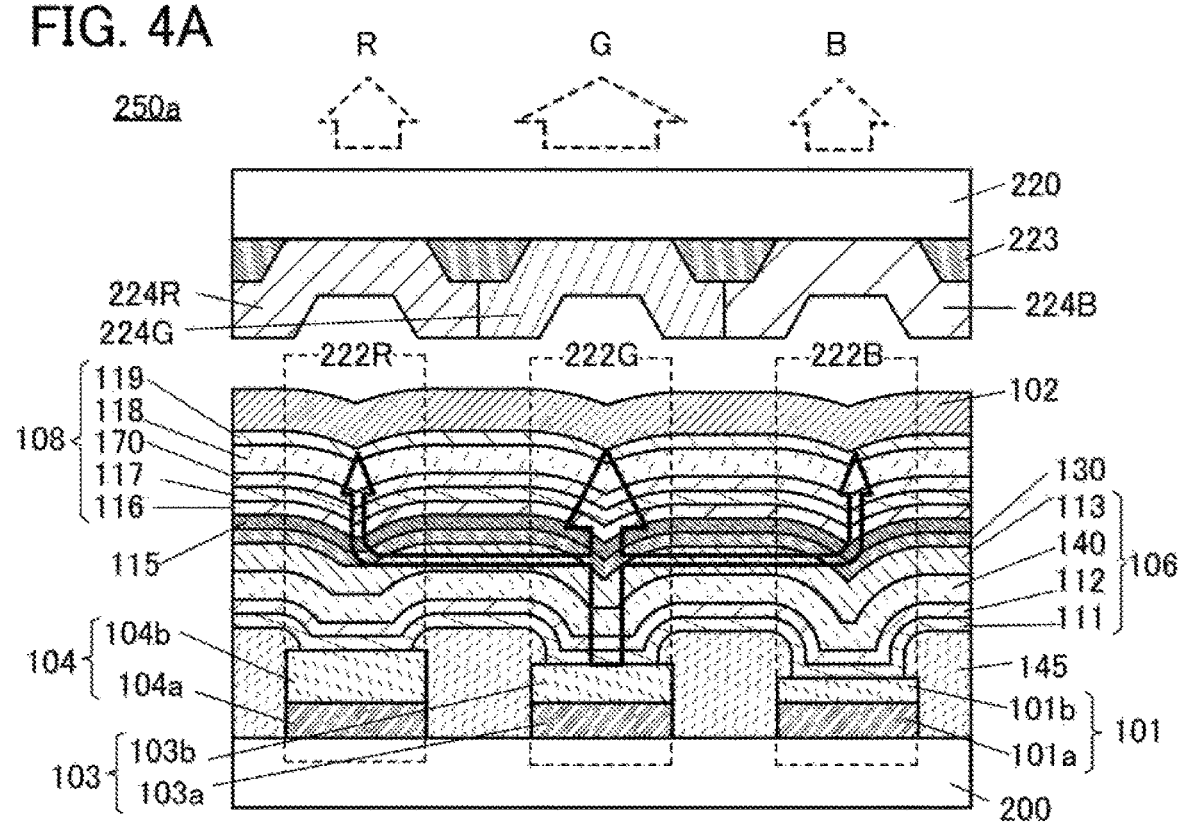
FIGS. 4A-4B are schematic cross-sectional views each illustrating a light-emitting device of one embodiment of the present invention.
Figure 4B:
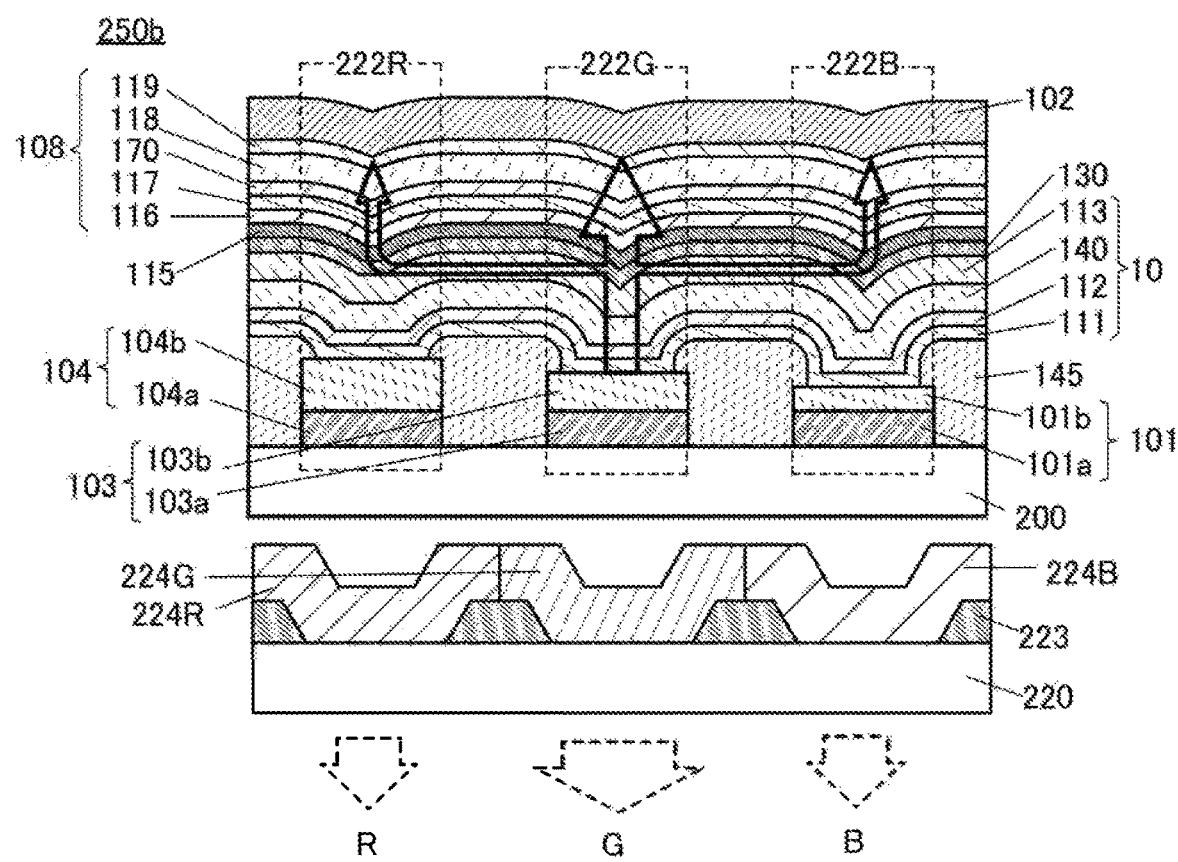

In order to reduce the driving voltage of the light-emitting device, a structure is preferable in which a barrier to electron injection from the charge-generation layer 115 to the electron-transport layer 113 is reduced to inject and transport electrons generated in the charge-generation layer 115 to the electron-transport layer 113 smoothly. Hence, the electron-injection layer 130 is preferably provided between the charge-generation layer 115 and the electron-transport layer 113. The electron-injection layer 119 and the electron-injection layer 130 are required to have a high electron-injection property, and accordingly, an alkali metal such as lithium (Li) or cesium (Cs), a compound thereof, an alkaline earth metal such as calcium (Ca), or a compound thereof is used for the electron-injection layers. However, in the case where the metal or the compound is used for the electron-injection layer 130, for example, as shown in FIG. 4, when current is made to flow in the region 222G by voltage application between the electrode 103 and the electrode 102, current flows also in the region 222B and the region 222R adjacent to the region 222G through the electron-injection layer 130 and the electron-transport layer 113, whereby a phenomenon in which light is emitted not only from the region 222G but also from the adjacent region 222B and region 222R (referred to as crosstalk) occurs in some cases. Note that in FIG. 4, current that flows in the region 222G, the region 222R, and the region 222B is indicated by a solid arrow.

In the case where the crosstalk occurs in the light-emitting devices, light is emitted not only from a desired region (e.g., the region 222G) but also from other regions (e.g., the regions 222B and 222R), which causes a reduction in the color purity or the intensity of light emitted from the light-emitting device 250a and the light-emitting device 250b in some cases.

A cause of the crosstalk is diffusion of an alkali metal, an alkaline earth metal, or a compound thereof from the electron-injection layer 130 sandwiched between the charge-generation layer 115 and electron-transport layer 113 to the electron-transport layer 113, which increases the conductivity of the electron-transport layer 113 (particularly, the conductivity in a direction perpendicular to the direction of voltage application). In particular, when a metal with a small atomic number, e.g., Li or Ca, or a compound thereof is used for the electron-injection layer 130, the metal with a small atomic number is easily diffused to the electron-transport layer 113. Therefore, it is preferable that an alkali metal and an alkaline earth metal not be included in the electron-injection layer 130 in terms of suppressing the crosstalk. On the other hand, in the case where an alkali metal, an alkaline earth metal, or a compound thereof is not used for the electron-injection layer 130, a barrier to electron injection from the charge-generation layer 115 to the electron-transport layer 113 is increased and electrons are not easily injected to the electron-transport layer 113, resulting in an increase in the driving voltage or a reduction in the emission efficiency of the light-emitting device in some cases.

Thus, in order to reduce the driving voltage of the light-emitting device, increase the emission efficiency, and suppress the crosstalk, a metal that has a high electron-injection property and is not easily diffused in an organic compound when mixed with the organic compound is preferably used for the electron-injection layer 130. It is preferable to use a metal with a long atomic radius as the metal that is not easily diffused and is used for the electron-injection layer 130. Furthermore, a metal with a large atomic weight is preferable.

Here, the light-emitting device of one embodiment of the present invention includes the composite material of a metal and an organic compound having a function of interacting with the metal as a tridentate or tetradentate ligand. As the metal, a metal that has a large atomic weight or a long atomic radius and belongs to any of Group 3 to Group 13 can be suitably used. Thus, one embodiment of the present invention can provide a light-emitting device in which crosstalk is suppressed.

In particular, a transition metal has a large atomic weight and is not easily diffused in an organic compound, and accordingly, a light-emitting device in which crosstalk is suppressed can be provided.

Note that the light-emitting unit 106, the light-emitting unit 108, and the charge-generation layer 115 can be formed by an evaporation method (including a vacuum evaporation method), an inkjet method, a coating method, a gravure printing method, or the like.

Note that the structures described in this embodiment can be used in an appropriate combination with any of the structures described in the other embodiments.

Embodiment 3

In this embodiment, a light-emitting apparatus including the light-emitting device described in Embodiment 1 and Embodiment 2 will be described with reference to FIGS. 5(A) and 5(B).

FIG. 5(A) is a top view of a light-emitting apparatus, and FIG. 5(B) is a cross-sectional view taken along a line A-B and a line C-D in FIG. 5(A). This light-emitting apparatus includes a driver circuit portion (a source side driver circuit) 601, a pixel portion 602, and a driver circuit portion (a gate side driver circuit) 603, which are indicated by dotted lines, as components controlling light emission from a light-emitting device. Furthermore, 604 denotes a sealing substrate, 625 denotes a desiccant, 605 denotes a sealant, and a portion surrounded by the sealant 605 is a space 607.

Note that a lead wiring 608 is a wiring for transmitting signals to be input to the source side driver circuit 601 and the gate side driver circuit 603 and receives a video signal, a clock signal, a start signal, a reset signal, and the like from an FPC (flexible printed circuit) 609 serving as an external input terminal. Although only the FPC is illustrated here, a printed wiring board (PWB) may be attached to the FPC. The light-emitting apparatus in this specification includes not only the light-emitting apparatus itself but also the light-emitting apparatus provided with the FPC or the PWB.

Next, a cross-sectional structure of the above light-emitting apparatus is described with reference to FIG. 5(B). The driver circuit portion and the pixel portion are formed over an element substrate 610; here, the source side driver circuit 601, which is the driver circuit portion, and one pixel in the pixel portion 602 are illustrated.

Note that in the source side driver circuit 601, a CMOS circuit in which an n-channel TFT 623 and a p-channel TFT 624 are combined is formed. The driver circuit may be formed of various CMOS circuits, PMOS circuits, or NMOS circuits. Although a driver-integrated type where the driver circuit is formed over the substrate is described in this embodiment, the driver circuit is not necessarily integrated and can be formed not over the substrate but outside the substrate.

The pixel portion 602 is formed of pixels including a switching TFT 611, a current controlling TFT 612, and a first electrode 613 electrically connected to a drain thereof. Note that an insulator 614 is formed to cover an end portion of the first electrode 613. The insulator 614 can be formed using a positive photosensitive resin film.

In order to improve the coverage with a film formed over the insulator 614, the insulator 614 is formed to have a surface with curvature at its upper end portion or lower end portion. For example, in the case where a photosensitive acrylic is used as a material of the insulator 614, only the upper end portion of the insulator 614 preferably has a curved surface. The radius of curvature of the curved surface is preferably greater than or equal to 0.2 μm and less than or equal to 0.3 μm. Either a negative photosensitive material or a positive photosensitive material can be used as the insulator 614.

An EL layer 616 and a second electrode 617 are formed over the first electrode 613. Here, as a material used for the first electrode 613 functioning as an anode, a material with a high work function is desirably used. For example, a single-layer film of an ITO film, an indium tin oxide film containing silicon, an indium oxide film containing zinc oxide at 2 wt % or higher and 20 wt % or lower, a titanium nitride film, a chromium film, a tungsten film, a Zn film, a Pt film, or the like, a stacked layer of titanium nitride and a film containing aluminum as its main component, a three-layer structure of a titanium nitride film, a film containing aluminum as its main component, and a titanium nitride film, or the like can be used. Note that the stacked-layer structure achieves low wiring resistance, a favorable ohmic contact, and a function as an anode.

The EL layer 616 is formed by any of a variety of methods such as an evaporation method using an evaporation mask, an inkjet method, and a spin coating method. A material included in the EL layer 616 may be a low molecular compound or a high molecular compound (including an oligomer or a dendrimer).

As a material used for the second electrode 617, which is formed over the EL layer 616 and functions as a cathode, a material with a low work function (e.g., Al, Mg, Li, Ca, or an alloy or a compound thereof (e.g., MgAg, MgIn, or AlLi)) is preferably used. Note that in the case where light generated in the EL layer 616 passes through the second electrode 617, a stacked layer of a thin metal film with a reduced thickness and a transparent conductive film (e.g., ITO, indium oxide containing zinc oxide at 2 wt % or higher and 20 wt % or lower, indium tin oxide containing silicon, or zinc oxide (ZnO)) is preferably used for the second electrode 617.

Note that the first electrode 613, the EL layer 616, and the second electrode 617 constitute a light-emitting device 618. The light-emitting device 618 is preferably the light-emitting device having the structure described in Embodiment 1 and Embodiment 2. In the light-emitting apparatus of this embodiment, the pixel portion, which includes a plurality of light-emitting devices, may include both the light-emitting device with the structure described in Embodiment 1 and Embodiment 2 and a light-emitting device with another structure.

The sealing substrate 604 and the element substrate 610 are attached to each other using the sealant 605, so that a structure in which a light-emitting device 618 is provided in the space 607 surrounded by the element substrate 610, the sealing substrate 604, and the sealant 605 is employed. Note that the space 607 is filled with a filler; as the filler, an inert gas (such as nitrogen or argon) or one or both of resin and desiccant is used in some cases.

Note that an epoxy-based resin or glass frit is preferably used for the sealant 605. Furthermore, these materials are preferably materials that transmit moisture or oxygen as little as possible. As the sealing substrate 604, in addition to a glass substrate and a quartz substrate, a plastic substrate formed of FRP (Fiber Reinforced Plastics), PVF (polyvinyl fluoride), polyester, acrylic, or the like can be used.

As described above, the light-emitting apparatus using the light-emitting device described in Embodiment 1 and Embodiment 2 can be obtained.

<Structure Example 1 of Light-Emitting Apparatus>

As an example of a display device, FIG. 6 shows a light-emitting apparatus including a light-emitting device exhibiting white light emission and a coloring layer (a color filter).

Figure 6A:
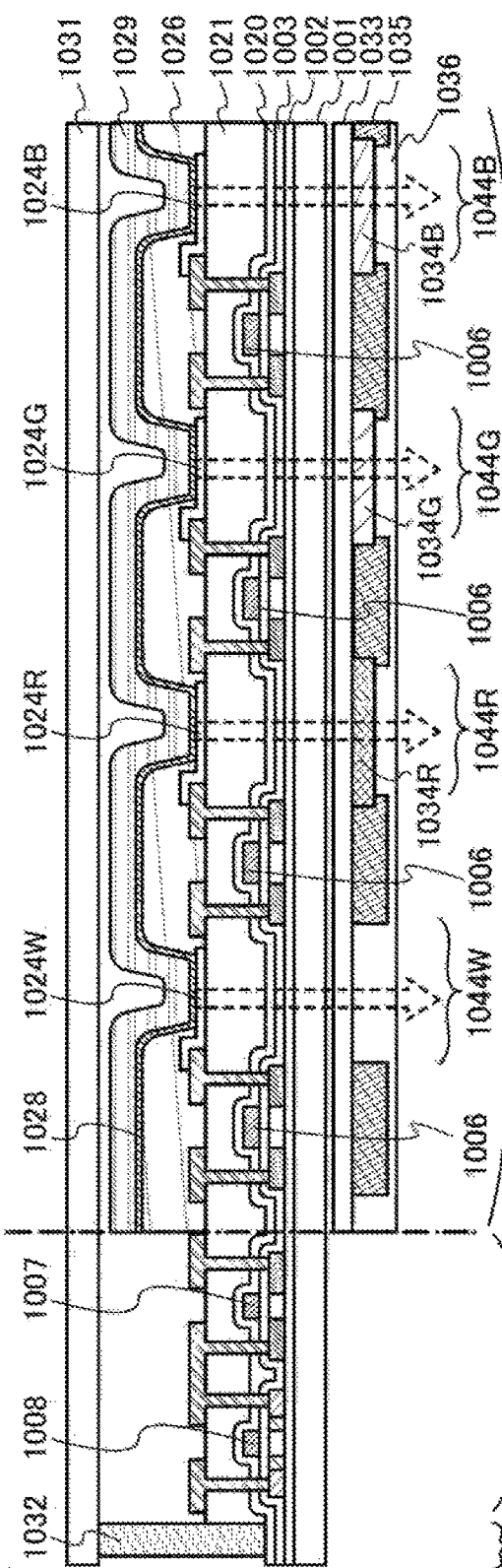
FIGS. 6A-6B are schematic cross-sectional views each illustrating a display device of one embodiment of the present invention.

FIG. 6(A) illustrates a substrate 1001, a base insulating film 1002, a gate insulating film 1003, gate electrodes 1006, 1007, and 1008, a first interlayer insulating film 1020, a second interlayer insulating film 1021, a peripheral portion 1042, a pixel portion 1040, a driver circuit portion 1041, first electrodes 1024W, 1024R, 1024G, and 1024B of light-emitting devices, a partition wall 1026, an EL layer 1028, a second electrode 1029 of the light-emitting devices, a sealing substrate 1031, a sealant 1032, a red pixel 1044R, a green pixel 1044G, a blue pixel 1044B, a white pixel 1044W, and the like.

Figure 6B:
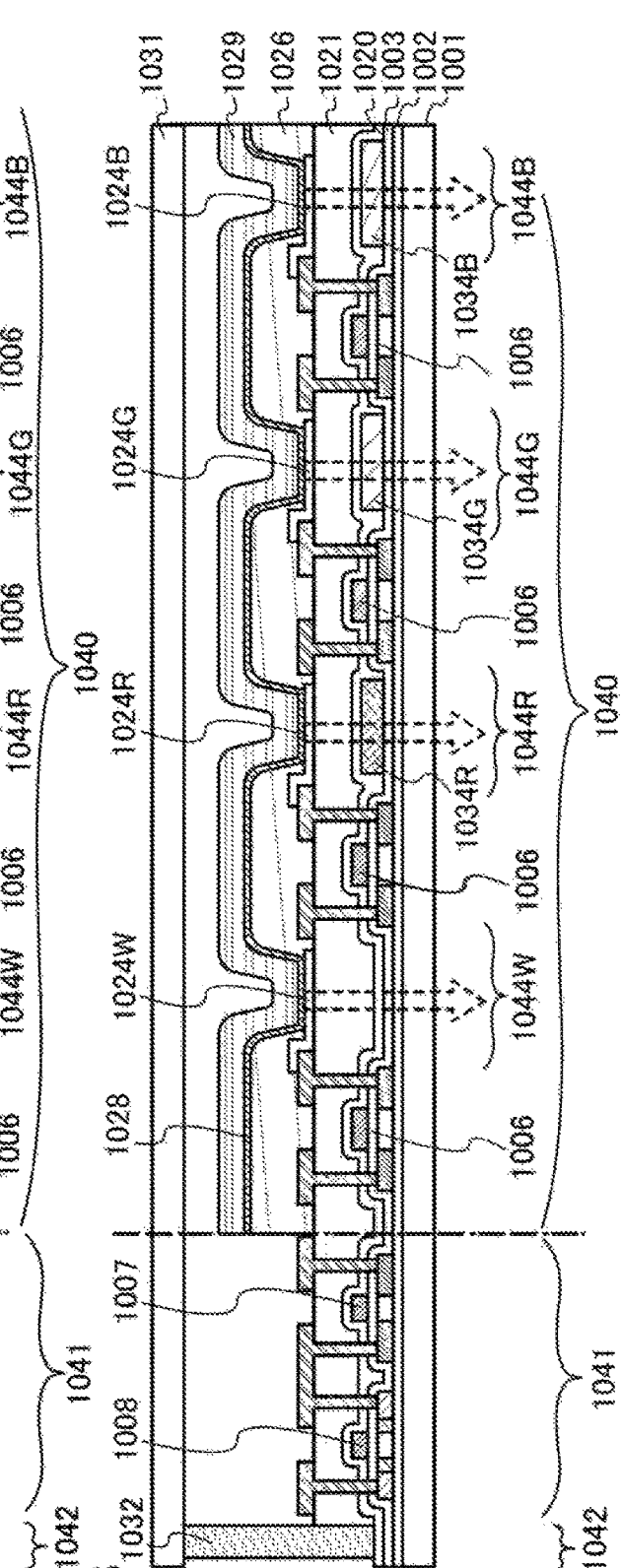

In FIG. 6(A) and FIG. 6(B), coloring layers (a red coloring layer 1034R, a green coloring layer 1034G, and a blue coloring layer 1034B) are provided on a transparent base material 1033. A black layer (black matrix) 1035 may be additionally provided. The transparent base material 1033 provided with the coloring layers and the black layer is positioned and fixed to the substrate 1001. Note that the coloring layers and the black layer are covered with an overcoat layer 1036. In FIG. 6(A), there is light extracted to the outside without passing through the coloring layers and light extracted to the outside after passing through the coloring layers of each color. The light that does not pass through the coloring layers is white, and the light that passes through the coloring layers is red, green, and blue, so that an image can be expressed with the pixels of four colors.

FIG. 6(B) shows an example in which the red coloring layer 1034R, the green coloring layer 1034G, and the blue coloring layer 1034B are formed between the gate insulating film 1003 and the first interlayer insulating film 1020. As shown in FIG. 6(B), the coloring layers may be provided between the substrate 1001 and the sealing substrate 1031.

The above-described light-emitting apparatus is a light-emitting apparatus having a structure in which light is extracted from the substrate 1001 side where the TFTs are formed (a bottom emission structure), but may be a light-emitting apparatus having a structure in which light is extracted from the sealing substrate 1031 side (a top emission structure).

<Structure Example 2 of Light-Emitting Apparatus>

Figures 7A, 7B:
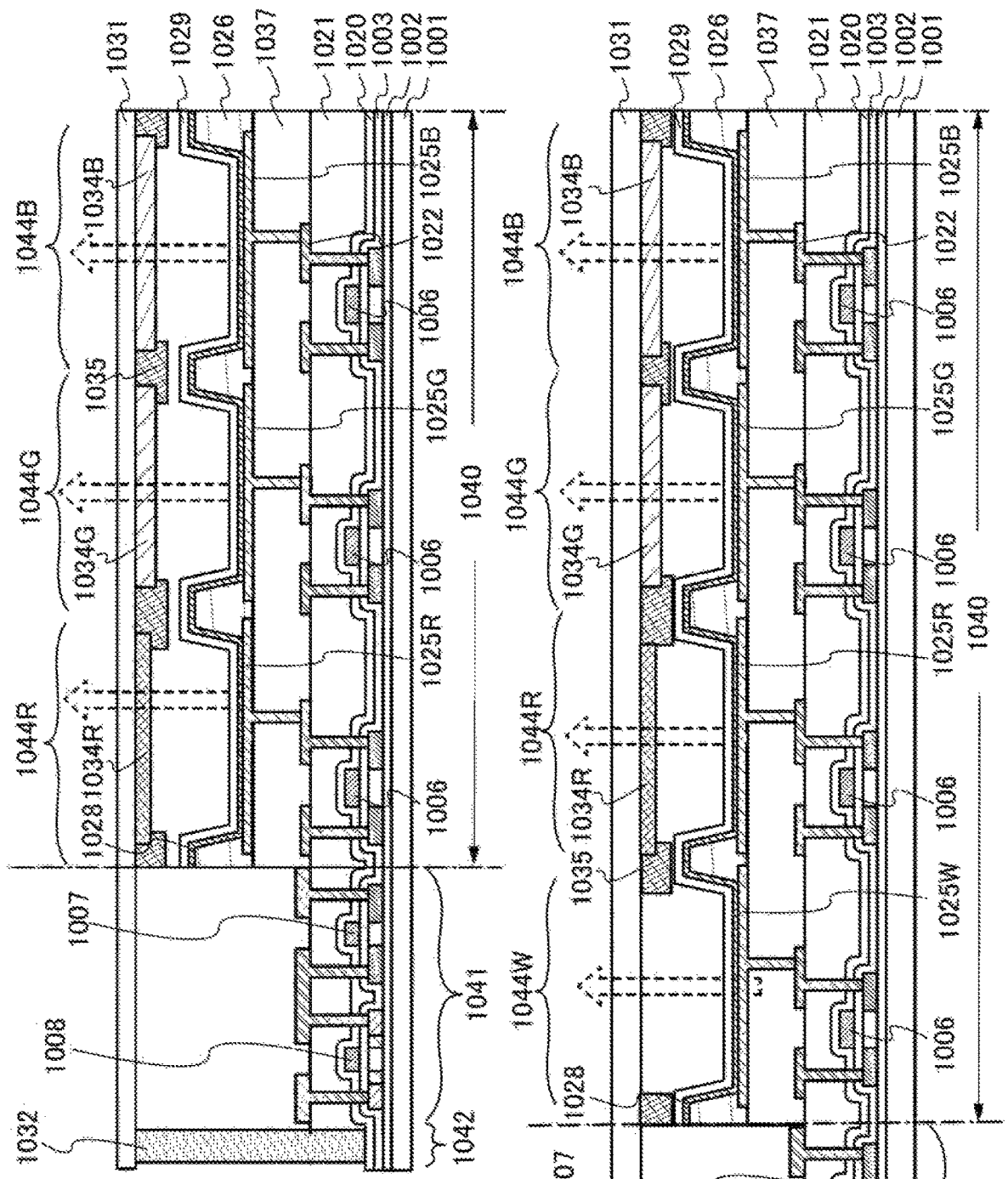
FIGS. 7A-7B are schematic cross-sectional views each illustrating a display device of one embodiment of the present invention.

FIGS. 7(A) and 7(B) shows a cross-sectional view of a top-emission light-emitting apparatus. In this case, a substrate that does not transmit light can be used as the substrate 1001. The process up to the formation of a connection electrode that connects the TFT and the anode of the light-emitting device is performed in a manner similar to that of a bottom-emission-type light-emitting apparatus. Then, a third interlayer insulating film 1037 is formed to cover an electrode 1022. This insulating film may have a planarization function. The third interlayer insulating film 1037 can be formed using a material similar to that of the second interlayer insulating film 1021 or using other various materials.

A lower electrode 1025W, a lower electrode 1025R, a lower electrode 1025G, and a lower electrode 1025B of the light-emitting device are anodes here, but may be cathodes. Furthermore, in the case of the top-emission light-emitting apparatus as illustrated in FIGS. 7(A) and 7(B), the lower electrode 1025W, the lower electrode 1025R, the lower electrode 1025G, and the lower electrode 1025B are preferably reflective electrodes. Note that the second electrode 1029 preferably has a function of reflecting light and a function of transmitting light. It is preferable that a microcavity structure be used between the second electrode 1029, and the lower electrode 1025W, the lower electrode 1025R, the lower electrode 1025G, and the lower electrode 1025B, in which case light with a specific wavelength is amplified. The EL layer 1028 has an device structure similar to the structures described in Embodiment 1 and Embodiment 2, with which white light emission can be obtained.

In FIG. 6(A), FIG. 6(B), and FIGS. 7(A) and 7(B), the structure of the EL layer for providing white light emission can be achieved by, for example, using a plurality of light-emitting layers or using a plurality of light-emitting units. Note that the structure for providing white light emission is not limited thereto.

In a top emission structure as shown in FIGS. 7(A) and 7(B), sealing can be performed with the sealing substrate 1031 on which the coloring layers (the red coloring layer 1034R, the green coloring layer 1034G, and the blue coloring layer 1034B) are provided. The sealing substrate 1031 may be provided with the black layer (black matrix) 1035 which is positioned between pixels. The coloring layers (the red coloring layer 1034R, the green coloring layer 1034G, and the blue coloring layer 1034B) and the black layer (black matrix) may be covered with the overcoat layer. Note that a substrate having a light-transmitting property is used as the sealing substrate 1031.

FIG. 7(A) illustrates a structure in which full color display is performed using three colors of red, green, and blue; alternatively, full color display may be performed using four colors of red, green, blue, and white as illustrated in FIG. 7(B). Note that the structure for performing full color display is not limited to them. For example, full color display using four colors of red, green, blue, and yellow may be performed.

In the light-emitting device of one embodiment of the present invention, a fluorescent material is used as a guest material. Since a fluorescent material has a sharper spectrum than a phosphorescent material, light emission with high color purity can be obtained. Accordingly, when the light-emitting device is used for the light-emitting apparatus described in this embodiment, a light-emitting apparatus with high color reproducibility can be obtained.

As described above, the light-emitting apparatus using the light-emitting device described in Embodiment 1 and Embodiment 2 can be obtained.

Note that this embodiment can be combined as appropriate with any of the other embodiments.

Embodiment 4

In this embodiment, electronic devices and display devices of embodiments of the present invention will be described.

In addition, an electronic device and a display device that have a flat surface, high emission efficiency, and high reliability can be manufactured according to one embodiment of the present invention. In addition, an electronic device and a display device that have a curved surface, high emission efficiency, and high reliability can be manufactured according to one embodiment of the present invention. Light with high color purity can be obtained from the light-emitting device of one embodiment of the present invention. Accordingly, with the use of the light-emitting device in the light-emitting apparatus described in this embodiment, an electronic device and a display device having high color reproducibility can be obtained.

Examples of the electronic devices include a television device, a desktop or laptop personal computer, a monitor of a computer or the like, a digital camera, a digital video camera, a digital photo frame, a mobile phone, a portable game machine, a portable information terminal, an audio reproducing device, and a large game machine such as a pachinko machine.

Figure 8A:
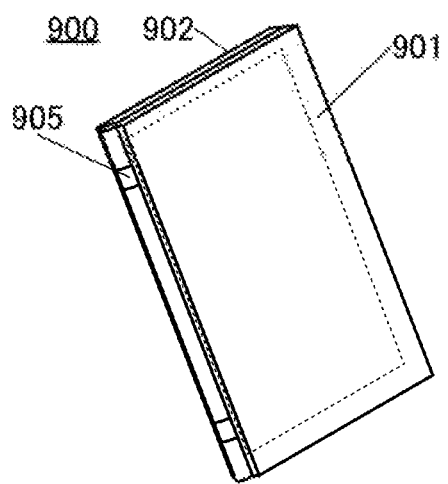
FIGS. 8A-8D are diagrams each illustrating an electronic device of one embodiment of the present invention.
Figure 8B:
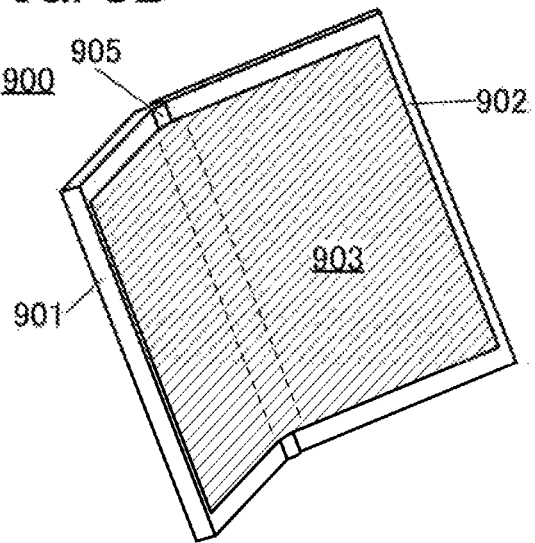

A portable information terminal 900 illustrated in FIGS. 8(A) and 8(B) includes a housing 901, a housing 902, a display portion 903, a hinge portion 905, and the like.

The housing 901 and the housing 902 are joined together by the hinge portion 905. The portable information terminal 900 can be opened as illustrated in FIG. 8(B) from a folded state (FIG. 8(A)). Thus, the portable information terminal 900 has high portability when carried and excellent visibility with its large display region when used.

In the portable information terminal 900, the flexible display portion 903 is provided across the housing 901 and the housing 902 which are joined together by the hinge portion 905.

The light-emitting apparatus manufactured using one embodiment of the present invention can be used for the display portion 903. Thus, a highly reliable portable information terminal can be manufactured.

The display portion 903 can display at least one of text information, a still image, a moving image, and the like. When text information is displayed on the display portion, the portable information terminal 900 can be used as an e-book reader.

When the portable information terminal 900 is opened, the display portion 903 is held in a state with a large radius of curvature. For example, the display portion 903 is held while including a curved portion with a radius of curvature of greater than or equal to 1 mm and less than or equal to 50 mm, preferably greater than or equal to 5 mm and less than or equal to 30 mm. Part of the display portion 903 can display an image while being curved since pixels are continuously arranged from the housing 901 to the housing 902.

The display portion 903 functions as a touch panel and can be controlled with a finger, a stylus, or the like.

The display portion 903 is preferably formed using one flexible display. Thus, a seamless continuous image can be displayed between the housing 901 and the housing 902. Note that each of the housing 901 and the housing 902 may be provided with a display.

The hinge portion 905 preferably includes a locking mechanism so that an angle formed between the housing 901 and the housing 902 does not become larger than a predetermined angle when the portable information terminal 900 is opened. For example, an angle at which they become locked (they are not opened any further) is preferably greater than or equal to 90° and less than 180° and can be typically 90°, 120°, 135°, 150°, 175°, or the like. In this way, the convenience, safety, and reliability of the portable information terminal 900 can be improved.

When the hinge portion 905 includes a locking mechanism, excessive force is not applied to the display portion 903; thus, breakage of the display portion 903 can be prevented. Therefore, a highly reliable portable information terminal can be achieved.

The housing 901 and the housing 902 may be provided with a power button, an operation button, an external connection port, a speaker, a microphone, or the like.

One of the housing 901 and the housing 902 is provided with a wireless communication module, and data can be transmitted and received through a computer network such as the Internet, a LAN (Local Area Network), or Wi-Fi (registered trademark).

Figure 8C:
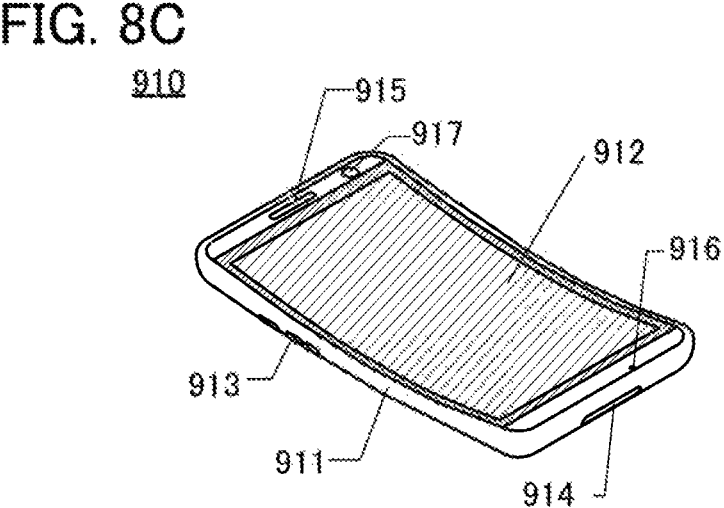

A portable information terminal 910 illustrated in FIG. 8(C) includes a housing 911, a display portion 912, an operation button 913, an external connection port 914, a speaker 915, a microphone 916, a camera 917, and the like.

The light-emitting apparatus fabricated using one embodiment of the present invention can be used for the display portion 912. Thus, the portable information terminal can be fabricated with a high yield.

The portable information terminal 910 includes a touch sensor in the display portion 912. A variety of operations such as making a call and inputting a character can be performed by touch on the display portion 912 with a finger, a stylus, or the like.

In addition, the operation of the operation button 913 can switch the power ON and OFF operations and types of images displayed on the display portion 912. For example, switching from a mail creation screen to a main menu screen can be performed.

When a sensing device such as a gyroscope sensor or an acceleration sensor is provided inside the portable information terminal 910, the direction of display on the screen of the display portion 912 can be automatically switched by determining the orientation (horizontal or vertical) of the portable information terminal 910. Furthermore, the direction of display on the screen can be switched by touch on the display portion 912, operation of the operation button 913, sound input using the microphone 916, or the like.

The portable information terminal 910 has, for example, one or more functions selected from a telephone set, a notebook, an information browsing system, and the like. Specifically, the portable information terminal can be used as a smartphone. The portable information terminal 910 is capable of executing a variety of applications such as mobile phone calls, e-mailing, text viewing and writing, music replay, video replay, Internet communication, and games, for example.

Figure 8D:
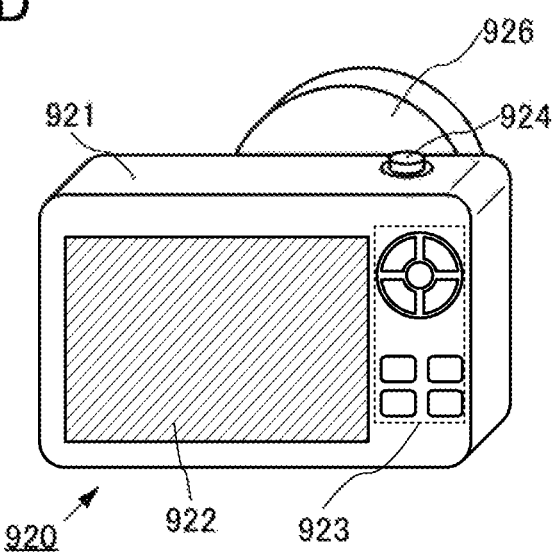

A camera 920 illustrated in FIG. 8(D) includes a housing 921, a display portion 922, operation buttons 923, a shutter button 924, and the like. Furthermore, a detachable lens 926 is attached to the camera 920.

The light-emitting apparatus fabricated using one embodiment of the present invention can be used for the display portion 922. Thus, a highly reliable camera can be fabricated.

Although the camera 920 here is configured such that the lens 926 is detachable from the housing 921 for replacement, the lens 926 may be integrated with the housing 921.

A still image or a moving image can be taken with the camera 920 at the press of the shutter button 924. In addition, the display portion 922 has a function of a touch panel, and images can also be taken by the touch on the display portion 922.

Note that a stroboscope, a viewfinder, or the like can be additionally attached to the camera 920. Alternatively, these may be incorporated into the housing 921.

Figure 9A:
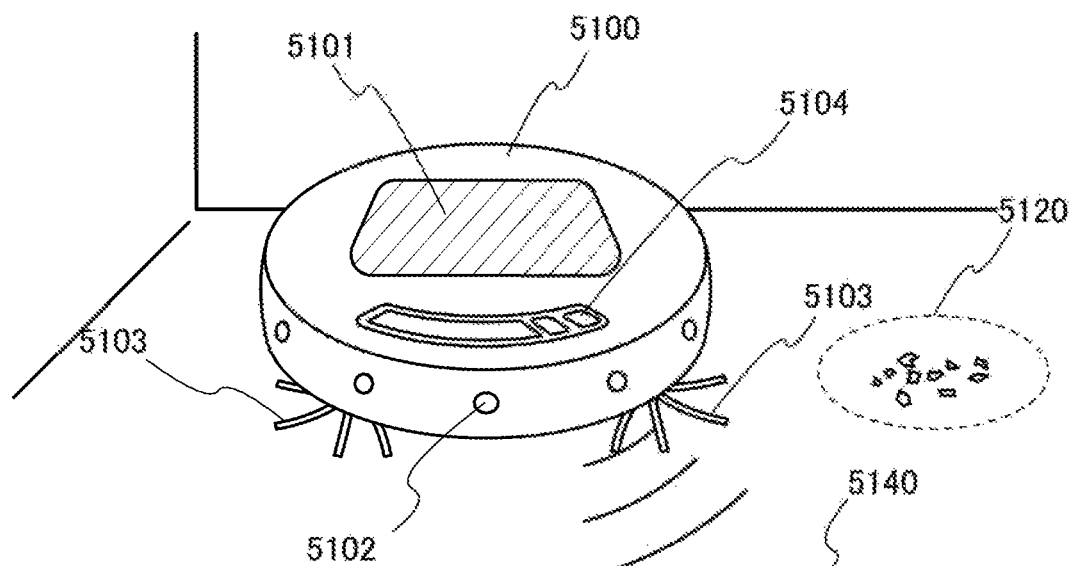
FIGS. 9A-9C are diagrams each illustrating an electronic device of one embodiment of the present invention.

FIG. 9(A) is a schematic view showing an example of a cleaning robot.

A cleaning robot 5100 includes a display 5101 placed on its top surface, a plurality of cameras 5102 placed on its side surface, a brush 5103, and an operation button 5104. Although not illustrated, the bottom surface of the cleaning robot 5100 is provided with a tire, an inlet, and the like. Furthermore, the cleaning robot 5100 includes various sensors such as an infrared sensor, an ultrasonic sensor, an acceleration sensor, a piezoelectric sensor, an optical sensor, and a gyroscope sensor. In addition, the cleaning robot 5100 has a wireless communication means.

The cleaning robot 5100 is self-propelled, detects dust 5120, and can suck up the dust through the inlet provided on the bottom surface.

The cleaning robot 5100 can determine whether there is an obstacle such as a wall, furniture, or a step by analyzing images taken by the cameras 5102. When an object that is likely to be caught in the brush 5103, such as a wire, is detected by image analysis, the rotation of the brush 5103 can be stopped.

The display 5101 can display the remaining capacity of a battery, the amount of vacuumed dust, and the like. The display 5101 may display the path on which the cleaning robot 5100 has run. The display 5101 may be a touch panel, and the operation button 5104 may be provided on the display 5101.

The cleaning robot 5100 can communicate with a portable electronic apparatus 5140 such as a smartphone. The portable electronic apparatus 5140 can display images taken by the cameras 5102. Accordingly, an owner of the cleaning robot 5100 can monitor the room even from the outside. The display on the display 5101 can be checked by the portable electronic device such as a smartphone.

The light-emitting apparatus of one embodiment of the present invention can be used for the display 5101.

Figure 9B:
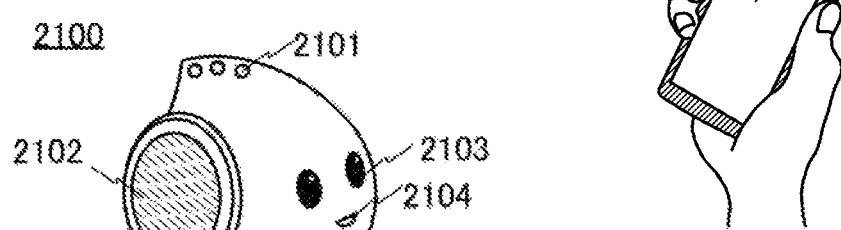

A robot 2100 illustrated in FIG. 9(B) includes an arithmetic device 2110, an illuminance sensor 2101, a microphone 2102, an upper camera 2103, a speaker 2104, a display 2105, a lower camera 2106, an obstacle sensor 2107, and a moving mechanism 2108.

The microphone 2102 has a function of detecting a speaking voice of a user, an environmental sound, and the like. The speaker 2104 has a function of outputting sound. The robot 2100 can communicate with a user using the microphone 2102 and the speaker 2104.

The display 2105 has a function of displaying various kinds of information. The robot 2100 can display information desired by a user on the display 2105. The display 2105 may be provided with a touch panel. Moreover, the display 2105 may be a detachable information terminal, in which case charging and data communication can be performed when the display 2105 is set at the home position of the robot 2100.

The upper camera 2103 and the lower camera 2106 each have a function of taking an image of the surroundings of the robot 2100. The obstacle sensor 2107 can detect the presence of an obstacle in the direction where the robot 2100 advances with the moving mechanism 2108. The robot 2100 can move safely by recognizing the surroundings with the upper camera 2103, the lower camera 2106, and the obstacle sensor 2107.

The light-emitting apparatus of one embodiment of the present invention can be used for the display 2105.

Figure 9C:
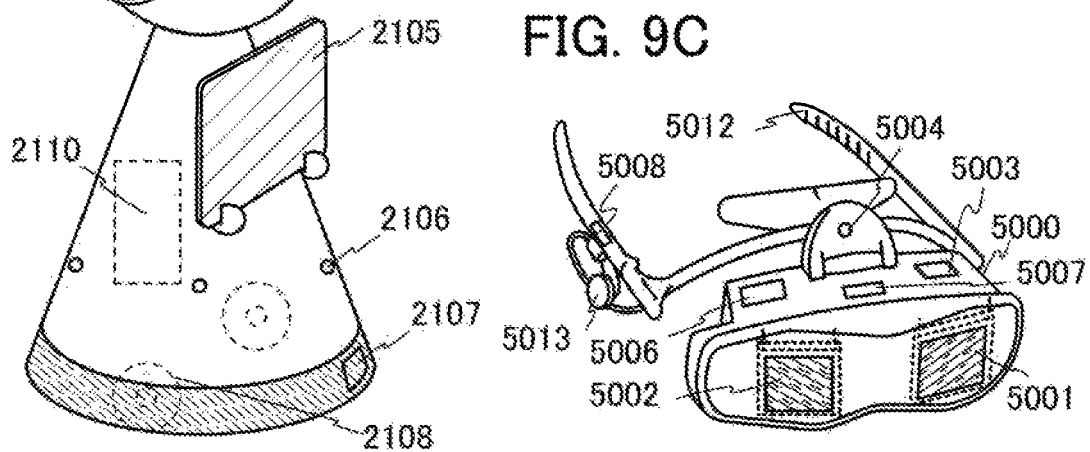

FIG. 9(C) illustrates an example of a goggle-type display. The goggle-type display includes, for example, a housing 5000, a display portion 5001, a speaker 5003, an LED lamp 5004, a connection terminal 5006, a sensor 5007 (a sensor having a function of measuring force, displacement, position, speed, acceleration, angular velocity, rotational frequency, distance, light, liquid, magnetism, temperature, chemical substance, sound, time, hardness, electric field, current, voltage, power, radiation, flow rate, humidity, gradient, oscillation, odor, or infrared ray), a microphone 5008, a second display portion 5002, a support 5012, and an earphone 5013.

The light-emitting apparatus of one embodiment of the present invention can be used for the display portion 5001 and the second display portion 5002.

Figure 10A:
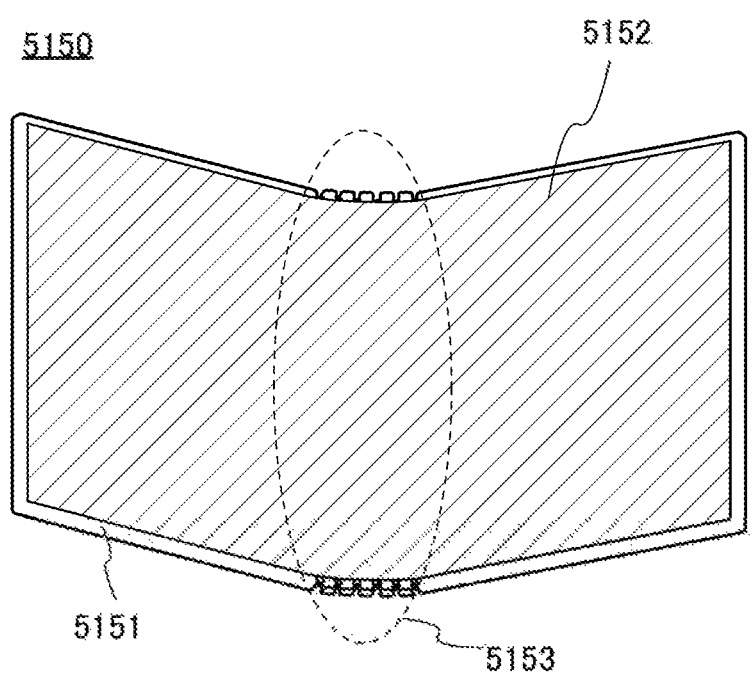
FIGS. 10A-10B are diagrams illustrating an electronic device of one embodiment of the present invention.
Figure 10B:
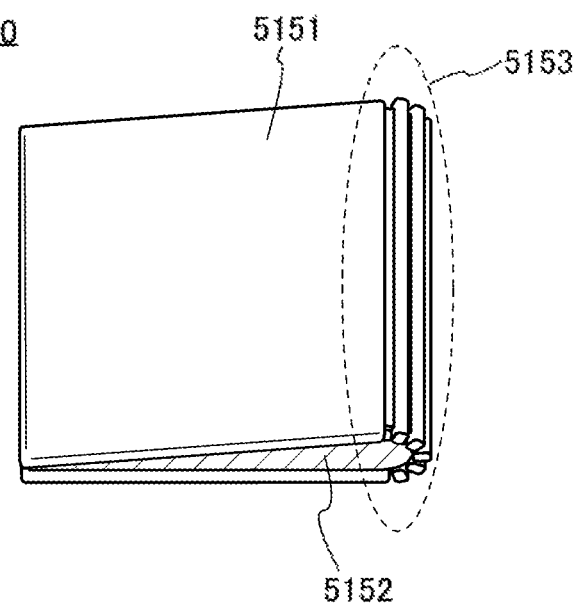

FIGS. 10(A) and 10(B) illustrate a foldable portable information terminal 5150. The foldable portable information terminal 5150 includes a housing 5151, a display region 5152, and a bend portion 5153. FIG. 10(A) illustrates the portable information terminal 5150 that is opened. FIG. 10(B) illustrates the portable information terminal 5150 that is folded. Despite its large display region 5152, the portable information terminal 5150 is compact in size and has excellent portability when folded.

The display region 5152 can be folded in half with the bend portion 5153. The bend portion 5153 is formed of a stretchable member and a plurality of supporting members. In the case where the display region is folded, the stretchable member stretches and the bend portion 5153 has a radius of curvature of 2 mm or more, preferably 5 mm or more.

Note that the display region 5152 may be a touch panel (an input/output device) including a touch sensor (an input device). The light-emitting apparatus of one embodiment of the present invention can be used for the display region 5152.

This embodiment can be combined with the other embodiments as appropriate.

Embodiment 5

In this embodiment, examples in which the light-emitting device of one embodiment of the present invention is used for various lighting devices will be described with reference to FIG. 11. With the use of the light-emitting device of one embodiment of the present invention, a highly reliable lighting device with high emission efficiency can be fabricated.

Fabricating the light-emitting device of one embodiment of the present invention over a substrate having flexibility enables an electronic device or a lighting device that has a light-emitting region with a curved surface to be achieved.

Furthermore, a light-emitting apparatus in which the light-emitting device of one embodiment of the present invention is used can also be used for lighting for motor vehicles; for example, such lighting can be provided on a windshield, a ceiling, and the like.

Figure 11:
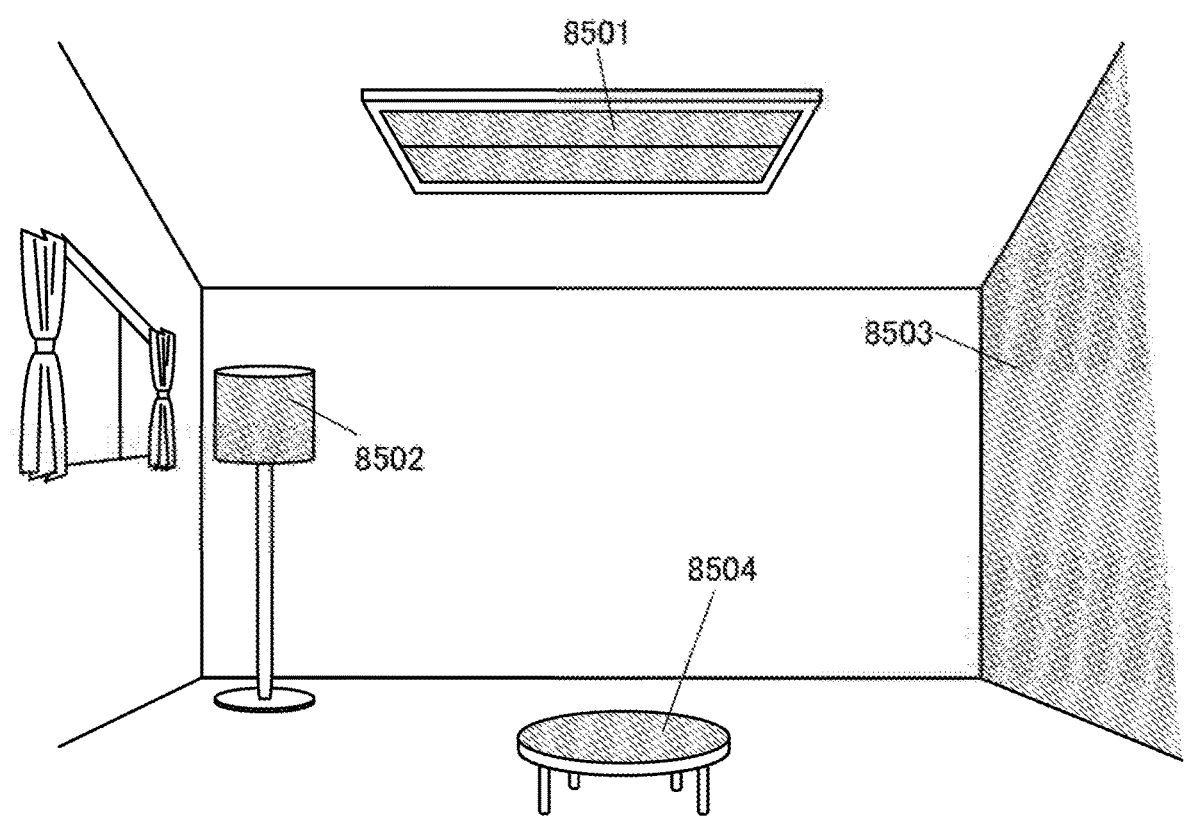
FIG. 11 is a diagram illustrating lighting devices of one embodiment of the present invention.

FIG. 11 shows an example in which the light-emitting device is used for an indoor lighting device 8501. Since the light-emitting device can have a larger area, a lighting device having a large area can also be formed. In addition, a lighting device 8502 in which a light-emitting region has a curved surface can also be formed with the use of a housing with a curved surface. A light-emitting device described in this embodiment is in the form of a thin film, which allows the housing to be designed more freely. Thus, the lighting device can be elaborately designed in a variety of ways. Furthermore, a wall of the room may be provided with a large-sized lighting device 8503. The lighting devices 8501, 8502, and 8503 may be provided with a touch sensor with which power-on or off is performed.

Moreover, when the light-emitting device is used on the surface side of a table, a lighting device 8504 which has a function of a table can be obtained. When the light-emitting device is used as part of other furniture, a lighting device having a function of the furniture can be obtained.

As described above, lighting devices and electronic devices can be obtained by application of the light-emitting apparatus of one embodiment of the present invention. Note that the light-emitting apparatus of one embodiment of the present invention can be used for lighting devices and electronic devices in a variety of fields without being limited to the lighting devices and the electronic devices described in this embodiment.

The structure described in this embodiment can be used in an appropriate combination with any of the structures described in the other embodiments.

Example 1

Described in this example are examples of fabricating a light-emitting device 2 to a light-emitting device 5 according to one embodiment of the present invention and a comparative light-emitting device 1. A schematic cross-sectional view of the light-emitting devices fabricated in this example is shown in FIG. 1(A), and details of the device structures are shown in Table 2 and Table 3. Chemical formulae of organic compounds used in this example are shown below. Note that Embodiment 1 above can be referred to for the structures and abbreviations of the other compounds.

[Chemical Formula 19]

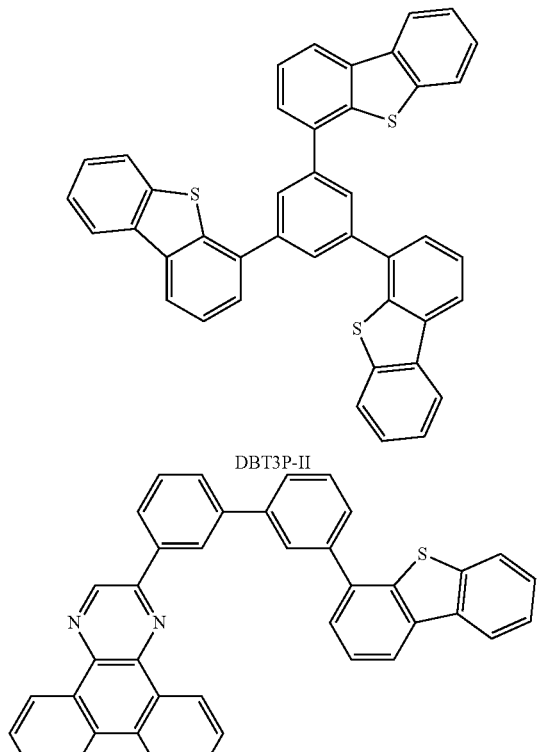

DBT3P-II

2mDBTBPDBq-II

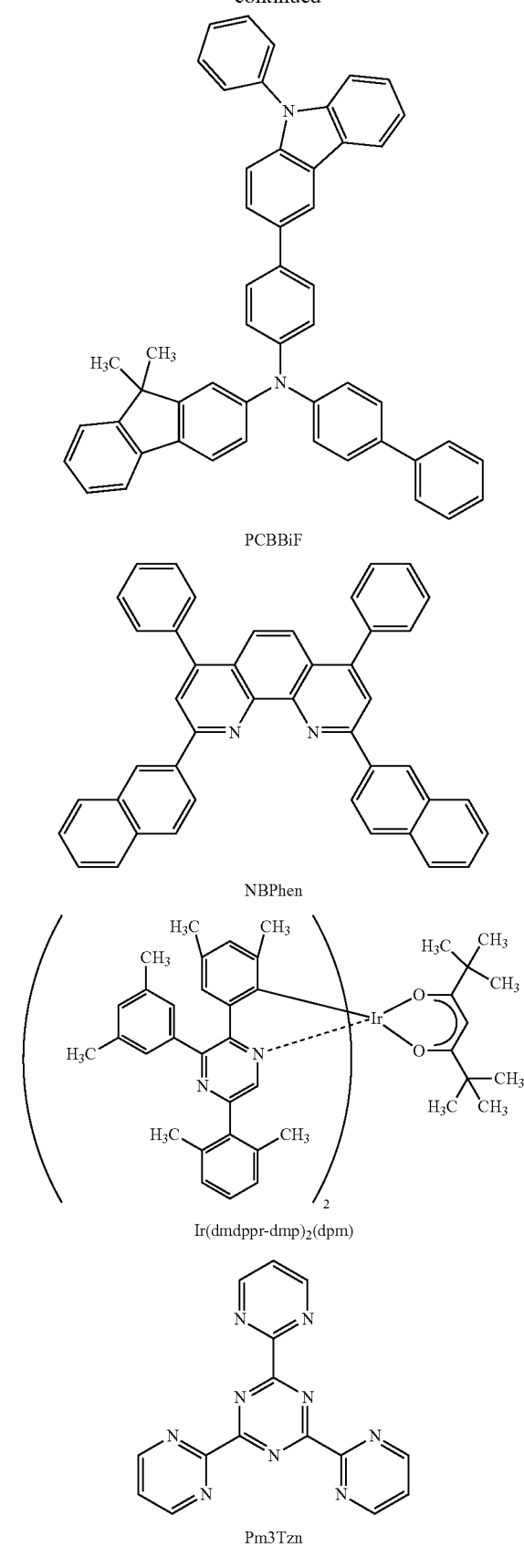

PCBBiF

NBPhen

Ir(dmdppr-dmp)₂(dpm)

Pm3Tzn

TABLE 2

| Layer | | Numeral | Thickness (nm) | Material | Weight ratio |
|---|---|---|---|---|---|
| Comparative light-emitting device 1 | Electrode | 102 | 200 | Al | — |
| | Electron-injection layer | 130 | 1 | LiF | — |
| | Electron-transport layer | 118(2) | 15 | NBPhen | — |
| | | 118(1) | 20 | 2mDBTBPDBq-II | — |
| | Light-emitting layer | 140 | 40 | 2mDBTBPDBq-II:PCBBiF: Ir(dmdppr-dmp)$_2$(dpm) | 0.75:0.25:0.08 |
| | Hole-transport layer | 112 | 20 | PCBBiF | — |
| | Hole-injection layer | 111 | 25 | DBT3P-II: MoO$_3$ | 1:0.5 |
| | Anode | 101 | 110 | ITSO | — |
| Comparative light-emitting device 2 | Electrode | 102 | 200 | Al | — |
| | Electron-injection layer | 130 | 5 | tPy2P:Ag | 1:0.3 |
| | Electron-transport layer | 118(2) | 15 | NBPhen | — |
| | | 118(1) | 20 | 2mDBTBPDBq-II | — |
| | Light-emitting layer | 140 | 40 | 2mDBTBPDBq-II:PCBBiF: Ir(dmdppr-dmp)$_2$(dpm) | 0.75:0.25:0.08 |
| | Hole-transport layer | 112 | 20 | PCBBiF | — |
| | Hole-injection layer | 111 | 25 | DBT3P-II:MoO$_3$ | 1:0.5 |
| | Anode | 101 | 110 | ITSO | — |
| Light-emitting device 3 | Electrode | 102 | 200 | Al | — |
| | Electron-injection layer | 130 | 5 | 2Py3Tzn:Cu | 1:0.3 |
| | Electron-transport layer | 118(2) | 15 | NBPhen | — |
| | | 118(1) | 20 | 2mDBTBPDBq-II | — |
| | Light-emitting layer | 140 | 40 | 2mDBTBPDBq-II:PCBBiF: Ir(dmdppr-dmp)$_2$(dpm) | 0.75:0.25:0.08 |
| | Hole-transport layer | 112 | 20 | PCBBiF | — |
| | Hole-injection layer | 111 | 25 | DBT3P-II:MoO$_3$ | 1:0.5 |
| | Anode | 101 | 110 | ITSO | — |

TABLE 3

| Layer | | Numeral | Thickness (nm) | Material | Weight ratio |
|---|---|---|---|---|---|
| Light-emitting device 4 | Electrode | 102 | 200 | Al | — |
| | Electron-injection layer | 130 | 5 | Pm3Tzn:Cu | 1:0.3 |
| | Electron-transport layer | 118(2) | 15 | NBPhen | — |
| | | 118(1) | 20 | 2mDBTBPDBq-II | — |
| | Light-emitting layer | 140 | 40 | 2mDBTBPDBq-II:PCBBiF: Ir(dmdppr-dmp)$_2$(dpm) | 0.75:0.25:0.08 |
| | Hole-transport layer | 112 | 20 | PCBBiF | — |
| | Hole-injection layer | 111 | 25 | DBT3P-II:MoO$_3$ | 1:0.5 |
| | Anode | 101 | 110 | ITSO | — |
| Light-emitting device 5 | Electrode | 102 | 200 | Al | — |
| | Electron-injection layer | 130 | 5 | tPy2P:Co | 1:0.2 |
| | Electron-transport layer | 118(2) | 15 | NBPhen | — |
| | | 118(1) | 20 | 2mDBTBPDBq-II | — |
| | Light-emitting layer | 140 | 40 | 2mDBTBPDBq-II:PCBBiF: Ir(dmdppr-dmp)$_2$(dpm) | 0.75:0.25:0.08 |
| | Hole-transport layer | 112 | 20 | PCBBiF | — |
| | Hole-injection layer | 111 | 25 | DBT3P-II:MoO$_3$ | 1:0.5 |
| | Anode | 101 | 110 | ITSO | — |

<Fabrication of Light-Emitting Devices>

Fabrication methods of the light-emitting devices in this example will be described below. The comparative light-emitting device 1 is a light-emitting device that uses LiF, which is a Li compound typically used for the electron-injection layer, and the light-emitting device 2 to the light-emitting device 5 are light-emitting devices each use for the electron-injection layer a composite material of a metal and an organic compound having a function of interacting with the metal as a tridentate or tetradentate ligand according to one embodiment of the present invention.

<<Fabrication of Comparative Light-Emitting Device 1>>

As the electrode 101, an ITSO film was formed to a thickness of 110 nm over a glass substrate. Note that the electrode area of the electrode 101 was set to 4 mm² (2 mm×2 mm).

Next, as the hole-injection layer 111, DBT3P-II and molybdenum oxide (MoO₃) were deposited over the electrode 101 by co-evaporation in a weight ratio (DBT3P-II: MoO₃) of 1:0.5 to a thickness of 25 nm.

Next, as the hole-transport layer 112, PCBBiF was deposited over the hole-injection layer 111 by evaporation to a thickness of 20 nm.

Then, as the light-emitting layer 140, 2mDBTBPDBq-II, PCBBiF, and Ir(dmdppr-dmp)₂(dpm) were deposited over the hole-transport layer 112 by co-evaporation in a weight ratio (2mDBTBPDBq-II: PCBBiF: Ir(dmdppr-dmp)₂(dpm)) of 0.75:0.25:0.08 to a thickness of 40 nm. Note that in the light-emitting layer 140, 2mDBTBPDBq-II and PCBBiF are host materials and Ir(dmdppr-dmp)₂(dpm) is a guest material (a phosphorescent compound).

Next, as an electron-transport layer 118(1), 2mDBTBPDBq-II was deposited over the light-emitting layer 140 by evaporation to a thickness of 20 nm.

Next, as an electron-transport layer 118(2), NBPhen was deposited over the electron-transport layer 118(1) by evaporation to a thickness of 15 nm.

As the electron-injection layer 130, lithium fluoride (LiF) was deposited over the electron-transport layer 118(2) by evaporation to a thickness of 1 nm.

Next, as the electrode 102, aluminum (Al) was formed over the electron-injection layer 130 to a thickness of 200 nm.

Then, heat treatment at 80° C. for one hour was performed in the air without sealing. Through the above steps, the comparative light-emitting device 1 was obtained.

<<<Fabrication of Light-Emitting Device 2 to Light-Emitting Device 5>>>

The light-emitting device 2 to the light-emitting device 5 were fabricated through steps similar to those for the comparative light-emitting device 1 except for the formation step of the electron-injection layer 130.

<Fabrication of Light-Emitting Device 2>

As the electron-injection layer 130, tPy2P and Ag were deposited over the electron-transport layer 118(2) by co-evaporation in a weight ratio (tPy2P: Ag) of 1:0.3 to a thickness of 5 nm.

<Fabrication of Light-Emitting Device 3>

As the electron-injection layer 130, 2Py3Tzn and Cu were deposited over the electron-transport layer 118(2) by co-evaporation in a weight ratio (2Py3Tzn: Cu) of 1:0.3 to a thickness of 5 nm.

<Fabrication of Light-Emitting Device 4>

As the electron-injection layer 130, Pm3Tzn and Cu were deposited over the electron-transport layer 118(2) by co-evaporation in a weight ratio (Pm3Tzn: Ag) of 1:0.3 to a thickness of 5 nm.

<Fabrication of Light-Emitting Device 5>

As the electron-injection layer 130, tPy2P and Co were deposited over the electron-transport layer 118(2) by co-evaporation in a weight ratio (tPy2P: Co) of 1:0.2 to a thickness of 5 nm.

<Characteristics of Light-Emitting Devices>

Next, the device characteristics of the fabricated comparative light-emitting device 1 and light-emitting device 2 to light-emitting device 5 were measured. Luminance and CIE chromaticity were measured with a luminance colorimeter (BM-5A manufactured by TOPCON TECHNOHOUSE CORPORATION), and electroluminescence spectra were measured with a multi-channel spectrometer (PMA-11 manufactured by Hamamatsu Photonics K.K.).

Figure 12:
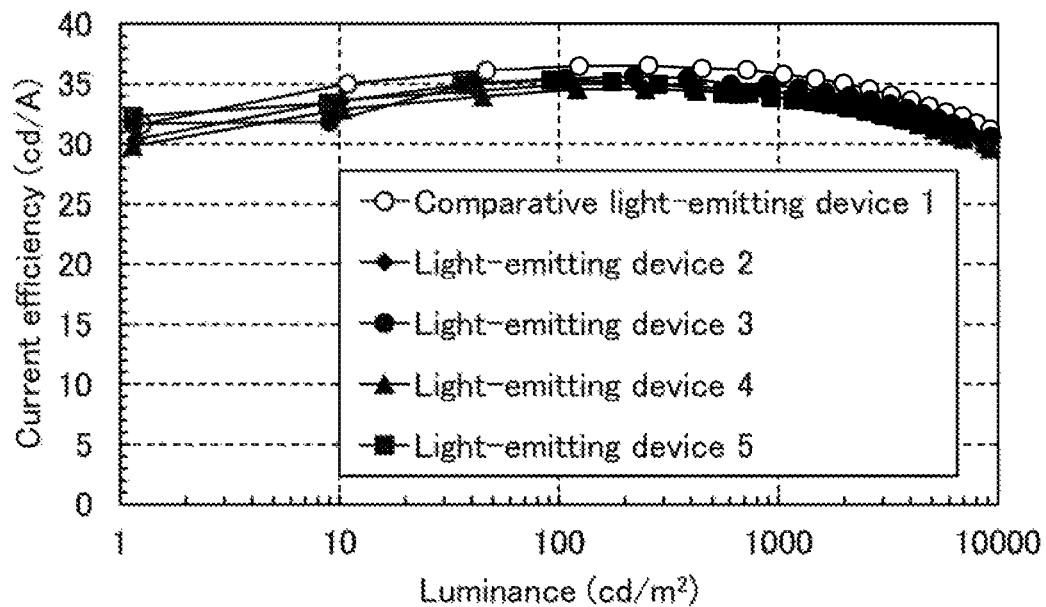
FIG. 12 is a diagram showing current efficiency-luminance characteristics of light-emitting devices in Example.
Figure 13:
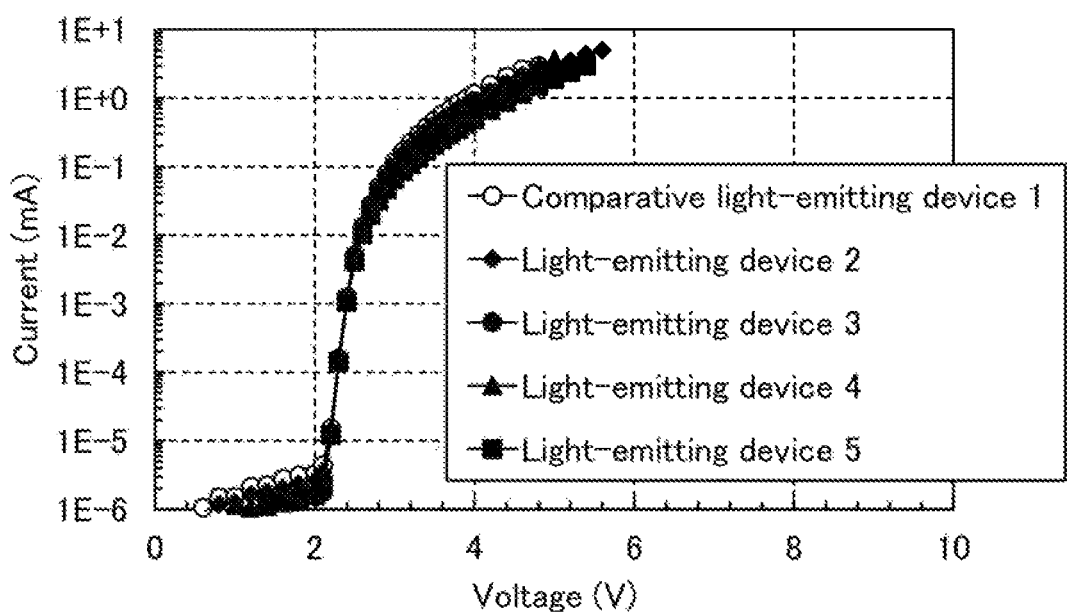
FIG. 13 is a diagram showing current-voltage characteristics of light-emitting devices in Example.
Figure 14:
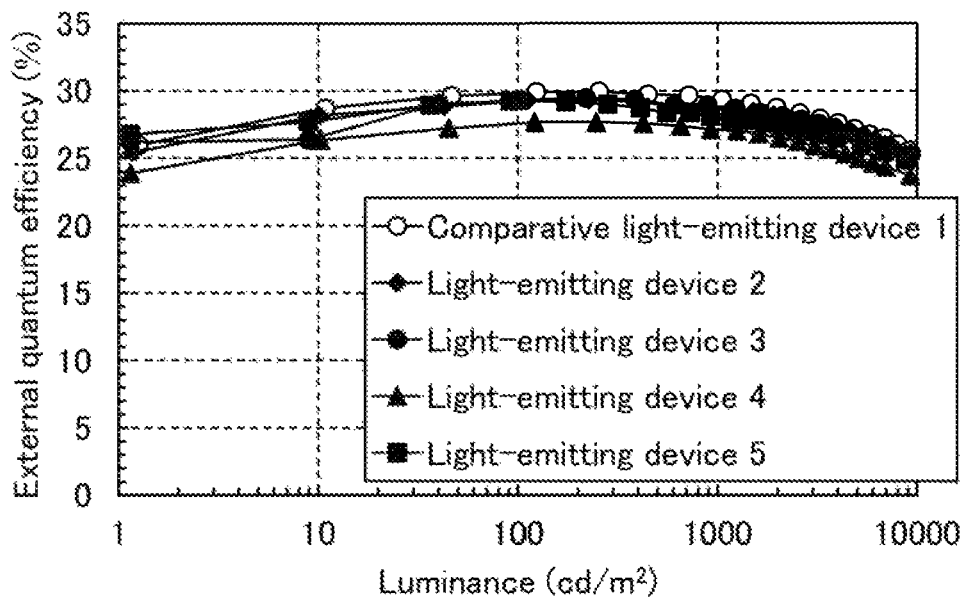
FIG. 14 is a diagram showing external quantum efficiency-luminance characteristics of light-emitting devices in Example.
Figure 15:
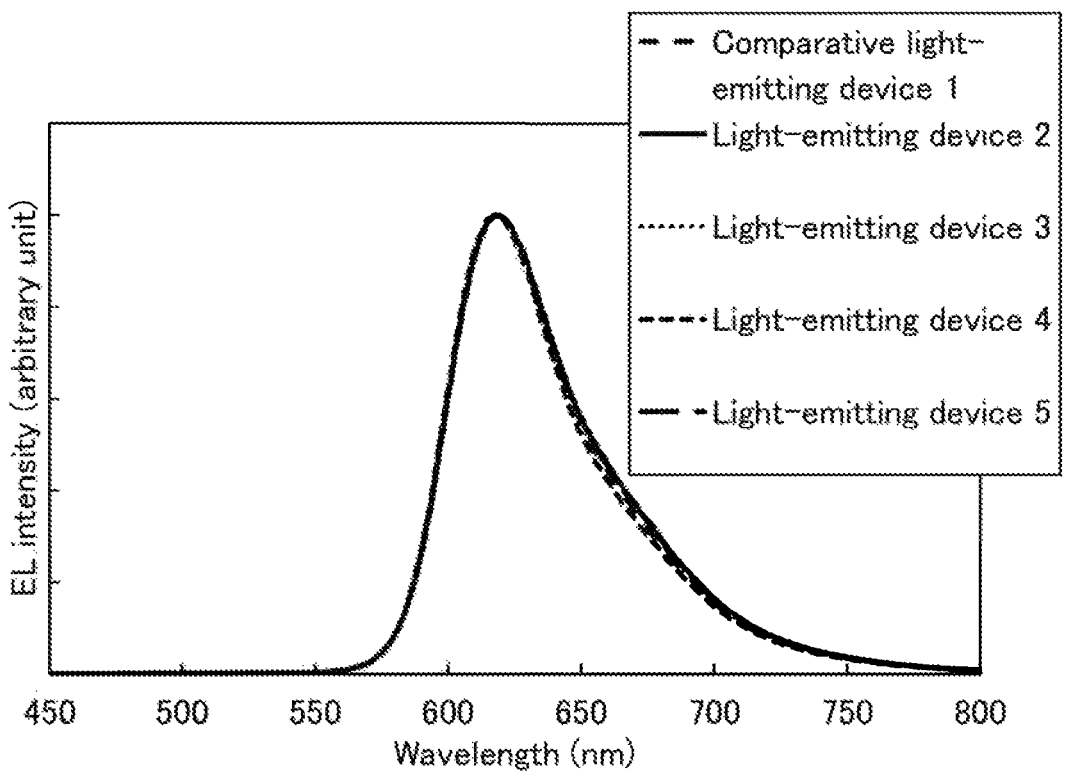
FIG. 15 is a diagram showing electroluminescence spectra of light-emitting devices in Example.

FIG. 12 shows the current efficiency-luminance characteristics of the fabricated comparative light-emitting device 1 and light-emitting device 2 to light-emitting device 5, FIG. 13 shows the current-voltage characteristics thereof, and FIG. 14 shows the external quantum efficiency-luminance characteristics thereof. Note that the measurement of the light-emitting devices was performed at room temperature (in an atmosphere maintained at 23° C.). FIG. 15 shows the electroluminescence spectra of the light-emitting devices through which current flows at a current density of 2.5 mA/cm². Note that the measurement was performed at room temperature.

Table 4 shows the device characteristics of the comparative light-emitting device 1 and the light-emitting device 2 to the light-emitting device 5 at around 1000 cd/m².

TABLE 4

|  | Voltage (V) | Current density (mA/cm²) | CIE chromaticity (x, y) | Luminance (cd/m²) | Current efficiency (cd/A) | Power efficiency (lm/W) | External quantum efficiency (%) |
|---|---|---|---|---|---|---|---|
| Comparative light-emitting device 1 | 3.00 | 2.95 | (0.665, 0.335) | 1054 | 35.8 | 37.5 | 29.3 |
| Light-emitting device 2 | 3.00 | 2.51 | (0.666, 0.334) | 862 | 34.4 | 36.0 | 28.8 |
| Light-emitting device 3 | 3.00 | 2.56 | (0.666, 0.335) | 893 | 34.9 | 36.6 | 28.9 |
| Light-emitting device 4 | 3.00 | 2.73 | (0.666, 0.334) | 924 | 33.9 | 35.5 | 27.1 |
| Light-emitting device 5 | 3.20 | 2.73 | (0.666, 0.335) | 925 | 33.9 | 33.3 | 28.1 |

As shown in FIG. 14 and Table 4, the comparative light-emitting device 1 and the light-emitting device 2 to the light-emitting device 5 each exhibited high emission efficiency with an external quantum efficiency exceeding 25%. The light-emitting device 2 to the light-emitting device 5 according to one embodiment of the present invention exhibited high efficiency equivalent to that of the comparative light-emitting device 1, which uses LiF typically used for the electron-injection layer.

As shown in FIG. 13 and Table 4, it was found that the comparative light-emitting device 1 and the light-emitting device 2 to the light-emitting device 5 exhibited favorable current-voltage characteristics. The light-emitting device 2 to the light-emitting device 5 exhibited current-voltage characteristics equivalent to those of the comparative light-emitting device 1, which shows that the composite material of a transition metal with a high work function (4.5 eV or more) such as Cu, Ag, or Co and an organic compound having a function of interacting with the metal as a tridentate or tetradentate ligand has an excellent electron-injection property equivalent to that of LiF, which is typically used for the electron-injection layer.

Furthermore, as shown in FIG. 15, the comparative light-emitting device 1 and the light-emitting device 2 to the light-emitting device 5 each exhibited red emission whose electroluminescence spectrum has a peak wavelength at approximately 619 nm and a full width at half maximum of approximately 58 nm. The obtained electroluminescence spectrum shows that the light is emitted from the guest material, Ir(dmdppr-dmp)$_2$(dpm).

<Results of Constant-Current Driving Test of Light-Emitting Devices>

Figure 16:
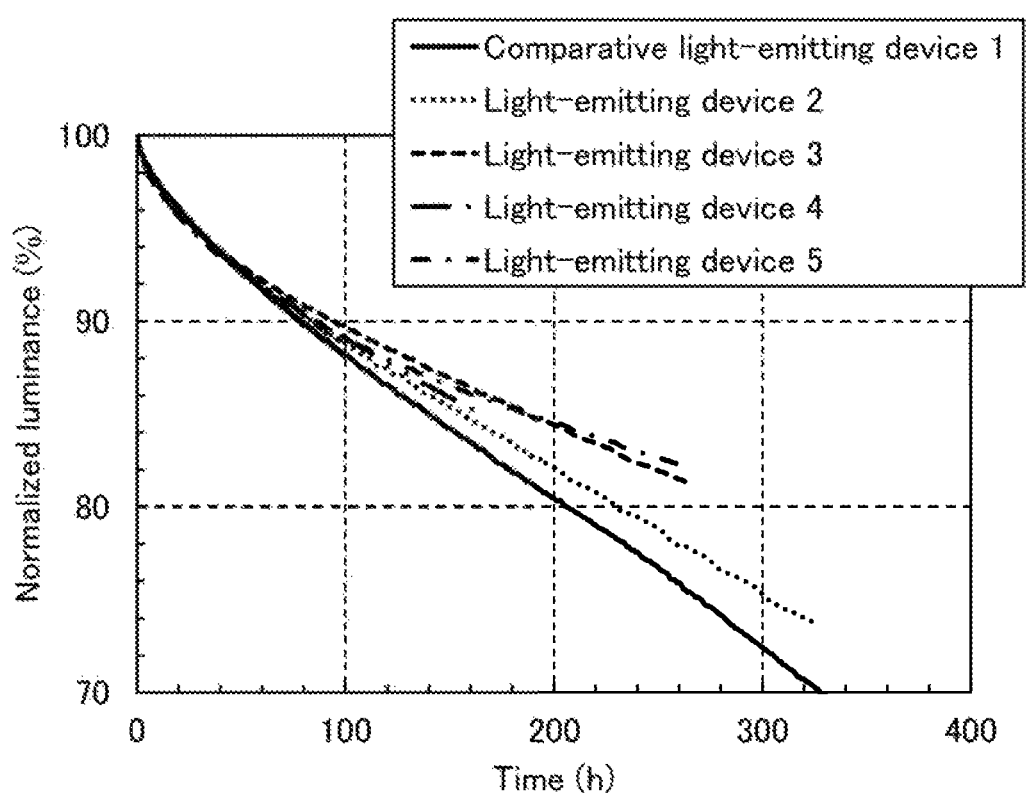
FIG. 16 is a diagram showing results of reliability tests of light-emitting devices in Example.

Next, the driving test at a constant current of 1.0 mA was performed on the comparative light-emitting device 1 and the light-emitting device 2 to the light-emitting device 5 in an air atmosphere. FIG. 16 shows the results. As described above, the comparative light-emitting device 1 and the light-emitting device 2 to the light-emitting device 5 were not sealed. As shown in FIG. 16, the light-emitting device 2 to the light-emitting device 5 were found to have more favorable reliability than the comparative light-emitting device 1 in an air atmosphere. The light-emitting device 1 uses a material including a metal with a low work function for the electron-injection layer. The metal with a low work function has high reactivity with water, and thus might allow moisture to enter the light-emitting device. Thus, in the case where the light-emitting device 1 is driven in an air atmosphere, the reliability is decreased due to the influence of moisture. In contrast, the light-emitting device of one embodiment of the present invention can use a metal that has low reactivity with water and a high work function for the electron-injection layer. Thus, moisture is less likely to enter the light-emitting device of one embodiment of the present invention, whereby the light-emitting device can have high reliability even when driven in an air atmosphere. In addition, the light-emitting device 3 to the light-emitting device 5 show high reliability. Thus, a light-emitting device having high reliability can be achieved with the use of a metal with a work function of 4.7 eV or more, such as Cu or Co.

Example 2

Described in this example are examples of fabricating a light-emitting device 7 to a light-emitting device 10 according to one embodiment of the present invention and a comparative light-emitting device 6. A schematic cross-sectional view of the light-emitting devices fabricated in this example is shown in FIG. 1(A), and details of the device structures are shown in Table 5 and Table 6. Embodiment 1 and Example 1 can be referred to for the structures and abbreviations of organic compounds used in this example.

TABLE 5

| | Layer | Numeral | Thickness (nm) | Material | Weight ratio |
|---|---|---|---|---|---|
| Comparative light-emitting device 6 | Electrode | 102 | 200 | Al | — |
| | Electron-injection layer | 130 | — | — | — |
| | Electron-transport layer | 118(2) | 15 | NBPhen | — |
| | | 118(1) | 20 | 2mDBTBPDBq-II | — |
| | Light-emitting layer | 140 | 40 | 2mDBTBPDBq-II:PCBBiF: Ir(dmdppr-dmp)$_2$(dpm) | 0.75:0.25:0.08 |
| | Hole-transport layer | 112 | 20 | PCBBiF | — |
| | Hole-injection layer | 111 | 25 | DBT3P-II:MoO$_3$ | 1:0.5 |
| | Anode | 101 | 110 | ITSO | — |
| Light-emitting device 7 | Electrode | 102 | 200 | Al | — |
| | Electron-injection layer | 130 | 5 | tPy2P:Au | 1:0.6 |
| | Electron-transport layer | 118(2) | 15 | NBPhen | — |
| | | 118(1) | 20 | 2mDBTBPDBq-II | — |
| | Light-emitting layer | 140 | 40 | 2mDBTBPDBq-II:PCBBiF: Ir(dmdppr-dmp)$_2$(dpm) | 0.75:0.25:0.08 |
| | Hole-transport layer | 112 | 20 | PCBBiF | — |
| | Hole-injection layer | 111 | 25 | DBT3P-II:MoO$_3$ | 1:0.5 |
| | Anode | 101 | 110 | ITSO | — |
| Light-emitting device 8 | Electrode | 102 | 200 | Al | — |
| | Electron-injection layer | 130 | 5 | 2Py3Tzn:Ag | 1:0.5 |
| | Electron-transport layer | 118(2) | 15 | NBPhen | — |
| | | 118(1) | 20 | 2mDBTBPDBq-II | — |
| | Light-emitting layer | 140 | 40 | 2mDBTBPDBq-II:PCBBiF: Ir(dmdppr-dmp)$_2$(dpm) | 0.75:0.25:0.08 |
| | Hole-transport layer | 112 | 20 | PCBBiF | — |
| | Hole-injection layer | 111 | 25 | DBT3P-II:MoO$_3$ | 1:0.5 |
| | Anode | 101 | 110 | ITSO | — |

TABLE 6

| Layer | | Numeral | Thickness (nm) | Material | Weight ratio |
|---|---|---|---|---|---|
| Light-emitting device 9 | Electrode | 102 | 200 | Al | — |
| | Electron-injection layer | 130 | 5 | tPy2P:Cu | 1:0.2 |
| | Electron-transport layer | 118(2) | 15 | NBPhen | — |
| | | 118(1) | 20 | 2mDBTBPDBq-II | — |
| | Light-emitting layer | 140 | 40 | 2mDBTBPDBq-II:PCBBiF: Ir(dmdppr-dmp)$_2$(dpm) | 0.75:0.25:0.08 |
| | Hole-transport layer | 112 | 20 | PCBBiF | — |
| | Hole-injection layer | 111 | 25 | DBT3P-II:MoO$_3$ | 1:0.5 |
| | Anode | 101 | 110 | ITSO | — |
| Light-emitting device 10 | Electrode | 102 | 200 | Al | — |
| | Electron-injection layer | 130 | 5 | 2Py3Tzn:Co | 1:0.3 |
| | Electron-transport layer | 118(2) | 15 | NBPhen | — |
| | | 118(1) | 20 | 2mDBTBPDBq-II | — |
| | Light-emitting layer | 140 | 40 | 2mDBTBPDBq-II:PCBBiF: Ir(dmdppr-dmp)$_2$(dpm) | 0.75:0.25:0.08 |
| | Hole-transport layer | 112 | 20 | PCBBiF | — |
| | Hole-injection layer | 111 | 25 | DBT3P-II:MoO$_3$ | 1:0.5 |
| | Anode | 101 | 110 | ITSO | — |

<Fabrication of Light-Emitting Devices>

Fabrication methods of the light-emitting devices in this example will be described below. The comparative light-emitting device 6 is alight-emitting device in which the electron-injection layer is not formed and the electrode and the electron-transport layer are in contact with each other, and the light-emitting device 7 to the light-emitting device 10 are light-emitting devices of one embodiment of the present invention in which the composite material of a metal and an organic compound having a function of interacting with the metal as a tridentate or tetradentate ligand is used for the electron-injection layer.

<Fabrication of Comparative Light-Emitting Device 6>>

The comparative light-emitting device 6 was fabricated through steps similar to those of the comparative light-emitting device 1 except for the formation step of the electron-injection layer 130.

The electron-injection layer 130 was not deposited in the comparative light-emitting device 6, and Al was deposited as the electrode 102 over the electron-transport layer 118 by evaporation to a thickness of 200 nm. In other words, the electrode 102 and the electron-transport layer 118 are in contact with each other in the comparative light-emitting device 6.

<<<Fabrication of Light-Emitting Device 7 to Light-Emitting Device 10>>

The light-emitting device 7 to the light-emitting device 10 were fabricated through steps similar to those of the comparative light-emitting device 1 except for the formation step of the electron-injection layer 130.

<Fabrication of Light-Emitting Device 7>

As the electron-injection layer 130, tPy2P and Au were deposited over the electron-transport layer 118(2) by co-evaporation in a weight ratio (tPy2P: Au) of 1:0.6 to a thickness of 5 nm.

<Fabrication of Light-Emitting Device 8>

As the electron-injection layer 130 of the light-emitting device 8, 2Py3Tzn and Ag were deposited over the electron-transport layer 118(2) by co-evaporation in a weight ratio (2Py3Tzn: Ag) of 1:0.5 to a thickness of 5 nm.

<Fabrication of Light-Emitting Device 9>

As the electron-injection layer 130 of the light-emitting device 9, tPy2P and Cu were deposited over the electron-transport layer 118(2) by co-evaporation in a weight ratio (tPy2P: Cu) of 1:0.2 to a thickness of 5 nm.

<Fabrication of Light-Emitting Device 10>

As the electron-injection layer 130 of the light-emitting device 10, 2Py3Tzn and Co were deposited over the electron-transport layer 118(2) by co-evaporation in a weight ratio (2Py3Tzn: Co) of 1:0.3 to a thickness of 5 nm.

<Characteristics of Light-Emitting Devices>

Next, the device characteristics of the fabricated comparative light-emitting device 6 and light-emitting device 7 to light-emitting device 10 were measured. The measurement was performed in a manner similar to that in Example 1.

Figure 17:
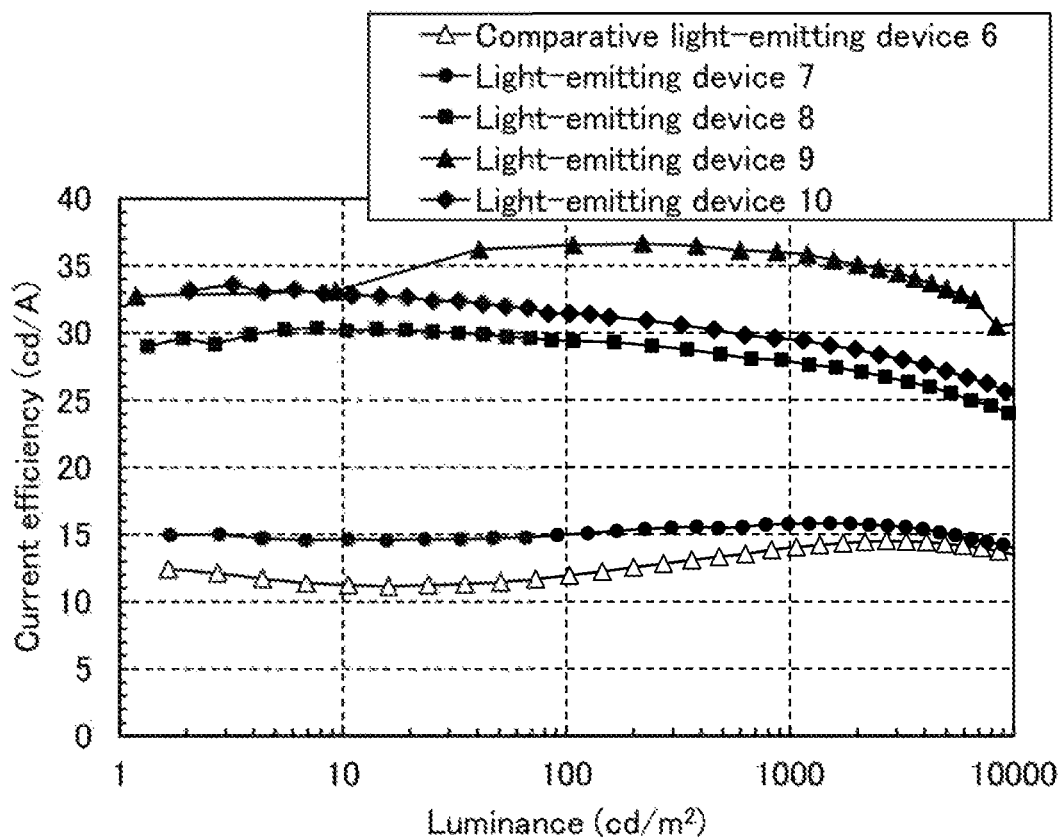
FIG. 17 is a diagram showing current efficiency-luminance characteristics of light-emitting devices in Example.
Figure 18:
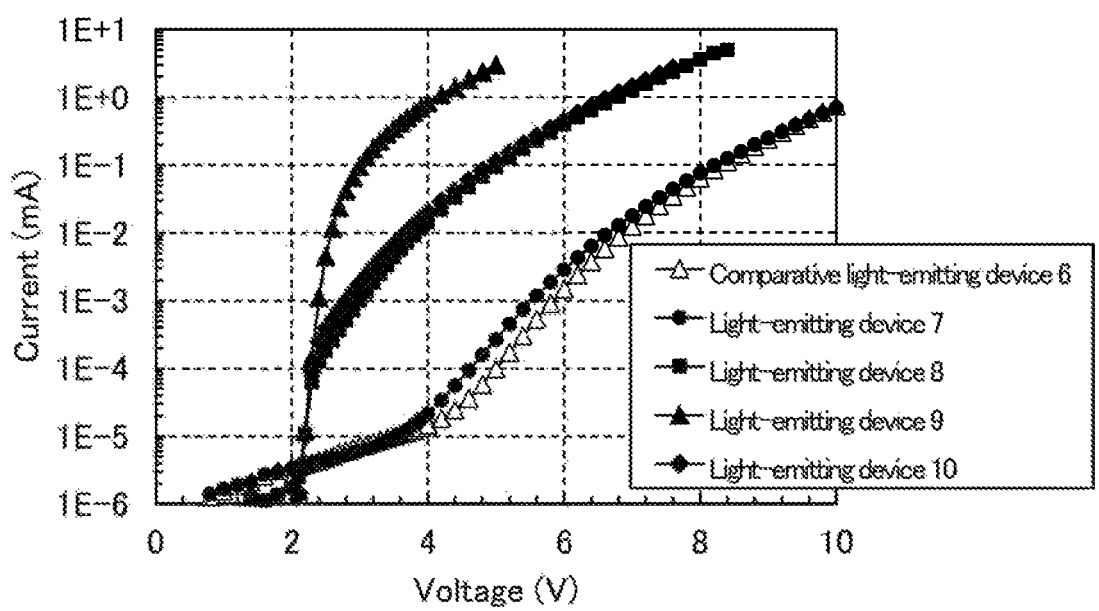
FIG. 18 is a diagram showing current-voltage characteristics of light-emitting devices in Example.
Figure 19:
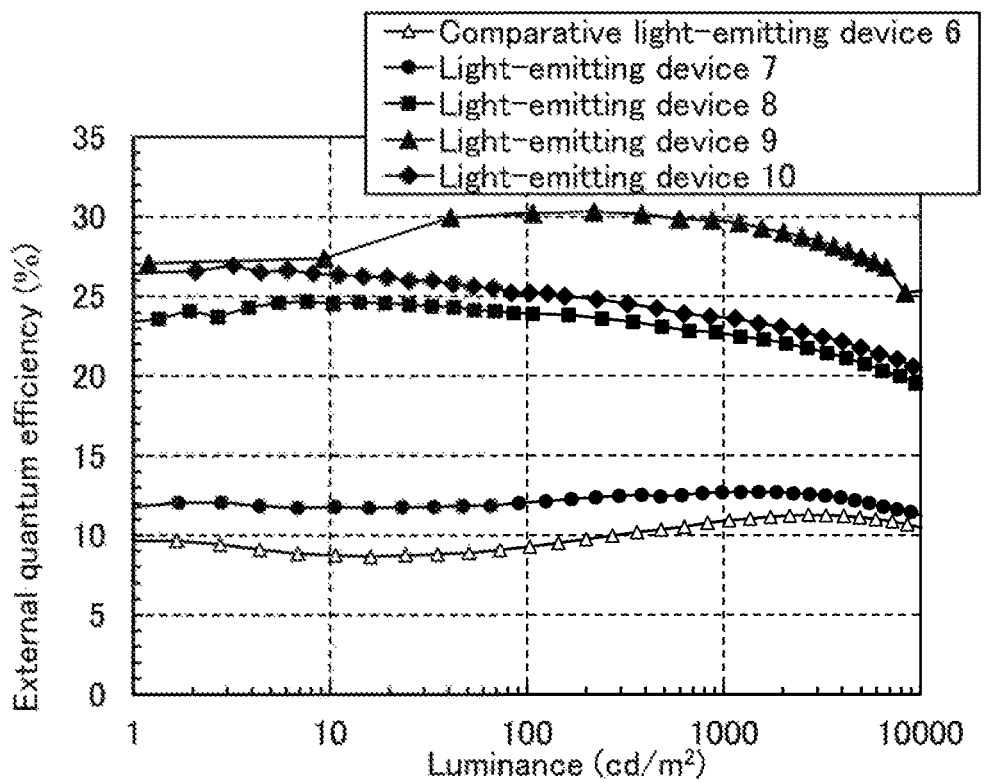
FIG. 19 is a diagram showing external quantum efficiency-luminance characteristics of light-emitting devices in Example.
Figure 20:
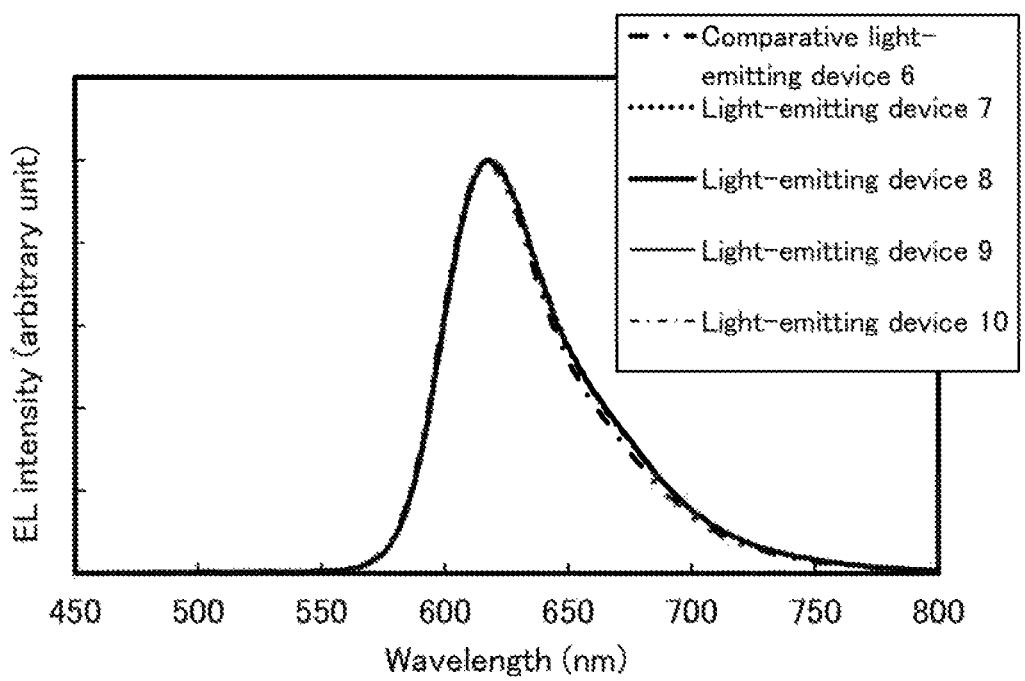
FIG. 20 is a diagram showing electroluminescence spectra of light-emitting devices in Example.

FIG. 17 shows the current efficiency-luminance characteristics of the fabricated comparative light-emitting device 6 and light-emitting device 7 to light-emitting device 10, FIG. 18 shows the current-voltage characteristics thereof, and FIG. 19 shows the external quantum efficiency-luminance characteristics thereof. Note that the measurement of the light-emitting devices was performed at room temperature (in an atmosphere maintained at 23° C.). FIG. 20 shows the electroluminescence spectra of the light-emitting devices through which current flows at a current density of 2.5 mA/cm$^2$. Note that the measurement was performed at room temperature.

Table 7 shows the device characteristics of the comparative light-emitting device 6 and the light-emitting device 7 to the light-emitting device 10 at around 1000 cd/m$^2$.

TABLE 7

| | Voltage (V) | Current density (mA/cm²) | CIE Chromaticity (x, y) | Luminance (cd/m²) | Current efficiency (cd/A) | Power efficiency (lm/W) | External quantum efficiency (%) |
|---|---|---|---|---|---|---|---|
| Comparative light-emitting device 6 | 9.20 | 7.59 | (0.662, 0.338) | 1066 | 14.0 | 4.8 | 10.9 |
| Light-emitting device 7 | 9.00 | 6.21 | (0.663, 0.337) | 980 | 15.8 | 5.5 | 12.7 |
| Light-emitting device 8 | 5.20 | 3.26 | (0.664, 0.336) | 913 | 28.0 | 16.9 | 22.8 |
| Light-emitting device 9 | 3.00 | 2.42 | (0.665, 0.335) | 874 | 36.0 | 37.7 | 29.8 |
| Light-emitting device 10 | 5.20 | 3.89 | (0.663, 0.337) | 1146 | 29.4 | 17.8 | 23.6 |

As shown in FIG. 19 and Table 7, the light-emitting device 7 to the light-emitting device 10 were found to show external quantum efficiency higher than that of the comparative light-emitting device 6. In particular, the light-emitting device 9 and the light-emitting device 10 showed high external quantum efficiency exceeding 25%. As shown in FIG. 18, the light-emitting device 7 to the light-emitting device 10 showed more favorable current-voltage characteristics than the comparative light-emitting device 6. In particular, the light-emitting device 9 showed excellent current-voltage characteristics. These results indicate that the light-emitting device 7 to the light-emitting device 10 have more favorable electron-injection properties than the comparative light-emitting device 6.

The electrode and the electron-transport layer are in contact with each other in the comparative light-emitting device 6, and a metal with a work function higher than the work function of Al, which is used for the electrode, is used for the electron-injection layer in the light-emitting device 7 to the light-emitting device 10. Thus, when attention is focused on the work function of the metal, the comparative light-emitting device 6 is expected to have a more favorable electron-injection property than the light-emitting device 7 to the light-emitting device 10. However, as described above, the light-emitting device 7 to the light-emitting device 10 have more favorable electron-injection properties than the comparative light-emitting device 6. Thus, in the light-emitting device of one embodiment of the present invention in which a composite material of a metal and an organic compound having a function of interacting with the metal as a tridentate or tetradentate ligand is used for the electron-injection layer, SOMO of the composite material is formed in the electron-injection layer; accordingly, favorable electron-injection properties can be obtained even when a metal with a work function higher than the work function of the electrode material is used for the electron-injection layer.

As shown in FIG. 20, the comparative light-emitting device 6 and the light-emitting device 7 to the light-emitting device 10 each exhibited red emission whose electroluminescence spectrum has a peak wavelength at approximately 619 nm and a full width at half maximum of approximately 58 nm. The obtained electroluminescence spectrum shows that the light is emitted from the guest material, Ir(dmdppr-dmp)$_2$(dpm).

<Results of Constant-Current Driving Test of Light-Emitting Devices>

Figure 21:
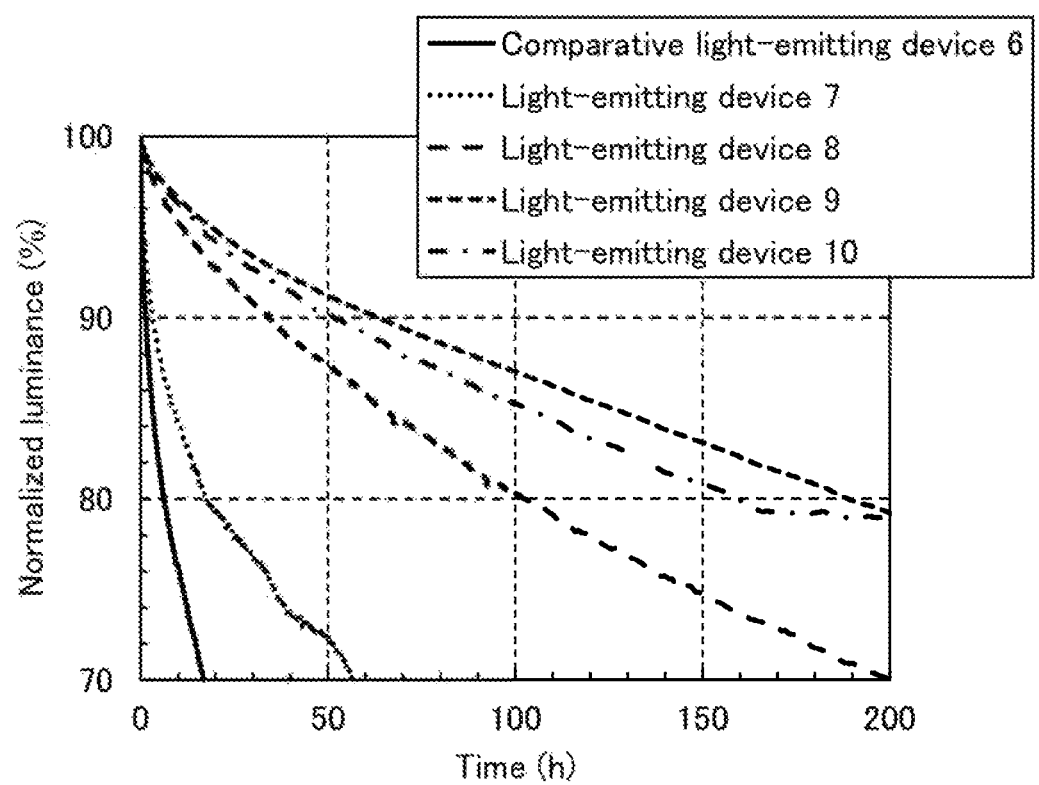
FIG. 21 is a diagram showing results of reliability tests of light-emitting devices in Example.

Next, the driving test at a constant current of 1.0 mA was performed on the comparative light-emitting device 6 and the light-emitting device 7 to the light-emitting device 10 in an air atmosphere. FIG. 21 shows the results. Note that the comparative light-emitting device 6 and the light-emitting device 7 to the light-emitting device 10 were not sealed. FIG. 21 shows that the light-emitting device 7 to the light-emitting device 10 have higher reliability than the comparative light-emitting device 6. Here, FIG. 18 and FIG. 19 show that the electron-injection property of the comparative light-emitting device 6 is inferior to those of the light-emitting device 7 to the light-emitting device 10, and the carrier balance of the comparative light-emitting device 6 is bad, both of which adversely affect the reliability. In contrast, the light-emitting device of one embodiment of the present invention has favorable electron-injection property and thus has favorable carrier balance in the light-emitting device, so that the light-emitting device can have high reliability.

Example 3

Described in this example are examples of fabricating a light-emitting device 12 to a light-emitting device 15 according to one embodiment of the present invention and a comparative light-emitting device 11. A schematic cross-sectional view of the light-emitting devices fabricated in this example is shown in FIG. 1(A), and details of the device structures are shown in Table 8 and Table 9. Chemical formulae of organic compounds used in this example are shown below. The above example and Embodiment 1 can be referred to for the structures and abbreviations of the other compounds.

[Chemical Formula 20]

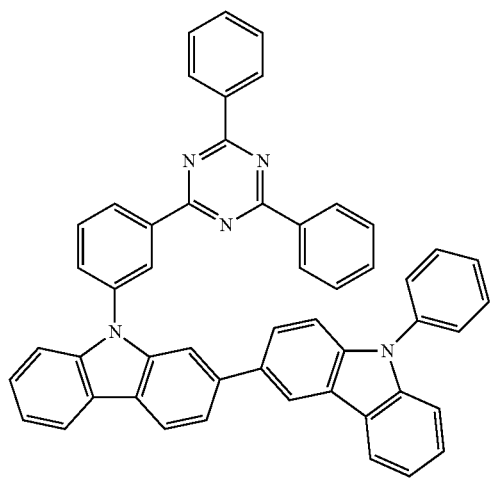

mPCCzPTzn-02

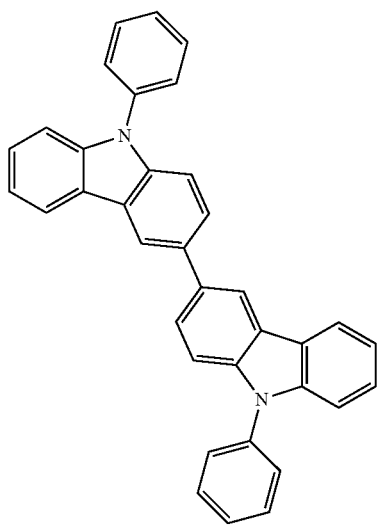

PCCP

TABLE 8

| Layer | | Numeral | Thickness (nm) | Material | Weight ratio |
|---|---|---|---|---|---|
| Comparative light-emitting device 11 | Electrode | 102 | 200 | Al | — |
| | Electron-injection layer | 130 | 1 | LiF | — |
| | Electron-transport layer | 118(2) | 15 | NBPhen | — |
| | | 118(1) | 10 | mPCCzPTzn-02 | — |
| | Light-emitting layer | 140 | 40 | mPCCzPTzn-02:PCCP: GD270 | 0.5:0.5:0.1 |
| | Hole-transport layer | 112 | 20 | PCCP | — |
| | Hole-injection layer | 111 | 40 | DBT3P-II:MoO$_3$ | 1:0.5 |
| | Anode | 101 | 70 | ITSO | — |
| Light-emitting device 12 | Electrode | 102 | 200 | Al | — |
| | Electron-injection layer | 130 | 5 | tPy2P:Ag | 1:0.3 |
| | Electron-transport layer | 118(2) | 15 | NBPhen | — |
| | | 118(1) | 10 | mPCCzPTzn-02 | — |
| | Light-emitting layer | 140 | 40 | mPCCzPTzn-02:PCCP: GD270 | 0.5:0.5:0.1 |
| | Hole-transport layer | 112 | 20 | PCCP | — |
| | Hole-injection layer | 111 | 40 | DBT3P-II:MoO$_3$ | 1:0.5 |
| | Anode | 101 | 70 | ITSO | — |
| Light-emitting device 13 | Electrode | 102 | 200 | Al | — |
| | Electron-injection layer | 130(2) | 5 | tPy2P:Au | 1:0.6 |
| | | 130(1) | 5 | NBPhen:Ag | 1:0.3 |
| | Electron-transport layer | 118(2) | 10 | NBPhen | — |
| | | 118(1) | 10 | mPCCzPTzn-02 | — |
| | Light-emitting layer | 140 | 40 | mPCCzPTzn-02:PCCP: GD270 | 0.5:0.5:0.1 |
| | Hole-transport layer | 112 | 20 | PCCP | — |
| | Hole-injection layer | 111 | 40 | DBT3P-II:MoO$_3$ | 1:0.5 |
| | Anode | 101 | 70 | ITSO | — |

TABLE 9

| Layer | | Numeral | Thickness (nm) | Material | Weight ratio |
|---|---|---|---|---|---|
| Light-emitting device 14 | Electrode | 102 | 200 | Al | — |
| | Electron-injection layer | 130 | 5 | 2Py3Tzn:Cu | 1:0.3 |
| | Electron-transport layer | 118(2) | 15 | NBPhen | — |
| | | 118(1) | 10 | mPCCzPTzn-02 | — |
| | light-emitting layer | 140 | 40 | mPCCzPTzn-02:PCCP: GD270 | 0.5:0.5:0.1 |

TABLE 9-continued

|  | Layer | Numeral | Thickness (nm) | Material | Weight ratio |
|---|---|---|---|---|---|
|  | Hole-transport layer | 112 | 20 | PCCP | — |
|  |  | 111 | 40 | DBT3P-II:MoO$_3$ | 1:0.5 |
|  | Anode | 101 | 70 | ITSO | — |
| Light-emitting device 15 | Electrode | 102 | 200 | Al | — |
|  | Electron-injection layer | 130(2) | 5 | 2Py3Tzn:Co | 1:0.2 |
|  |  | 130(1) | 5 | NBPhen:Cu | 1:0.2 |
|  | Electron-transport layer | 118(2) | 10 | NBPhen | — |
|  |  | 118(1) | 10 | mPCCzPTzn-02 | — |
|  | light-emitting layer | 140 | 40 | mPCCzPTzn-02:PCCP: GD270 | 0.5:0.5:0.1 |
|  | Hole-transport layer | 112 | 20 | PCCP | — |
|  | Hole-injection layer | 111 | 40 | DBT3P-II:MoO$_3$ | 1:0.5 |
|  | Anode | 101 | 70 | ITSO | — |

<Fabrication of Light-Emitting Devices>

Fabrication methods of the light-emitting devices in this example will be described below. The comparative light-emitting device 11 is alight-emitting device that uses LiF, which is a Li compound typically used for the electron-injection layer, and the light-emitting device 12 to the light-emitting device 15 are light-emitting devices each use for the electron-injection layer a composite material of a metal and an organic compound having a function of interacting with the metal as a tridentate or tetradentate ligand according to one embodiment of the present invention.

<Fabrication of Comparative Light-Emitting Device 11>>

As the electrode 101, an ITSO film was formed to a thickness of 70 nm over a glass substrate. Note that the electrode area of the electrode 101 was set to 4 mm$^2$ (2 mm×2 mm).

Next, as the hole-injection layer 111, DBT3P-II and molybdenum oxide (MoO$_3$) were deposited over the electrode 101 by co-evaporation in a weight ratio (DBT3P-II: MoO$_3$) of 1:0.5 to a thickness of 40 nm.

Then, as the hole-transport layer 112, PCCP was deposited over the hole-injection layer 111 by evaporation to a thickness of 20 nm.

Next, as the light-emitting layer 140, 9-[3-(4,6-diphenyl-1,3,5-triazin-2-yl)phenyl]-9'-phenyl-2,3'-bi-9H-carbazole (abbreviation: mPCCzPTzn-02), PCCP, and GD270 (manufactured by Jilin Optical and Electronic Materials Co., Ltd.) were deposited over the hole-transport layer 112 by co-evaporation in a weight ratio (mPCCzPTzn-02:PCCP: GD270) of 0.5:0.5:0.1 to a thickness of 40 nm. Note that in the light-emitting layer 140, mPCCzPTzn and PCCP are host materials and GD270 is a guest material (phosphorescent compound).

Next, as the electron-transport layer 118(1), mPCCzPTzn-02 was deposited over the light-emitting layer 140 by evaporation to a thickness of 10 nm.

Next, as the electron-transport layer 118(2), NBPhen was deposited over the electron-transport layer 118(1) by evaporation to a thickness of 15 nm.

As the electron-injection layer 130, LiF was deposited over the electron-transport layer 118(2) by evaporation to a thickness of 1 nm.

Next, as the electrode 102, aluminum (Al) was formed over the electron-injection layer 130 to a thickness of 200 nm.

Then, heat treatment at 80° C. for one hour was performed in the air without sealing. Through the above steps, the comparative light-emitting device 11 was obtained.

<<<Fabrication of Light-Emitting Device 12 to Light-Emitting Device 15>>>

The light-emitting device 12 to the light-emitting device 15 were fabricated through steps similar to those for the comparative light-emitting device 11 except for the formation step of the electron-transport layer 118(2) and the electron-injection layer 130.

<Fabrication of Light-Emitting Device 12>

Next, as the electron-transport layer 118(2), NBPhen was deposited over the electron-transport layer 118(1) by evaporation to a thickness of 15 nm. Next, as the electron-injection layer 130, tPy2P and Ag were deposited over the electron-transport layer 118(2) by co-evaporation in a weight ratio (tPy2P: Ag) of 1:0.3 to a thickness of 5 nm.

<Fabrication of Light-Emitting Device 13>

As an electron-transport layer 118(2), NBPhen was deposited over the electron-transport layer 118(1) by evaporation to a thickness of 10 nm. Next, as the electron-injection layer 130, NBPhen and Ag were deposited over the electron-transport layer 118(2) by co-evaporation in a weight ratio (NBPhen: Ag) of 1:0.3 to a thickness of 5 nm, and tPy2P and Au were deposited thereover by co-evaporation in a weight ratio (tPy2P: Au) of 1:0.6 to a thickness of 5 nm.

<Fabrication of Light-Emitting Device 14>

Next, as the electron-transport layer 118(2), NBPhen was deposited over the electron-transport layer 118(1) by evaporation to a thickness of 15 nm. Then, as the electron-injection layer 130, 2Py3Tzn and Cu were deposited over the electron-transport layer 118(2) by co-evaporation in a weight ratio (2Py3Tzn: Cu) of 1:0.3 to a thickness of 5 nm.

<Fabrication of Light-Emitting Device 15>

Then, as an electron-transport layer 118(2), NBPhen was deposited over the electron-transport layer 118(1) by evaporation to a thickness of 10 nm. Next, as the electron-injection layer 130, NBPhen and Cu were deposited over the electron-transport layer 118(2) by co-evaporation in a weight ratio (NBPhen: Cu) of 1:0.2 to a thickness of 5 nm, and 2Py3Tzn and Co were deposited thereover by co-evaporation in a weight ratio (2Py3Tzn: Co) of 1:0.2 to a thickness of 5 nm.

<Characteristics of Light-Emitting Devices>

Next, the device characteristics of the fabricated comparative light-emitting device 11 and light-emitting device 12 to light-emitting device 15 were measured. The measurement was performed in a manner similar to that in Example 1.

Figure 22:
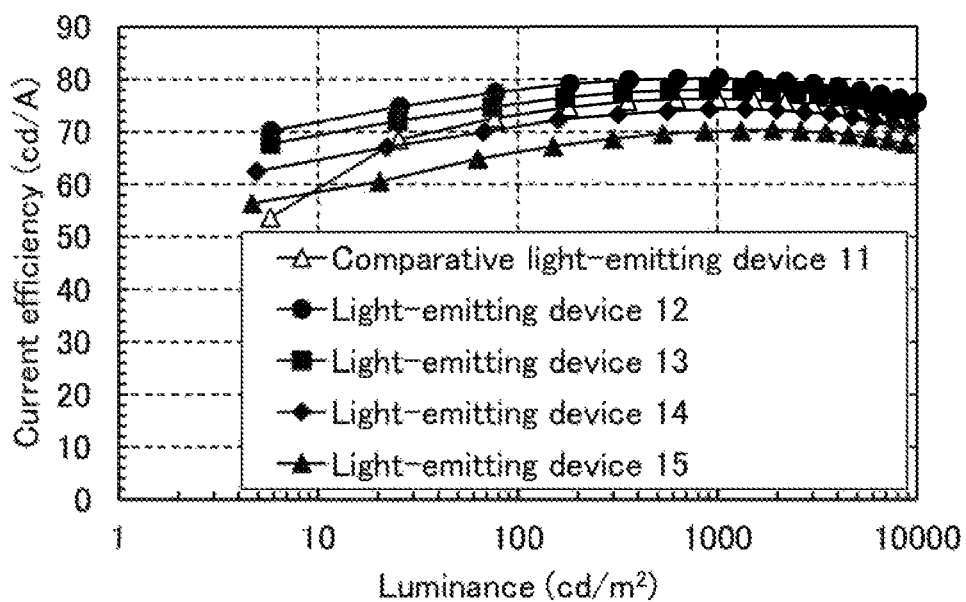
FIG. 22 is a diagram showing current efficiency-luminance characteristics of light-emitting devices in Example.
Figure 23:
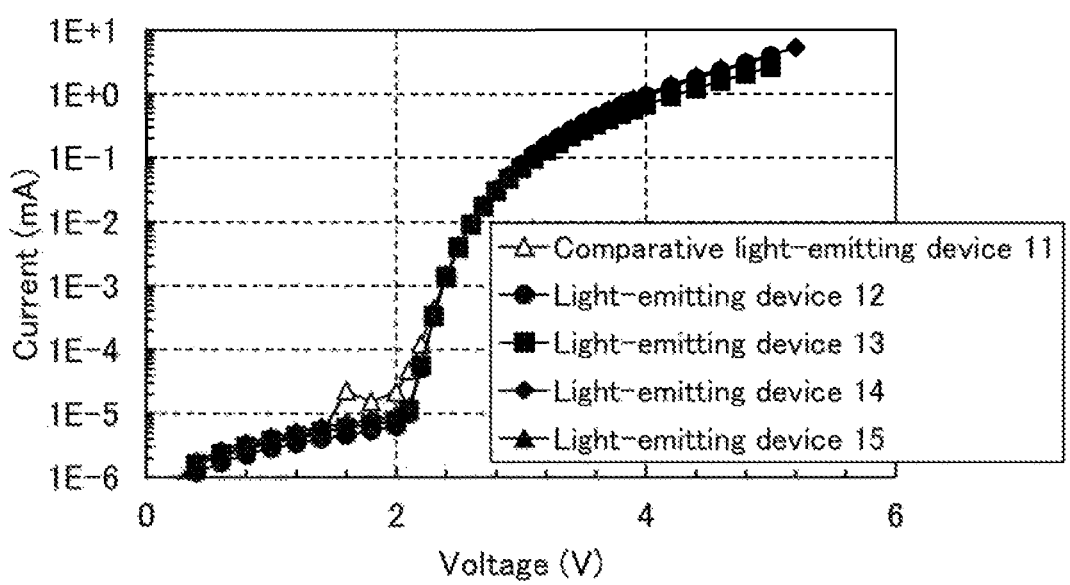
FIG. 23 is a diagram showing current-voltage characteristics of light-emitting devices in Example.
Figure 24:
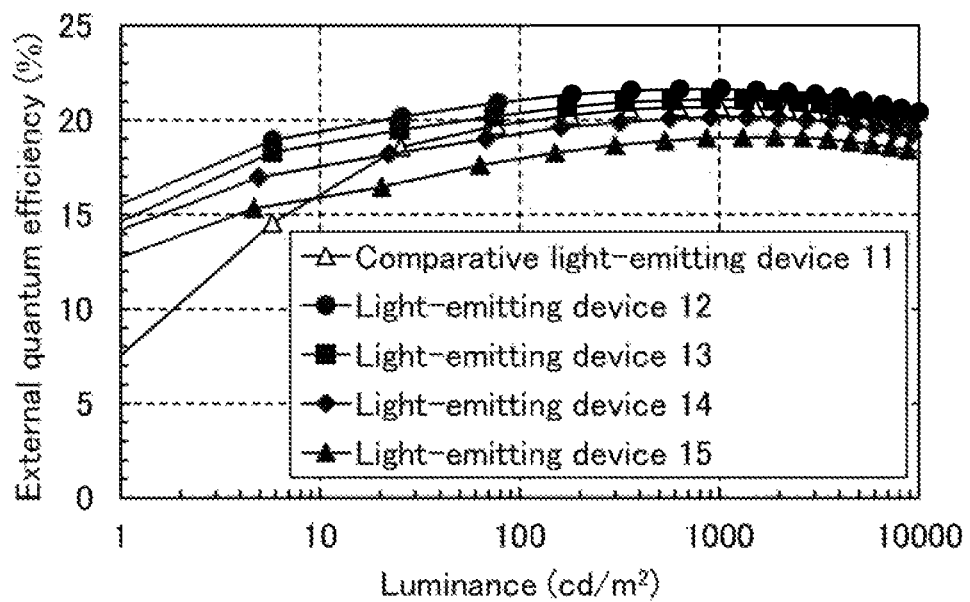
FIG. 24 is a diagram showing external quantum efficiency-luminance characteristics of light-emitting devices in Example.
Figure 25:
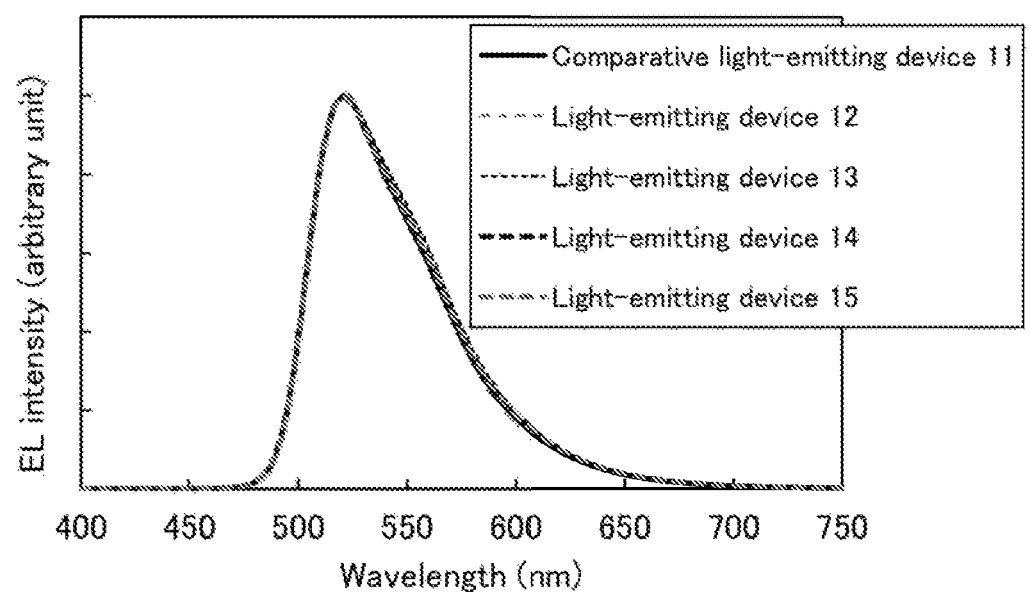
FIG. 25 is a diagram showing electroluminescence spectra of light-emitting devices in Example.

FIG. 22 shows the current efficiency-luminance characteristics of the fabricated comparative light-emitting device 11 and light-emitting device 12 to light-emitting device 15, FIG. 23 shows the current-voltage characteristics thereof, and FIG. 24 shows the external quantum efficiency-luminance characteristics thereof. Note that the measurement of the light-emitting devices was performed at room temperature (in an atmosphere maintained at 23° C.). FIG. 25 shows the electroluminescence spectra of the light-emitting devices through which current flows at a current density of 2.5 mA/cm$^2$. Note that the measurement was performed at room temperature.

Table 10 shows the device characteristics of the comparative light-emitting device 11 and the light-emitting device 12 to the light-emitting device 15 at around 1000 cd/m$^2$.

TABLE 10

| | Voltage (V) | Current density (mA/cm$^2$) | CIE Chromaticity (x, y) | Luminance (cd/m$^2$) | Current efficiency (cd/A) | Power efficiency (lm/W) | External quantum efficiency (%) |
|---|---|---|---|---|---|---|---|
| Comparative light-emitting device 11 | 2.90 | 1.32 | (0.292, 0.666) | 1000 | 76.2 | 82.5 | 20.7 |
| Light-emitting device 12 | 2.90 | 1.27 | (0.297, 0.664) | 1020 | 80.2 | 86.8 | 21.6 |
| Light-emitting device 13 | 2.90 | 1.16 | (0.299, 0.662) | 908 | 78.0 | 84.5 | 21.1 |
| Light-emitting device 14 | 2.90 | 1.22 | (0.297, 0.662) | 908 | 74.2 | 80.4 | 20.1 |
| Light-emitting device 15 | 2.90 | 1.23 | (0.297, 0.663) | 866 | 70.1 | 75.9 | 19.0 |

As shown in FIG. 24 and Table 10, it was found that the comparative light-emitting device 11 and the light-emitting device 12 to the light-emitting device 15 exhibited almost the same external quantum efficiency. In addition, the light-emitting device 12 to the light-emitting device 14 also exhibited high external quantum efficiency exceeding 20%. Furthermore, as shown in FIG. 23 and Table 10, the comparative light-emitting device 11 and the light-emitting device 12 to the light-emitting device 15 showed almost the same current-voltage characteristics. These results indicate that the light-emitting device 12 to the light-emitting device 15 have electron-injection properties equivalent to that of the comparative light-emitting device 11, which uses LiF typically used in the electron-injection layer.

As shown in FIG. 25, the comparative light-emitting device 11 and the light-emitting device 12 to the light-emitting device 15 each exhibited green emission whose electroluminescence spectrum has a peak wavelength at approximately 520 nm and a full width at half maximum of approximately 63 nm. The obtained electroluminescence spectrum shows that light is emitted from the guest material, GD270.

<Reliability Evaluation of Light-Emitting Devices>

Next, a preservation test under constant temperature and humidity was performed on the comparative light-emitting device 11 and the light-emitting device 12 to the light-emitting device 15. Since each of the light-emitting devices is not sealed, the cathode and the EL layer are exposed to the atmosphere of the test environment. In general, moisture entering the light-emitting device causes dark spots (non-emission regions in a light-emitting portion) or shrinkage (non-emission regions at the end portion of the light-emitting portion), thereby adversely affecting the reliability of the light-emitting device. Thus, the preservation test under constant temperature and humidity allows evaluation of the reliability of the light-emitting device against moisture.

In a thermostatic bath kept at a temperature of 40° C. and a humidity of 90%, the comparative light-emitting device 11 and the light-emitting device 12 to the light-emitting device 15 were placed for 350 hours; then, the emission state of each light-emitting device was measured.

The emission state was evaluated by estimating the proportion of the emission area before and after the preservation test under constant temperature and humidity. The results are shown in Table 11.

TABLE 11

| | Proportion of emission area |
|---|---|
| Comparative light-emitting device 11 | 0% |
| Light-emitting device 12 | 95% |
| Light-emitting device 13 | 88% |
| Light-emitting device 14 | 55% |
| Light-emitting device 15 | 57% |

In Table 11, the proportion of emission area (%) is the emission area after the preservation test under constant temperature and humidity/the emission area before the preservation test under constant temperature and humidity×100. Table 11 shows that the comparative light-emitting device 11 that uses LiF, which is an alkali metal compound, for the electron-injection layer deteriorates due to the preservation test and emits no light. Meanwhile, the light-emitting device 12 to the light-emitting device 15 that are light-emitting devices of one embodiment of the present invention each have a higher proportion of emission area than the comparative light-emitting device 11. This indicates that the light-emitting devices of one embodiment of the present invention have higher moisture resistance than the light-emitting device that uses for the electron-injection layer a material with a low work function, e.g., an alkali metal. This is because the material with a low work function has high reactivity with water, allowing moisture to enter the light-emitting device. In contrast, moisture does not easily enter the light-emitting devices of one embodiment of the present invention, which can use a transition metal with a high work function. Hence, highly moisture resistant light-emitting devices can be achieved.

From the above, the light-emitting device of one embodiment of the present invention has a favorable electron-injection property, and thus is a light-emitting device having a low driving voltage and a high emission efficiency. In addition, the light-emitting device has high moisture resistance because it can use a material with a high work function. The structures shown in this example can be used in appropriate combination with any of the other embodiments and examples.

Example 4

In this example, an example of an organic compound that can be used for the light-emitting device of one embodiment of the present invention and a synthesis example thereof will be described.

Synthesis of 4'-[4-(10-phenyl-9-anthryl)phenyl]-2,2':6',2''-terpyridine (Abbreviation: PAtPy) (Structural Formula (200))

To a 100-mL three-neck flask were added 1.0 g (2.6 mmol) of 4'-(4-bromophenyl)-2,2':6',2''-terpyridine, 0.86 g (2.9 mmol) of 10-phenyl-9-anthrylboronic acid, 0.85 g (8.0 mmol) of sodium carbonate, 20 mL of toluene, 5 mL of ethanol, and 5 mL of water. This mixture was degassed by being stirred under reduced pressure, and the air in the flask was replaced with nitrogen. To the mixture, 65 mg (56 µmol) of tetrakis(triphenylphosphine)palladium(0) was added, and the mixture was refluxed at 100° C. under nitrogen stream for 8 hours. After the stirring, the reaction mixture was cooled to room temperature, and the precipitated solid was collected by suction filtration. The chloroform solution of the obtained solid was washed with water, a saturated aqueous solution of sodium hydrogencarbonate, and saturated brine, and dried with magnesium sulfate. The mixture of the chloroform solution and the magnesium sulfate was subjected to gravity filtration and the filtrate was concentrated, whereby a solid was obtained. A methanol suspension of the obtained solid was irradiated with ultrasonic waves, and a solid was collected by suction filtration. Furthermore, the obtained solid was recrystallized with toluene, whereby 1.2 g of a pale red powder, which was the target substance, was obtained in a yield of 81%. The synthesis scheme is shown in the following formula (a-1).

[Chemical Formula 21]

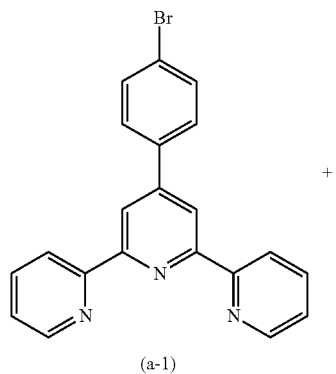

(a-1)

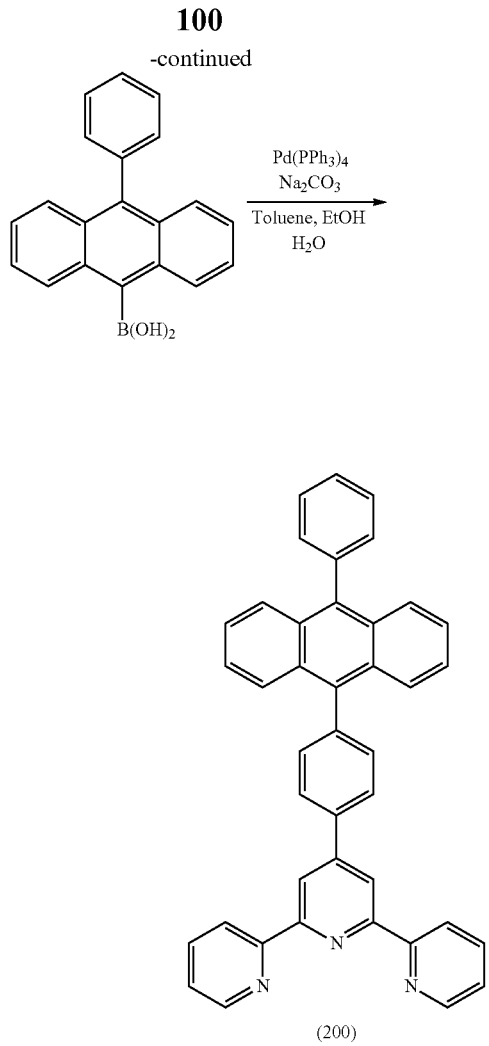

(200)

By a train sublimation method, 1.2 g of the obtained pale red powder was sublimated and purified. The sublimation purification was performed by heating PAtPy at 290° C. under the conditions where the pressure was 4.5 Pa and the argon flow rate was 10 mL/min. After the sublimation purification of PAtPy, 0.55 g of the pale red powder was obtained at a collection rate of 47%.

The obtained pale red powder was measured by nuclear magnetic resonance spectrometry ($^1$H-NMR). The analysis results are shown below.

$^1$H-NMR (CDCl$_3$, 300 MHz): δ=7.34-7.40 (m, 6H), 7.49-7.79 (m, 11H), 7.91 (dt, J=1.5 Hz, 7.2 Hz, 2H), 8.16 (d, J=7.8 Hz, 2H), 8.72-8.78 (m, 4H), 8.93 (s, 2H).

Figure 26A:
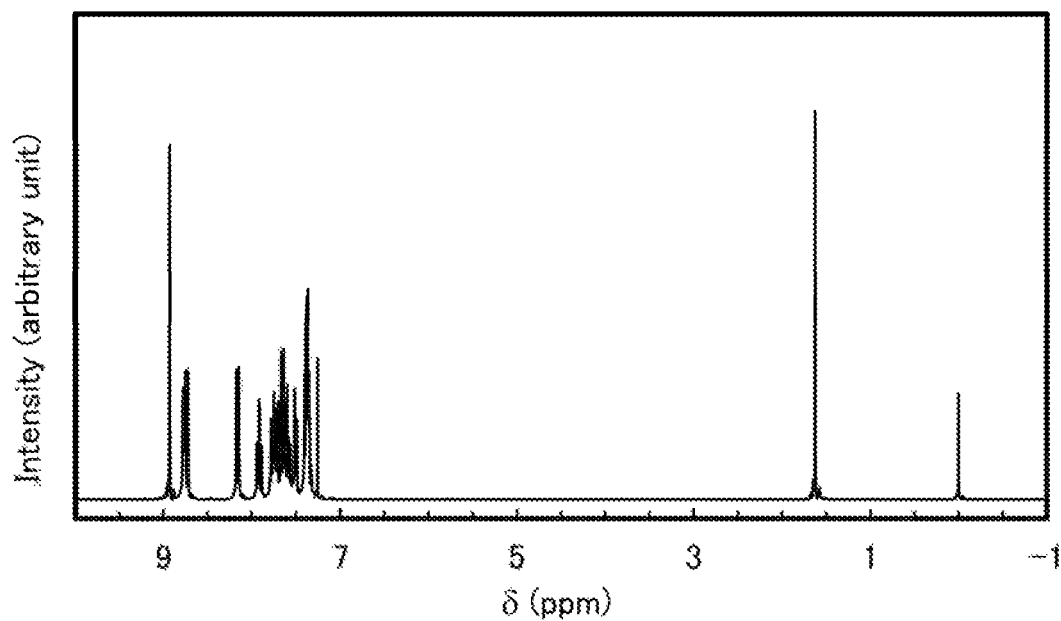
FIGS. 26A-26B are diagrams showing-NMR spectra of compounds in Example.
Figure 26B:
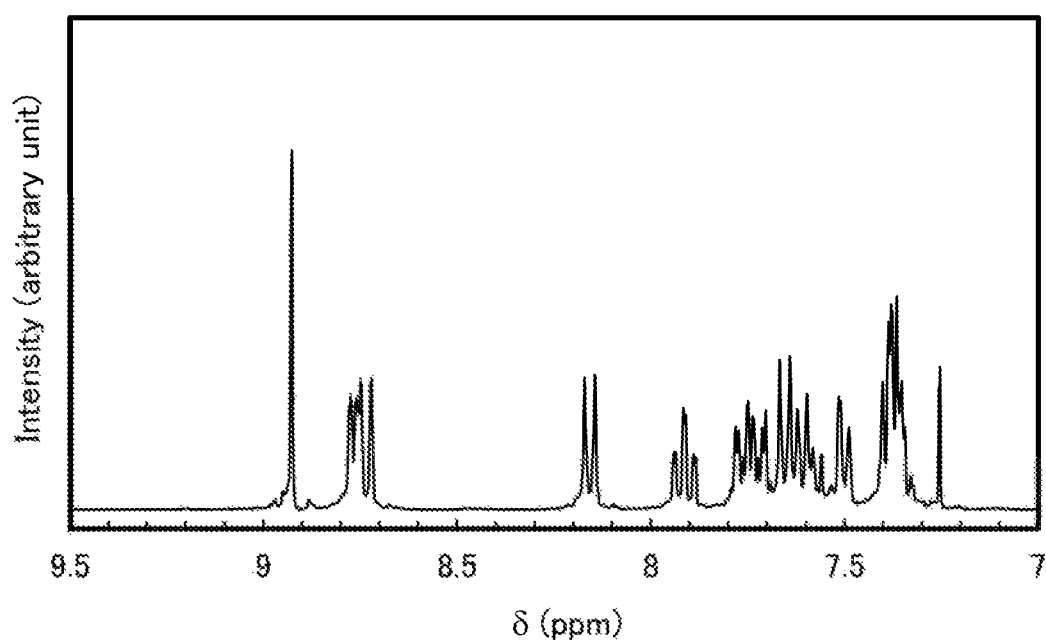

FIGS. 26(A) and 26(B) show $^1$H-NMR charts of the obtained pale red powder. Note that FIG. 26(B) is an enlarged diagram of the range of 7.0 ppm to 9.5 ppm of FIG. 26(A). The measurement results indicate that PAtPy, which was the target substance, was obtained.

Example 5

In this example, an example of an organic compound that can be used for the light-emitting device of one embodiment of the present invention and a synthesis example thereof will be described.

Synthesis of 2-[4'-(2,2':6',2''-terpyridine-4'-yl)biphenyl-4-yl]benzoxazole (Abbreviation: BOxtPy) (Structural Formula (201))

To a 100-mL three-neck flask were added 1.0 g (2.6 mmol) of 4'-(4-bromophenyl)-2,2':6',2''-terpyridine, 0.68 g (2.9 mmol) of 4-(benzoxazol-2-yl)phenylboronic acid, 0.62 g (5.8 mmol) of sodium carbonate, 20 mL of toluene, 5 mL of ethanol, and 3 mL of water. This mixture was degassed by being stirred under reduced pressure, and the air in the flask was replaced with nitrogen. To the mixture, 63 mg (55 µmol) of tetrakis(triphenylphosphine)palladium(0) was added, and the mixture was refluxed at 100° C. under nitrogen stream for 5 hours. After the reflux, the reaction mixture was cooled to room temperature, and the precipitated solid was collected by suction filtration. The chloroform solution of the obtained solid was washed with water, a saturated aqueous solution of sodium hydrogencarbonate, and saturated brine, and dried with magnesium sulfate. The mixture of the chloroform solution and the magnesium sulfate was subjected to gravity filtration and the filtrate was concentrated, whereby a solid was obtained. The obtained solid was recrystallized with toluene, whereby 1.0 g of a pale red powder, which was the target substance, was obtained in a yield of 78%. The synthesis scheme is shown in the following formula (b-1).

[Chemical Formula 22]

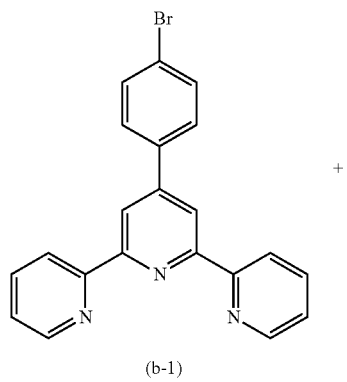

(b-1)

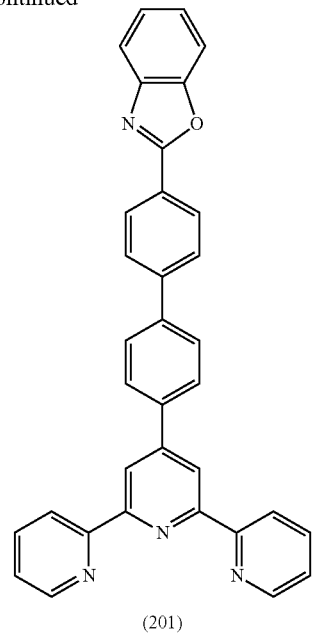

(201)

By a train sublimation method, 1.0 g of the powder of BOxtPy was sublimated and purified. The sublimation purification was performed by heating BOxtPy at 280° C. under the conditions where the pressure was 4.4 Pa and the argon flow rate was 10 mL/min. After the sublimation purification of BOxtPy, 0.64 g of the pale red powder was obtained at a collection rate of 63%.

The obtained pale red powder was measured by nuclear magnetic resonance spectrometry ($^1$H-NMR). The analysis results are shown below.

$^1$H-NMR (CDCl$_3$, 300 MHz): δ=7.32-7.41 (m, 4H), 7.59-7.65 (m, 1H), 7.78-7.93 (m, 7H), 8.05 (d, J=8.4 Hz, 2H), 8.37 (d, J=7.8 Hz, 2H), 8.70 (d, J=7.8 Hz, 2H), 8.75-8.77 (m, 2H), 8.81 (s, 2H).

Figure 27A:
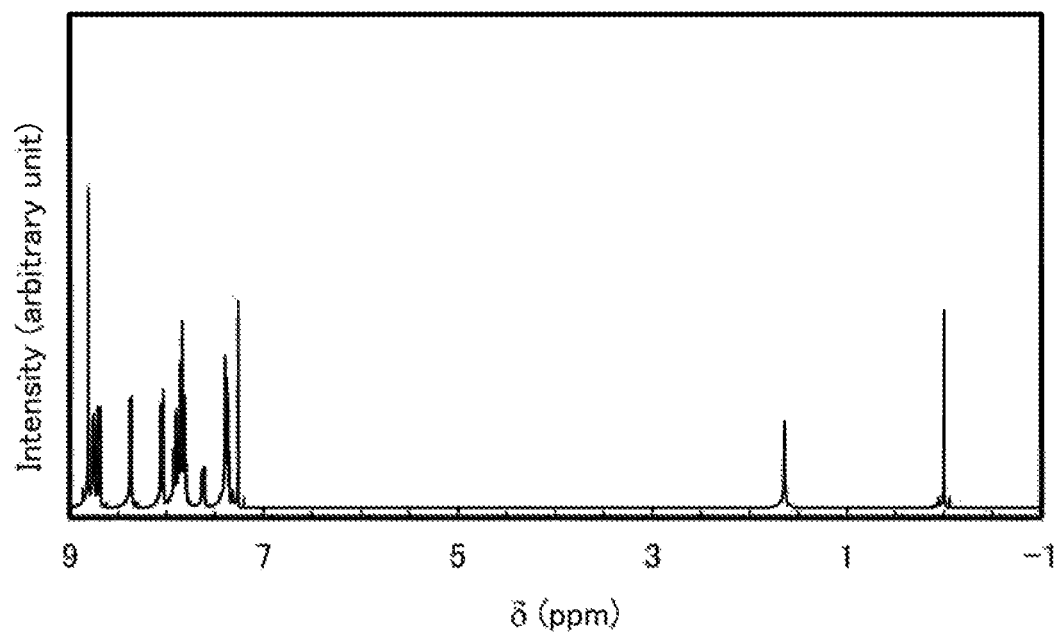
FIGS. 27A-27B are diagrams showing-NMR spectra of compounds in Example.
Figure 27B:
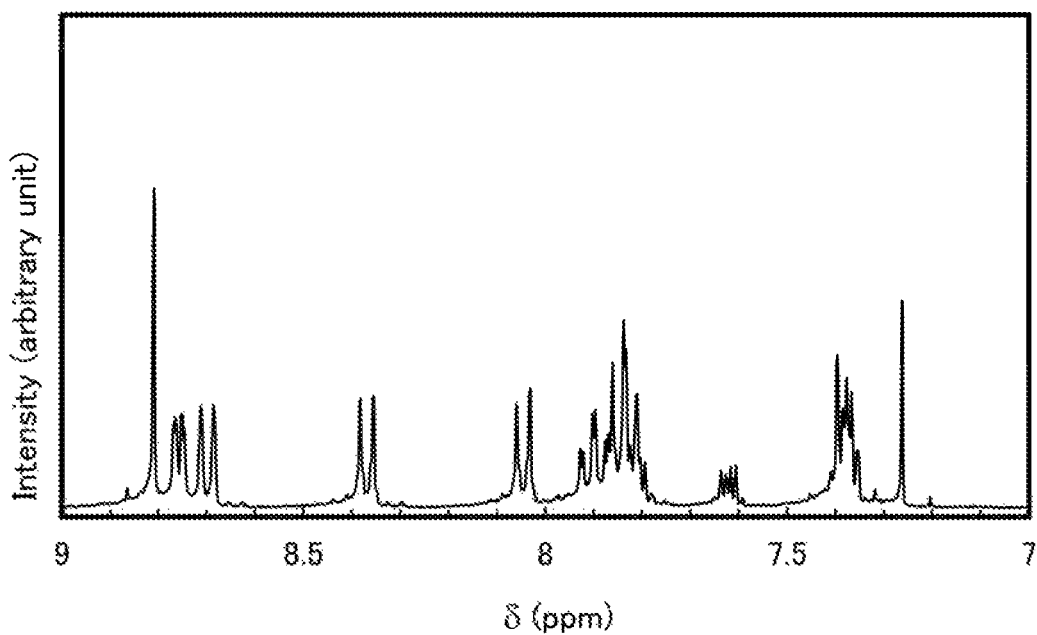

FIGS. 27(A) and 27(B) show $^1$H-NMR charts of the obtained pale red powder. Note that FIG. 27(B) is an enlarged diagram of the range of 7.0 ppm to 9.0 ppm of FIG. 27(A). The measurement results indicate that BOxtPy, which was the target substance, was obtained.

Example 6

In this example, an example of an organic compound that can be used for the light-emitting device of one embodiment of the present invention and a synthesis example thereof will be described.

Synthesis of 4'-{4-[4-(5-phenyl-1,3,4-oxadiazole-2-yl)phenyl]phenyl}-2,2':6',2''-terpyridine (Abbreviation: O11tPy) (Structural Formula (202))

To a 100-mL three-neck flask were added 1.0 g (2.6 mmol) of 4'-(4-bromophenyl)-2,2':6',2''-terpyridine, 0.73 g (2.7 mmol) of 4-(5-phenyl-1,3,4-oxadiazol-2-yl)phenylboronic acid, 0.71 g (6.7 mmol) of sodium carbonate, 20 mL of toluene, 5 mL of ethanol, and 3 mL of water. This mixture was degassed by being stirred under reduced pressure, and the air in the flask was replaced with nitrogen. To the mixture, 68 mg (59 µmol) of tetrakis(triphenylphosphine)palladium(0) was added. The mixture was refluxed at 100° C. under nitrogen stream for 9 hours. After the stirring, the mixture was cooled to room temperature, and the precipitated solid was collected by suction filtration. The chloroform solution of the obtained solid was washed with water, a saturated aqueous solution of sodium hydrogencarbonate, and saturated brine, and dried with magnesium sulfate. The mixture was subjected to gravity filtration and the filtrate was concentrated, whereby a solid was obtained. The obtained solid was washed with methanol and then recrystallized with toluene, whereby 0.72 g of a white powder, which was the target substance, was obtained in a yield of 51%. The synthesis scheme is shown in the following formula (c-1).

[Chemical Formula 23]

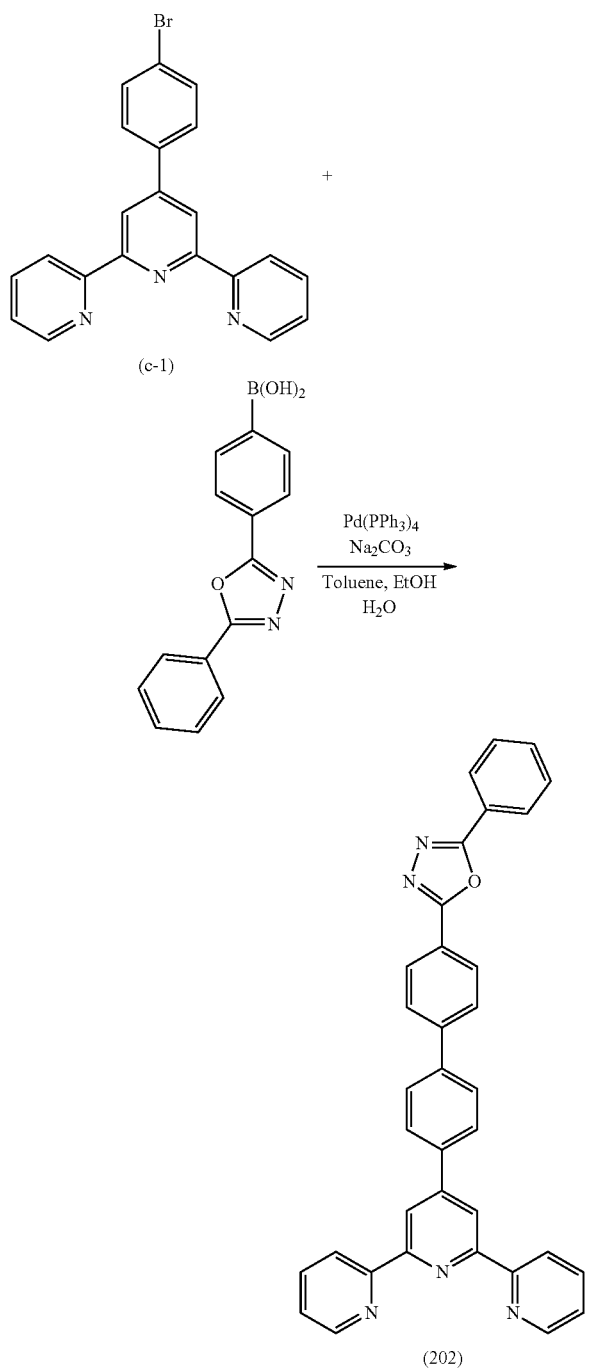

By a train sublimation method, 0.71 g of the powder of O11tPy was sublimated and purified. The sublimation purification was performed by heating O11tPy at 270° C. under the conditions where the pressure was 4.0 Pa and the argon flow rate was 10 mL/min. After the sublimation purification, 0.29 g of the white powder, which was O11tPy, was obtained at a collection rate of 41%.

The obtained white powder was measured by nuclear magnetic resonance spectrometry ($^1$H-NMR). The analysis results are shown below.

$^1$H-NMR (CDCl$_3$, 300 MHz): δ=7.35-7.39 (m, 2H), 7.52-7.58 (m, 3H), 7.79-7.93 (m, 6H), 8.04 (d, J=8.4 Hz, 2H), 8.16-8.19 (m, 2H), 8.24 (d, J=8.4 Hz, 2H), 8.69 (d, J=7.8 Hz, 2H), 8.74-8.76 (m, 2H), 8.80 (s, 2H).

Figure 28A:
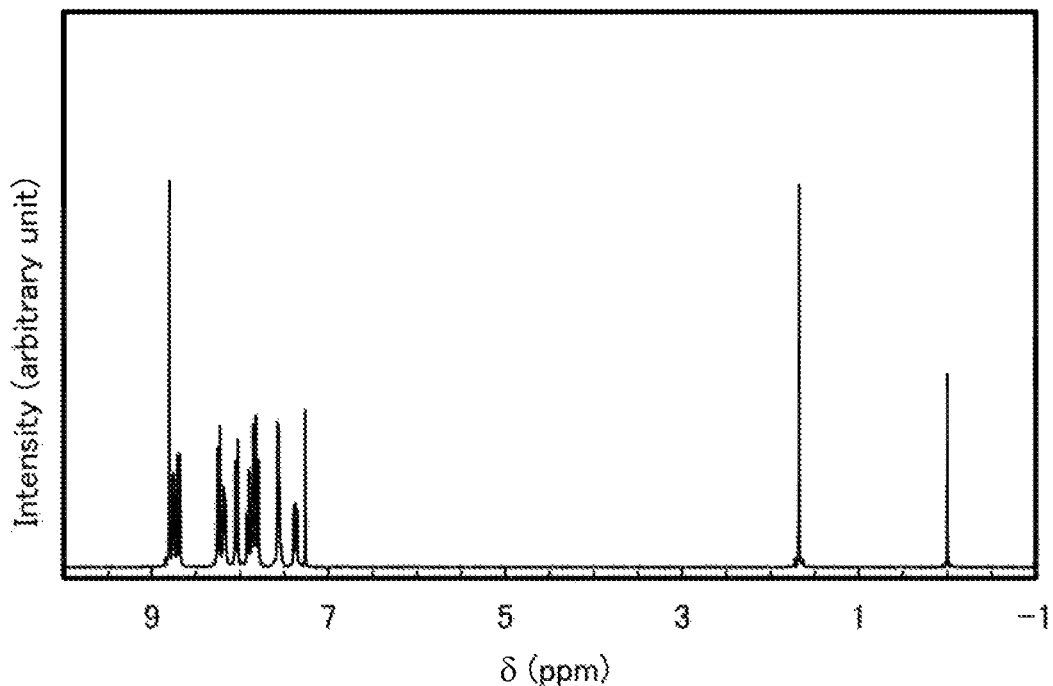
FIGS. 28A-28B are diagrams showing-NMR spectra of compounds in Example.
Figure 28B:
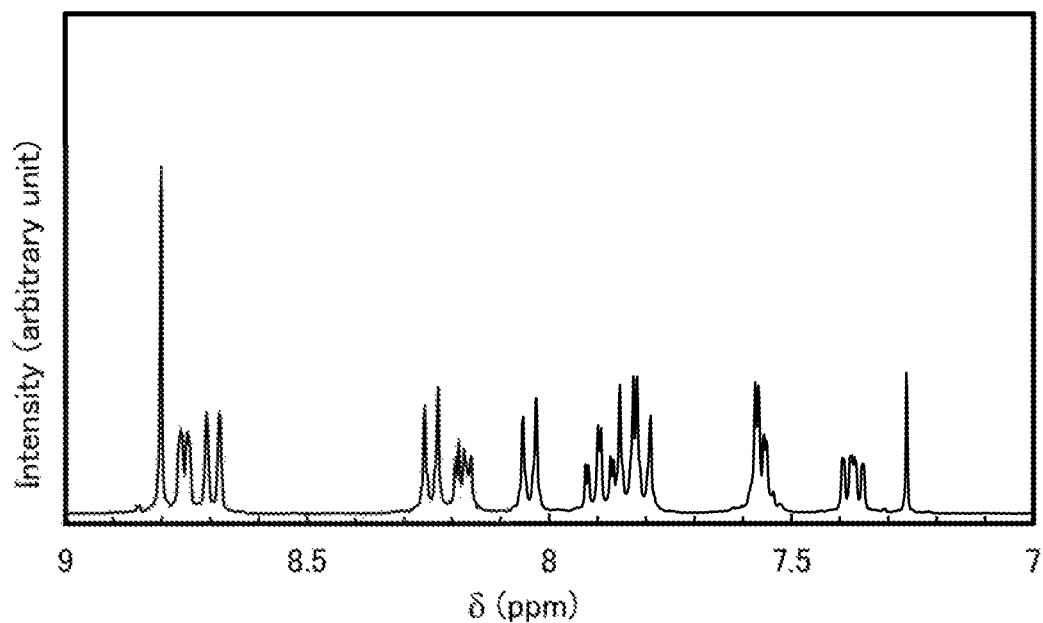

FIGS. 28(A) and 28(B) show $^1$H-NMR charts of the obtained white powder. Note that FIG. 28(B) is an enlarged diagram of the range of 7.0 ppm to 9.0 ppm of FIG. 28(A). The measurement results indicate that O11tPy, which was the target substance, was obtained.

Example 7

In this example, examples of an organic compound and a synthesis example thereof, which can be used for the light-emitting device of one embodiment of the present invention, will be described.

Synthesis of 9,9'-[5-(2,2':6',2"-terpyridine-4'-yl)-1,3-phenylene]bis(9H-carbazole) (Abbreviation: Cz2PtPy) (Structural Formula (203)

To a 100-mL three-neck flask were added 0.94 g (3.0 mmol) of 4'-(4-bromophenyl)-2,2':6',2"-terpyridine, 1.4 g (3.2 mmol) of 3,5-bis(9H-carbazol-9-yl)phenylboronic acid, 0.86 g (6.2 mmol) of sodium carbonate, 30 mL of toluene, 5 mL of ethanol, and 3 mL of water. This mixture was degassed by being stirred under reduced pressure, and the air in the flask was replaced with nitrogen. To the mixture, 72 mg (62 μmol) of tetrakis(triphenylphosphine)palladium(0) was added. The mixture was stirred at 80° C. under nitrogen stream for 7 hours. After the stirring, an aqueous layer of the mixture was subjected to extraction with toluene, the extracted solution and an organic layer were combined, washed with a saturated aqueous solution of sodium hydrogen carbonate and a saturated aqueous solution of sodium, and then dried with magnesium sulfate. The mixture was cooled to room temperature, and the precipitated solid was collected by suction filtration. The chloroform solution of the obtained solid was washed with water, a saturated aqueous solution of sodium hydrogencarbonate, and saturated brine, and dried with magnesium sulfate. The mixture was subjected to gravity filtration and the filtrate was concentrated, whereby a solid was obtained. The obtained solid was washed with methanol and then recrystallized with toluene, whereby 1.1 g of a white powder, which was the target substance, was obtained in a yield of 55%. The synthesis scheme is shown in the following formula (d-1).

[Chemical Formula 24]

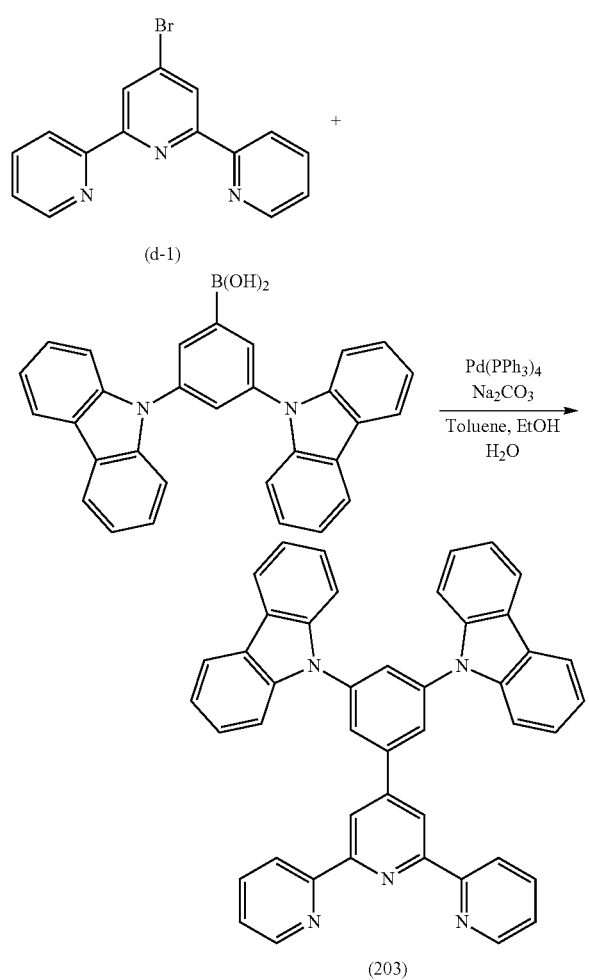

By a train sublimation method, 0.83 g of the obtained powder of Cz2PtPy was sublimated and purified. The sublimation purification was performed by heating Cz2PtPy at 290° C. under the conditions where the pressure was 3.2 Pa and the argon flow rate was 5.0 mL/min. After the sublimation purification of Cz2PtPy, 0.71 g of the white powder was obtained at a collection rate of 86%.

The obtained white powder was measured by nuclear magnetic resonance spectrometry ($^1$H-NMR). The analysis results are shown below.

$^1$H-NMR (CDCl$_3$, 300 MHz): δ=7.31-7.37 (m, 6H), 7.47 (dt, J=0.9 Hz, 7.2 Hz, 4H), 7.59 (d, J=8.1 Hz, 4H), 7.85-7.92 (m, 3H), 8.17-8.22 (m, 6H), 8.66-8.69 (m, 4H), 8.82 (s, 2H).

Figure 29A:
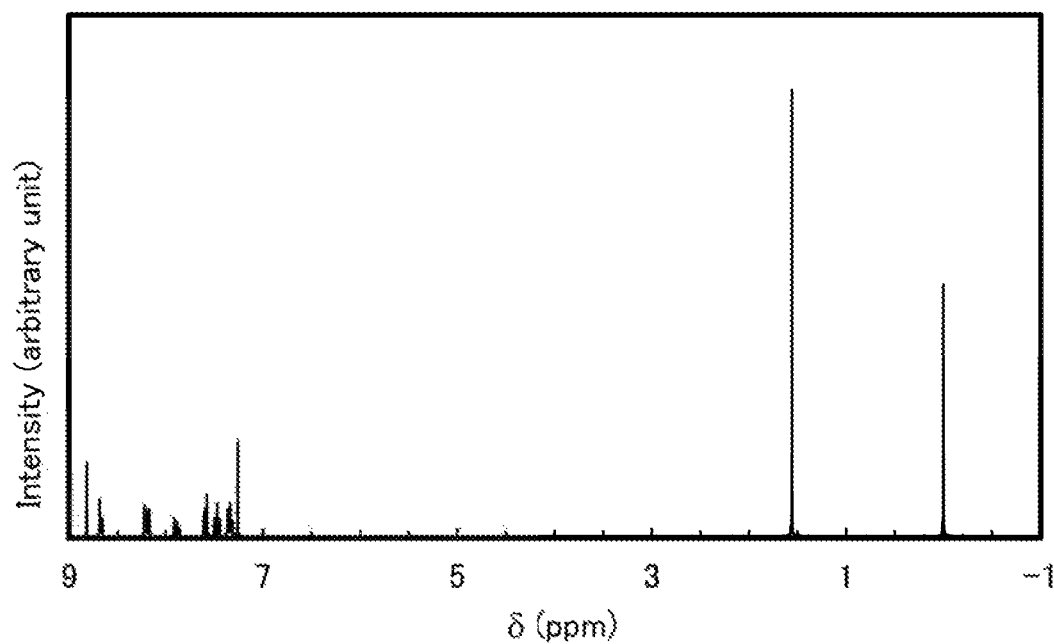
FIGS. 29A-29B are diagrams showing-NMR spectra of compounds in Example.
Figure 29B:
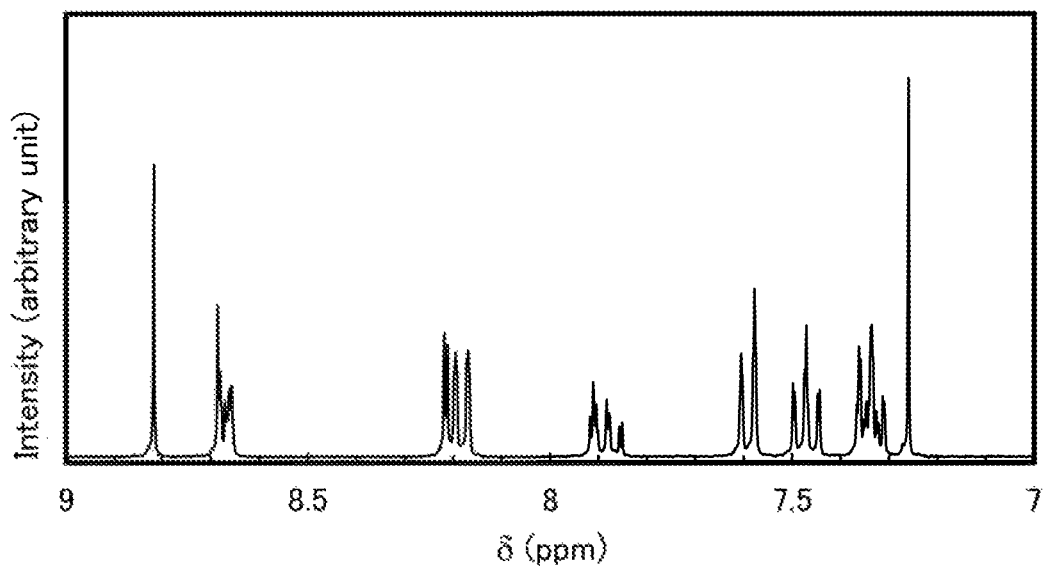

FIGS. 29(A) and 29(B) show $^1$H-NMR charts of the obtained white powder. Note that FIG. 29(B) is an enlarged diagram of the range of 7.0 ppm to 9.0 ppm of FIG. 29(A). The measurement results indicate that Cz2PtPy, which was the target substance, was obtained.

Example 8

In this example, an example of an organic compound that can be used for the light-emitting device of one embodiment of the present invention and a synthesis example thereof will be described.

Synthesis of 2,4,6-tris(5-phenyl-2-pyrimidine-2-yl)-1,3,5-triazine (Abbreviation: PPm3Tzn) (Structural Formula (105)

To a 50-mL two-neck flask were added 0.80 g (4.0 mmol) of 5-phenylpyrimidine-2-carboximidamide, 1.4 g (7.7 mmol) of 2-cyano-5-phenylpyrimidine, 2 mL of diglyme, 1 mL of 1,2,3,4-tetrahydronaphthalene. The mixture was stirred at 180° C. under nitrogen stream for 29 hours and at 200° C. for 100 hours. After the stirring, the mixture was cooled to room temperature and washed with ethyl acetate, whereby 0.82 g of a brown powder was obtained. The synthesis scheme is shown in the following formula (e-1). In addition, in the measurement of $^1$H-NMR before the sublimation purification that is to be described later, the proton ratio was PPm3Tzn: 5-phenylpyrimidine-2-carboximidamide=1:1.7, which indicates that the target substance and a raw material are mixed in the brown powder. Furthermore, a signal derived from 2-cyano-5-phenylpyrimidine was not observed.

[Chemical Formula 25]

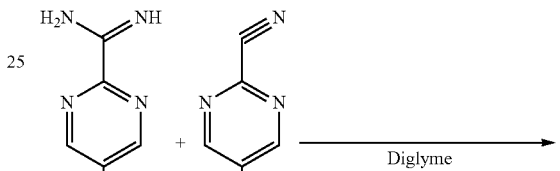

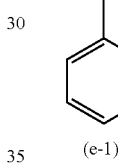

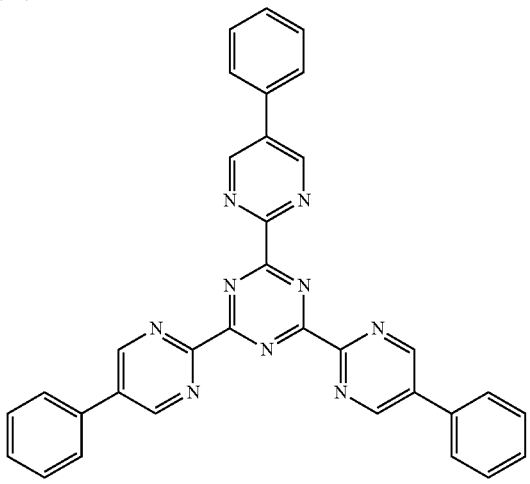

By the train sublimation method, 0.79 g of the obtained brown powder was sublimated and purified. The sublimation purification was performed by heating at 310° C. under the conditions where the pressure was 3.7 Pa and the argon flow rate was 15 mL/min. After the sublimation purification, 0.19 g of a pale brown powder, which was 2,4,6-tris (5-phenyl-2-pyrimidine-2-yl)-1,3,5-triazine, was obtained. The $^1$H-NMR measurement after the sublimation purification revealed that a signal derived from 5-phenylpyrimidine-2-carboximidamide disappeared. Accordingly, it is found that the target substance can be easily purified by sublimation purification.

The obtained pale brown powder was measured by nuclear magnetic resonance spectrometry ($^1$H-NMR). The analysis results are shown below.

$^1$H-NMR (CDCl$_3$, 300 MHz): δ=7.52-7.63 (m, 9H), 7.73 (dd, J=1.5 Hz, 7.8 Hz, 6H), 9.35 (s, 6H).

Figure 30A:
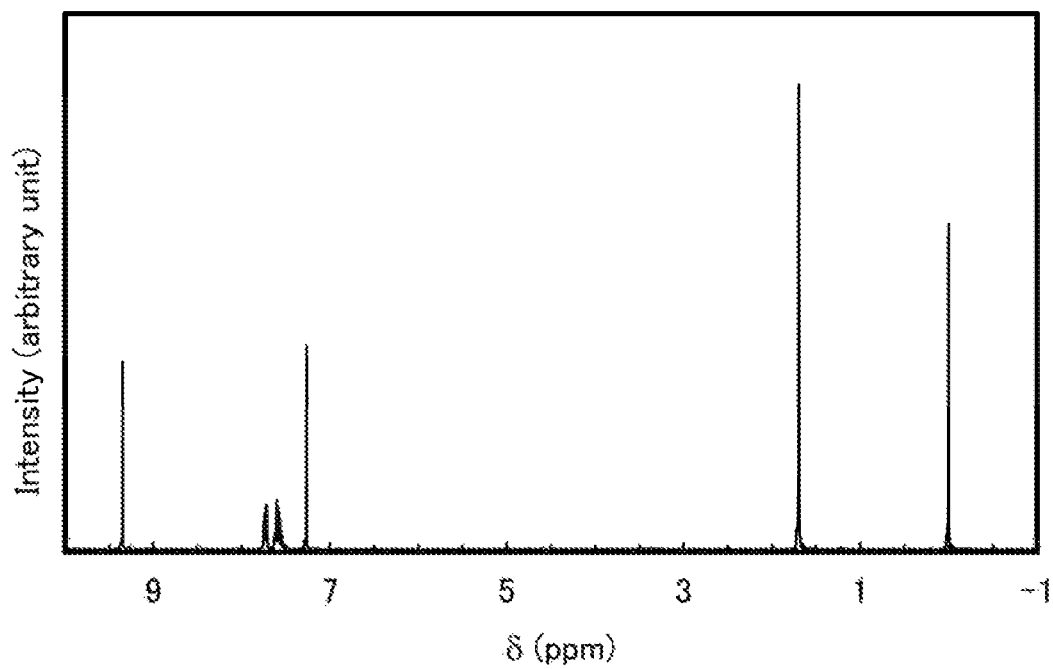
FIGS. 30A-30B are diagrams showing-NMR spectra of compounds in Example.
Figure 30B:
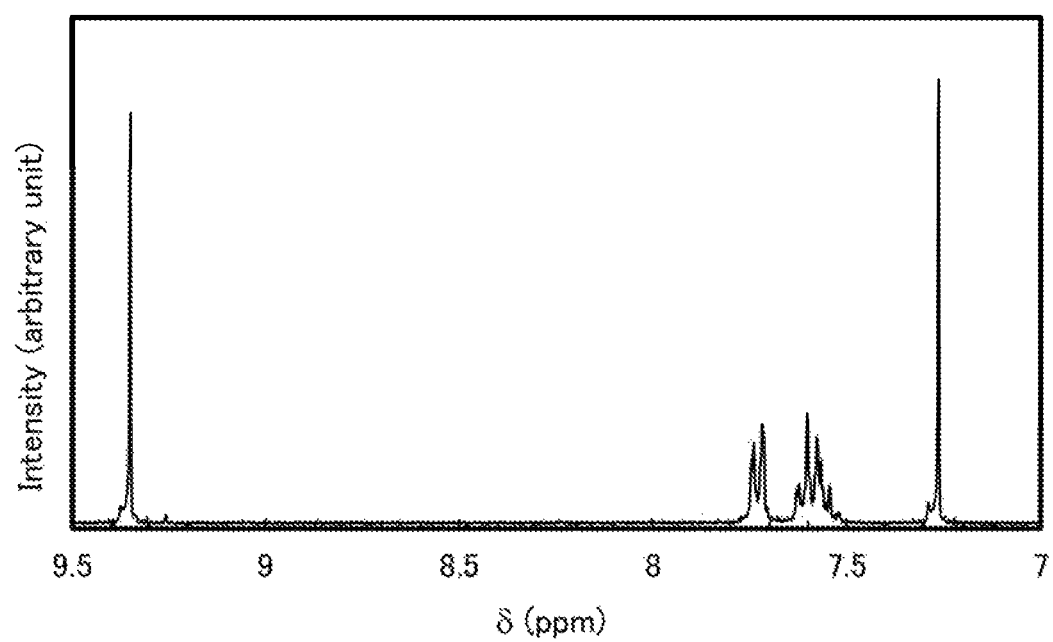

FIGS. 30(A) and 30(B) show $^1$H-NMR charts of the obtained pale brown powder. Note that FIG. 30(B) is an enlarged diagram of the range of 7.0 ppm to 9.5 ppm of FIG. 30(A). The measurement results indicate that PPm3Tzn, which was the target substance, was obtained.

Example 9

Figure 31:
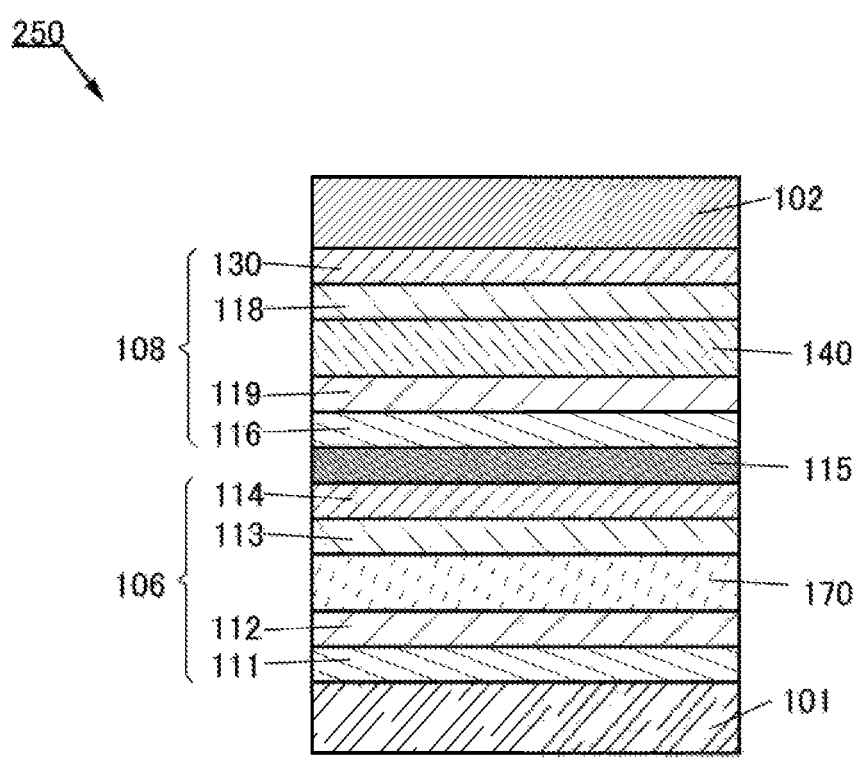
FIG. 31 is a schematic cross-sectional view illustrating a light-emitting device of one embodiment of the present invention.

Fabrication examples of a light-emitting device 16 to a light-emitting device 21, which are light-emitting devices of one embodiment of the present invention and examples of a tandem element to be described later, and a comparative light-emitting device 33 and a comparative light-emitting device 34 will be described. A schematic cross-sectional view of the light-emitting devices fabricated in this example is shown in FIG. 31, and details of the device structures are shown in Table 12 to Table 14. Chemical formulae of organic compounds used in this example are shown below. The above examples and Embodiment 1 can be referred to for the structures and abbreviations of the other compounds. Note that the light-emitting device 16 to the light-emitting device 21 are examples of an element in which a plurality of EL layers are connected in series between a pair of electrodes with a charge-generation layer therebetween (also referred to as a tandem element) and the composite material of a metal and an organic compound having a function of interacting with the metal as a tridentate or tetradentate ligand is used in the electron-injection layer (the electron-injection layer 114 in FIG. 31) that is in contact with the charge-generation layer (the charge-generation layer 115 in FIG. 31) between the EL layers.

[Chemical Formula 26]

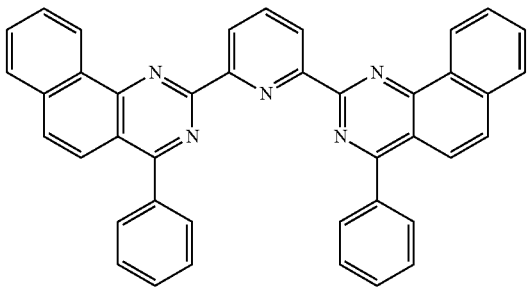

2,6(P-Bqn)2Py

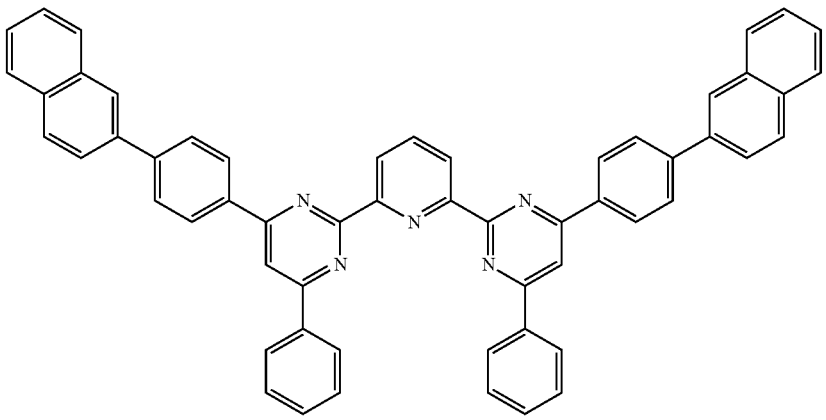

2,6(NP-PPm)2Py

TABLE 12

| | Layer | Numeral | Thickness (nm) | Material | Weight ratio |
|---|---|---|---|---|---|
| Light-emitting device 16 | Electrode | 102 | 200 | Al | — |
| | Electron-injection layer | 130 | 5 | NBPhen:Cu | 1:0.2 |
| | Electron-transport layer | 118(2) | 10 | NBPhen | — |
| | | 118(1) | 25 | 2mDBTBPDBq-II | — |
| | Light-emitting layer | 140 | 40 | 2mDBTBPDBq-II:PCBBiF: Ir(dmdppr-dmp)$_2$(dpm) | 0.75:0.25:0.08 |
| | Hole-transport layer | 119 | 20 | PCBBiF | — |
| | Charge-generation layer | 115 | 80 | DBT3P-II:MoO$_3$ | 1:0.5 |
| | Electron-injection layer | 114 | 5 | 2,6(P-Bqn)2Py:Cu | 1:0.2 |
| | Electron-transport layer | 113(2) | 15 | NBPhen | — |
| | | 113(1) | 10 | 2mDBTBPDBq-II | — |

TABLE 12-continued

|  | Layer | Numeral | Thickness (nm) | Material | Weight ratio |
|---|---|---|---|---|---|
|  | Light-emitting layer | 170 | 40 | 2mDBTBPDBq-II:PCBBiF: Ir(dmdppr-dmPp)$_2$(dpm) | 0.75:0.25:0.08 |
|  | Hole-transport layer | 112 | 20 | PCBBiF | — |
|  | Hole-injection layer | 111 | 25 | DBT3P-II:MoO$_3$ | 1:0.5 |
|  | Electrode | 101 | 110 | ITSO | — |
| Light-emitting device 17 | Electrode | 102 | 200 | Al | — |
|  | Electron-injection layer | 130 | 5 | NBPhen:Cu | 1:0.2 |
|  | Electron-transport layer | 118(2) | 10 | NBPhen | — |
|  |  | 118(1) | 25 | 2mDBTBPDBq-II | — |
|  | Light-emitting layer | 140 | 40 | 2mDBTBPDBq-II:PCBBiF: Ir(dmdppr-dmp)$_2$(dpm) | 0.75:0.25:0.08 |
|  | Hole-transport layer | 119 | 20 | PCBBiF | — |
|  | Charge-generation layer | 115 | 80 | DBT3P-II:MoO$_3$ | 1:0.5 |
|  | Electron-injection layer | 114 | 5 | 2,6(NP-PPm)2P:Cu | 1:0.2 |
|  | Electron-transport layer | 113(2) | 15 | NBPhen | — |
|  |  | 113(1) | 10 | 2mDBTBPDBq-II | — |
|  | Light-emitting layer | 170 | 40 | 2mDBTBPDBq-II:PCBBiF: Ir(dmdppr-dmp)$_2$(dpm) | 0.75:0.25:0.08 |
|  | Hole-transport layer | 112 | 20 | PCBBiF | — |
|  | Hole-injection layer | 111 | 25 | DBT3P-II:MoO$_3$ | 1:0.5 |
|  | Electrode | 101 | 110 | ITSO | — |
| Light-emitting device 18 | Electrode | 102 | 200 | Al | — |
|  | Electron-injection layer | 130 | 5 | NBPhen:Ag | 1:0.3 |
|  | Electron-transport layer | 118(2) | 10 | NBPhen | — |
|  |  | 118(1) | 25 | 2mDBTBPDBq-II | — |
|  | Light-emitting layer | 140 | 40 | 2mDBTBPDBq-II:PCBBiF: Ir(dmdppr-dmp)$_2$(dpm) | 0.75:0.25:0.08 |
|  | Hole-transport layer | 119 | 20 | PCBBiF | — |
|  | Charge-generation layer | 115 | 80 | DBT3P-II:MoO$_3$ | 1:0.5 |
|  | Electron-injection layer | 114(2) | 5 | tPy2P:Ag | 1:0.3 |
|  |  | 114(1) | 5 | NBPhen:Ag | 1:0.3 |
|  | Electron-transport layer | 113(2) | 10 | NBPhen | — |
|  |  | 113(1) | 10 | 2mDBTBPDBq-II | — |
|  | Light-emitting layer | 170 | 40 | 2mDBTBPDBq-II:PCBBiF: Ir(dmdppr-dmp)$_2$(dpm) | 0.75:0.25:0.08 |
|  | Hole-transport layer | 112 | 20 | PCBBiF | — |
|  | Hole-injection layer | 111 | 25 | DBT3P-II:MoO$_3$ | 1:0.5 |
|  | Electrode | 101 | 110 | ITSO | — |

TABLE 13

|  | Layer | Numeral | Thickness (nm) | Material | Weight ratio |
|---|---|---|---|---|---|
| Light-emitting device 19 | Electrode | 102 | 200 | Al | — |
|  | Electron-injection layer | 130 | 5 | NBPhen:Ag | 1:0.3 |
|  | Electron-transport layer | 118(2) | 10 | NBPhen | — |
|  |  | 118(1) | 25 | 2mDBTBPDBq-II | — |
|  | Light-emitting layer | 140 | 40 | 2mDBTBPDBq-II:PCBBiF: Ir(dmdppr-dmp)$_2$(dpm) | 0.75:0.25:0.08 |
|  | Hole-transport layer | 119 | 20 | PCBBiF | — |
|  | Charge-generation layer | 115 | 80 | DBT3P-II:MoO$_3$ | 1:0.5 |
|  | Electron-injection layer | 114(2) | 5 | tPy2P:In | 1:0.3 |
|  |  | 114(1) | 5 | NBPhen:Ag | 1:0.3 |
|  | Electron-transport layer | 113(2) | 15 | NBPhen | — |
|  |  | 113(1) | 10 | 2mDBTBPDBq-II | — |
|  | Light-emitting layer | 170 | 40 | 2mDBTBPDBq-II:PCBBiF: Ir(dmdppr-dmp)$_2$(dpm) | 0.75:0.25:0.08 |
|  | Hole-transport layer | 112 | 20 | PCBBiF | — |
|  | Hole-injection layer | 111 | 25 | DBT3P-II:MoO$_3$ | 1:0.5 |
|  | Electrode | 101 | 110 | ITSO | — |
| Light-emitting device 20 | Electrode | 102 | 200 | Al | — |
|  | Electron-injection layer | 130 | 5 | NBPhen:Cu | 1:0.2 |
|  | Electron-transport layer | 118(2) | 10 | NBPhen | — |
|  |  | 118(1) | 25 | 2mDBTBPDBq-II | — |
|  | Light-emitting layer | 140 | 40 | 2mDBTBPDBq-II:PCBBiF: Ir(dmdppr-dmp)$_2$(dpm) | 0.75:0.25:0.08 |
|  | Hole-transport layer | 119 | 20 | PCBBiF | — |
|  | Charge-generation layer | 115 | 70 | DBT3P-II:MoO$_3$ | 1:0.5 |
|  | Electron-injection layer | 114 | 5 | 6,6'(P-Bqn)2BPy:Cu | 1:0.2 |
|  | Electron-transport layer | 113(2) | 15 | NBPhen | — |
|  |  | 113(1) | 10 | 2mDBTBPDBq-II | — |
|  | Light-emitting layer | 170 | 40 | 2mDBTBPDBq-II:PCBBiF: Ir(dmdppr-dmp)$_2$(dpm) | 0.75:0.25:0.08 |

TABLE 13-continued

| | Layer | Numeral | Thickness (nm) | Material | Weight ratio |
|---|---|---|---|---|---|
| | Hole-transport layer | 112 | 20 | PCBBiF | — |
| | Hole-injection layer | 111 | 25 | DBT3P-II:MoO$_3$ | 1:0.5 |
| | Electrode | 101 | 110 | ITSO | — |
| Light-emitting device 21 | Electrode | 102 | 200 | Al | — |
| | Electron-injection layer | 130 | 5 | NBPhen:Cu | 1:0.2 |
| | Electron-transport layer | 118(2) | 10 | NBPhen | — |
| | | 118(1) | 25 | 2mDBTBPDBq-II | — |
| | Light-emitting layer | 140 | 40 | 2mDBTBPDBq-II:PCBBiF: Ir(dmdppr-dmp)$_2$(dpm) | 0.75:0.25:0.08 |
| | Hole-transport layer | 119 | 20 | PCBBiF | — |
| | Charge-generation layer | 115 | 70 | DBT3P-II:MoO$_3$ | 1:0.5 |
| | Electron-injection layer | 114 | 5 | tPy2P:Cu | 1:0.2 |
| | Electron-transport layer | 113(2) | 15 | NBPhen | — |
| | | 113(1) | 10 | 2mDBTBPDBq-II | — |
| | Light-emitting layer | 170 | 40 | 2mDBTBPDBq-II:PCBBiF: Ir(dmdppr-dmp)$_2$(dpm) | 0.75:0.25:0.08 |
| | Hole-transport layer | 112 | 20 | PCBBiF | — |
| | Hole-injection layer | 111 | 25 | DBT3P-II:MoO$_3$ | 1:0.5 |
| | Electrode | 101 | 110 | ITSO | — |

TABLE 14

| | Layer | Numeral | Thickness (nm) | Material | Weight ratio |
|---|---|---|---|---|---|
| Comparative light-emitting device 33 | Electrode | 102 | 200 | Al | — |
| | Electron-injection layer | 130 | 5 | NBPhen:Ag | 1:0.3 |
| | Electron-transport layer | 118(2) | 10 | NBPhen | — |
| | | 118(1) | 25 | 2mDBTBPDBq-II | — |
| | Light-emitting layer | 140 | 40 | 2mDBTBPDBq-II:PCBBiF: Ir(dmdppr-dmp)$_2$(dpm) | 0.75:0.25:0.08 |
| | Hole-transport layer | 119 | 20 | PCBBiF | — |
| | Charge-generation layer | 115 | 80 | DBT3P-II:MoO$_3$ | 1:0.5 |
| | Electron-injection layer | 114 | 0.2 | Li$_2$O | — |
| | Electron-transport layer | 113(2) | 20 | NBPhen | — |
| | | 113(1) | 10 | 2mDBTBPDBq-II | — |
| | Light-emitting layer | 170 | 40 | 2mDBTBPDBq-II:PCBBiF: Ir(dmdppr-dmp)$_2$(dpm) | 0.75:0.25:0.08 |
| | Hole-transport layer | 112 | 20 | PCBBiF | — |
| | Hole-injection layer | 111 | 25 | DBT3P-II:MoO$_3$ | 1:0.5 |
| | Electrode | 101 | 110 | ITSO | — |
| Comparative light-emitting device 34 | Electrode | 102 | 200 | Al | — |
| | Electron-injection layer | 130 | 5 | NBPhen:Ag | 1:0.3 |
| | Electron-transport layer | 118(2) | 10 | NBPhen | — |
| | | 118(1) | 25 | 2mDBTBPDBq-II | — |
| | Light-emitting layer | 140 | 40 | 2mDBTBPDBq-II:PCBBiF: Ir(dmdppr-dmp)$_2$(dpm) | 0.75:0.25:0.08 |
| | Hole-transport layer | 119 | 20 | PCBBiF | — |
| | Charge-generation layer | 115 | 80 | DBT3P-II:MoO$_3$ | 1:0.5 |
| | Electron-injection layer | 114 | — | — | — |
| | Electron-transport layer | 113(2) | 20 | NBPhen | — |
| | | 113(1) | 10 | 2mDBTBPDBq-II | — |
| | Light-emitting layer | 170 | 40 | 2mDBTBPDBq-II:PCBBiF: Ir(dmdppr-dmp)$_2$(dpm) | 0.75:0.25:0.08 |
| | Hole-transport layer | 112 | 20 | PCBBiF | — |
| | Hole-injection layer | 111 | 25 | DBT3P-II:MoO$_3$ | 1:0.5 |
| | Electrode | 101 | 110 | ITSO | — |

<<<Fabrication of Light-Emitting Device 16>>

As the electrode 101, an ITSO film was formed to a thickness of 110 nm over a glass substrate. The electrode area was set to 4 mm$^2$ (2 mm×2 mm).

Next, as the hole-injection layer 111, DBT3P-II and molybdenum oxide (MoO$_3$) were deposited over the electrode 101 by co-evaporation in a weight ratio (DBT3P-II: MoO$_3$) of 1:0.5 to a thickness of 25 nm.

Next, as the hole-transport layer 112, PCBBiF was deposited over the hole-injection layer 111 by evaporation to a thickness of 20 nm.

Then, as the light-emitting layer 170, 2mDBTBPDBq-II, PCBBiF, and Ir(dmdppr-dmp)$_2$(dpm) were deposited over the hole-transport layer 112 by co-evaporation in a weight ratio (2mDBTBPDBq-II: PCBBiF: Ir(dmdppr-dmp)$_2$(dpm)) of 0.75:0.25:0.08 to a thickness of 40 nm. Note that in the light-emitting layer 170, 2mDBTBPDBq-II and PCBBiF are host materials and Ir(dmdppr-dmp)$_2$(dpm) is a guest material (a phosphorescent compound).

Next, as an electron-transport layer 113(1), 2mDBTBPDBq-II was deposited over the light-emitting layer 170 by evaporation to a thickness of 10 nm. Then, NBPhen was deposited to a thickness of 15 nm as the electron-transport layer 113(2).

As the electron-injection layer 114, 2,2'-(pyridine-2,6-diyl)bis(4-phenylbenzo[h]quinazoline) (abbreviation: 2,6(P-Bqn)2Py) and Cu were deposited over the electron-transport layer 113(2) by co-evaporation in a weight ratio (2,6(P-Bqn) 2Py: Cu) of 1:0.2 to a thickness of 5 nm.

Then, as the charge-generation layer 115, DBT3P-II and MoO$_3$ were deposited over the electron-injection layer 114 by co-evaporation in a weight ratio (DBT3P-II: MoO$_3$) of 1:0.5 to a thickness of 80 nm.

Next, as the hole-transport layer 119, PCBBiF was deposited over the charge-generation layer 115 by evaporation to a thickness of 20 nm.

Then, as the light-emitting layer 140, 2mDBTBPDBq-II, PCBBiF, and Ir(dmdppr-dmp)$_2$(dpm) were deposited over the hole-transport layer 119 by co-evaporation in a weight ratio (2mDBTBPDBq-II: PCBBiF: Ir(dmdppr-dmp)$_2$(dpm)) of 0.75:0.25:0.08 to a thickness of 40 nm.

Next, as the electron-transport layer 118(1), 2mDBTBPDBq-II was deposited over the light-emitting layer 140 by evaporation to a thickness of 25 nm. Then, as the electron-transport layer 118(2), NBPhen was deposited over the electron-transport layer 118(1) by evaporation to a thickness of 10 nm.

As the electron-injection layer 130, NBPhen and Cu were deposited over the electron-transport layer 118(2) by co-evaporation in a weight ratio (NBPhen: Cu) of 1:0.2 to a thickness of 5 nm.

Then, as the electrode 102, Al was deposited over the electron-injection layer 130 by evaporation to a thickness of 200 nm.

Next, in a glove box containing a nitrogen atmosphere, the light-emitting device 16 was sealed by fixing a glass substrate for sealing to the glass substrate on which the organic materials were formed using a sealant for organic EL. Specifically, the sealant was applied to the periphery of the organic materials formed on the glass substrate, the glass substrate was bonded to the glass substrate for sealing, irradiation with ultraviolet light having a wavelength of 365 nm at 6 J/cm$^2$ was performed, and heat treatment at 80° C. for one hour was performed. Through the above steps, the light-emitting device 16 was obtained.

<<<Fabrication of Light-Emitting Device 17 to Light-Emitting Device 21, Comparative Light-Emitting Device 33, and Comparative Light-Emitting Device 34>>

The light-emitting device 17 to the light-emitting device 21, the comparative light-emitting device 33, and the comparative light-emitting device 34 were fabricated in a manner similar to that of the above-described light-emitting device 16. The details of the device structures are shown in Table 12 to Table 14; thus, the details of the fabrication methods are omitted.

<<<Measurement of Light-Emitting Devices>>

Next, the device characteristics of the fabricated light-emitting device 16 to light-emitting device 21, comparative light-emitting device 33, and comparative light-emitting device 34 were measured. Luminance and CIE chromaticity were measured with a luminance colorimeter (BM-5A manufactured by TOPCON TECHNOHOUSE CORPORATION), and electroluminescence spectra were measured with a multi-channel spectrometer (PMA-11 manufactured by Hamamatsu Photonics K.K.).

Figure 32:
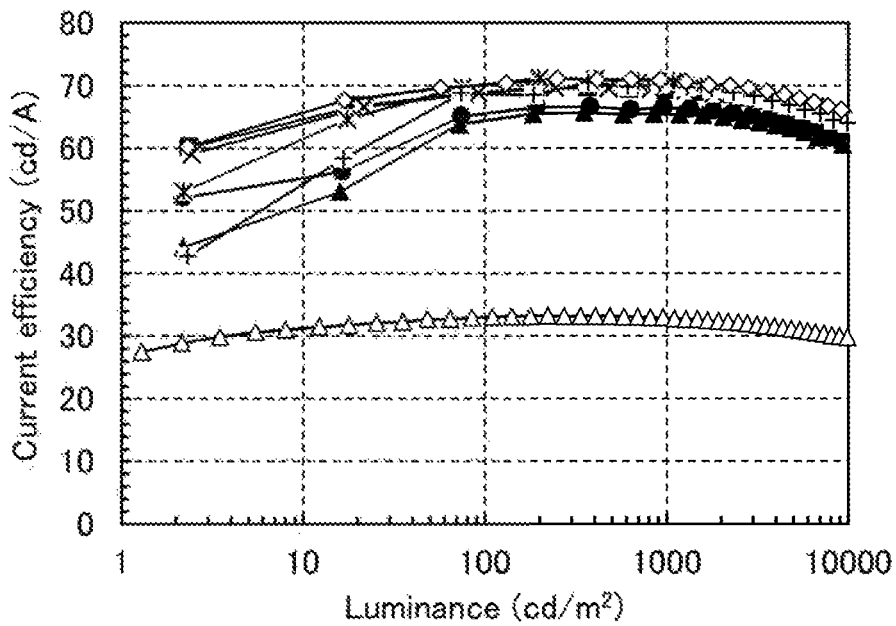
FIG. 32 is a diagram showing current efficiency-luminance characteristics of light-emitting devices in Example.
Figure 33:
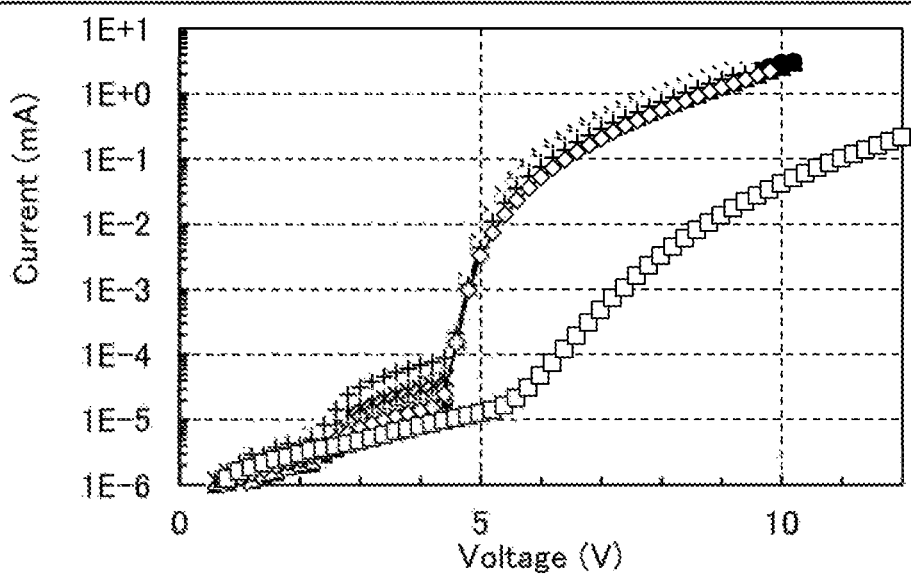
FIG. 33 is a diagram showing current-voltage characteristics of light-emitting devices in Example.
Figure 34:
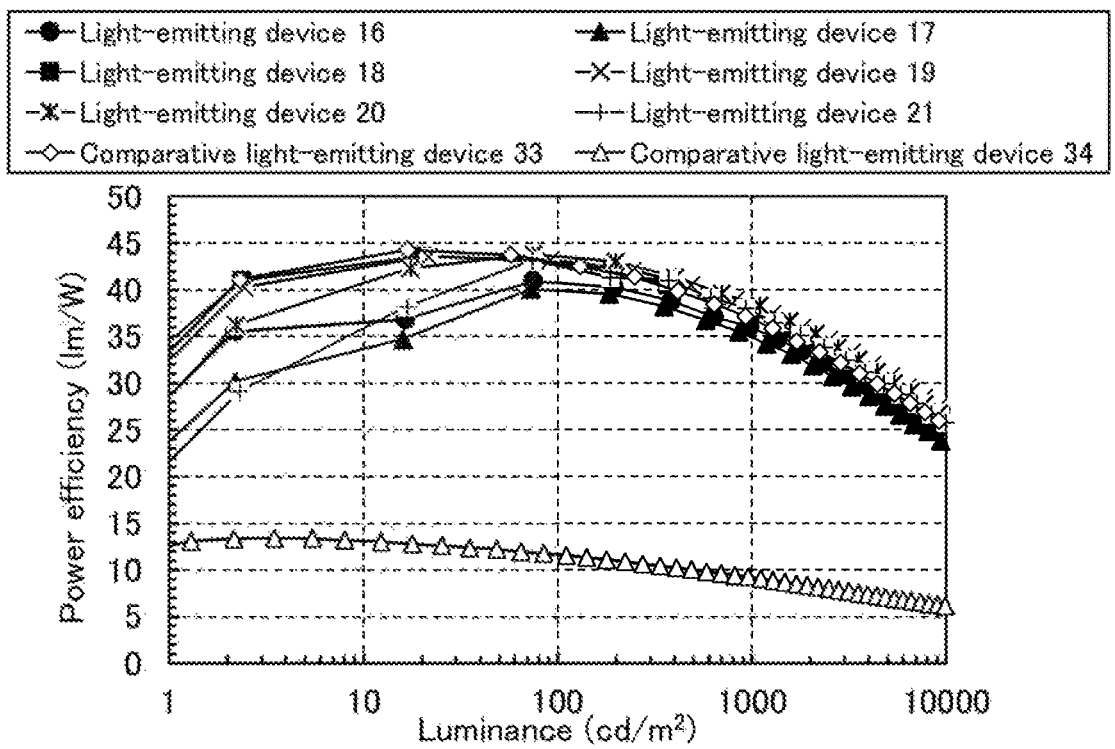
FIG. 34 is a diagram showing power efficiency-luminance characteristics of light-emitting devices in Example.
Figure 35:
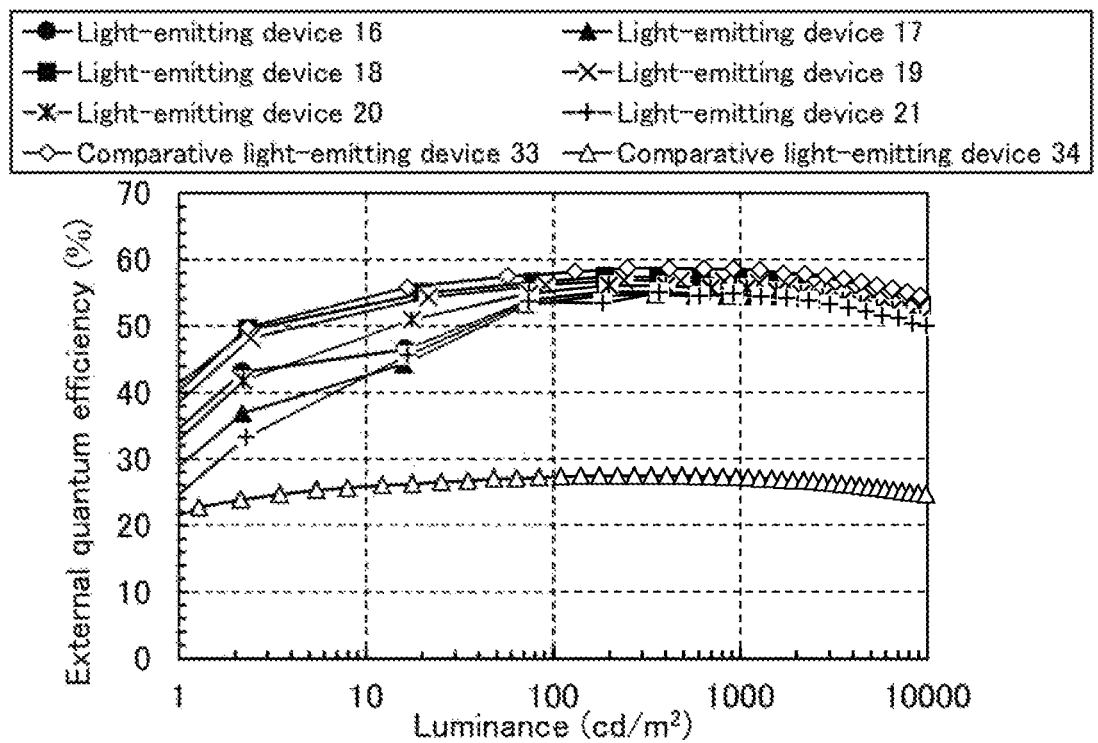
FIG. 35 is a diagram showing external quantum efficiency-luminance characteristics of light-emitting devices in Example.
Figure 36:
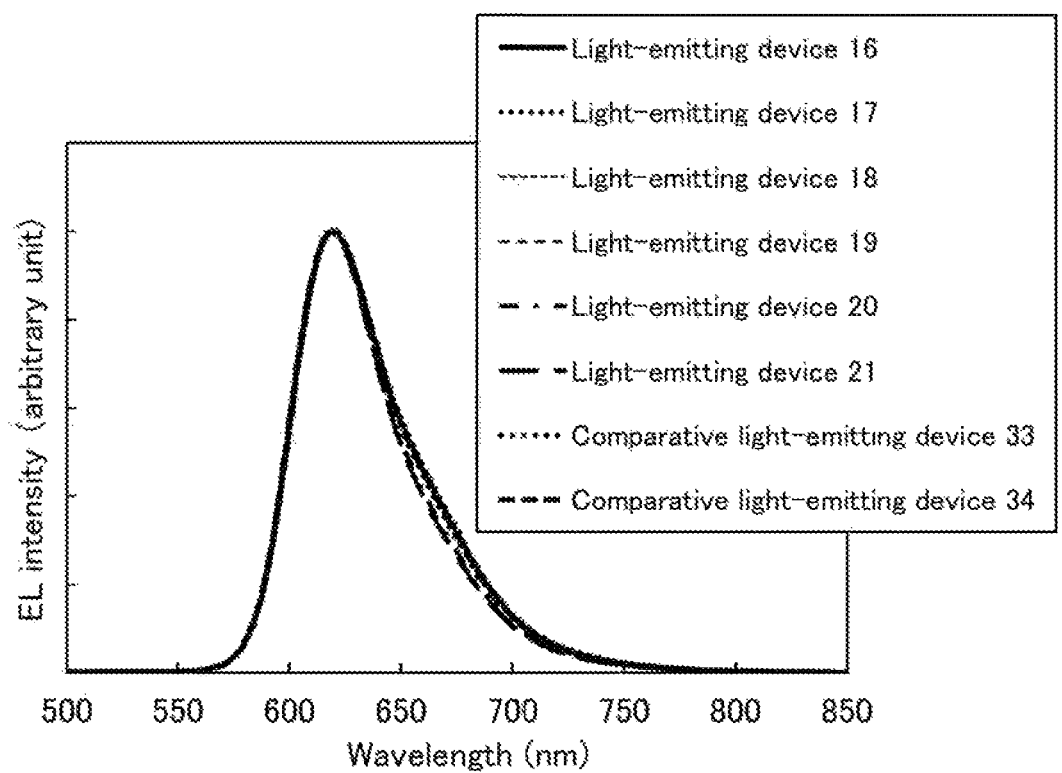
FIG. 36 is a diagram showing electroluminescence spectra of light-emitting devices in Example.

FIG. 32 shows the current efficiency-luminance characteristics of the fabricated light-emitting device 16 to the light-emitting device 21, the comparative light-emitting device 33, and the comparative light-emitting device 34, FIG. 33 shows the current-voltage characteristics thereof, FIG. 34 shows the power efficiency-luminance characteristics thereof, and FIG. 35 shows the external quantum efficiency-luminance characteristics thereof. Note that the measurement of the light-emitting devices was performed at room temperature (in an atmosphere maintained at 23° C.). FIG. 36 shows the electroluminescence spectra of the light-emitting devices through which current flows at a current density of 2.5 mA/cm$^2$. Note that the measurement was performed at room temperature.

Table 15 shows the device characteristics of the light-emitting device 16 to the light-emitting device 21, the comparative light-emitting device 33, and the comparative light-emitting device 34 at around 1000 cd/m$^2$.

TABLE 15

|  | Voltage (V) | Current density (mA/cm$^2$) | CIE Chromaticity (x, y) | Luminance (cd/m$^2$) | Current efficiency (cd/A) | Power efficiency (lm/W) | External quantum efficiency (%) |
|---|---|---|---|---|---|---|---|
| Light-emitting device 16 | 5.80 | 1.45 | (0.669, 0.331) | 967 | 66.5 | 36.0 | 55.0 |
| Light-emitting device 17 | 5.80 | 1.30 | (0.671, 0.329) | 852 | 65.4 | 35.4 | 54.5 |
| Light-emitting device 18 | 5.80 | 1.42 | (0.671, 0.329) | 981 | 69.2 | 37.5 | 57.0 |
| Light-emitting device 19 | 5.60 | 1.18 | (0.671, 0.328) | 822 | 69.4 | 39.0 | 56.6 |
| Light-emitting device 20 | 5.80 | 1.54 | (0.668, 0.332) | 1091 | 70.7 | 38.3 | 55.7 |
| Light-emitting device 21 | 5.80 | 1.31 | (0.672, 0.328) | 923 | 70.2 | 38.0 | 54.8 |
| Comparative light-emitting device 33 | 6.00 | 1.30 | (0.671, 0.328) | 923 | 70.9 | 37.1 | 58.6 |
| Comparative light emitting device 34 | 11.20 | 2.89 | (0.668, 0.331) | 952 | 32.9 | 9.2 | 27.2 |

As shown in FIG. 36, the light-emitting device 16 to the light-emitting device 21, the comparative light-emitting device 33, and the comparative light-emitting device 34 each have a peak wavelength of the electroluminescence spectrum at approximately 620 nm, and the light-emitting device 16 to the light-emitting device 21, the comparative light-emitting device 33, and the comparative light-emitting device 34 are found to exhibit light emission derived from Ir(dmdppr-dmp)$_2$(dpm), which is a guest material included in each light-emitting device.

Furthermore, as shown in FIG. 35 and Table 15, the light-emitting device 16 to the light-emitting device 21 each exhibited extremely high emission efficiency with an external quantum efficiency exceeding 50%, which is equivalent to that of the comparative light-emitting device 33. They also exhibited high current efficiency and high power efficiency as shown in FIG. 32 and FIG. 34. In contrast, the comparative light-emitting device 34 had low external quantum efficiency of 27.2%, which was not sufficient as the efficiency of a tandem element. These results show that the light-emitting device 16 to the light-emitting device 21 have an electron-injection property equivalent to that of the comparative light-emitting device 33 that uses Li$_2$O, which is a Li compound typically used for an electron-injection layer in contact with a charge-generation layer between EL layers.

As shown in FIG. 33 and Table 15, the light-emitting device 16 to the light-emitting device 21 showed favorable current-voltage characteristics with a low driving voltage as compared with the comparative light-emitting device 33 and the comparative light-emitting device 34. In addition, it was found that the comparative light-emitting device 34 had an extremely high driving voltage and had a problem with the electron-injection property from the charge-generation layer. These results reveal that the light-emitting device 16 to the light-emitting device 21 have more favorable electron-injection properties than the comparative light-emitting device 33 that uses Li$_2$O, which is a Li compound typically used for an electron-injection layer in contact with a charge-generation layer between EL layers. Accordingly, it was found that the composite material of a metal and an organic compound having a function of interacting with the metal as a tridentate or tetradentate ligand exhibited favorable driving voltage characteristics, even when used for the electron-injection layer in contact with the charge-generation layer between EL layers in a tandem element.

<Results of Constant-Current Driving Test of Light-Emitting Devices>

Figure 52:
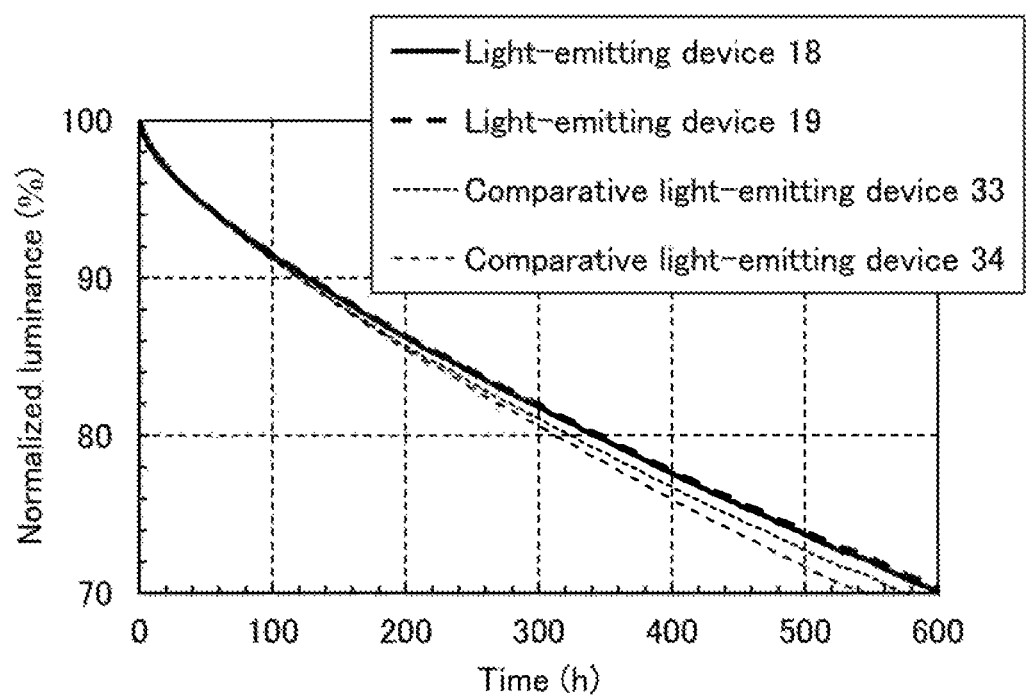
FIG. 52 is a diagram showing results of reliability tests of light-emitting devices in Example.

Next, the driving test at a constant current of 1.0 mA was performed on the light-emitting device 18, the light-emitting device 19, the comparative light-emitting device 33, and the comparative light-emitting device 34 at room temperature. The results are shown in FIG. 52. As shown in FIG. 52, the light-emitting device 18 and the light-emitting device 19 have more favorable reliability than the comparative light-emitting device 33 and the comparative light-emitting device 34. These results show that the light-emitting device 18 and the light-emitting device 19 have more favorable reliability than the comparative light-emitting device 33 that uses Li$_2$O, which is a Li compound typically used for an electron-injection layer in contact with a charge-generation layer between EL layers, and the comparative light-emitting device 34 that does not include the electron-injection layer in contact with the charge-generation layer. Accordingly, using the composite material of a metal and an organic compound having a function of interacting with the metal as a tridentate or tetradentate ligand for the electron-injection layer in contact with the charge-generation layer between EL layers can achieve a light-emitting device having high reliability.

From the above, the light-emitting device of one embodiment of the present invention has a favorable electron-injection property, and thus is a light-emitting device having a low driving voltage and high emission efficiency. In addition, the light-emitting device can use a material with a high work function, and thus has high moisture resistance and high reliability. The structures shown in this example can be used in appropriate combination with any of the other examples and embodiments.

Example 10

Described are examples of fabricating a light-emitting device 22 to a light-emitting device 25 as the light-emitting device of one embodiment of the present invention. A schematic cross-sectional view of the light-emitting devices fabricated in this example is shown in FIG. 1, and details of the device structures are shown in Table 16. The above examples and Embodiment 1 can be referred to for the structures and abbreviations of the other compounds. Note that the light-emitting device 22 to the light-emitting device 25 are light-emitting devices that use In, which is a metal belonging to Group 13, as a metal used in the composite material of a metal and an organic compound having a function of interacting with the metal as a tridentate or tetradentate ligand.

TABLE 16

|  | Layer | Numeral | Thickness (nm) | Material | Weight ratio |
|---|---|---|---|---|---|
| Light-emitting device 22 | Electrode | 102 | 200 | Al | — |
|  | Electron-injection layer | 130 | 5 | tPy2P:In | 1:0.4 |
|  | Electron-transport layer | 118(2) | 15 | NBPhen | — |
|  |  | 118(1) | 20 | 2mDBTBPDBq-II | — |
|  | Light-emitting layer | 140 | 40 | 2mDBTBPDBq-II:PCBBiF: Ir(dmdppr-dmp)$_2$(dpm) | 0.75:0.25:0.08 |
|  | Hole-transport layer | 112 | 20 | PCBBiF | — |
|  | Hole-injection layer | 111 | 25 | DBT3P-II:MoO$_3$ | 1:0.5 |
|  | Anode | 101 | 110 | ITSO | — |

TABLE 16-continued

| | Layer | Numeral | Thickness (nm) | Material | Weight ratio |
|---|---|---|---|---|---|
| Light-emitting device 23 | Electrode | 102 | 200 | Al | — |
| | Electron-injection layer | 130(2) | 5 | 2Py3Tzn:In | 1:0.6 |
| | | 130(1) | 5 | NBPhen:Ag | 1:0.3 |
| | Electron-transport layer | 118(2) | 10 | NBPhen | — |
| | | 118(1) | 20 | 2mDBTBPDBq-II | — |
| | Light-emitting layer | 140 | 40 | 2mDBTBPDBq-II:PCBBiF:Ir(dmdppr-dmp)$_2$(dpm) | 0.75:0.25:0.08 |
| | Hole-transport layer | 112 | 20 | PCBBiF | — |
| | Hole-injection layer | 111 | 25 | DBT3P-II:MoO$_3$ | 1:0.5 |
| | Anode | 101 | 110 | ITSO | — |
| Light-emitting device 24 | Electrode | 102 | 200 | Al | — |
| | Electron-injection layer | 130(2) | 5 | 2,6(P-Bqn)2Py:In | 1:0.3 |
| | | 130(1) | 5 | NBPhen:Ag | 1:0.3 |
| | Electron-transport layer | 118(2) | 10 | NBPhen | — |
| | | 118(1) | 20 | 2mDBTBPDBq-II | — |
| | Light-emitting layer | 140 | 40 | 2mDBTBPDBq-II:PCBBiF:Ir(dmdppr-dmp)$_2$(dpm) | 0.75:0.25:0.08 |
| | Hole-transport layer | 112 | 20 | PCBBiF | — |
| | Hole-injection layer | 111 | 25 | DBT3P-II:MoO$_3$ | 1:0.5 |
| | Anode | 101 | 110 | ITSO | — |
| Light-emitting device 25 | Electrode | 102 | 200 | Al | — |
| | Electron-injection layer | 130(2) | 5 | 2,6(NP-PPm)2Py:In | 1:0.3 |
| | | 130(1) | 5 | NBPhen:Ag | 1:0.3 |
| | Electron-transport layer | 118(2) | 10 | NBPhen | — |
| | | 118(1) | 20 | 2mDBTBPDBq-II | — |
| | Light-emitting layer | 140 | 40 | 2mDBTBPDBq-II:PCBBiF:Ir(dmdppr-dmp)$_2$(dpm) | 0.75:0.25:0.08 |
| | Hole-transport layer | 112 | 20 | PCBBiF | — |
| | Hole-injection layer | 111 | 25 | DBT3P-II:MoO$_3$ | 1:0.5 |
| | Anode | 101 | 110 | ITSO | — |

<Fabrication of Light-Emitting Device 22>>

The light-emitting device 22 was fabricated through the steps similar to those for the comparative light-emitting device 1 except for the formation step of the electron-injection layer 130.

As the electron-injection layer 130 of the light-emitting device 22, tPy2P and In were deposited over the electron-transport layer 118(2) by co-evaporation in a weight ratio (tPy2P: In) of 1:0.4 to a thickness of 5 nm.

<<<Fabrication of Light-Emitting Device 23>>

The light-emitting device 23 was fabricated through the steps similar to those for the comparative light-emitting device 1 except for the formation step of the electron-transport layer 118(2) and the electron-injection layer 130.

As the electron-transport layer 118(2) of the light-emitting device 23, NBPhen was deposited over the electron-transport layer 118(1) by evaporation to a thickness of 10 nm.

Next, as an electron-injection layer 130(1), NBPhen and Ag were deposited over the electron-transport layer 118(2) by co-evaporation in a weight ratio (NBPhen: Ag) of 1:0.3 to a thickness of 5 nm. Then, as the electron-injection layer 130(2), 2Py3Tzn and In were deposited over the electron-injection layer 130(1) by co-evaporation in a weight ratio (2Py3Tzn: In) of 1:0.6 to a thickness of 5 nm.

<<<Fabrication of Light-Emitting Device 24 and Light-Emitting Device 25>>

The light-emitting device 24 and the light-emitting device 25 were fabricated through steps similar to those for the light-emitting device 23 except for the formation step of the electron-injection layer 130(2).

<Fabrication of Light-Emitting Device 24>

As the electron-injection layer 130(2) of the light-emitting device 24, 2,6(P-Bqn)2Py and In were deposited over the electron-transport layer 130(1) by co-evaporation in a weight ratio of (2,6(P-Bqn)2Py: In) of 1:0.3 to a thickness of 5 nm.

<Fabrication of Light-Emitting Device 25>

As the electron-injection layer 130(2) of the light-emitting device 25, 2,6(NP-PPm)2Py and In were deposited over the electron-transport layer 130(1) by co-evaporation in a weight ratio of (2,6(NP-PPm)2Py: In) of 1:0.3 to a thickness of 5 nm.

Note that in the light-emitting device 22 to the light-emitting device 25, a cathode was fabricated in a manner similar to that of the comparative light-emitting device 1, and then heat treatment was performed at 80° C. in an air for one hour without sealing.

<<Measurement of Light-Emitting Devices>>

The device characteristics of the fabricated light-emitting device 22 to the light-emitting device 25 were measured. Luminance and CIE chromaticity were measured with a luminance colorimeter (BM-5A manufactured by TOPCON TECHNOHOUSE CORPORATION), and electroluminescence spectra were measured with a multi-channel spectrometer (PMA-11 manufactured by Hamamatsu Photonics K.K.).

Figure 37:
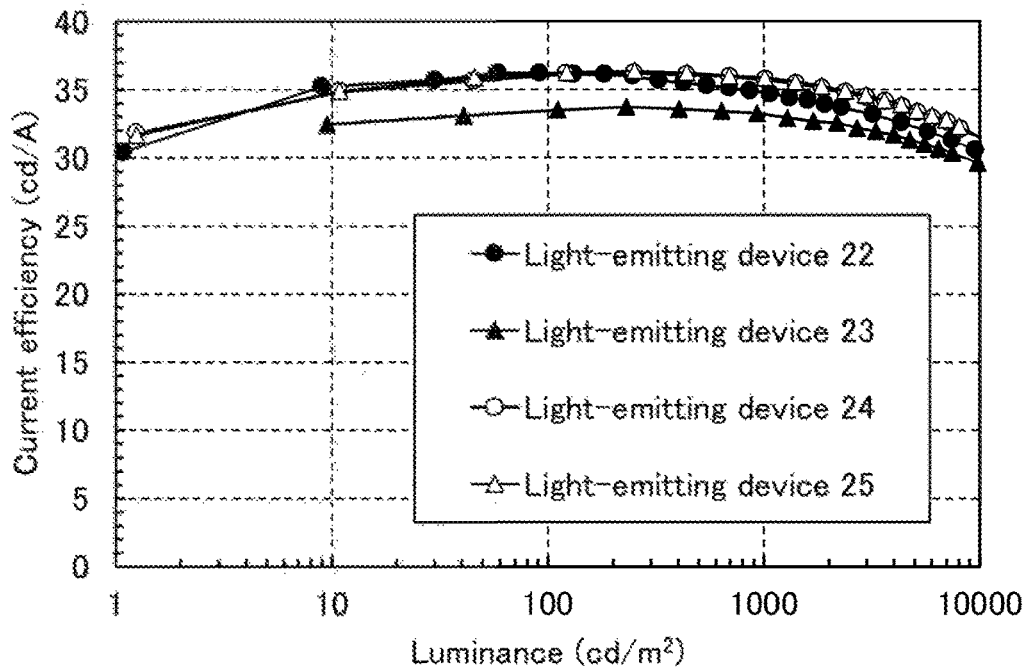
FIG. 37 is a diagram showing current efficiency-luminance characteristics of light-emitting devices in Example.
Figure 38:
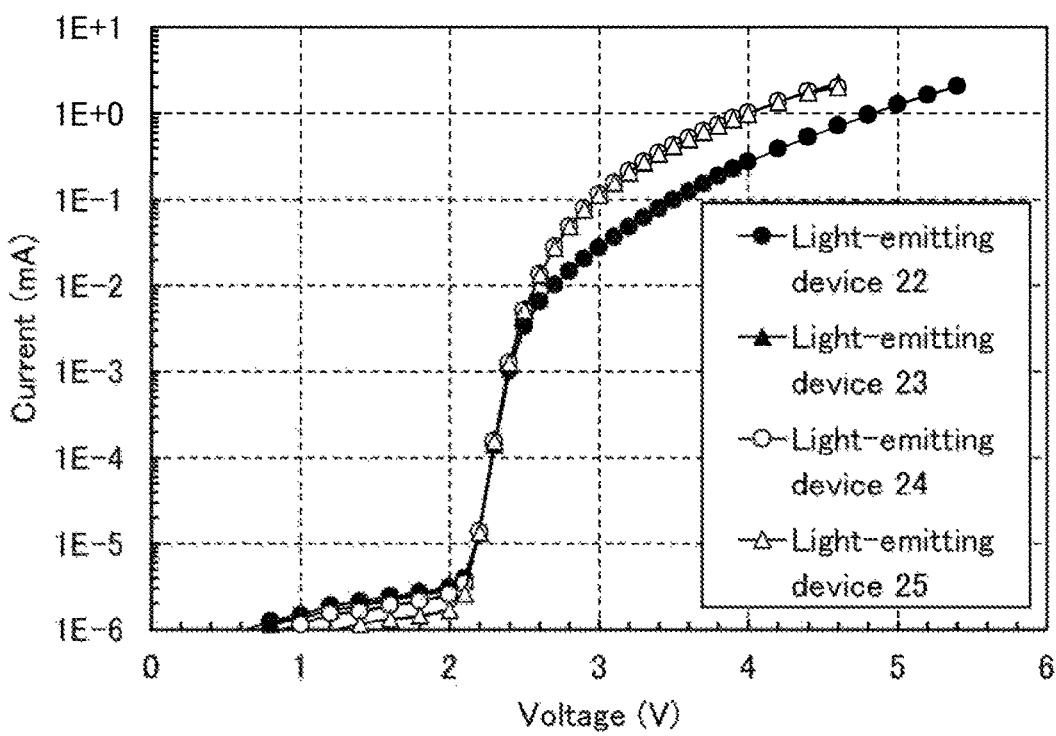
FIG. 38 is a diagram showing current-voltage characteristics of light-emitting devices in Example.
Figure 39:
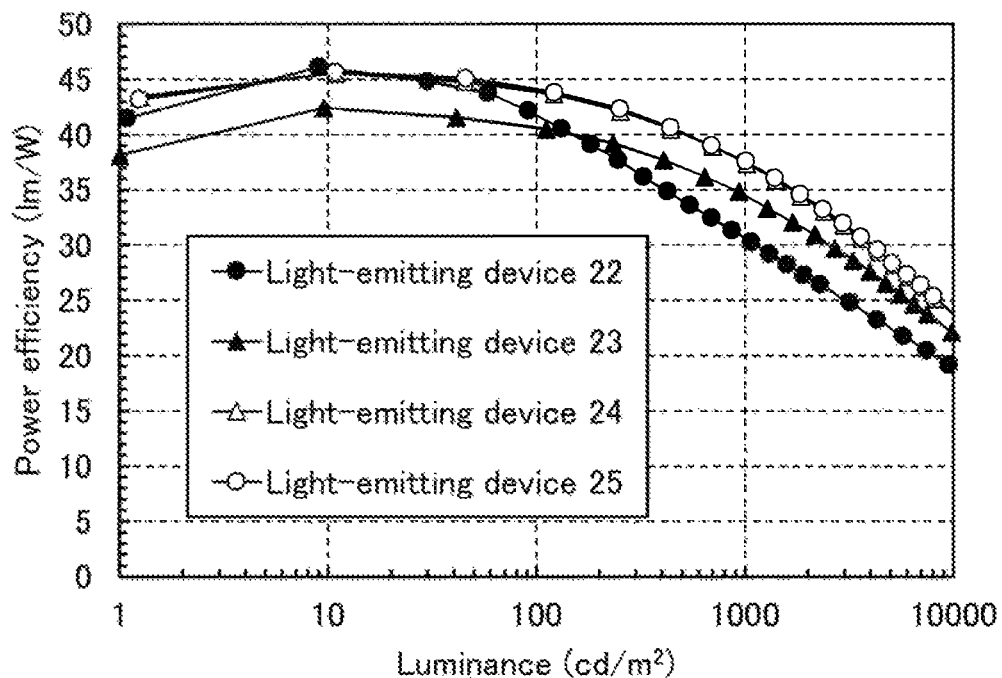
FIG. 39 is a diagram showing power efficiency-luminance characteristics of light-emitting devices in Example.
Figure 40:
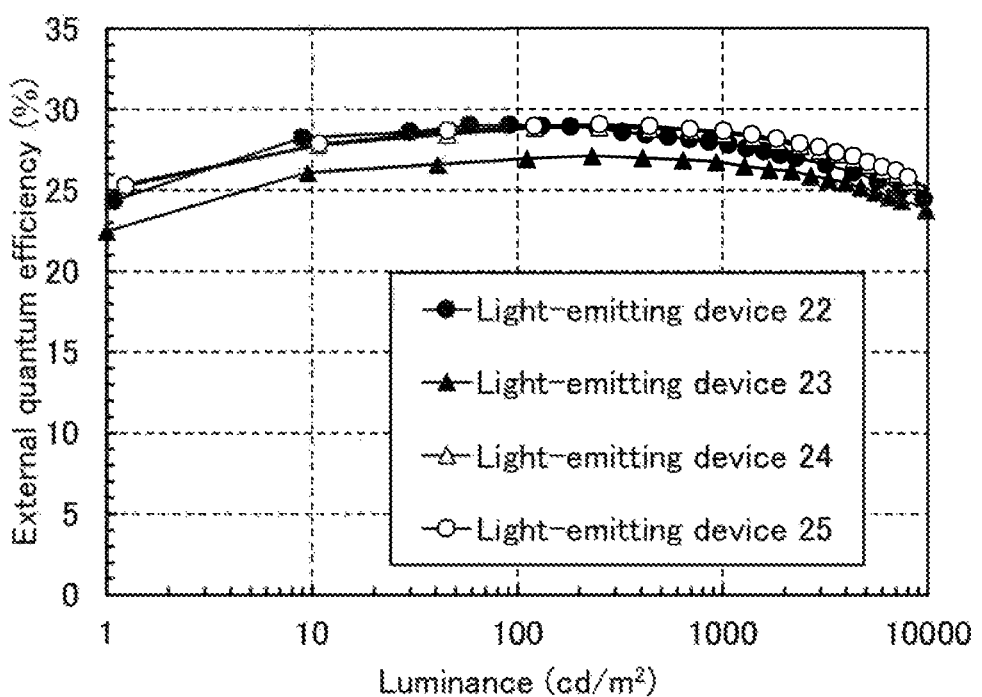
FIG. 40 is a diagram showing external quantum efficiency-luminance characteristics of light-emitting devices in Example.
Figure 41:
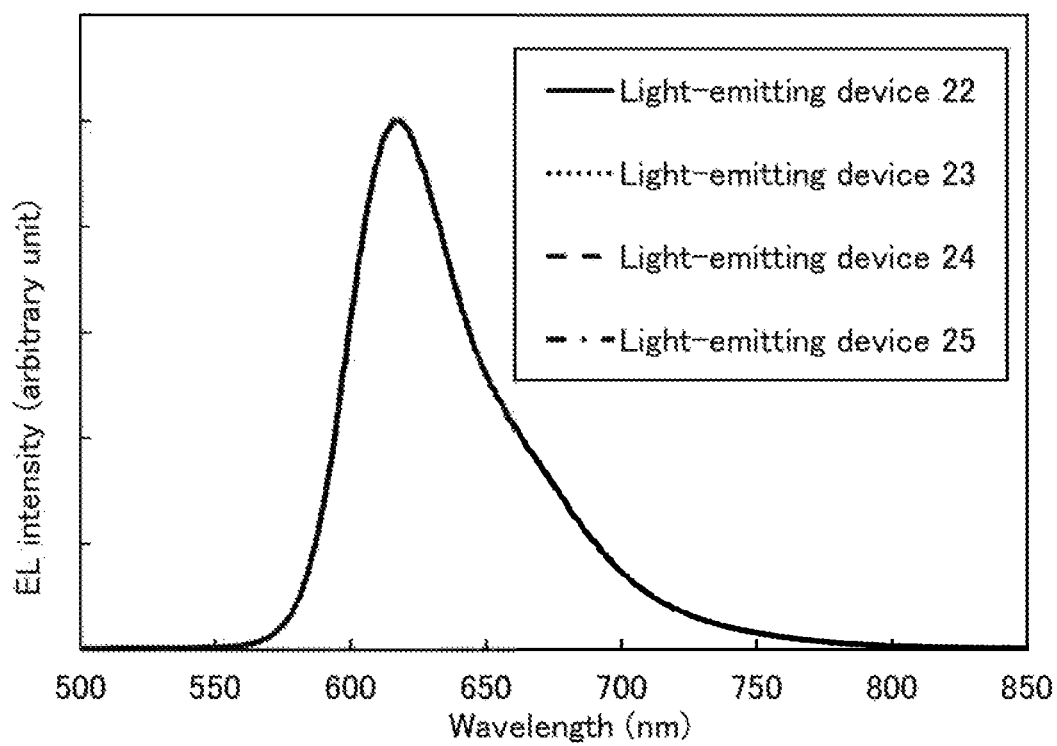
FIG. 41 is a diagram showing electroluminescence spectra of light-emitting devices in Example.

FIG. 37 shows the current efficiency-luminance characteristics of the fabricated light-emitting device 22 to the light-emitting device 25, FIG. 38 shows the current-voltage characteristics thereof, FIG. 39 shows the power efficiency-luminance characteristics thereof, and FIG. 40 shows the external quantum efficiency-luminance characteristics thereof. Note that the measurement of the light-emitting devices was performed at room temperature (in an atmosphere maintained at 23° C.). FIG. 41 shows the electroluminescence spectra of the light-emitting devices through which current flows at a current density of 2.5 mA/cm$^2$. Note that the measurement was performed at room temperature.

Table 17 shows the device characteristics of the light-emitting device 22 to the light-emitting device 25 at around 1000 cd/m$^2$.

TABLE 17

| | Voltage (V) | Current density (mA/cm$^2$) | CIE Chromaticity (x, y) | Luminance (cd/m$^2$) | Current efficiency (cd/A) | Power efficiency (lm/W) | External quantum efficiency (%) |
|---|---|---|---|---|---|---|---|
| Light-emitting device 22 | 3.60 | 3.09 | (0.664, 0.335) | 1073 | 34.7 | 30.3 | 27.8 |
| Light-emitting device 23 | 3.00 | 2.80 | (0.665, 0.334) | 933 | 33.3 | 34.8 | 26.8 |
| Light-emitting device 24 | 3.00 | 2.85 | (0.665, 0.335) | 1017 | 35.7 | 37.4 | 28.5 |
| Light-emitting device 25 | 3.00 | 2.83 | (0.665, 0.335) | 1013 | 35.8 | 37.5 | 28.6 |

As shown in FIG. 41, the electroluminescence spectra of the light-emitting device 22 to the light-emitting device 25 each have a peak wavelength of the electroluminescence spectrum at approximately 615 nm, which shows that the light-emitting device 22 to the light-emitting device 25 exhibit light emission derived from Ir(dmdppr-dmp)$_2$(dpm), which is a guest material included in each light-emitting device.

Furthermore, as shown in FIG. 40 and Table 17, the light-emitting device 22 to the light-emitting device 25 each exhibited extremely high emission efficiency with external quantum efficiency exceeding 25%. They also exhibited high current efficiency and high power efficiency as shown in FIG. 37 and FIG. 39. Thus, it was found that In was suitable as the metal used for the composite material of a metal and an organic compound having a function of interacting with the metal as a tridentate or tetradentate ligand.

As shown in FIG. 38, the light-emitting device 22 to the light-emitting device 25 exhibited favorable current-voltage characteristics. Thus, it was found that In was suitable as a metal used for the composite material of a metal and an organic compound having a function of interacting with the metal as a tridentate or tetradentate ligand.

From the above, the light-emitting device of one embodiment of the present invention has a favorable electron-injection property, and thus is a light-emitting device having a low driving voltage and high emission efficiency. In addition, the light-emitting device can use a material with a high work function, and thus has high moisture resistance. The structures shown in this example can be used in appropriate combination with any of the other examples and embodiments.

Example 11

Described are examples of fabricating a light-emitting device 26 to a light-emitting device 28 that are examples of one embodiment of the present invention. A schematic cross-sectional view of the light-emitting devices fabricated in this example is shown in FIG. 1, and details of the device structures are shown in Table 18. Chemical formulae of organic compounds used in this example are shown below. The above examples and Embodiment 1 can be referred to for the structures and abbreviations of the other compounds. Note that the light-emitting device 26 to the light-emitting device 28 are examples of the light-emitting device that uses an organic compound having a triazine skeleton or a bipyridine skeleton as the organic compound used for the composite material of a metal and an organic compound having a function of interacting with the metal as a tridentate or tetradentate ligand. Note that in this example, the composite material of a metal and an organic compound having a function of interacting with the metal as a tridentate or tetradentate ligand is used for the electron-injection layer 130.

[Chemical Formula 27]

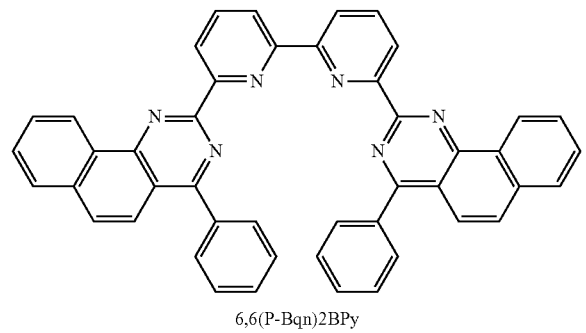

6,6(P-Bqn)2BPy

TABLE 18

| | Layer | Numeral | Thickness (nm) | Material | Weight ratio |
|---|---|---|---|---|---|
| Light-emitting device 26 | Electrode | 102 | 200 | Al | — |
| | Electron-injection layer | 130 | 5 | PPm3Tzn:Cu | 1:0.2 |
| | Electron-transport layer | 118(2) | 15 | NBPhen | — |
| | | 118(1) | 20 | 2mDBTBPDBq-II | — |
| | Light-emitting layer | 140 | 40 | 2mDBTBPDBq-II:PCBBiF: Ir(dmdppr-dmp)$_2$(dpm) | 0.75:0.25:0.08 |
| | Hole-transport layer | 112 | 20 | PCBBiF | — |
| | Hole-injection layer | 111 | 25 | DBT3P-II:MoO$_3$ | 1:0.5 |
| | Anode | 101 | 110 | ITSO | — |

TABLE 18-continued

| Layer | | Numeral | Thickness (nm) | Material | Weight ratio |
|---|---|---|---|---|---|
| Light-emitting device 27 | Electrode | 102 | 200 | Al | — |
| | Electron-injection layer | 130 | 5 | 6,6'(P-Bqn)2BPy:Ag | 1:0.3 |
| | Electron-transport layer | 118(2) | 15 | NBPhen | — |
| | | 118(1) | 20 | 2mDBTBPDBq-II | — |
| | Light-emitting layer | 140 | 40 | 2mDBTBPDBq-II:PCBBiF:Ir(dmdppr-dmp)$_2$(dpm) | 0.75:0.25:0.08 |
| | Hole-transport layer | 112 | 20 | PCBBiF | — |
| | Hole-injection layer | 111 | 25 | DBT3P-II:MoO$_3$ | 1:0.5 |
| | Anode | 101 | 110 | ITSO | — |
| Light-emitting device 28 | Electrode | 102 | 200 | Al | — |
| | Electron-injection layer | 130 | 5 | 6,6'(P-Bqn)2BPy:Cu | 1:0.2 |
| | Electron-transport layer | 118(2) | 15 | NBPhen | — |
| | | 118(1) | 20 | 2mDBTBPDBq-II | — |
| | Light-emitting layer | 140 | 40 | 2mDBTBPDBq-II:PCBBiF:Ir(dmdppr-dmp)$_2$(dpm) | 0.75:0.25:0.08 |
| | Hole-transport layer | 112 | 20 | PCBBiF | — |
| | Hole-injection layer | 111 | 25 | DBT3P-II:MoO$_3$ | 1:0.5 |
| | Anode | 101 | 110 | ITSO | — |

<<Fabrication of Light-Emitting Device 26 to Light-Emitting Device 28>>

The light-emitting device 26 to the light-emitting device 28 were fabricated through the steps similar to those for the comparative light-emitting device 1 except for the formation step of the electron-injection layer 130.

As the electron-injection layer 130 of the light-emitting device 26, PPm3Tzn and Cu were deposited over the electron-transport layer 118(2) by co-evaporation in a weight ratio (PPm3Tzn: Cu) of 1:0.2 to a thickness of 5 nm. Note that PPm3Tzn is an example of an organic compound having a triazine skeleton. Furthermore, it can be said that PPm3Tzn is an organic compound having a pyrimidine skeleton.

As the electron-injection layer 130 of the light-emitting device 27, 2,2'-(2,2'-bipyridine-6,6'-diyl)bis(4-phenylbenzo[h]quinazoline (abbreviation: 6,6'(P-Bqn)2BPy) and Ag were deposited over the electron-transport layer 118(2) in a weight ratio (6,6'(P-Bqn)2BPy: Ag) of 1:0.3 to a thickness of 5 nm. Note that 6,6'(P-Bqn)2BPy is an example of an organic compound having a bipyridine skeleton. In addition, it can be said that 6,6'(P-Bqn)2BPy is an organic compound having a quinazoline skeleton.

As the electron-injection layer 130 of the light-emitting device 28, 6,6'(P-Bqn)2BPy and Cu were deposited over the electron-transport layer 118(2) in a weight ratio (6,6'(P-Bqn)2BPy: Cu) of 1:0.3 to a thickness of 5 nm.

Note that in the light-emitting device 26 to the light-emitting device 28, a cathode was fabricated in a manner similar to that of the comparative light-emitting device 1, and then heat treatment was performed at 80° C. in an air for one hour without sealing.

<<<Measurement of Light-Emitting Devices>>>

The device characteristics of the fabricated light-emitting device 26 to light-emitting device 28 were measured. Luminance and CIE chromaticity were measured with a luminance colorimeter (BM-5A manufactured by TOPCON TECHNOHOUSE CORPORATION), and electroluminescence spectra were measured with a multi-channel spectrometer (PMA-11 manufactured by Hamamatsu Photonics K.K.).

Figure 42:
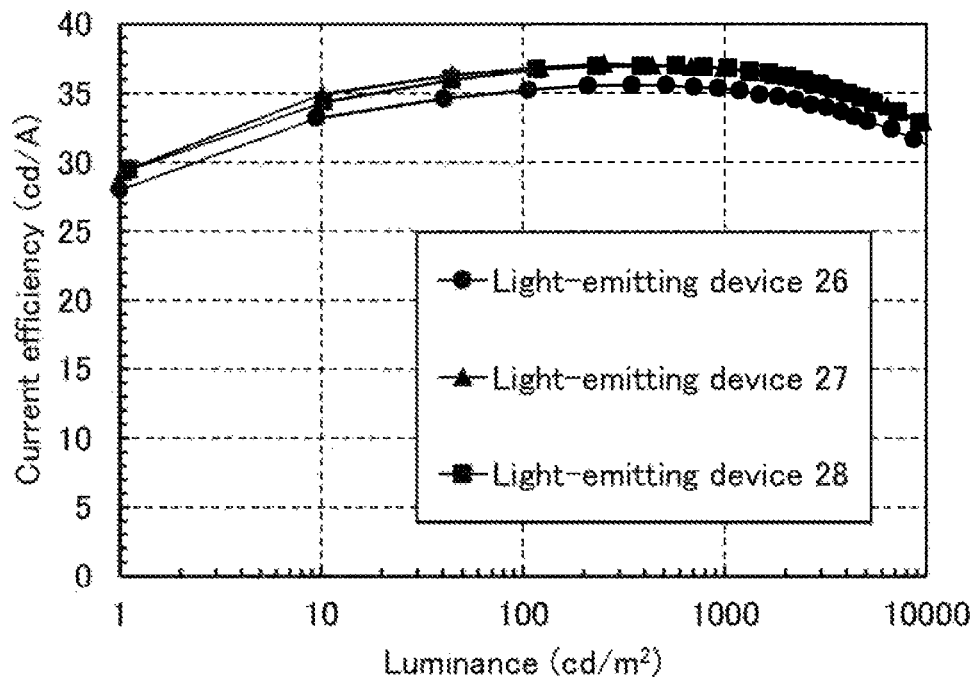
FIG. 42 is a diagram showing current efficiency-luminance characteristics of light-emitting devices in Example.
Figure 43:
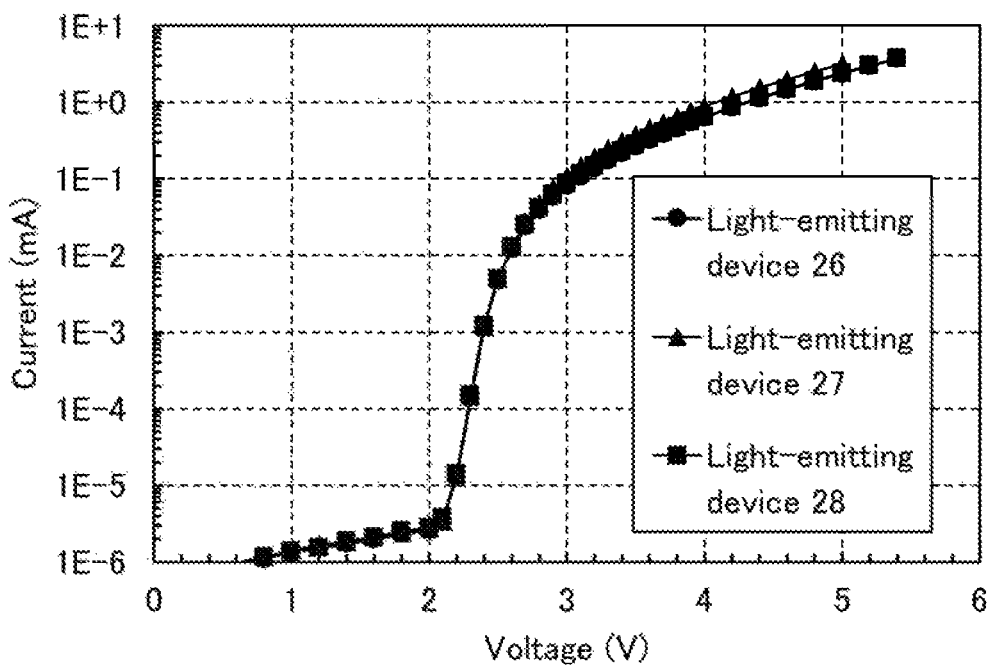
FIG. 43 is a diagram showing current-voltage characteristics of light-emitting devices in Example.
Figure 44:
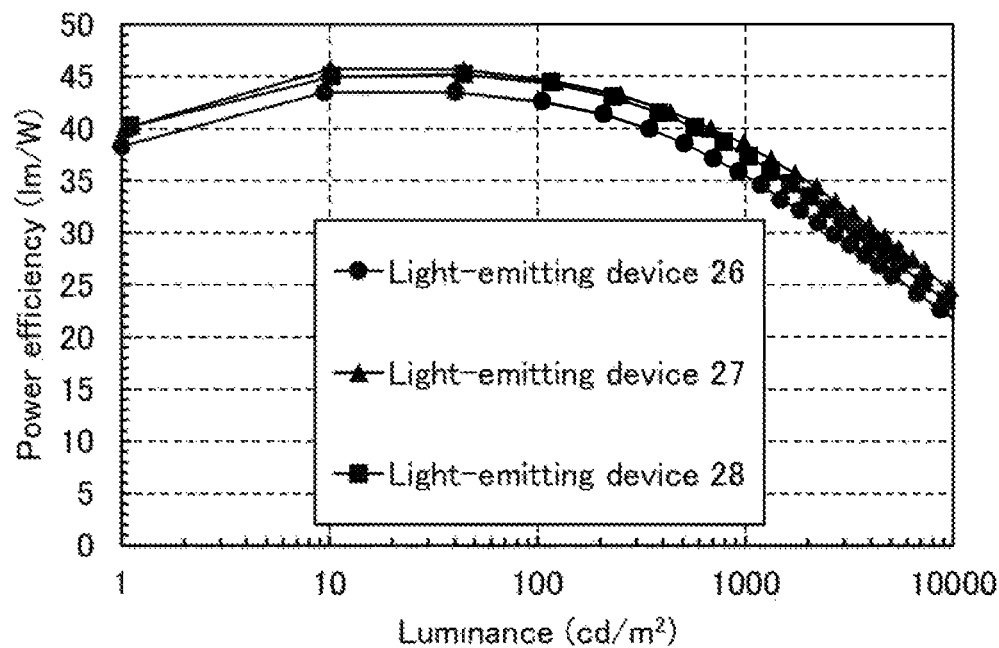
FIG. 44 is a diagram showing power efficiency-luminance characteristics of light-emitting devices in Example.
Figure 45:
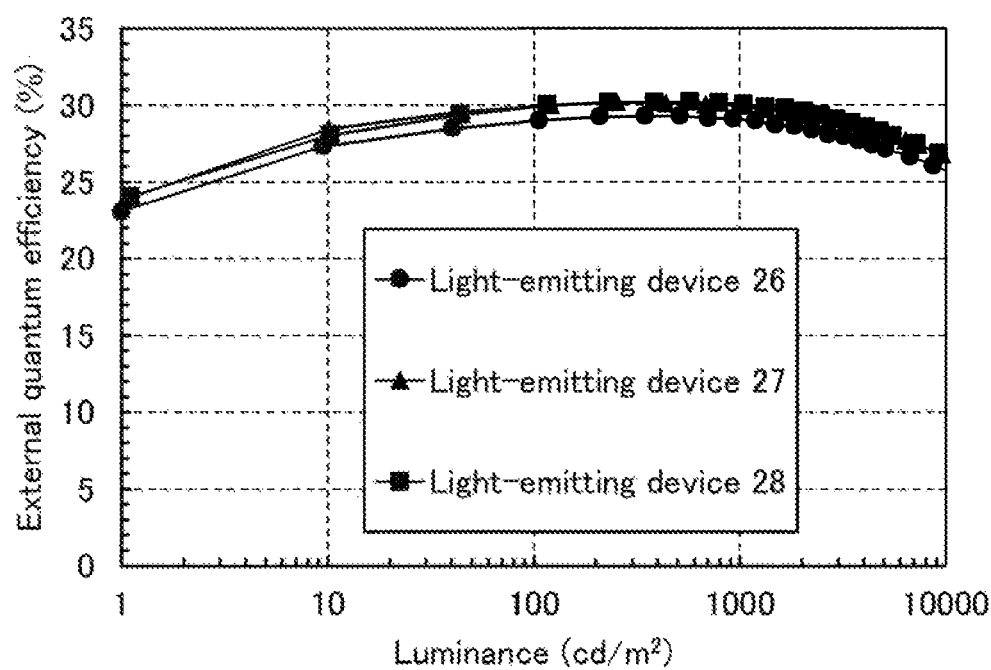
FIG. 45 is a diagram showing external quantum efficiency-luminance characteristics of light-emitting devices in Example.
Figure 46:
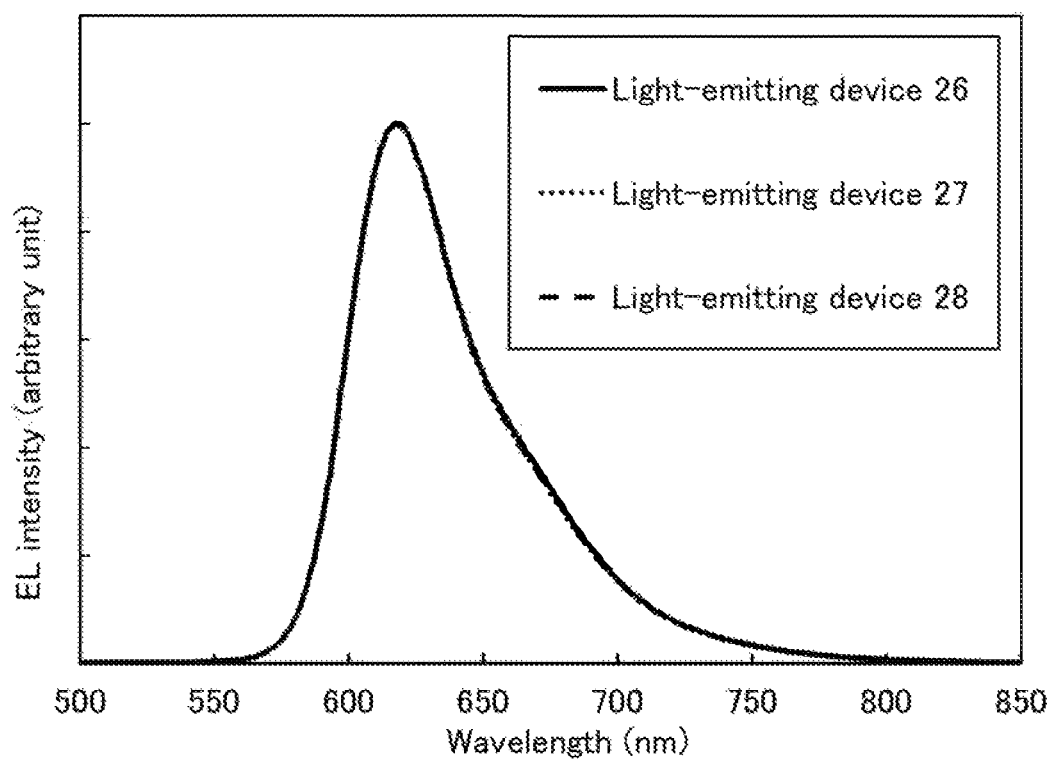
FIG. 46 is a diagram showing electroluminescence spectra of light-emitting devices in Example.

FIG. 42 shows the current efficiency-luminance characteristics of the fabricated light-emitting device 26 to light-emitting device 28, FIG. 43 shows the current-voltage characteristics thereof, FIG. 44 shows the power efficiency-luminance characteristics thereof, and FIG. 45 shows the external quantum efficiency-luminance characteristics thereof. Note that the measurement of the light-emitting devices was performed at room temperature (in an atmosphere maintained at 23° C.). FIG. 46 shows the electroluminescence spectra of the light-emitting devices through which current flows at a current density of 2.5 mA/cm$^2$. Note that the measurement was performed at room temperature.

Table 19 shows the device characteristics of the light-emitting device 26 to the light-emitting device 28 at around 1000 cd/m$^2$.

TABLE 19

| | Voltage (V) | Current density (mA/cm$^2$) | CIE Chromaticity (x, y) | Luminance (cd/m$^2$) | Current efficiency (cd/A) | Power efficiency (lm/W) | External quantum efficiency (%) |
|---|---|---|---|---|---|---|---|
| Light-emitting device 26 | 3.10 | 2.64 | (0.666, 0.333) | 932 | 35.3 | 35.8 | 29.1 |
| Light-emitting device 27 | 3.00 | 2.67 | (0.665, 0.334) | 983 | 36.8 | 38.5 | 29.9 |
| Light-emitting device 28 | 3.10 | 2.85 | (0.667, 0.333) | 1048 | 36.8 | 37.3 | 30.0 |

As shown in FIG. 46, the electroluminescence spectra of the light-emitting device 26 to the light-emitting device 28 each have a peak wavelength of the electroluminescence spectrum at approximately 618 nm, which shows that the light-emitting device 26 to the light-emitting device 28 exhibit light emission derived from Ir(dmdppr-dmp)$_2$(dpm), which is a guest material included in each light-emitting device.

Furthermore, as shown in FIG. 45 and Table 19, the light-emitting device 26 to the light-emitting device 28 each exhibited extremely high emission efficiency with external quantum efficiency exceeding 29%. They also exhibited high current efficiency and high power efficiency as shown in FIG. 42 and FIG. 44. Thus, it was found that the organic compound having a triazine skeleton (or a pyrimidine skeleton) or a bipyridine skeleton (or a quinazoline skeleton) was suitable as the organic compound used for the composite material of a metal and an organic compound having a function of interacting with the metal as a tridentate or tetradentate ligand.

As shown in FIG. 43, the light-emitting device 26 to the light-emitting device 28 exhibited favorable current-voltage characteristics. Thus, it was found that the organic compound having a triazine skeleton (or a pyrimidine skeleton) or a bipyridine skeleton (or a quinazoline skeleton) was suitable as the organic compound used for the composite material of a metal and an organic compound having a function of interacting with the metal as a tridentate or tetradentate ligand.

From the above, the light-emitting device of one embodiment of the present invention has a favorable electron-injection property, and thus is a light-emitting device having a low driving voltage and high emission efficiency. In addition, the light-emitting device has high moisture resistance because it can use a material with a high work function. The structures shown in this example can be used in appropriate combination with any of the other examples and embodiments.

Example 12

Described are examples of fabricating a light-emitting device 29 to a light-emitting device 32 that are examples of one embodiment of the present invention. A schematic cross-sectional view of the light-emitting devices fabricated in this example is shown in FIG. 1, and details of the device structures are shown in Table 20. Chemical formulae of organic compounds used in this example are shown below. The above examples and Embodiment 1 can be referred to for the structures and abbreviations of the other compounds. Note that the light-emitting device 29 to the light-emitting device 32 are examples of the light-emitting device that uses an organic compound having a pyridine skeleton as the organic compound used for the composite material of a metal and an organic compound having a function of interacting with the metal as a tridentate or tetradentate ligand. Note that in this example, the composite material of a metal and an organic compound having a function of interacting with the metal as a tridentate or tetradentate ligand is used for the electron-injection layer 130.

TABLE 20

| | Layer | Numeral | Thickness (nm) | Material | Weight ratio |
|---|---|---|---|---|---|
| Light-emitting device 29 | Electrode | 102 | 200 | Al | — |
| | Electron-injection layer | 130 | 5 | 2,6(P-Bqn)2Py:Ag | 1:0.3 |
| | Electron-transport layer | 118(2) | 15 | NBPhen | — |
| | | 118(1) | 20 | 2mDBTBPDBq-II | — |
| | Light-emitting layer | 140 | 40 | 2mDBTBPDBq-II:PCBBiF:Ir(dmdppr-dmp)$_2$(dpm) | 0.75:0.25:0.08 |
| | Hole-transport layer | 112 | 20 | PCBBiF | — |
| | Hole-injection layer | 111 | 25 | DBT3P-II:MoO$_3$ | 1:0.5 |
| | Anode | 101 | 110 | ITSO | — |
| Light-emitting device 30 | Electrode | 102 | 200 | Al | — |
| | Electron-injection layer | 130 | 5 | 2,6(P-Bqn)2Py:Cu | 1:0.2 |
| | Electron-transport layer | 118(2) | 15 | NBPhen | — |
| | | 118(1) | 20 | 2mDBTBPDBq-II | — |
| | Light-emitting layer | 140 | 40 | 2mDBTBPDBq-II:PCBBiF:Ir(dmdppr-dmp)$_2$(dpm) | 0.75:0.25:0.08 |
| | Hole-transport layer | 112 | 20 | PCBBiF | — |
| | Hole-injection layer | 111 | 25 | DBT3P-II:MoO$_3$ | 1:0.5 |
| | Anode | 101 | 110 | ITSO | — |
| Light-emitting device 31 | Electrode | 102 | 200 | Al | — |
| | Electron-injection layer | 130 | 5 | 2,6(NP-PPm)2Py:Ag | 1:0.3 |
| | Electron-transport layer | 118(2) | 15 | NBPhen | — |
| | | 118(1) | 20 | 2mDBTBPDBq-II | — |
| | Light-emitting layer | 140 | 40 | 2mDBTBPDBq-II:PCBBiF:Ir(dmdppr-dmp)$_2$(dpm) | 0.75:0.25:0.08 |
| | Hole-transport layer | 112 | 20 | PCBBiF | — |
| | Hole-injection layer | 111 | 25 | DBT3P-II:MoO$_3$ | 1:0.5 |
| | Anode | 101 | 110 | ITSO | — |
| Light-emitting device 32 | Electrode | 102 | 200 | Al | — |
| | Electron-injection layer | 130 | 5 | 2,6(NP-PPm)2Py:Cu | 1:0.2 |
| | Electron-transport layer | 118(2) | 15 | NBPhen | — |
| | | 118(1) | 20 | 2mDBTBPDBq-II | — |
| | Light-emitting layer | 140 | 40 | 2mDBTBPDBq-II:PCBBiF:Ir(dmdppr-dmp)$_2$(dpm) | 0.75:0.25:0.08 |
| | Hole-transport layer | 112 | 20 | PCBBiF | — |
| | Hole-injection layer | 111 | 25 | DBT3P-II:MoO$_3$ | 1:0.5 |
| | Anode | 101 | 110 | ITSO | — |

<Fabrication of Light-Emitting Device 29 to Light-Emitting Device 32>>

The light-emitting device 29 to the light-emitting device 32 were fabricated through the steps similar to those for the comparative light-emitting device 1 except for the formation step of the electron-injection layer 130.

As the electron-injection layer 130 of the light-emitting device 29, 2,6(P-Bqn)2Py and Ag were deposited over the electron-transport layer 118(2) by co-evaporation in a weight ratio (2,6(P-Bqn)2Py: Ag) of 1:0.3 to a thickness of 5 nm. Note that 2,6(P-Bqn)2Py is an example of the organic compound having a pyridine skeleton. Furthermore, it can be said that 2,6(P-Bqn)2Py is an organic compound having a quinazoline skeleton.

As the electron-injection layer 130 of the light-emitting device 30, 2,6(P-Bqn)2Py and Cu were deposited over the electron-transport layer 118(2) by co-evaporation in a weight ratio (2,6(P-Bqn)2Py: Cu) of 1:0.2 to a thickness of 5 nm.

As the electron-injection layer 130 of the light-emitting device 31, 2,6(NP-PPm)2Py and Ag were deposited over the electron-transport layer 118(2) by co-evaporation in a weight ratio (2,6(NP-PPm)2Py: Ag) of 1:0.3 to a thickness of 5 nm. Note that 2,6(NP-PPm)2Py is an example of the organic compound having a pyridine skeleton. Furthermore, it can be said that 2,6(NP-PPm)2Py is an organic compound having a pyrimidine skeleton.

Note that in the light-emitting device 29 to the light-emitting device 32, a cathode was fabricated in a manner similar to that of the comparative light-emitting device 1, and then heat treatment was performed at 80° C. in an air for one hour without sealing <<<Measurement of Light-Emitting Devices>>

The device characteristics of the fabricated light-emitting device 29 to light-emitting device 32 were measured. Luminance and CIE chromaticity were measured with a luminance colorimeter (BM-5A manufactured by TOPCON TECHNOHOUSE CORPORATION), and electroluminescence spectra were measured with a multi-channel spectrometer (PMA-11 manufactured by Hamamatsu Photonics K.K.).

Figure 47:
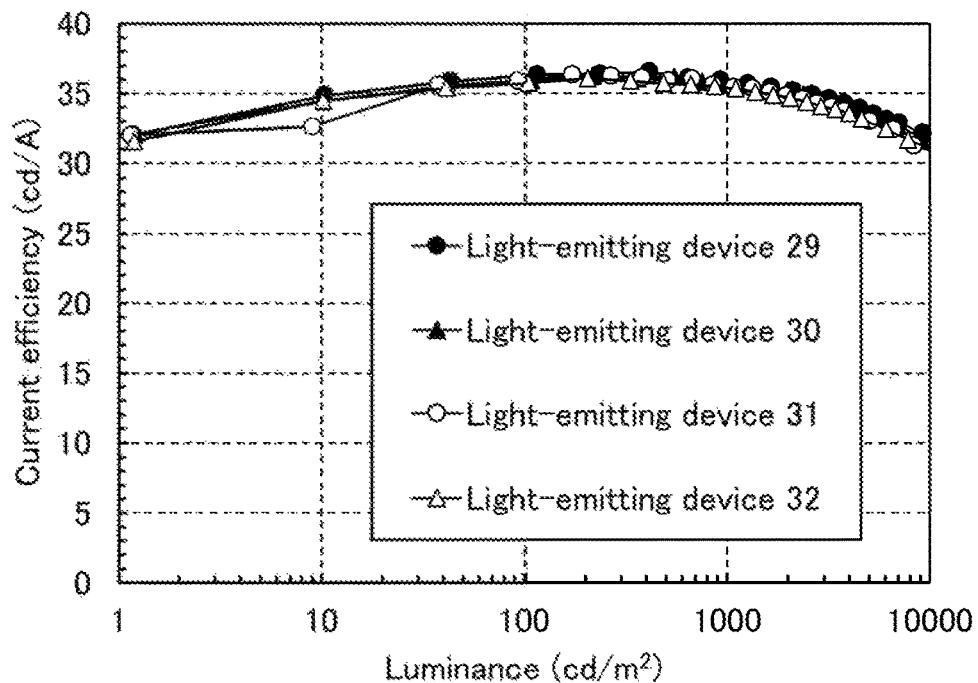
FIG. 47 is a diagram showing current efficiency-luminance characteristics of light-emitting devices in Example.
Figure 48:
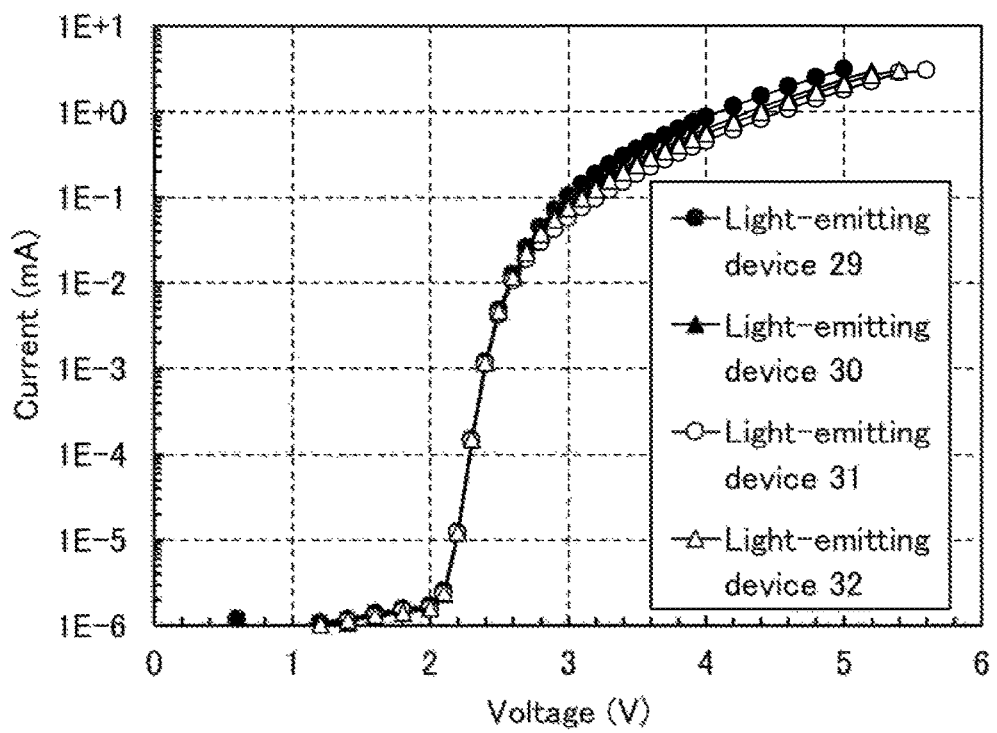
FIG. 48 is a diagram showing current-voltage characteristics of light-emitting devices in Example.
Figure 49:
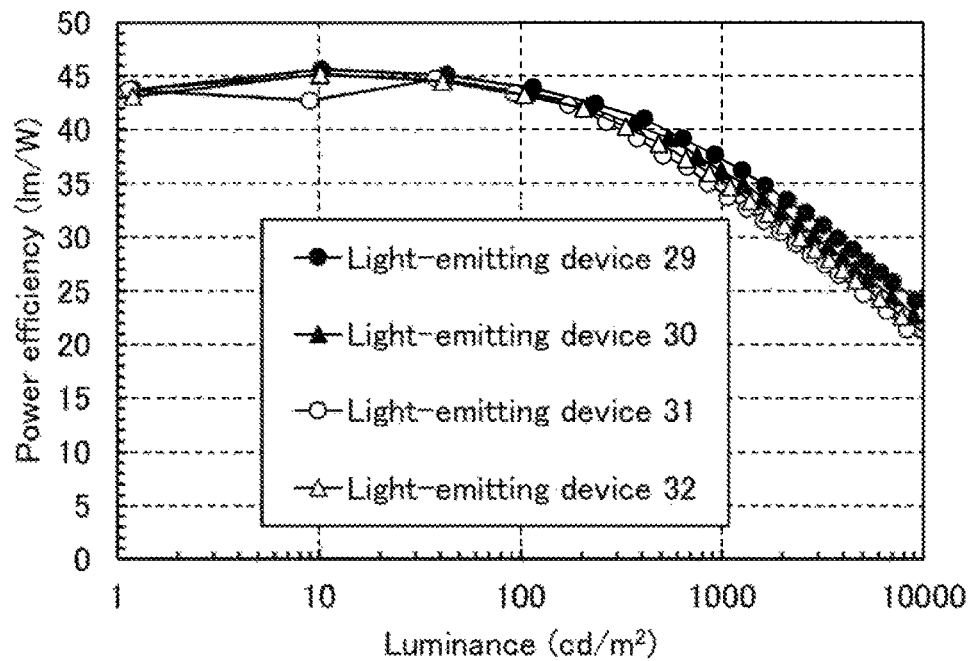
FIG. 49 is a diagram showing power efficiency-luminance characteristics of light-emitting devices in Example.
Figure 50:
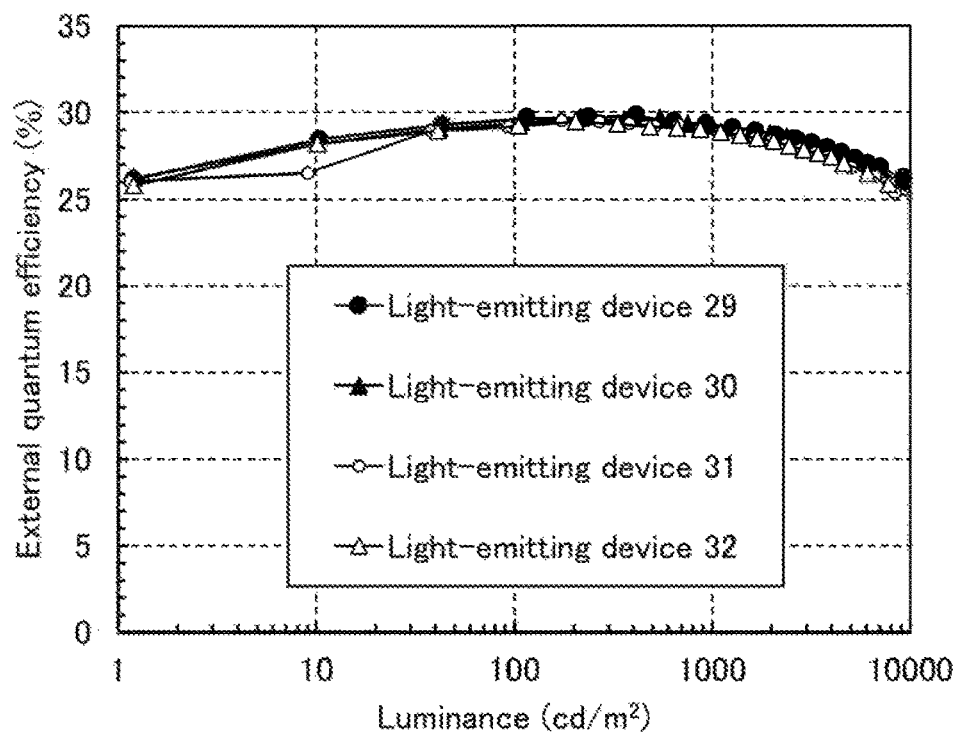
FIG. 50 is a diagram showing external quantum efficiency-luminance characteristics of light-emitting devices in Example.
Figure 51:
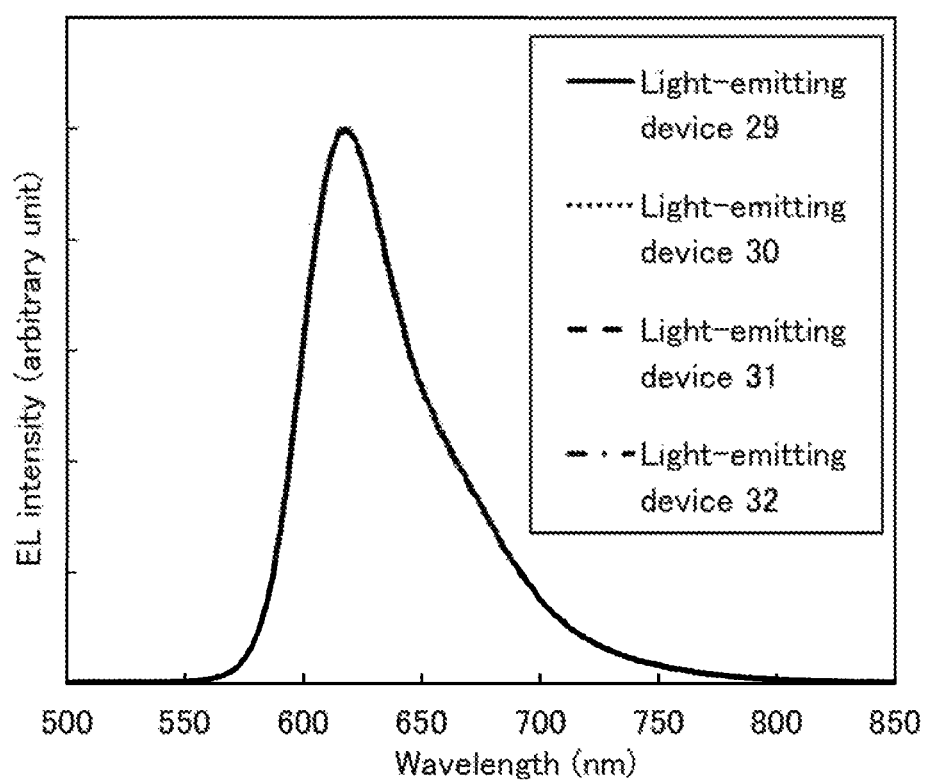
FIG. 51 is a diagram showing electroluminescence spectra of light-emitting devices in Example.

FIG. 47 shows the current efficiency-luminance characteristics of the fabricated light-emitting device 29 to light-emitting device 32, FIG. 48 shows the current-voltage characteristics thereof, FIG. 49 shows the power efficiency-luminance characteristics thereof, and FIG. 50 shows the external quantum efficiency-luminance characteristics thereof. Note that the measurement of the light-emitting devices was performed at room temperature (in an atmosphere maintained at 23° C.). FIG. 51 shows the electroluminescence spectra of the light-emitting devices through which current flows at a current density of 2.5 mA/cm$^2$. Note that the measurement was performed at room temperature.

Table 21 shows the device characteristics of the light-emitting device 29 to the light-emitting device 32 at around 1000 cd/m$^2$.

TABLE 21

| | Voltage (V) | Current density (mA/cm$^2$) | CIE Chromaticity (x, y) | Luminance (cd/m$^2$) | Current efficiency (cd/A) | Power efficiency (lm/W) | External quantum efficiency (%) |
|---|---|---|---|---|---|---|---|
| Light-emitting device 29 | 3.00 | 2.60 | (0.667, 0.333) | 935 | 35.9 | 37.6 | 29.3 |
| Light-emitting device 30 | 3.10 | 2.80 | (0.667, 0.333) | 998 | 35.7 | 36.2 | 29.2 |
| Light-emitting device 31 | 3.30 | 3.06 | (0.666, 0.334) | 1085 | 35.4 | 33.7 | 28.8 |
| Light-emitting device 32 | 3.20 | 3.13 | (0.666, 0.334) | 1105 | 35.3 | 34.7 | 28.9 |

As shown in FIG. 51, the electroluminescence spectra of the light-emitting device 29 to the light-emitting device 32 each have a peak wavelength of the electroluminescence spectrum at approximately 618 nm, which shows that the light-emitting device 29 to the light-emitting device 32 exhibit light emission derived from Ir(dmdppr-dmp)$_2$(dpm), which is a guest material included in each light-emitting device.

Furthermore, as shown in FIG. 50 and Table 21, the light-emitting device 29 to the light-emitting device 32 each exhibited extremely high emission efficiency with external quantum efficiency exceeding 28%. They also exhibited high current efficiency and high power efficiency as shown in FIG. 47 and FIG. 49. Thus, it was found that the organic compound having a pyridine skeleton (a pyrimidine skeleton or a quinazoline skeleton) was suitable as the organic compound used for the composite material of a metal and an organic compound having a function of interacting with the metal as a tridentate or tetradentate ligand.

In addition, as shown in FIG. 48, the light-emitting device 29 to the light-emitting device 32 exhibited favorable current density-voltage characteristics. Thus, it was found that the organic compound having a triazine skeleton (or a pyrimidine skeleton) or a bipyridine skeleton (or a quinazoline skeleton) was suitable as the organic compound used for the composite material of a metal and an organic compound having a function of interacting with the metal as a tridentate or tetradentate ligand.

From the above, the light-emitting device of one embodiment of the present invention has a favorable electron-injection property, and thus is a light-emitting device having a low driving voltage and high emission efficiency. In addition, the light-emitting device has high moisture resistance because it can use a material with a high work function. The structures shown in this example can be used in appropriate combination with any of the other examples and embodiments.

REFERENCE NUMERALS

100: EL layer, 101: electrode, 101a: conductive layer, 101b: conductive layer, 102: electrode, 103: electrode, 103a: conductive layer, 103b: conductive layer, 104: electrode, 104a: conductive layer, 104b: conductive layer, 106: light-emitting unit, 108: light-emitting unit, 110: EL layer, 111: hole-injection layer, 112: hole-transport layer, 113: electron-transport layer, 115: charge generation layer, 116: hole-injection layer, 117: hole-transport layer, 118: electron-transport layer, 119: electron-injection layer, 127: buffer layer, 129: charge generation layer, 130: electron-injection layer, 131: compound, 132: metal, 133: compound, 140: light-emitting layer, 145: partition wall, 150: light-emitting element, 152: light-emitting element, 154: light-emitting element, 170: light-emitting layer, 200: substrate, 220: substrate, 222B: region, 222G: region, 222R: region, 223: light-blocking layer, 224B: optical element, 224G: optical element, 224R: optical element, 250a: light-emitting element, 250b: light-emitting element, 601: source side driver circuit, 602: pixel portion, 603: gate side driver circuit, 604: sealing substrate, 605: sealant, 607: space, 608: wiring, 610: element substrate, 611: switching TFT, 612: current control TFT, 613: electrode, 614: insulator, 616: EL layer, 617: electrode, 618: light-emitting element, 623: n-channel TFT, 624: p-channel TFT, 900: portable information terminal, 901: housing, 902: housing, 903: display portion, 905: hinge portion, 910: portable information terminal, 911: housing, 912: display portion, 913: operation button, 914: external connection port, 915: speaker, 916: microphone, 917: camera, 920: camera, 921: housing, 922: display portion, 923: operation button, 924: shutter button, 926: lens, 1001: substrate, 1002: base insulating film, 1003: gate insulating film, 1006: gate electrode, 1007: gate electrode, 1008: gate electrode, 1020: interlayer insulating film, 1021: interlayer insulating film, 1022: electrode, 1024B: electrode, 1024G: electrode, 1024R: electrode, 1024W: electrode, 1025B: lower electrode, 1025G: lower electrode, 1025R: lower electrode, 1025W: lower electrode, 1026: partition wall, 1028: EL layer, 1029: electrode, 1031: sealing substrate, 1032: sealant, 1033: base material, 1034B: coloring layer, 1034G: coloring layer, 1034R: coloring layer, 1036: overcoat layer, 1037: interlayer insulating film, 1040: pixel portion, 1041: driver circuit portion, 1042: peripheral portion, 2100: robot, 2101: illuminance sensor, 2102: microphone, 2103: upper camera, 2104: speaker, 2105: display, 2106: lower camera, 2107: obstacle sensor, 2108: moving mechanism, 2110: arithmetic device, 5000: housing, 5001: display portion, 5002: display portion, 5003: speaker, 5004: LED lamp, 5005: control key, 5006: connection terminal, 5007: sensor, 5008: microphone, 5012: support, 5013: earphone, 5100: cleaning robot, 5101: display, 5102: camera, 5103: brush, 5104: operation button, 5120: dust, 5140: portable electronic apparatus, 5150: portable information terminal, 5151: housing, 5152: display region, 5153: bend portion, 8501: lighting device, 8502: lighting device, 8503: lighting device, 8504: lighting device This application is based on Japanese Patent Application Serial No. 2017-246022 filed with Japan Patent Office on Dec. 22, 2017, the entire contents of which are hereby incorporated herein by reference.

The invention claimed is:

1. A light-emitting device comprising:
    a light-emitting layer between an anode and a cathode; and
    a first layer between the light-emitting layer and the cathode,
    wherein the first layer comprises a first organic compound and a metal,
    wherein the metal belongs to any of Group 3 to Group 13 of a periodic table,
    wherein the first organic compound comprises a substituted or unsubstituted heteroaromatic ring having 1 to 30 carbon atoms,
    wherein the first organic compound has a three or four coordination positions,
    wherein each of the three or four coordination positions is included in a heteroaromatic ring comprising nitrogen,
    wherein the first organic compound is capable of interacting with the metal by the three or four coordination positions, and
    wherein the first organic compound and the metal form SOMO.

2. The light-emitting device according to claim 1, further comprising:
    a first light-emitting unit and a second light-emitting unit between the anode and the cathode,
    wherein the first light-emitting unit comprises the light-emitting layer and the first layer.

3. The light-emitting device according to claim 1,
    wherein the first organic compound is represented by formula (G0):

[Chemical formula 1]

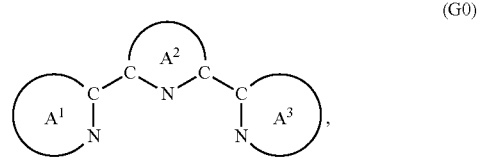

(G0)

and
    wherein each of $A^1$, $A^2$ and $A^3$ independently represents a substituted or unsubstituted heteroaromatic ring having 1 to 30 carbon atoms.

4. The light-emitting device according to claim 3,
    wherein the first organic compound is represented by formula (G1):

[Chemical Formula 2]

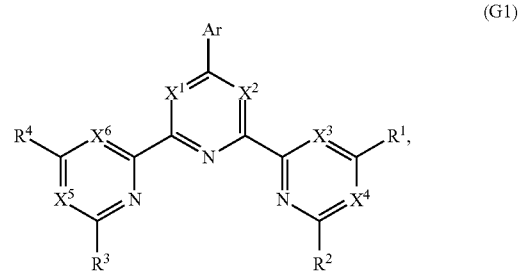

(G1)

and
    wherein:
    each of $X^1$ to $X^6$ independently represents carbon or nitrogen;
    the carbon bonds to any one of hydrogen, an alkyl group having 1 to 4 carbon atoms, a substituted or unsubstituted cycloalkyl group having 3 to 7 carbon atoms, a substituted or unsubstituted aromatic hydrocarbon group having 6 to 25 carbon atoms, and a substituted or unsubstituted heteroaromatic hydrocarbon group having 3 to 30 carbon atoms;
    each of $R^1$ to $R^4$ independently represents any one of hydrogen, an alkyl group having 1 to 4 carbon atoms, a substituted or unsubstituted cycloalkyl group having 3 to 7 carbon atoms, a substituted or unsubstituted aromatic hydrocarbon group having 6 to 25 carbon atoms, and a substituted or unsubstituted heteroaromatic hydrocarbon group having 3 to 30 carbon atom; and Ar represents any one of hydrogen, an alkyl group having 1 to 4 carbon atoms, a substituted or unsubstituted cycloalkyl group having 3 to 7 carbon atoms, a substituted or unsubstituted aromatic hydrocarbon group having 6 to 60 carbon atoms, and a substituted or unsubstituted heteroaromatic hydrocarbon group having 2 to 60 carbon atoms.

5. The light-emitting device according to claim 3, wherein the first organic compound is represented by formula (G2):

[Chemical Formula 3]

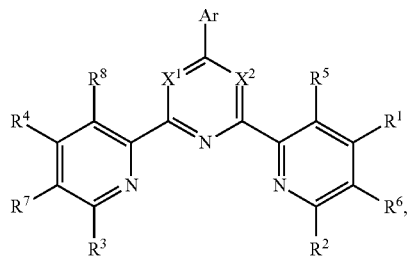

(G2)

and
wherein:
each of $X^1$ and $X^2$ independently represent carbon (C) or nitrogen (N); the carbon comprises any one of hydrogen, an alkyl group having 1 to 4 carbon atoms, a substituted or unsubstituted cycloalkyl group having 3 to 7 carbon atoms, a substituted or unsubstituted aromatic hydrocarbon group having 6 to 25 carbon atoms, and a substituted or unsubstituted heteroaromatic hydrocarbon group having 3 to 30 carbon atoms;

each of $R^1$ to $R^8$ independently represents any one of hydrogen, an alkyl group having 1 to 4 carbon atoms, a substituted or unsubstituted cycloalkyl group having 3 to 7 carbon atoms, a substituted or unsubstituted aromatic hydrocarbon group having 6 to 25 carbon atoms, and a substituted or unsubstituted heteroaromatic hydrocarbon group having 3 to 30 carbon atoms; and Ar represents any one of hydrogen, an alkyl group having 1 to 4 carbon atoms, a substituted or unsubstituted cycloalkyl group having 3 to 7 carbon atoms, a substituted or unsubstituted aromatic hydrocarbon group having 6 to 60 carbon atoms, and a substituted or unsubstituted heteroaromatic hydrocarbon group having 2 to 60 carbon atoms.

6. The light-emitting device according to claim 3, wherein the first organic compound is represented by any one of formulae (G3-1) to (G3-3):

[Chemical Formula 4]

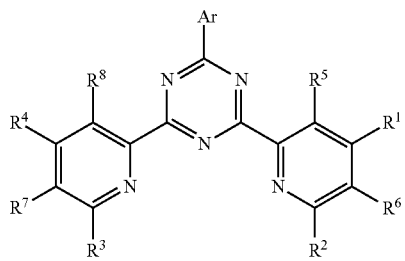

(G3-1)

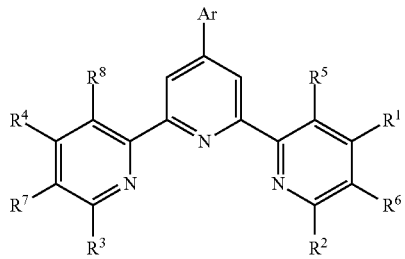

(G3-2)

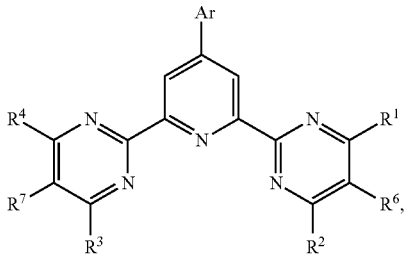

(G3-3)

and
wherein:
each of $R^1$ to $R^8$ independently represents any one of hydrogen, an alkyl group having 1 to 4 carbon atoms, a substituted or unsubstituted cycloalkyl group having 3 to 7 carbon atoms, a substituted or unsubstituted aromatic hydrocarbon group having 6 to 25 carbon atoms, and a substituted or unsubstituted heteroaromatic hydrocarbon group having 3 to 30 carbon atoms, and Ar represents any one of hydrogen, an alkyl group having 1 to 4 carbon atoms, a substituted or unsubstituted cycloalkyl group having 3 to 7 carbon atoms, a substituted or unsubstituted aromatic hydrocarbon group having 6 to 60 carbon atoms, and a substituted or unsubstituted heteroaromatic hydrocarbon group having 2 to 60 carbon atoms.

7. The light-emitting device according to claim 3, wherein the first organic compound is represented by any one of formulae (G4-1) to (G4-3):

[Chemical Formula 5]

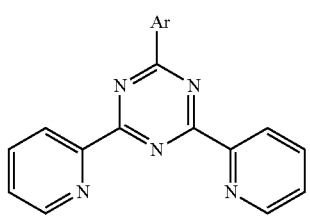

(G4-1)

-continued (G4-2)
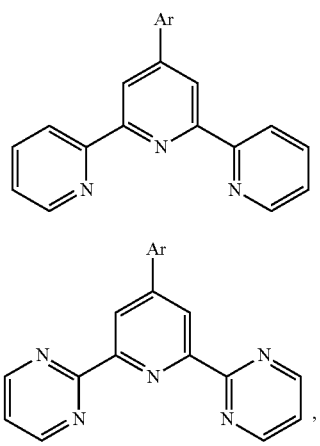

(G4-3)
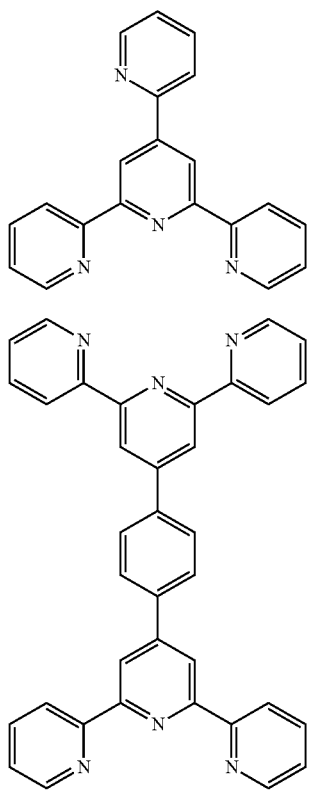

and wherein Ar represents any one of hydrogen, an alkyl group having 1 to 4 carbon atoms, a substituted or unsubstituted cycloalkyl group having 3 to 7 carbon atoms, a substituted or unsubstituted aromatic hydrocarbon group having 2 to 60 carbon atoms, and a substituted or unsubstituted heteroaromatic hydrocarbon group having 2 to 60 carbon atoms.

8. The light-emitting device according to claim 3, wherein the first organic compound is represented by any one of formulae (100) to (103):

[Chemical Formula 6]

-continued (102)
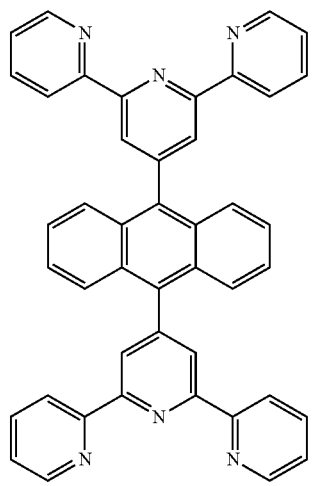

(103)
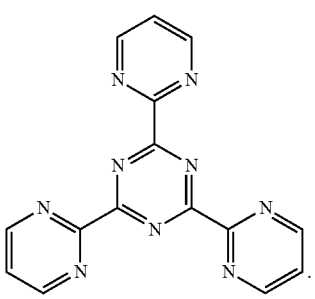

9. The light-emitting device according to claim 1, wherein a work function of the metal is higher than or equal to 4.0 eV and lower than or equal to 5.3 eV.

10. The light-emitting device according to claim 1, wherein the metal is a transition metal.

11. The light-emitting device according to claim 1, wherein the metal belongs to any of Group 5, Group 7, Group 9, and Group 11 of the periodic table.

12. The light-emitting device according to claim 1, wherein the metal belongs to Group 11 of the periodic table.

13. The light-emitting device according to claim 1, wherein the metal is Ag or Cu.

14. The light-emitting device according to claim 1, wherein the heteroaromatic ring comprises an electron deficient heteroaromatic ring.

15. The light-emitting device according to claim 14, wherein the electron deficient heteroaromatic ring is any one of a pyridine ring, a diazine ring and a triazine ring.

16. The light-emitting device according to claim 1, wherein a LUMO level of the first organic compound is higher than or equal to 3.6 eV and lower than or equal to 2.3 eV.

17. The light-emitting device according to claim 1, further comprising:

a second layer between the cathode and the first layer, wherein the second layer comprises a second organic compound comprising an electron deficient heteroaromatic ring.

18. The light-emitting device according to claim 17, wherein a LUMO level of the second organic compound is lower than an energy level of the SOMO.

19. The light-emitting device according to claim 1, wherein the first layer comprises neither an alkali metal nor an alkaline earth metal.

20. The light-emitting device according to claim 1, wherein a molar ratio of the metal to the first organic compound in the first layer is higher than or equal to 0.2 and lower than or equal to 0.8.

21. The light-emitting device according to claim 1, wherein the cathode comprises the metal.

22. The light-emitting device according to claim 1, wherein the cathode and the first layer are in contact with each other.

23. The light-emitting device according to claim 1, wherein a work function of the metal is higher than or equal to a work function of a metal included in the cathode.

24. A light-emitting apparatus comprising:
the light-emitting device according to of claim 1; and
at least one of a color filter and a transistor.

25. An electronic device comprising:
the light-emitting apparatus according to claim 24; and
at least one of a housing and a display portion.

26. A lighting device comprising:
the light-emitting device according to claim 1; and
a housing.

27. An organic compound represented by any one of formulae (200) to (203):

(200)
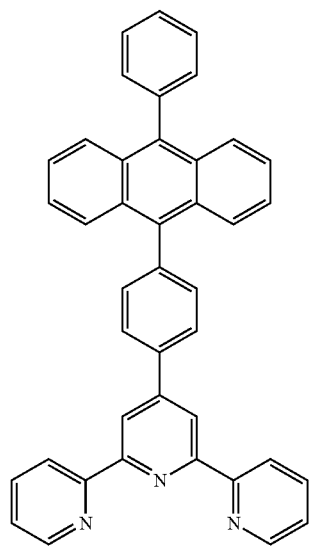

-continued (201)
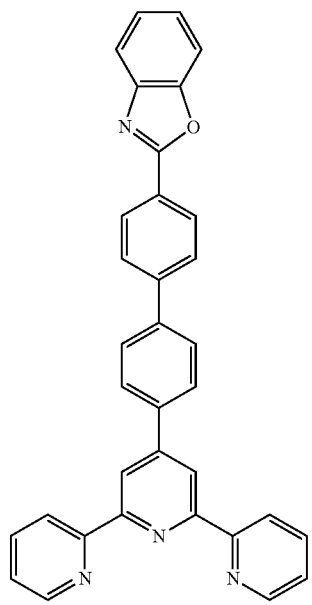

(202)
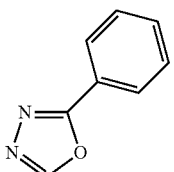
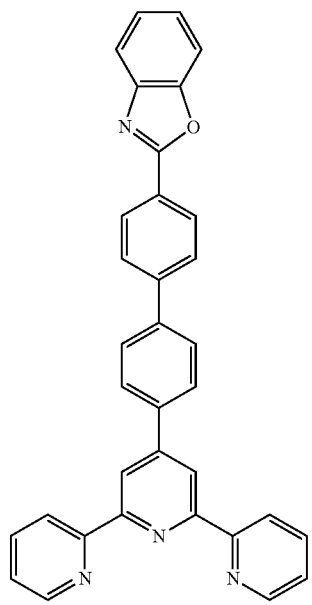

(203)
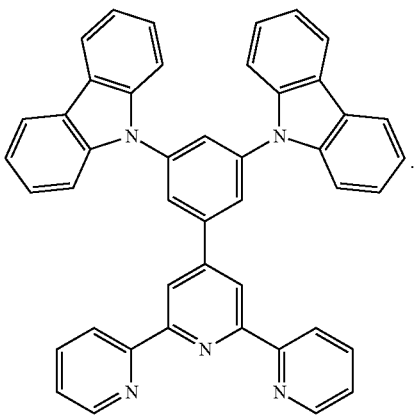

28. A light-emitting device comprising any one of the organic compound according to claim 27,
   wherein the light-emitting device optionally further comprises one or more compounds represented by formulae (200) to (203) other than the organic compound according to claim 27.

29. The light-emitting device according to claim 3, wherein $R^1$, $R^2$ and $R^3$ form one condensed ring.

* * * * *